US009468675B2

(12) United States Patent
Teschner et al.

(10) Patent No.: US 9,468,675 B2
(45) Date of Patent: Oct. 18, 2016

(54) REMOVAL OF SERINE PROTEASES BY TREATMENT WITH FINELY DIVIDED SILICON DIOXIDE

(71) Applicants: Baxalta Incorporated, Bannockburn, IL (US); Baxalta GmbH, Glattpark (Opfikon) (CH)

(72) Inventors: Wolfgang Teschner, Vienna (AT); Hans-Peter Schwarz, Vienna (AT); Ruth Madlener, Vienna (AT); Sonja Svatos, Berg (AT); Azra Pljevljakovic, Vienna (AT); Alfred Weber, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/296,319

(22) Filed: Jun. 4, 2014

(65) Prior Publication Data
US 2014/0336122 A1 Nov. 13, 2014

Related U.S. Application Data

(60) Division of application No. 13/117,028, filed on May 26, 2011, now Pat. No. 8,772,462, which is a continuation-in-part of application No. 12/789,365, filed on May 27, 2010, now Pat. No. 8,993,734, and a continuation-in-part of application No. 12/842,944, filed on Jul. 23, 2010, now Pat. No. 8,304,524.

(30) Foreign Application Priority Data

May 26, 2010 (AU) ................................ 2010202125

(51) Int. Cl.
*A61K 39/395* (2006.01)
*A61K 9/00* (2006.01)
*A61K 9/08* (2006.01)
*A61K 38/17* (2006.01)
*A61K 47/18* (2006.01)
*C07K 1/30* (2006.01)
*C07K 1/36* (2006.01)
*C07K 16/06* (2006.01)
*A61K 35/16* (2015.01)

(52) U.S. Cl.
CPC ....... *A61K 39/39525* (2013.01); *A61K 9/0019* (2013.01); *A61K 9/08* (2013.01); *A61K 35/16* (2013.01); *A61K 38/1709* (2013.01); *A61K 47/183* (2013.01); *C07K 1/30* (2013.01); *C07K 1/36* (2013.01); *C07K 16/065* (2013.01)

(58) Field of Classification Search
None
See application file for complete search history.

(56) References Cited

U.S. PATENT DOCUMENTS

| 3,998,946 A | 12/1976 | Condie et al. |
| 4,056,614 A | 11/1977 | Bonneau et al. |
| 4,136,094 A | 1/1979 | Condie |
| 4,216,205 A | 8/1980 | Radowitz |
| 4,228,154 A | 10/1980 | Fisher et al. |
| 4,272,523 A | 6/1981 | Kotitschke et al. |
| 4,296,027 A | 10/1981 | Condie |
| 4,318,902 A | 3/1982 | Stephan |
| 4,378,346 A | 3/1983 | Tankersley |
| 4,439,358 A | 3/1984 | Coan et al. |
| 4,476,109 A | 10/1984 | Kimura et al. |
| 4,499,073 A | 2/1985 | Tenold |
| 4,503,039 A | 3/1985 | Kotitschke et al. |
| 4,550,019 A | 10/1985 | Polson |
| 4,624,780 A | 11/1986 | Chang |
| 5,055,447 A | 10/1991 | Palladino et al. |
| 5,061,237 A | 10/1991 | Gessler et al. |
| 5,122,373 A | 6/1992 | Eibl et al. |
| 5,130,451 A | 7/1992 | Pourreau et al. |
| 5,136,094 A | 8/1992 | Listemann et al. |
| 5,177,194 A | 1/1993 | Sarno et al. |
| 5,324,425 A | 6/1994 | Ellison |
| 5,886,154 A | 3/1999 | Lebing et al. |
| 6,069,236 A | 5/2000 | Burnouf-Radosevich et al. |
| 6,093,324 A | 7/2000 | Bertolini et al. |

(Continued)

FOREIGN PATENT DOCUMENTS

| AU | 2010202125 B1 | 9/2010 |
| AU | 2010224461 A1 | 10/2010 |

(Continued)

OTHER PUBLICATIONS

Ahrer, K. et al., "Effects of ultra-/diafiltration conditions on present aggregates in human immunoglobulin G preparations," *Journal of Membrane Science*, 2006, vol. 274, pp. 108-115.

(Continued)

*Primary Examiner* — Suzanne M Noakes
(74) *Attorney, Agent, or Firm* — Morgan, Lewis & Bockius LLP

(57) ABSTRACT

The present invention provides novel methods for reducing the serine protease and/or serine protease zymogen content of a plasma-derived protein composition. Also provided are methods for manufacturing plasma-derived protein compositions having reduced serine protease and\or serine protease zymogen content. Among yet other aspects, the present invention provides aqueous and lyophilized compositions of plasma-derived proteins having reduced serine protease and/or serine protease zymogen content. Yet other aspects include methods for treating, managing, and/or preventing a disease comprising the administration of a plasma-derived protein composition having a reduced serine protease or serine protease zymogen content.

20 Claims, 3 Drawing Sheets

(56) References Cited

U.S. PATENT DOCUMENTS

| | | | |
|---|---|---|---|
| 6,124,437 | A | 9/2000 | Hirao et al. |
| 6,159,471 | A | 12/2000 | Hirao et al. |
| 6,835,379 | B2 | 12/2004 | Andersson et al. |
| 7,186,410 | B2 | 3/2007 | Chtourou et al. |
| 7,553,938 | B2 | 6/2009 | Buchacher et al. |
| 7,932,365 | B2 | 4/2011 | Lim et al. |
| 8,304,524 | B2 | 11/2012 | Bairstow et al. |
| 8,841,248 | B2 * | 9/2014 | Bairstow et al. ............. 514/1.4 |
| 8,993,734 | B2 | 3/2015 | Bruckschwaiger et al. |
| 2002/0098182 | A1 | 7/2002 | Weisbart et al. |
| 2002/0114802 | A1 | 8/2002 | Tjellstrom et al. |
| 2003/0099635 | A1 | 5/2003 | Barstow et al. |
| 2003/0190732 | A1 | 10/2003 | Josic |
| 2007/0020647 | A1 | 1/2007 | Hageman et al. |
| 2008/0318841 | A1 | 12/2008 | Chtourou et al. |
| 2009/0118163 | A1 | 5/2009 | Gronski et al. |
| 2009/0148463 | A1 | 6/2009 | Reipert et al. |
| 2009/0203580 | A1 | 8/2009 | Dinarello et al. |
| 2010/0330071 | A1 | 12/2010 | Teschner et al. |
| 2011/0021432 | A1 | 1/2011 | Bairstow et al. |

FOREIGN PATENT DOCUMENTS

| | | |
|---|---|---|
| DE | 35 23 615 A1 | 1/1987 |
| DE | 100 08 619 A1 | 9/2011 |
| EP | 0 222 611 A2 | 5/1987 |
| EP | 0 440 509 A2 | 8/1991 |
| EP | 0 893 450 A1 | 1/1999 |
| GB | 1 344 340 | 9/1972 |
| SE | 348 942 | 9/1972 |
| WO | WO 95/11260 A1 | 4/1995 |
| WO | WO 99/43362 A1 | 9/1999 |
| WO | WO 03/034982 A2 | 5/2003 |
| WO | WO 2004/060528 A1 | 7/2004 |
| WO | WO 2005/026197 A1 | 3/2005 |
| WO | WO 2005/046587 A2 | 5/2005 |
| WO | WO 2005/073252 A1 | 8/2005 |
| WO | WO 2007/038995 A1 | 4/2007 |
| WO | WO 2007/066017 A2 | 6/2007 |
| WO | WO 2007/066017 A3 | 6/2007 |
| WO | WO 2007/085626 A1 | 8/2007 |
| WO | WO 2008/113589 A1 | 9/2008 |
| WO | WO 2009/005877 A2 | 8/2009 |
| WO | WO 2009/154695 A1 | 12/2009 |
| WO | WO 2010/056909 A1 | 5/2010 |
| WO | WO 2010/138736 A2 | 12/2010 |
| WO | WO 2011/011753 A1 | 1/2011 |
| WO | WO 2011/149472 A1 | 12/2011 |
| WO | WO 2011/150284 A2 | 12/2011 |
| WO | WO 2012/012773 A1 | 1/2012 |

OTHER PUBLICATIONS

Barandun, S. et al., "Intravenous Administration of Human y-Globulin," *Vox Sanguinis*, 1962, pp. 157-174, vol. 7.
Bee, W.H. et al., "Effects of Recombinant Human Hyaluronidase (rHuPH20) on Subcutaneous Administration of 10% and 20% IgC in Yucatan Mini Pigs," *J. Allergy Clin. Immunol.*, Feb. 2010, 2 pages (p. Abstracts AB139), Abstract No. 547, vol. 125, No. 2, Suppl 2.
Buchacher, et al., "Purification of intravenous immunoglobulin G from human plasma—aspects of yield and virus safety," *Biotechnol. J.*, 2006, 1, pp. 148-163.
Cammarata, P.S. et al., "Fractionation and Properties of Glutamic-Oxalacetic Transaminase," *The Journal of Biological Chemistry*, Nov. 1951, vol. 193, No. 1, pp. 53-62.
Celite Material Safety Data Sheet, No. 2402, Rev. No. 9, Date Revised Jun. 30, 2012, pp. 1-2.
Cochrane, C.G. et al., "Molecular Assembly in the Contact Phase of the Hageman Factor System," *The American Journal of Medicine*, Oct. 1979, vol. 67, pp. 657-664.
Cohn, E.J. et al., "A System for the Separation of the Components of Human Blood: Quantitative Procedures for the Separation of the Protein Components of Human Plasma," *Separation of Protein Components of Human Plasma*, Jan. 1950, vol. 72, pp. 465-474.
Cohn, E.J. et al., "Preparation and Properties of Serum and Plasma Proteins. IV. A System for the Separation into Fractions of the Protein and Lipoprotein Components of Biological Tissues and Fluids," *J. Am. Chem. Soc.*, Mar. 1946, pp. 459-475, vol. 68, No. 3.
Curling, J.M. ed., *Methods of Plasma Protein Fractionation*, 1980, Academic Press, pp. 12-13. 248-249, Table 1.
Falksveden, L.-G. et al., "Ion Exchange and Polyethylene Glycol Precipitation of Immunoglobulin G," in *Methods of Plasma Protein Fractionation*, Curling, J.M. ed., 1980, pp. 93-103, Academic Press, New York, NY.
Foster, P.R., "Assessment of the potential of plasma fractionation processes to remove causative agents of transmissible spongiform encephalopathy," *Transfusion Medicine*, 1999, vol. 9, pp. 3-14.
Goldsmith, et al., "The Activation of Plasminogen by Hageman Factor (Factor XII) and Hageman Factor Fragments," *J. Clin. Invest.*, 1978, 62,(1), pp. 54-60.
Guerffroy, "A guide for the preparation and use of buffers in biological systems," © 1975 by Behring Diagnostics, pp. 1-25.
Gun'Ko, V.M. et al., "Aqueous Suspensions of Fumed Silica and Adsorption of Proteins," *Journal of Colloid and Interface Science*, 1997, vol. 192, pp. 166-178.
Hermann, C. et al., "Analysis of Fc-Receptor-Mediated Activities of New IgG Products Using a Novel THP-1 Cell-based Assay," *J. Allergy Clin. Immunol.*, Feb. 2010, 2 pages (p. Abstracts AB79), Abstract No. 312, vol. 125, No. 2, Suppl 1.
Hofmeister, Y. et al., "Human IgG Subclasses: In Vitro Neutralization of and In Vivo Protection against West Nile Virus," *Journal of Virology*, Feb. 2011, pp. 1896-1899, vol. 85, No. 4.
Hoppe, Von H.H. et al., "Herstellung von Anti-Rh-Gammaglobulin zur Immunisierungs-Prophylaxe," *Münchener Medizinische Wochenschrift*, Jul. 7, 1967, vol. 34, pp. 1749-1752.
Jourdain, M. et al., "Effects of Inter-α-inhibitor in Experimental Endotoxic Shock and Disseminated Intravascular Coagulation," *Am J Respir Crit Care Med*, 1997, vol. 156, pp. 1825-1833.
Kistler, P. et al., "Large Scale Production of Human Plasma Fractions," *Vox Sang.*, 1962, vol. 7, pp. 414-424.
Koblet, H. et al., "Turnover of Standard-Gammaglobulin, pH-4-Gammaglobulin and Pepsin Desaggregated Gammaglobulin and Clinical Implications," *Vox Sanguinis*, 1967, pp. 93-102, vol. 13.
Kreil, T.R. et al., "Development of a New 10% Liquid, Triple Virus Reduced Intra-venous Immune-Globulin Product, New Generation IGIV," *J. Allergy Immunol.*, Feb. 2004, p. S128 Abstracts, Abstract No. 410.
Kreil, T.R. et al., "Pathogen Safety Profile of a New 10% Liquid, Triple Virus Reduced Intravenous Immune Globulin Product, New Generation IGIV (NG IGIV)—Further Studies," *J. Allergy Clin. Immunol.*, Feb. 2005, p. S156 Abstracts, Abstract No. 623.
Kreil, T.R. et al., "Removal of small nonenveloped viruses by antibody-enhanced nanofiltration during the manufacture of plasma derivatives," *Transfusion*, Jul. 2006, pp. 1143-1151, vol. 46.
Lebing, W. et al., "Properties of a new intravenous immunoglobulin (IGIV-C, 10%) produced by virus inactivation with caprylate and col. chromatography," Vox Sanguinis, 2003, pp. 193-201, vol. 84.
Leesch, V.W. et al., "30-Day Pharmacokinetic Evaluation of IV versus Subcutaneous Administration of Immunoglobulin with and without Recombinant Human Hyaluronidase in Dogs," *J. Allergy Clin. Immunol.*, Feb. 2009, p. S10 Abstracts, Abstract No. 24.
Lim, Y-P. et al., "Affinity purification and enzymatic cleavage of inter-alpha inhibitor proteins using antibody and elastase immobilized on CIM monolithic disks," *Journal of Chromatography A*, 2005, vol. 1065, pp. 39-43.
Lim, Y-P. et al., "Correlation between Mortality and the Levels of Inter-Alpha Inhibitors in the Plasma of Patients with Severe Sepsis," *The Journal of Infectious Diseases*, Sep. 15, 2003, vol. 188, pp. 919-926.
McCann, K.B. et al., "Evaluation of expanded bed adsorption chromatography for extraction of prothrombin complex from Cohn Supernatant I," *Biologicals*, 2008, vol. 36, pp. 227-223.
Michalski, C. et al., "Preparation and Properties of a Therapeutic Inter-Alpha-Trypsin Inhibitor Concentrate from Human Plasma," *Vox Sang*, 1994, vol. 67, pp. 329-336.

(56) References Cited

OTHER PUBLICATIONS

Mizon, C. et al., "Human pre-α-inhibitor: isolation from a by-product of industrial scale plasma fractionation and structural analysis of its H3 heavy chain," *Journal of Chromatography B*, 1997, vol. 692, pp. 281-291.

Nitschmann, H., et al., "Vereinfachtes Verfahren zur Gewinnung von Humanem Albumin and Gamma-Globulin aus Blutplasma Mittels Alkoholfaellung," Helvetica Chimica Acta, Verlag Helvetica Chimica Acta, vol. 37, Jan. 1, 1954 (Jan. 1, 1954), pp. 866-873.

Olas, K. et al., "Immunomodulatory properties of human serum immunoglobulin A: anti-inflammatory and pro-inflammatory activities in human monocytes and peripheral blood mononuclear cells," *Clinical and Experimental Immunology*, 2005, pp. 478-490, vol. 140.

Olas, K. et al., "Natural anti-amyloid beta antibodies in intravenous immunoglobulin prevent amyloid beta-induced neurotoxicity in vitro," *Immunology*, 2008, p. 19, Abstract No. 3.5, vol. 125, Suppl 1.

Oncley, J.L et al., "The Separation of the Antibodies, Isoagglutinins, Prothrombin, Plasminogen and $\beta_1$-Lipoprotein into Subfractions of Human Plasma," *J. Am. Chem. Soc.*, Feb. 1949, pp. 541-550, vol. 71.

Opal, S.M. et al., "Longitudinal studies of inter-alpha inhibitor proteins in severely septic patients: A potential clinical marker and mediator of severe sepsis," *Crit Care Med*, 2007, vol. 35, No. 2, pp. 387-392.

Poelsler, G. et al., "A new liquid intravenous immunoglobulin with three dedicated virus reduction steps: virus and prion reduction capacity," *Vox Sanguinis*, 2007, pp. 1-9.

Radosevich, M. et al., "Intravenous immunoglobulin G; trends in production methods, quality control and quality assurance," *Vox Sanguinis*, 2010, vol. 98, pp. 12-28.

Reipert, B.M. et al., "Evaluating the Fc-Function of Intravenous Immunoglobulin Products by Flow Cytometry," *J. Allergy Clin. Immunol.*, Feb. 2004, p. S214 Abstracts, Abstract No. 751.

Reipert, B.M. et al "Fc function of a new intravenous immunoglobulin product: IGIV 10% triple virally inactivated solution," *Vox Sanguinis*, 2006, pp. 256-263, vol. 91.

Salier, J-P. et al., "The inter-α-inhibitor family: from structure to regulation," *Biochem J.*, 1996, vol. 315, pp. 1-9.

Schiffman, S. et al, "Partial Purification and Characterization of Contact Activation Cofactor," *The Journal of Clinical Investigation*, Nov. 1975, vol. 56, pp. 1082-1092.

Schultze, H.E. et al. *Molecular Biology of Human Proteins, vol. 1: Nature and Metabolism of Extracellular Proteins*, 1966, Elsevier Publishing Company, pp. 236-317.

Tanaka, K. et al., "High quality human immunoglobulin G purified from Cohn fractions by liquid chromatography," *Brazilian Journal of Medical and Biological Research*, 2000, pp. 27-30, vol. 33, No. 1.

Teschner, IV, W. et al., "Preclinical Characterization of a New Liquid 'Immune Globulin Intravenous (Human), 10% Triple Virally Reduced Solution' (IGIV, 10%TVR)," *J. Allergy Clin. Immunol.*, Feb. 2004, 2 pages, (p. Abstracts S45), Abstract No. 79, vol. 113, No. 2, Suppl 1.

Teschner, W. et al., "A new liquid, intravenous immunoglobulin product (IGIV 10%) highly purified by a state-of-the-art process," *Vox Sanguinis*, 2007, pp. 42-55, vol. 92.

U.S. Appl. No. 61/227,968, filed Jul. 23, 2009, "Factor H(Fh) and FH-Derivative Used to Treat Adult Macular Degeneration and Other Diseases," Johnson, R. et al., 21 pages.

Weber, A. et al., "Intravenous Immunoglobulin (IVIG) Gammagard Liquid Contains Anti-Rage IGG and SLRP," *Alzheimer's & Dementia: The Journal of the Alzheimer's Association*, Jul. 2009, 3 pages (p. P416), Abstract No. P3-248, vol. 5, No. 4, Suppl.

Wu, R. et al., "Delayed administration of human inter-α inhibitor proteins reduces mortality in sepsis," *Crit Care Med*, 2004, vol. 32, No. 8, pp. 1747-1752.

Yang, S. et al., "Administration of human inter-α-inhibitors maintains hemodynamic stability and improves survival during sepsis," *Crit Care Med*, 2002, vol. 30, No. 3, pp. 617-622.

Zhuo, L. et al., "Inter-α-trypsin Inhibitor, a Covalent Protein-Glycosaminoglycan-Protein Complex," *The Journal of Biological Chemistry*, Sep. 10, 2004, vol. 279, No. 37, pp. 38079-38082.

\* cited by examiner

REMOVAL OF SERINE PROTEASES BY TREATMENT WITH FINELY DIVIDED SILICON DIOXIDE

CROSS-REFERENCES TO RELATED APPLICATIONS

This application is a Divisional of U.S. patent application Ser. No. 13/117,028, filed May 26, 2011 (now issued as U.S. Pat. No. 8,772,462), which is a Continuation-in-part of U.S. patent application Ser. No. 12/789,365, filed May 27, 2010, and is a Continuation-in-part of U.S. patent application Ser. No. 12/842,944, filed Jul. 23, 2010 (now issued as U.S. Pat. No. 8,304,524), which claims priority to AU Patent Application No. 2010202125, filed May 26, 2010, (now issued as Australian Patent No. 2010202125), the disclosures of which are hereby incorporated herein by reference in their entireties for all purposes.

BACKGROUND OF THE INVENTION

Plasma-derived blood products are used to treat not only a variety of blood disorders, but diseases of other origin. For example, immune globulin (IgG) products from human plasma were first used in 1952 to treat immune deficiency. Since then, IgG preparations have found widespread use in at least three main categories of medical conditions: (1) immune deficiencies such as X-linked agammaglobulinemia, hypogammaglobulinemia (primary immune deficiencies), and acquired compromised immunity conditions (secondary immune deficiencies), featuring low antibody levels; (2) inflammatory and autoimmune diseases; and (3) acute infections.

Likewise, Factor H has been implicated as a potential therapeutic agent for several human disease states, including age-related macular degeneration (AMD), hemolytic uremic syndrome (aHUS) and membranoproliferative glomerulonephritis (MPGN). Specifically, a causal relationship between the single nucleotide polymorphism (SNP) in complement control protein (CCP) module 7 of Factor H and age-related macular degeneration (AMD) has been characterized.

Studies have shown correlations between decreased plasma levels of Inter-alpha-Inhibitor proteins (IaIp) and mortality in patients with severe sepsis (Lim et al., J Infect Dis. (2003) Sep. 15; 188(6):919-26 and Opal et al., Crit Care Med. (2007) February; 35(2):387-92). Furthermore, several studies have shown that the administration of IaIp reduces mortality associated with sepsis and septic shock (Jourdain et al., Am J Respir Crit Care Med. (1997) December; 156(6):1825-33; Yang et al., Crit Care Med. (2002) March; 30(3):617-22; Lim et al., J Infect Dis. (2003) Sep. 15; 188(6):919-26; and Wu et al., Crit Care Med. (2004) August; 32(8):1747-52; the disclosures of which are incorporated by reference herein in their entireties for all purposes).

Various safety precautions must be taken into consideration when manufacturing and formulating plasma-derived biologic therapies. These include methods for removing and/or inactivating blood borne pathogens (e.g., viral and bacterial pathogens), anticomplement activity, and other unwanted contaminants arising from the use of donated plasma. Studies have suggested that administration of high levels of amidolytic activity may result in unwanted thromboembolic events (Wolberg A S et al., Coagulation factor XI is a contaminant in intravenous immunoglobulin preparations. Am J Hematol 2000; 65:30-34; and Alving B M et al., Contact-activated factors: contaminants of immunoglobulins preparations with coagulant and vasoactive properties. J Lab Clin Med 1980; 96:334-346; the disclosures of which are hereby incorporated by reference in their entireties for all purposes). Highlighting this concern was the recent voluntary withdrawal of Octagam® (Octapharma) in the US and suspension of marketing authorization for Octagam® and octagam 10% by the European Commission following increased reports of thromboembolic events. It is likely that the increased thrombolic events were caused by high levels of amidolytic activity in the biologic, caused by serine protease and serine protease zymogen impurities, such as Factor XI, Factor XIa, Factor XII and Factor XIIa (FDA Notice: Voluntary Market Withdrawal—Sep. 23, 2010 Octagam [Immune Globulin Intravenous (Human)]5% Liquid Preparation; Octagam 50 mg/ml, solution pour perfusion—Octapharma France—Mise en quarantaine de tous les lots, published online Sep. 9, 2010 by the AFSSAPS; and Questions and answers on the suspension of the marketing authorisations for Octagam (human normal immunoglobulin 5% and 10%), published online Sep. 23, 2010 by the European Medicines Agency).

Dedicated serine proteases, generically known as coagulation factors, are integral components of both the contact activation and tissue factor pathways of the coagulation cascade. Upon a stimulus of the coagulation pathways, serine protease zymogens, which are inactive enzyme precursors, become activated proteases that catalyze the activation of the next protease zymogen, resulting in an activation cascade. This coagulation cascade culminates in the activation of Thrombin (Factor IIa) and Factor XIIa, which function to convert Fibrinogen (Factor I) into Fibrin (Factor Ia) and cross-link fibrin to form a fibrin clot, respectively.

The contact activation pathway, also known as the intrinsic coagulation pathway, begins with the activation of Kallikrein and Factor XIIa (FXIIa) from Prekallikrein and Factor XII, respectively. The activated serine protease FXIIa cleaves Factor XI (FXI), converting the zymogen into Factor XIa (FXIa), an active serine protease which participates in the subsequent activation of Factor Xa (FXa).

Due to rising concerns over the presence of serine protease and serine protease zymogens in plasma-derived protein compositions, there remains a need in the art for methods for reducing the levels of these contaminants, and particularly FXI, FXIa, FXII, and FXIIa. The present invention fulfils these and other needs by providing such methods and plasma-derived protein compositions with reduced levels of serine protease and serine protease zymogen.

BRIEF SUMMARY OF THE INVENTION

In one aspect, the present invention is based on the surprising finding that serine proteases and serine protease zymogens, and specifically, FXI, FXIa, FXII, and FXIIa, can be removed from plasma-derived protein compositions by treatment with finely divided silicon dioxide ($SiO_2$). In this fashion the present invention provides methods for reducing the serine protease activity, serine protease content, and serine protease zymogen content of plasma-derived protein compositions. Also provided are therapeutic plasma-derived protein compositions having reduced serine protease activity, serine protease content, and serine protease zymogen content, as well as methods for treating or preventing disease by the administration of the same.

In a first aspect, the present invention provides a method for reducing the amount of a serine protease or a serine protease zymogen in a plasma-derived target protein composition, the method comprising the steps of: (a) contacting the composition with finely divided silicon dioxide ($SiO_2$)

under conditions suitable to bind at least one serine protease or serine protease zymogen; and (b) separating the SiO$_2$ from the composition to remove the bound serine protease. In a preferred embodiment, the serine protease or serine protease zymogen is Factor XIa (FXIa), Factor XIIa (FXIIa), Factor XI (FXI), or Factor XII (FXII).

In certain embodiments, the method described above further comprises the step of performing a first target protein enrichment step to form a first enriched composition, prior to contacting the composition with finely divided silicon dioxide (SiO$_2$). In one embodiment, the first target protein enrichment step is a protein precipitation step. In a specific embodiment, the protein precipitation step is an alcohol fractionation step. In another embodiment, the first target protein enrichment step is an ultrafiltration/diafiltration step.

In other embodiments of the methods described above, the method further comprises the step of performing a second target protein enrichment step prior to contacting the enriched composition with finely divided silicon dioxide (SiO$_2$). In one embodiment, the second target protein enrichment step is a protein precipitation step. In a specific embodiment, the protein precipitation step is an alcohol fractionation step. In another embodiment, the second target protein enrichment step is an ultrafiltration/diafiltration step. In yet another embodiment, the second target protein enrichment step is a chromatographic enrichment step.

In other embodiments of the methods described above, the method further comprises the step of performing a third target protein enrichment step after contacting the composition with finely divided silicon dioxide (SiO$_2$). In one embodiment, the third target protein enrichment step is a protein precipitation step. In a specific embodiment, the protein precipitation step is an alcohol fractionation step. In another embodiment, the third target protein enrichment step is an ultrafiltration/diafiltration step. In yet another embodiment, the third target protein enrichment step is a chromatographic enrichment step.

In certain embodiments of the methods described above, the chromatographic enrichment step comprises the sub-steps of: (i) contacting the plasma-derived target protein composition with a chromatographic resin under conditions suitable to bind the plasma-derived target protein; and (ii) eluting the plasma-derived target protein from the chromatographic resin. In a specific embodiment, the impurity does not bind to the chromatographic resin in sub-step (i). In another specific embodiment, the impurity binds to the chromatographic resin in sub-step (i), but is not eluted from the chromatographic resin in sub-step (ii).

In other certain embodiments of the methods described above, the chromatographic enrichment step comprises the sub-steps of: (i) contacting the first enriched plasma-derived target protein composition with a chromatographic resin under conditions suitable to bind at least one impurity; and (ii) separating the resin from the plasma-derived protein composition, wherein the plasma-derived target protein does not bind to the chromatographic resin in sub-step (i).

In certain embodiments of the methods comprising a chromatographic enrichment step described above, the chromatographic resin is selected from the group consisting of an anion exchange resin, a cation exchange resin, a hydrophobic interaction resin, a mixed mode resin, a hydroxyapatite resin, a ligand affinity resin, an immunoaffinity resin, and a size exclusion resin.

In other certain embodiments of the methods comprising a chromatographic enrichment step described above, the chromatographic enrichment step comprises separating at least one impurity from the target protein by size and/or shape using size exclusion chromatography.

In certain embodiments of the methods described above, the plasma-derived target protein is selected from an immunoglobulin (Ig), albumin, alpha-1-antitrypsin (A1PI), butyrylcholinesterase, a protein of the complement system, and an inter-alpha-trypsin inhibitor (IαI). In a specific embodiment, the protein of the complement system is selected from the group consisting of Factor H (FH), Factor D, complement protein C3, and C4 binding protein.

In yet another embodiment of the methods described above, the plasma-derived target protein composition is a manufacturing intermediate.

In a second aspect, the present invention provides a method for preparing a plasma-derived Factor H composition having a reduced amount of a serine protease or a serine protease zymogen, the method comprising the steps of: (a) contacting a composition containing Factor H and at least one serine protease or serine protease zymogen with finely divided silicon dioxide (SiO$_2$) under conditions suitable to bind the Factor H and at least one serine protease or serine protease zymogen; (b) separating the SiO$_2$ from the composition; (c) eluting the serine protease or serine protease zymogen from the SiO$_2$ under a solution condition in which the Factor H remains bound; and (d) eluting the Factor H from the SiO$_2$.

In certain embodiment of the methods described above, the solution condition under which the serine protease or serine protease zymogen is eluted from the SiO$_2$ and the Factor H remains bound comprises a pH greater than about 6.0. In another embodiment, the solution condition under which the serine protease or serine protease zymogen is eluted from the SiO$_2$ and the Factor H remains bound comprises a pH greater than about 6.5. In another embodiment, the solution condition under which the serine protease or serine protease zymogen is eluted from the SiO$_2$ and the Factor H remains bound comprises a pH greater than about 7.0. In yet another embodiment, the solution condition under which the serine protease or serine protease zymogen is eluted from the SiO$_2$ and the Factor H remains bound comprises a pH of at least about 7.5.

In certain embodiment of the methods described above, the solution condition comprises a pH of no more than 11.0. In another embodiment, the solution condition comprises a pH of no more than 10.0. In another embodiment, the solution condition comprises a pH of no more than 9.0.

In certain embodiments of the methods described above, the solution condition under which the serine protease or serine protease zymogen is eluted from the SiO$_2$ and the Factor H remains bound comprises a conductivity of greater than about 10 mS/cm. In another embodiment of the methods described above, the solution condition under which the serine protease or serine protease zymogen is eluted from the SiO$_2$ and the Factor H remains bound comprises a conductivity of greater than about 20 mS/cm. In another embodiment of the methods described above, the solution condition under which the serine protease or serine protease zymogen is eluted from the SiO$_2$ and the Factor H remains bound comprises a conductivity of between about 10 mS/cm and about 50 mS/cm. In yet another embodiment of the methods described above, the solution condition under which the serine protease or serine protease zymogen is eluted from the SiO$_2$ and the Factor H remains bound comprises a conductivity between about 20 mS/cm and about 50 mS/cm.

In a third aspect, the present invention provides a method for preparing a Factor H composition having a reduced amount of a serine protease or a serine protease zymogen, the method comprising the steps of: (a) contacting a composition containing Factor H and at least one serine protease or serine protease zymogen with finely divided silicon dioxide ($SiO_2$) under conditions suitable to bind the Factor H and at least one serine protease; (b) separating the $SiO_2$ from the composition; and (c) eluting the Factor H from the $SiO_2$ under conditions in which the serine protease or serine protease zymogen remains bound to the $SiO_2$.

In certain embodiment of the methods described above, the solution condition under which the Factor H is eluted from the $SiO_2$ and the serine protease or serine protease zymogen remains bound comprises a pH greater than about 6.0. In another embodiment, the solution condition under which the Factor H is eluted from the $SiO_2$ and the serine protease or serine protease zymogen remains bound comprises a pH greater than about 6.5. In another embodiment, the solution condition under which the Factor H is eluted from the $SiO_2$ and the serine protease or serine protease zymogen remains bound comprises a pH greater than about 7.0. In yet another embodiment, the solution condition under which the Factor H is eluted from the $SiO_2$ and the serine protease or serine protease zymogen remains bound comprises a pH of at least about 7.5.

In certain embodiment of the methods described above, the solution condition comprises a pH of no more than 11.0. In another embodiment, the solution condition comprises a pH of no more than 10.0. In another embodiment, the solution condition comprises a pH of no more than 9.0.

In certain embodiment of the methods described above, the solution condition under which the Factor H is eluted from the $SiO_2$ and the serine protease or serine protease zymogen remains bound comprises a conductivity of less than about 20 mS/cm. In another embodiment, the solution condition under which the Factor H is eluted from the $SiO_2$ and the serine protease or serine protease zymogen remains bound comprises a conductivity of less than about 10 mS/cm. In another embodiment of the methods described above, the solution condition under which the Factor H is eluted from the $SiO_2$ and the serine protease or serine protease zymogen remains bound comprises a conductivity between about 2 mS/cm and about 20 mS/cm. In yet another embodiment of the methods described above, the solution condition under which the Factor H is eluted from the $SiO_2$ and the serine protease or serine protease zymogen remains bound comprises a conductivity between about 2 mS/cm and about 10 mS/cm.

In a fourth aspect, the present invention provides a method for preparing a Factor H composition having a reduced amount of a serine protease or a serine protease zymogen, the method comprising the steps of: (a) contacting a composition containing Factor H and at least one serine protease or serine protease zymogen with finely divided silicon dioxide ($SiO_2$) under conditions suitable to bind the Factor H but not the at least one serine protease or serine protease zymogen; (b) separating the $SiO_2$ from the composition; and (c) eluting the Factor H from the $SiO_2$.

In certain embodiment of the methods described above, the solution condition under which the Factor H binds to the $SiO_2$ and the serine protease or serine protease zymogen does not comprises a pH greater than about 6.0. In another embodiment, the solution condition under which the Factor H binds to the $SiO_2$ and the serine protease or serine protease zymogen does not comprises a pH greater than about 6.5. In another embodiment, the solution condition under which the Factor H binds to the $SiO_2$ and the serine protease or serine protease zymogen does not comprises a pH greater than about 7.0. In yet another embodiment, the solution condition under which the Factor H binds to the $SiO_2$ and the serine protease or serine protease zymogen does not comprises a pH of at least about 7.5.

In certain embodiment of the methods described above, the solution condition comprises a pH of no more than 11.0. In another embodiment, the solution condition comprises a pH of no more than 10.0. In another embodiment, the solution condition comprises a pH of no more than 9.0.

In certain embodiment of the methods described above, the solution condition under which the Factor H binds to the $SiO_2$ and the serine protease or serine protease zymogen does not comprises a conductivity of greater than about 10 mS/cm. In another embodiment of the methods described above, the solution condition under which the Factor H binds to the $SiO_2$ and the serine protease or serine protease zymogen does not comprises a conductivity of greater than about 20 mS/cm. In another embodiment of the methods described above, the solution condition under which the Factor H binds to the $SiO_2$ and the serine protease or serine protease zymogen does not comprises a conductivity between about 10 mS/cm and about 50 mS/cm. In yet another embodiment of the methods described above, the solution condition under which the Factor H binds to the $SiO_2$ and the serine protease or serine protease zymogen does not comprises a conductivity between about 20 mS/cm and about 50 mS/cm.

In a fifth aspect, the present invention provides a method for preparing a Factor H composition having a reduced amount of a serine protease or a serine protease zymogen, the method comprising the steps of: (a) contacting a composition containing Factor H and at least one serine protease or serine protease zymogen with finely divided silicon dioxide ($SiO_2$) under conditions suitable to bind the at least one serine protease or serine protease zymogen but not the Factor H and (b) separating the $SiO_2$ from the composition.

In certain embodiment of the methods described above, the solution condition under which the serine protease or serine protease zymogen binds to the $SiO_2$ and the Factor H does not comprises a pH greater than about 6.0. In another embodiment, the solution condition under which the serine protease or serine protease zymogen binds to the $SiO_2$ and the Factor H does not comprises a pH greater than about 6.5. In another embodiment, the solution condition under which the serine protease or serine protease zymogen binds to the $SiO_2$ and the Factor H does not comprises a pH greater than about 7.0. In yet another embodiment, the solution condition under which the serine protease or serine protease zymogen binds to the $SiO_2$ and the Factor H does not comprises a pH of at least about 7.5.

In certain embodiment of the methods described above, the solution condition comprises a pH of no more than 11.0. In another embodiment, the solution condition comprises a pH of no more than 10.0. In another embodiment, the solution condition comprises a pH of no more than 9.0.

In certain embodiment of the methods described above, the solution condition under which the serine protease or serine protease zymogen binds to the $SiO_2$ and the Factor H does not comprises a conductivity of less than about 20 mS/cm. In another embodiment, the solution condition under which the serine protease or serine protease zymogen binds to the $SiO_2$ and the Factor H does not comprises a conductivity of less than about 10 mS/cm. In another embodiment of the methods described above, the solution condition under which the serine protease or serine protease zymogen binds to the $SiO_2$ and the Factor H does not comprises a conductivity between about 2 mS/cm and about 20 mS/cm. In yet another embodiment of the methods described above, the solution condition under which the serine protease or serine protease zymogen binds to the $SiO_2$ and the Factor H does not comprises a conductivity between about 2 mS/cm and about 10 mS/cm.

In a sixth aspect, the present invention provides a method for preparing an inter-alpha-trypsin inhibitor (IαI) composition having reduced serine protease activity, the method comprising the steps of: (a) contacting a solution containing IαI and at least one serine protease with finely divided silicon dioxide ($SiO_2$) under conditions suitable to bind the IαI and at least one serine protease; (b) separating the $SiO_2$ from the composition; (c) eluting the serine protease from the $SiO_2$ under conditions in which the IαI remains bound; and (d) eluting the IαI from the $SiO_2$.

In a seventh aspect, the present invention provides a method for preparing an inter-alpha-trypsin inhibitor (IαI) composition having reduced serine protease activity, the method comprising the steps of: (a) contacting a solution containing IαI and at least one serine protease with finely divided silicon dioxide ($SiO_2$) under conditions suitable to bind the IαI and at least one serine protease; (b) separating the $SiO_2$ from the composition; and (c) eluting the IαI from the $SiO_2$ under conditions in which the serine protease remains bound to the $SiO_2$.

In an eighth aspect, the present invention provides a method for preparing an inter-alpha-trypsin inhibitor (IαI) composition having reduced serine protease activity, the method comprising the steps of: (a) contacting a solution containing IαI and at least one serine protease with finely divided silicon dioxide ($SiO_2$) under conditions suitable to bind the IαI but not the least one serine protease; (b) separating the $SiO_2$ from the composition; and (c) eluting the IαI from the $SiO_2$.

In a ninth aspect, the present invention provides a method for preparing a inter-alpha-trypsin inhibitor (IαI) composition having reduced serine protease activity, the method comprising the steps of: (a) contacting a solution containing inter-alpha-trypsin inhibitor (IαI) and at least one serine protease with finely divided silicon dioxide ($SiO_2$) under conditions suitable to bind the serine protease but not the inter-alpha-trypsin inhibitor (IαI); and (b) separating the $SiO_2$ from the composition.

In certain embodiments of the aspects described above, the composition is contacted with $SiO_2$ at a final concentration of at least 1 g $SiO_2$/g protein. In another embodiment of the aspects described above, the composition is contacted with $SiO_2$ at a final concentration of at least 2 g $SiO_2$/g protein. In another embodiment of the aspects described above, the composition is contacted with $SiO_2$ at a final concentration of at least 2.5 g $SiO_2$/g protein.

In certain embodiments of the aspects described above, the serine protease or serine protease zymogen is Factor XI. In another embodiment of the aspects described above, the serine protease or serine protease zymogen is Factor XIa. In another embodiment of the aspects described above, the serine protease or serine protease zymogen is Factor XII. In yet another embodiment of the aspects described above, the serine protease or serine protease zymogen is Factor XIIa.

In a tenth aspect, the present invention provides a plasma-derived protein composition prepared by a process comprising a method for reducing serine protease activity according to any one of the aspects described above. In one embodiment, the composition is formulated for administration to a subject. In a specific embodiment, the composition is formulated for intravenous, intramuscular, or subcutaneous administration. In one embodiment, the composition is aqueous. In another embodiment, the composition is lyophilized.

In an eleventh aspect, the present invention provides a method for treating a disease associated with aberrant activity of a plasma protein in a subject in need thereof, the method comprising administering a plasma-derived protein composition according to the aspect outlined above. In certain embodiments, the composition comprises a plasma-derived protein is selected from an immunoglobulin (Ig), albumin, alpha-1-antitrypsin (A1PI), butyrylcholinesterase, a protein of the complement system, and an inter-alpha-trypsin inhibitor (IαI).

In a twelfth aspect, the present invention provides a method for preparing a Factor H composition comprising the steps of (a) contacting a suspended plasma precipitate fraction containing Factor H with finely divided silicon dioxide ($SiO_2$), (b) washing the $SiO_2$ with a wash buffer comprising a low pH and a low conductivity, and (c) eluting Factor H from the $SiO_2$ with an elution buffer comprising a pH between 7.0 and 8.0 and a conductivity of at least 10 mS/cm. In specific embodiments, the plasma precipitate fraction containing Factor H is a Cohn fraction II+III precipitate, a Cohn fraction I+II+III precipitate, a Kistler/Nitschmann Precipitate A, or a Kistler/Nitschmann Precipitate B. In certain embodiments, the methods further comprises one or more additional steps selected from (d) precipitating and removing at least one impurity from the Factor H elution, (e) precipitating and recovering Factor H from the enriched composition, (f) further enriching Factor H by anion exchange chromatography, (g) further enriching Factor H by heparin affinity chromatography, (h) a dedicated viral inactivation step, and (i) concentrating the enriched Factor H composition by ultrafiltration/diafiltration.

In one embodiment, the present invention provides a method for reducing the amount of a serine protease or a serine protease zymogen in a plasma-derived target protein composition, the method comprising the steps of: (a) contacting the composition with finely divided silicon dioxide (SiO2) under conditions suitable to bind at least one serine protease or serine protease zymogen; and (b) separating the SiO2 from the composition to remove the bound serine protease, wherein the at least one serine protease or serine protease zymogen is Factor XIa (FXIa), Factor XIIa (FXIIa), Factor XI (FXI), or Factor XII (FXII).

In a specific embodiment of the methods described above, the method further comprises the step of performing a first target protein enrichment step to form a first enriched composition, prior to contacting the composition with finely divided silicon dioxide (SiO2). In one embodiment, the first target protein enrichment step is a protein precipitation step. In a specific embodiment, the protein precipitation step is an alcohol fractionation step. In another specific embodiment, the first target protein enrichment step is an ultrafiltration/diafiltration step.

In a specific embodiment of the methods described above, the method further comprises the step of performing a second target protein enrichment step prior to contacting the enriched composition with finely divided silicon dioxide (SiO2). In one embodiment, the second target protein enrichment step is a protein precipitation step. In a specific embodiment, the protein precipitation step is an alcohol fractionation step. In one embodiment, the second target protein enrichment step is an ultrafiltration/diafiltration step. In one embodiment, the second target protein enrichment step is a chromatographic enrichment step.

In a specific embodiment of the methods described above, the method further comprises the step of performing a third target protein enrichment step after contacting the composition with finely divided silicon dioxide (SiO2). In one embodiment, the third target protein enrichment step is a protein precipitation step. In a specific embodiment, the protein precipitation step is an alcohol fractionation step. In one embodiment, the third target protein enrichment step is an ultrafiltration/diafiltration step. In one embodiment, the third target protein enrichment step is a chromatographic enrichment step.

In a specific embodiment of the methods described above, the chromatographic enrichment step comprises the sub-steps of: (i) contacting the plasma-derived target protein composition with a chromatographic resin under conditions suitable to bind the plasma-derived target protein; and (ii) eluting the plasma-derived target protein from the chromatographic resin. In one specific embodiment, at least one impurity does not bind to the chromatographic resin in sub-step (i). In another specific embodiment, at least one impurity binds to the chromatographic resin in sub-step (i), but is not eluted from the chromatographic resin in sub-step (ii).

In a specific embodiment of the methods described above, the chromatographic enrichment step comprises the sub-steps of: (i) contacting the first enriched plasma-derived target protein composition with a chromatographic resin under conditions suitable to bind at least one impurity; and (ii) separating the resin from the plasma-derived protein composition, wherein the plasma-derived target protein does not bind to the chromatographic resin in sub-step (i).

In a specific embodiment of the methods described above, the chromatographic resin is selected from the group consisting of an anion exchange resin, a cation exchange resin, a hydrophobic interaction resin, a mixed mode resin, a hydroxyapatite resin, a ligand affinity resin, an immunoaffinity resin, and a size exclusion resin. In one embodiment, the chromatographic resin is an anion exchange resin. In one embodiment, the chromatographic resin is a cation exchange resin. In one embodiment, the chromatographic resin is a hydrophobic interaction resin. In one embodiment, the chromatographic resin is a mixed mode resin. In one embodiment, the chromatographic resin is a hydroxyapatite resin. In one embodiment, the chromatographic resin is a ligand affinity resin. In one embodiment, the chromatographic resin is an immunoaffinity resin. In one embodiment, the chromatographic enrichment step comprises separating at least one impurity from the target protein by size and/or shape using size exclusion chromatography.

In a specific embodiment of the methods described above, the plasma-derived target protein is selected from an immunoglobulin (Ig), albumin, alpha-1-antitrypsin (A1PI), butyrylcholinesterase, a protein of the complement system, and an inter-alpha-trypsin inhibitor (IαI). In one embodiment, the plasma-derived protein is an immunoglobulin (Ig). In one embodiment, the plasma-derived protein is albumin. In one embodiment, the plasma-derived protein is alpha-1-antitrypsin. In one embodiment, the plasma-derived protein is butyrylcholinesterase. In one embodiment, the plasma-derived protein is a protein of the complement system. In one embodiment, the protein of the complement system is selected from the group consisting of Factor H (FH), Factor D, complement protein C3, and C4 binding protein. In one embodiment, the plasma-derived protein is an inter-alpha-trypsin inhibitor.

In a specific embodiment of the methods described above, the plasma-derived target protein composition is a manufacturing intermediate.

In one embodiment, the present invention provides a method for preparing a plasma-derived Factor H composition having a reduced amount of a serine protease or a serine protease zymogen, the method comprising the steps of: (a) contacting a composition containing Factor H and at least one serine protease or serine protease zymogen with finely divided silicon dioxide (SiO2) under conditions suitable to bind the Factor H and at least one serine protease or serine protease zymogen; (b) separating the SiO2 from the composition; (c) eluting the serine protease or serine protease zymogen from the SiO2 under a solution condition in which a substantial fraction of Factor H remains bound; and (d) eluting the Factor H from the SiO2.

In a specific embodiment of the methods described above, the solution condition under which the Factor H and at least one serine protease or serine protease zymogen bind the SiO2 comprises a pH below 7.0 and a conductivity of less than 11 mS/cm.

In a specific embodiment of the methods described above, the solution condition under which the Factor H and at least one serine protease or serine protease zymogen bind the SiO2 comprises a pH between 4.5 and 6.5 and a conductivity of less than 6 mS/cm.

In a specific embodiment of the methods described above, the solution condition under which the Factor H and at least one serine protease or serine protease zymogen bind the SiO2 comprises a pH between 4.5 and 6.5 and a conductivity between 0.5 mS/cm and 5 mS/cm.

In a specific embodiment of the methods described above, the solution condition under which the serine protease or serine protease zymogen is eluted from the SiO2 and a substantial fraction of the Factor H remains bound comprises a pH below 7.0 and a conductivity of less than 11 mS/cm.

In a specific embodiment of the methods described above, the solution condition under which the serine protease or serine protease zymogen is eluted from the SiO2 and a substantial fraction of the Factor H remains bound comprises a pH between 4.5 and 6.5 and a conductivity of less than 6 mS/cm.

In a specific embodiment of the methods described above, the solution condition under which the serine protease or serine protease zymogen is eluted from the SiO2 and a substantial fraction of the Factor H remains bound comprises a pH between 5.0 and 6.5 and a conductivity between 0.5 mS/cm and 5 mS/cm.

In a specific embodiment of the methods described above, the solution condition under which the Factor H is eluted from the SiO2 comprises an ionic strength of at least 6 mS/cm.

In a specific embodiment of the methods described above, the solution condition under which the Factor H is eluted from the SiO2 comprises an ionic strength of at least 11 mS/cm.

In a specific embodiment of the methods described above, the solution condition under which the Factor H is eluted from the SiO2 comprises a pH between 5.0 and 7.0.

In a specific embodiment of the methods described above, the solution condition under which the Factor H is eluted from the SiO2 comprises a pH between 7.0 and 8.0 and an ionic strength of between 4 mS/cm and 7 mS/cm.

In one embodiment, the present invention provides a method for preparing a Factor H composition having a reduced amount of a serine protease or a serine protease zymogen, the method comprising the steps of: (a) contacting a composition containing Factor H and at least one serine protease or serine protease zymogen with finely divided silicon dioxide (SiO2) under conditions suitable to bind the Factor H and at least one serine protease; (b) separating the SiO2 from the composition; and (c) eluting the Factor H from the SiO2 under conditions in which a substantial fraction of the serine protease or serine protease zymogen remains bound to the SiO2.

In a specific embodiment of the methods described above, the solution condition under which the Factor H and at least one serine protease or serine protease zymogen bind the SiO2 comprises a pH below 7.0 and a conductivity of less than 11 mS/cm.

In a specific embodiment of the methods described above, the solution condition under which the serine protease or serine protease zymogen is eluted from the SiO2 and a substantial fraction of the Factor H remains bound comprises a pH between 4.5 and 6.5 and a conductivity of less than 6 mS/cm.

In a specific embodiment of the methods described above, the solution condition suitable to bind the Factor H and at least one serine protease or serine protease zymogen comprises a pH between 5.0 and 6.0 and a conductivity of between 0.5 mS/cm and 5.0 mS/cm.

In a specific embodiment of the methods described above, the solution condition under which the Factor H is eluted from the SiO2 and a substantial fraction of the serine protease or serine protease zymogen remains bound comprises a pH between 5.0 and 7.0 and a conductivity of at least 11 mS/cm.

In a specific embodiment of the methods described above, the solution condition under which the Factor H is eluted from the SiO2 and a substantial fraction of the serine protease or serine protease zymogen remains bound comprises a pH between 7.0 and 8.0 and a conductivity of between 2 mS/cm and 10 mS/cm.

In a specific embodiment of the methods described above, the conductivity of the solution condition is between 4 mS/cm and 7 mS/cm.

In a specific embodiment of the methods described above, the conductivity of the solution condition is between 5 mS/cm and 6 mS/cm.

In one embodiment, the present invention provides method for preparing a Factor H composition having a reduced amount of a serine protease or a serine protease zymogen, the method comprising the steps of: (a) contacting a composition containing Factor H and at least one serine protease or serine protease zymogen with finely divided silicon dioxide (SiO2) under conditions suitable to bind the Factor H but not a substantial fraction of the at least one serine protease or serine protease zymogen; (b) separating the SiO2 from the composition; and (c) eluting the Factor H from the SiO2.

In a specific embodiment of the methods described above, the solution condition under which the Factor H binds to the SiO2 and a substantial fraction of the serine protease or serine protease zymogen does not bind to the SiO2 comprises a pH of between 5.0 and 7.0 and a conductivity of no more than 14 mS/cm.

In a specific embodiment of the methods described above, the conductivity of the solution condition is between 9 mS/cm and 14 mS/cm.

In one embodiment, the present invention provides a method for preparing a Factor H composition having a reduced amount of a serine protease or a serine protease zymogen, the method comprising the steps of: (a) contacting a composition containing Factor H and at least one serine protease or serine protease zymogen with finely divided silicon dioxide (SiO2) under conditions suitable to bind the at least one serine protease or serine protease zymogen but not a substantial fraction of the Factor H; and (b) separating the SiO2 from the composition.

In a specific embodiment of the methods described above, the solution condition under which the serine protease or serine protease zymogen binds to the SiO2 and a substantial fraction of the Factor H does not bind to the SiO2 comprises a pH between 5.0 and 7.0 and a conductivity of at least 11 mS/cm.

In a specific embodiment of the methods described above, the solution condition under which the serine protease or serine protease zymogen binds to the SiO2 and a substantial fraction of the Factor H does not bind to the SiO2 comprises a pH between 7.0 and 8.0 and a conductivity of between 2 mS/cm and 10 mS/cm.

In a specific embodiment of the methods described above, the conductivity of the solution condition is between 4 mS/cm and 7 mS/cm.

In a specific embodiment of the methods described above, the conductivity of the solution condition is between 5 mS/cm and 6 mS/cm.

In one embodiment, the present invention provides a method for preparing a Factor H composition, the method comprising the steps of: (a) contacting a composition containing Factor H and at least one serine protease or serine protease zymogen with finely divided silicon dioxide (SiO2) under conditions suitable to bind the Factor H; (b) washing the SiO2 with a solution comprising a pH between 5.0 and 7.0 and a conductivity of less than 4 mS/cm; and (c) eluting Factor H from the SiO2 with a solution comprising a pH between 7.0 and 8.0 and a conductivity greater than 10 mS/cm.

In a specific embodiment of the methods described above, the solution used to wash the SiO2 comprises a pH between 5.5 and 6.5.

In a specific embodiment of the methods described above, the solution used to wash the SiO2 comprises a pH between of 6.0±0.2.

In a specific embodiment of the methods described above, the solution used to elute Factor H comprises a conductivity of at least 20 mS/cm.

In a specific embodiment of the methods described above, the solution used to elute Factor H comprises a conductivity of between 25 mS/cm and 40 mS/cm.

In a specific embodiment of the methods described above, the starting composition containing Factor H is a suspended Cohn fraction II+III precipitate, or equivalent fraction thereof.

In a specific embodiment of the methods described above, the starting composition containing Factor H is a suspended Kistler/Nitschmann Precipitate A, or equivalent fraction thereof.

In a specific embodiment of the methods described above, the starting composition containing Factor H is a suspended Kistler/Nitschmann Precipitate B, or equivalent fraction thereof.

In a specific embodiment of the methods described above, the method further comprises the step of precipitating at least one impurity from the recovered Factor H solution, wherein Factor H is not precipitated.

In a specific embodiment of the methods described above, the precipitation step is PEG precipitation.

In a specific embodiment of the methods described above, the PEG precipitation comprises precipitation with PEG 4000 at a final concentration between 3% and 7%.

In a specific embodiment of the methods described above, the final concentration of PEG 4000 is 5±0.5%.

In a specific embodiment of the methods described above, the method further comprises the step of precipitating Factor H from the recovered Factor H solution.

In a specific embodiment of the methods described above, the precipitation step is PEG precipitation.

In a specific embodiment of the methods described above, the PEG precipitation comprises precipitation with PEG 4000 at a final concentration between 10% and 15%.

In a specific embodiment of the methods described above, the final concentration of PEG 4000 is 12±0.5%.

In a specific embodiment of the methods described above, the method further comprises a step of enriching Factor H by chromatography.

In a specific embodiment of the methods described above, the chromatographic enrichment step comprises anion exchange chromatography.

In a specific embodiment of the methods described above, the chromatographic enrichment step comprises heparin affinity chromatography.

In a specific embodiment of the methods described above, the chromatographic enrichment step comprises anion exchange chromatography followed by heparin affinity chromatography.

In a specific embodiment of the methods described above, the method further comprises at least one dedicated viral removal or inactivation step.

In a specific embodiment of the methods described above, the method comprises a nanofiltration step.

In a specific embodiment of the methods described above, the method further comprises a step of concentrating the Factor H composition comprising ultrafiltration/diafiltration.

In one embodiment, the present invention provides a method for preparing an inter-alpha-trypsin inhibitor (I$\alpha$I) composition having a reduced amount of a serine protease or a serine protease zymogen, the method comprising the steps of: (a) contacting a solution containing I$\alpha$I and at least one serine protease with finely divided silicon dioxide (SiO2) under conditions suitable to bind the I$\alpha$I and at least one serine protease; (b) separating the SiO2 from the composition; (c) eluting the serine protease or serine protease zymogen from the SiO2 under conditions in which a substantial fraction of the I$\alpha$I remains bound; and (d) eluting the I$\alpha$I from the SiO2.

In one embodiment, the present invention provides a method for preparing an inter-alpha-trypsin inhibitor (I$\alpha$I) composition having a reduced amount of a serine protease or a serine protease zymogen, the method comprising the steps of: (a) contacting a solution containing I$\alpha$I and at least one serine protease with finely divided silicon dioxide (SiO2) under conditions suitable to bind the I$\alpha$I and at least one serine protease; (b) separating the SiO2 from the composition; and (c) eluting the I$\alpha$I from the SiO2 under conditions in which a substantial fraction of the serine protease or serine protease zymogen remains bound to the SiO2.

In one embodiment, the present invention provides a method for preparing an inter-alpha-trypsin inhibitor (I$\alpha$I) composition having a reduced amount of a serine protease or a serine protease zymogen, the method comprising the steps of: (a) contacting a solution containing I$\alpha$I and at least one serine protease with finely divided silicon dioxide (SiO2) under conditions suitable to bind the I$\alpha$I but not a substantial fraction of the least one serine protease or serine protease zymogen; (b) separating the SiO2 from the composition; and (c) eluting the I$\alpha$I from the SiO2.

In one embodiment, the present invention provides a method for preparing a inter-alpha-trypsin inhibitor (I$\alpha$I) composition having a reduced amount of a serine protease or a serine protease zymogen, the method comprising the steps of: (a) contacting a solution containing inter-alpha-trypsin inhibitor (I$\alpha$I) and at least one serine protease with finely divided silicon dioxide (SiO2) under conditions suitable to bind the serine protease or serine protease zymogen but not the inter-alpha-trypsin inhibitor (I$\alpha$I); and (b) separating the SiO2 from the composition.

In one embodiment, the present invention provides a method for preparing an Immunoglobulin G (IgG) composition having a reduced amount of a serine protease or a serine protease zymogen, the method comprising the steps of: (a) precipitating a cryo-poor plasmid fraction, in a first precipitation step, with between about 6% and about 10% alcohol at a pH of between about 7.0 and about 7.5 to obtain a first precipitate and a first supernatant; (b) precipitating IgG from the first supernatant, in a second precipitation step, with between about 20% and about 25% alcohol at a pH of between about 6.7 and about 7.3 to form a second precipitate; (c) re-suspending the second precipitate to form a suspension; (d) contacting the suspension with finely divided silicon dioxide (SiO2) under a solution condition suitable to bind a serine protease or serine protease zymogen; and (e) separating the SiO2 from the suspension to form a clarified suspension.

In a specific embodiment of the methods described above, the method further comprises the steps of: (f) precipitating IgG from the clarified suspension formed in step (e), in a third precipitation step, with between about 22% and about 28% alcohol at a pH of between about 6.7 and about 7.3 to form a third precipitate; (g) re-suspending the third precipitate to form a suspension; and (h) separating the soluble fraction from the suspension formed in step (e), thereby forming an enriched IgG composition.

In a specific embodiment of the methods described above, the method further comprises an anion exchange chromatography enrichment step.

In a specific embodiment of the methods described above, the method further comprises a cation exchange chromatography enrichment step.

In a specific embodiment of the methods described above, the method further comprises at least one dedicated viral inactivation or removal step.

In a specific embodiment of the methods described above, the method comprises a solvent/detergent (S/D) viral inactivation step.

In a specific embodiment of the methods described above, the method comprises a nanofiltration step.

In a specific embodiment of the methods described above, the method comprises an incubation step at low pH.

In a specific embodiment of the methods described above, step (b) comprises adjusting the ethanol concentration of the first supernatant formed in step (a) to about 25% (v/v) at a temperature between about −7° C. and about −9° C.

In a specific embodiment of the methods described above, the temperature is about −9° C.

In a specific embodiment of the methods described above, step (c) comprises re-suspending the precipitate of step (b) with a buffer containing phosphate and acetate, wherein the pH of the buffer is adjusted with between 300 mL and 700 mL of glacial acetic acid per 1000 L of buffer.

In a specific embodiment of the methods described above, step (d) comprises the addition SiO2 to a final concentration of between about 0.02 grams per gram precipitate formed in step (b) and about 0.06 grams per gram precipitate formed in step (b).

In a specific embodiment of the methods described above, the solution condition suitable to bind a serine protease or serine protease zymogen comprises a pH between 4.5 and 6.0 and a conductivity of between 0.1 mS/cm and 3 mS/cm.

In a specific embodiment of the methods described above, the pH is between 4.9 and 5.3.

In a specific embodiment of the methods described above, the conductivity is between 0.5 mS/cm and 2 mS/cm.

In a specific embodiment of the methods described above, step (e) comprises the sub-steps of: (i) washing the filter press with at least 3 filter press dead volumes of a buffer containing phosphate and acetate, wherein the pH of the buffer is adjusted with between 50 mL and 200 mL of glacial acetic acid per 1000 L of buffer, thereby forming a wash solution; and (ii) combining the filtrate of step (f) with the wash solution of step (g), thereby forming a solution.

In a specific embodiment of the methods described above, further comprising the sub-step of: (iii) treating the solution with a detergent.

In a specific embodiment of the methods described above, step (h) further comprises solvent and detergent (S/D) treatment of the enriched IgG composition.

In a specific embodiment of the methods described above, the enriched IgG composition obtained in step (h) contains at least 85% of the IgG content found in the cryo-poor plasma fraction used in step (a).

In a specific embodiment of the methods described above, the enriched IgG composition obtained in step (h) contains at least 90% of the IgG content found in the cryo-poor plasma fraction used in step (a).

In a specific embodiment of the methods described above, the amount of a serine protease or a serine protease zymogen has been reduced by at least 90%.

In a specific embodiment of the methods described above, the amount of a serine protease or a serine protease zymogen has been reduced by at least 95%.

In a specific embodiment of the methods described above, the amount of a serine protease or a serine protease zymogen has been reduced by at least 98%.

In a specific embodiment of the methods described above, the amount of a serine protease or a serine protease zymogen has been reduced by at least 99%.

In a specific embodiment of the methods described above, the serine protease or a serine protease zymogen is FXIa.

In a specific embodiment of the methods described above, the composition is contacted with SiO2 at a final concentration of at least 1 g SiO2/g protein.

In a specific embodiment of the methods described above, the composition is contacted with SiO2 at a final concentration of at least 2 g SiO2/g protein.

In a specific embodiment of the methods described above, the composition is contacted with SiO2 at a final concentration of at least 2.5 g SiO2/g protein.

In a specific embodiment of the methods described above, the serine protease or serine protease zymogen is Factor XI.

In a specific embodiment of the methods described above, the serine protease or serine protease zymogen is Factor XII.

In a specific embodiment of the methods described above, the serine protease or serine protease zymogen is Factor XIa.

In a specific embodiment of the methods described above, the serine protease or serine protease zymogen is Factor XIIa.

In one embodiment, the present invention provides a plasma-derived protein composition prepared by a process comprising a method for reducing serine protease activity according to any one of the preceding claims.

In a specific embodiment of the compositions described above, the composition is formulated for administration to a subject.

In a specific embodiment of the compositions described above, the composition is formulated for intravenous, intramuscular, or subcutaneous administration.

In a specific embodiment of the compositions described above, the composition is aqueous.

In a specific embodiment of the compositions described above, the composition is lyophilized.

In one embodiment, the present invention provides a method for treating a disease associated with aberrant activity of a plasma protein in a subject in need thereof, the method comprising administering a plasma-derived protein composition according to any one of claims 124 to 128. In one embodiment, the composition comprises a plasma-derived protein is selected from an immunoglobulin (Ig), albumin, alpha-1-antitrypsin (A1PI), butyrylcholinesterase, a protein of the complement system, and an inter-alpha-trypsin inhibitor (IαI).

DETAILED DESCRIPTION OF THE INVENTION

I. Introduction

Figure 1:
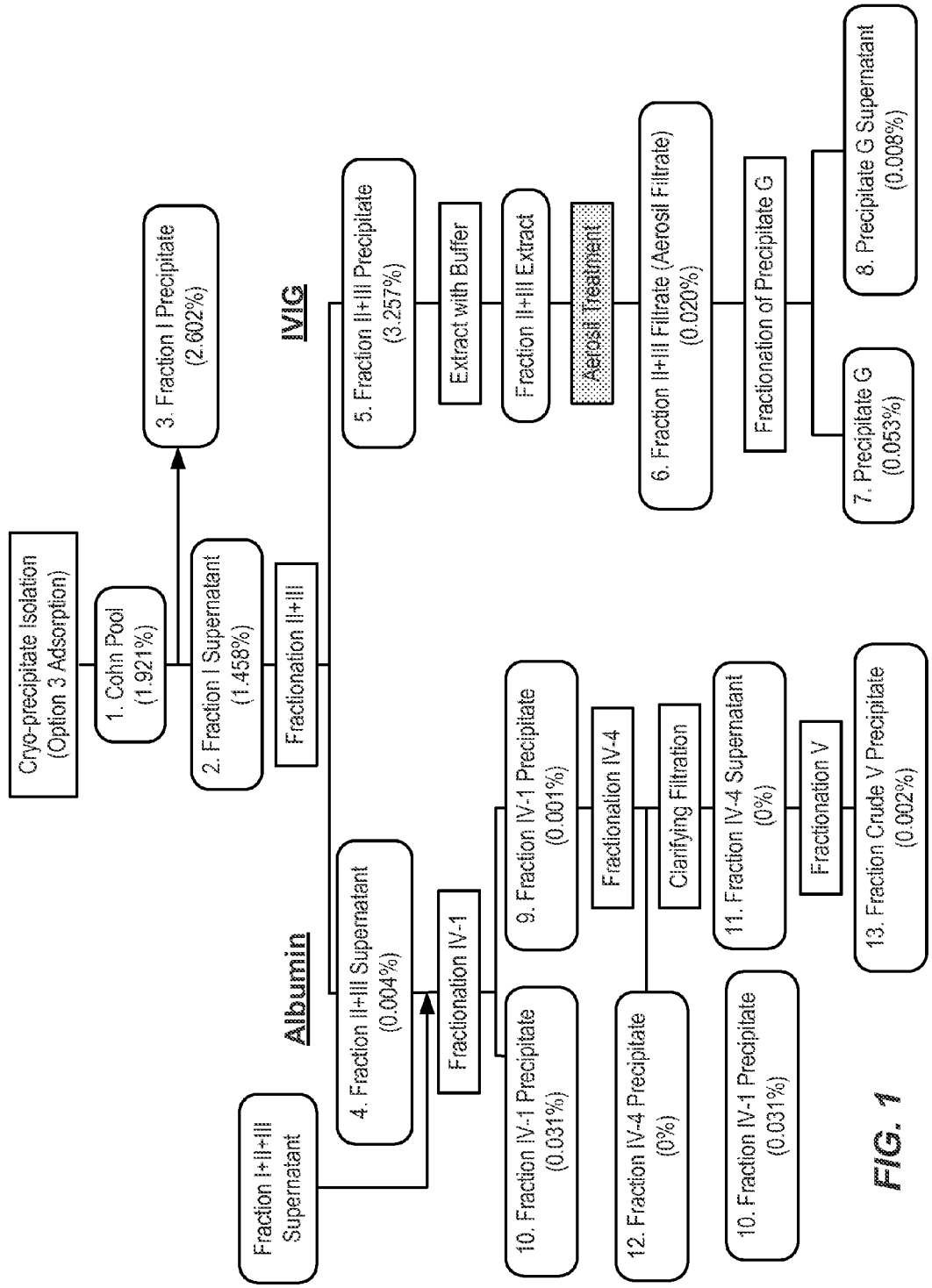
FIG. 1. Overview of an exemplary plasma fractionation scheme.

Given the broad use of therapeutic plasma-derived blood protein compositions, such as immune globulin compositions, blood coagulation factors, coagulation factor inhibitors, and proteins of the complement system, ensuring the safety of these compositions is of paramount importance. Recent concerns over the amidolytic content of these compositions paired with the occurrence of thromboembolic events in patients being administered plasma-derived protein compositions, has highlighted a need in the art for method for reducing serine proteases (e.g., FXIa and FXIIa) and serine protease zymogens (e.g., FXI and FXII) during the manufacturing of these biologics. Advantageously, the present invention is based at least in part on the surprising finding that finely divided silicon dioxide ($SiO_2$) can be used to bind serine proteases and serine protease zymogens present in plasma-derived protein compositions. As such, methods are provided herein for reducing the concentration of serine proteases and serine protease zymogens during the manufacture of plasma-derived protein compositions.

In certain aspects, the present invention provides manufacturing methods based on the surprising finding that finely divided silicon dioxide ($SiO_2$) can be used to remove significant amounts of serine protease (e.g., FXIa and FXIIa) and serine protease zymogen (e.g., FXI and FXII) from plasma-derived protein solutions. As such, the methods provided herein may be easily integrated into existing manufacturing procedures, for example, the fractionation of pooled plasma samples, preferably human plasma samples, by ethanol in the cold (reviewed in Schultze H E, Heremans J F; Molecular Biology of Human Proteins. Volume I: Nature and Metabolism of Extracellular Proteins 1966, Elsevier Publishing Company; p. 236-317). However, the methods provided herein are in no way limited in their use to manufacturing methods including ethanol fractionation.

Other methodologies for the purification of plasma-derived proteins are also compatible with the methods provided herein, for example, polymer (e.g., PEG) fractionation and chromatographic methodologies (e.g., anion and/or cation exchange chromatography, affinity chromatography, immuno-affinity chromatography, size exclusion chromatography, hydrophobic interaction chromatography, mixed mode chromatography, and the like).

Furthermore, unlike other biologics that are produced via recombinant expression of DNA vectors in host cell lines, plasma-derived proteins are fractionated from human blood and plasma donations. Thus, the supply of these products cannot be increased by simply increasing the volume of production. Rather the level of commercially available blood products is limited by the available supply of blood and plasma donations. This dynamic results in a shortage in the availability of raw human plasma for the manufacture of new plasma-derived blood factors that have lesser established commercial markets, including Complement Factor H (CFH) and inter-alpha-trypsin inhibitor proteins (IαIp).

Due to the lack of plasma available for the manufacture of new plasma-derived products, their manufacture must be integrated into the existing framework of the established manufacturing processes for plasma-derived products such as immunoglobulins and albumin. Factor H, implicated as a potential therapeutic for AMD, aHUS, and MPGN, among other conditions, is one such plasma-derived blood product that is gaining the attention of physicians. However, due to the resources devoted to, for example, IgG gamma globulin manufacture, methods are needed for the manufacture of Factor H that can be introduced into the existing manufacturing schemes. Several methods have been suggested to achieve just this, however, many of these proposed solutions require modification of the existing manufacturing scheme for established products. Such changes will require new regulatory approvals for the established products and may even result in alterations of the characteristics of the established products.

For example, WO 2007/066017 describes methods for the production of Factor H preparations from the supernatant of a cryoprecipitate. The disclosed method consists of preparing a supernatant of a cryoprecipitate, submitting the supernatant to anion exchange chromatography (AEC), submitting the flow through from the AEC to heparin affinity chromatography (HAC), submitting the relevant eluate from the HAC to strong cation exchange chromatography (CEC), submitting the relevant eluate from the CEC to strong anion exchange chromatography (sAEC) and eluting the Factor H from the sAEC. Disadvantageously, cryoprecipitate supernatants are common intermediate fractions in the manufacturing processes of many commercially important plasma-derived blood products, including IgG gamma globulins (IVIG and subcutaneous) and albumin. Submitting this fraction to chromatography steps will alter the cryoprecipitate supernatant and would require that the manufacturing processes of the established downstream blood products be adapted in unknown fashions. In addition to requiring a complete revalidation and possible redesign of these manufacturing processes, regulatory re-approval of the manufacturing procedures from key regulatory agencies is needed.

Likewise, WO 2008/113589 describes methods for the production of Factor H preparations from human plasma. Specifically, this publication describes the purification of Factor H from three known plasma processing fractions, namely a Cohn-Oncley Fraction I supernatant, a Cohn-Oncley Fraction III precipitate, and a Kistler/Nitschmann Precipitate B fraction. With respect to the first method, WO 2008/113589 discloses that Factor H can be removed from a Cohn-Oncley Fraction I supernatant by the addition of a heparin affinity chromatography step. Disadvantageously, the Cohn-Oncley Fraction I supernatant is a common intermediate fraction in the manufacturing processes of many commercially important plasma-derived blood products, including IgG gamma globulins (IVIG and subcutaneous) and albumin. Similarly, many immunoglobulin (e.g., IgG, IVIG, etc.) manufacturing processes do not rely on Cohn-Oncley Fraction III precipitation or Kistler/Nitschmann Precipitate B steps, for example Gammagard® Liquid and Kiovig (Baxter International Inc.). The disadvantage of the introduction of additional steps, such as a heparin affinity chromatography, Fraction III precipitation, or Precipitate B steps, into the manufacturing schemes of established blood products, as outlined above, is that it requires revalidation of the manufacturing procedure, regulatory re-approval of the manufacturing procedures from key regulatory agencies, and may further have unforeseen consequences for the yield and/or purity of the otherwise established product.

As such, a need remains in the art for methods of manufacturing Factor H that do not require the use of additional input plasma or the redesign and regulatory re-approval of existing manufacturing processes for commercially important plasma-derived blood products, such as albumin and IgG gamma globulins for intravenous (IVIG) or subcutaneous administration. Advantageously, the present invention is based at least in part on the surprising discovery that Factor H, serine proteases, and serine protease zymogens can be simultaneously bound to finely divided silicon dioxide ($SiO_2$) thereby separating serine proteases and serine protease zymogen from a first protein of interest not bound to (e.g., IgG) and then separated by differentially eluting Factor H and the serine protease and serine protease zymogens from the $SiO_2$. Similarly, the present invention is based at least in part on the surprising discovery that IαIp, serine proteases, and serine protease zymogens can be simultaneously bound to finely divided silicon dioxide ($SiO_2$) and then separated by differentially eluting IαIp and the serine protease and serine protease zymogens from the $SiO_2$.

II. Definitions

As used herein, "Factor H" refers to a protein component of the alternative pathway of complement encoded by the complement factor H gene (for example, CFH; NM000186; GeneID:3075; UniProt ID P08603; Ripoche et al., Biochem. J. 249:593-602(1988)). Factor H is translated as a 1,213 amino acid precursor polypeptide which is processed by removal of an 18 amino acid signal peptide, resulting in the mature Factor H protein (amino acids 19-1231). As used in the present invention, Factor H encompasses any natural variants, alternative sequences, isoforms or mutant proteins that can be found in a plasma sample, for example a human plasma sample. Examples of Factor H mutations found in the human population include, without limitation, Y402H; V62I; R78G; R127L; Δ224; Q400K; C431S; T493R; C536R; I551T; R567G; C630W; C673S; C673Y; E850K; S890I; H893R; C915S; E936D; Q950H; Y951H; T956M; C959Y; W978C; N997T; V1007I; V1007L; A1010T; T1017I; Y1021F; C1043R; N1050Y; I1059T; Q1076R; R1078S; D1119G; V1134G; Y1142D; Q1143E; W1157R; C1163W; W1183L; W1183R; T1184R; L1189R; S1191L; G1194D; V1197A; E1198A; F1199S; R1210C; R1215G; R1215Q; YPTCAKR1225:1231FQS; and P1226S. Many of the these mutations have been found to be associated with a variety of diseases and disorders, including, atypical haemolytic uremic syndrome (aHUS), age-related macular degeneration (AMD), membranoproliferative glomulonephritis type II (MPGNII), CFH deficiency, and basal laminar drusen. Factor H also includes proteins containing post-translational modifications. For example, Factor H is believed to be modified by N-acetylglucosamine (GlcNAc) at residues 529, 718, 802, 822, 882, 911, 1029, and 1095.

As used herein, "Inter-alpha-Inhibitor proteins" or "IαIp" refers to a family of plasma protease inhibitors comprised of polypeptides encoded by one or more of the Alpha-1-microglobulin/bikunin precursor gene (AMBP; UniGene ID:231948, bikunin polypeptide), Inter-alpha (globulin) inhibitor H1 gene (ITIH1; UniGene ID:224173, H1 polypeptide), Inter-alpha (globulin) inhibitor H2 gene (ITIH2; Unigene ID: 139782, H2 polypeptide), Inter-alpha (globulin) inhibitor H3 gene (ITIH3; UniGene ID:140017, H3 polypeptide), or Inter-alpha (globulin) inhibitor H4 (plasma Kallikrein-sensitive glycoprotein, H4 polypeptide) gene (ITIH4; UniGene ID:3321613). Exemplary IαI p protease inhibitors include, without limitation, IαI (bikunin, H1, and H2 polypeptides); PαI (bikunin and H3 polypeptides), IaLI (bikunin and H2 polypeptides), IaIH4P (H4 polypeptide), and bikunin (Salier, J, et al., supra).

As used herein, "cryo-poor plasma" refers to the supernatant created after the removal of cryo-precipitate formed by thawing plasma or pooled plasma at temperatures near freezing, e.g., at temperatures below about 10° C., preferably at a temperature no higher than about 6° C. In the context of the present invention, plasma may refer interchangeably to recovered plasma (i.e., plasma that has been separated from whole blood ex vivo) or source plasma (i.e., plasma collected via plasmapheresis). Cryo-precipitation is commonly performed, for example, by thawing previously frozen pooled plasma, which has already been assayed for safety and quality considerations, although fresh plasma may also be used. After complete thawing of the frozen plasma at low temperature, separation of the solid cryo-precipitates from the liquid supernatant is performed in the cold (e.g., ≤6° C.) by centrifugation of filtration.

As used herein, a "Cohn pool" refers to the starting material used for the fractionation of a plasma sample or pool of plasma samples. Cohn pools include whole plasma, cryo-poor plasma samples, and pools of cryo-poor plasma samples that may or may not have been subjected to a pre-processing step. In certain embodiments, a Cohn pool is a cryo-poor plasma sample from which one or more blood factor have been removed in a pre-processing step, for example, adsorption onto a solid phase (e.g., aluminum hydroxide, finely divided silicon dioxide, etc.), or chromatographic step (e.g., ion exchange or heparin affinity chromatography). Various blood factors, including but not limited to Factor Eight Inhibitor Bypass Activity (FEIBA), Factor IX-complex, Factor VII-concentrate, or Antithrombin III-complex, may be isolated from the cryo-poor plasma sample to form a Cohn pool.

As used herein, a "Fraction I+III filter cake" refers to a solid phase recovered after the filtration or centrifugation of a Cohn-Oncley or equivalent Fraction II+III paste suspension. In a preferred embodiment, a Fraction II+III suspension will be treated with an adsorptive material, for example, finely divided silicon dioxide, to remove impurities such as lipids, fibrinogen, amidolytic activity, prekallikren activity, and lipoproteins. In another preferred embodiment, filter aid may be added to the Fraction II+III suspension prior to centrifugation or filtration. In a most preferred embodiment, a Fraction II+III suspension will be treated with both an adsorptive material and a filter aid prior to centrifugation or filtration. Upon separation of the clarified Fraction II+III suspension supernatant, the recovered solid phase material is referred to as the Fraction II+III filter cake.

As used herein, "finely divided silicon dioxide" or "finely divided silica" refers to an oxide of silicon having the formula $SiO_2$, manufactured in a fashion that allows for the adsorption of Factor H onto its surface. Exemplary forms of finely divided silicon dioxide suitable for use in the methods of the present invention include, without limitation, fumed silica, pyrogenic silica, Aerosil®, Cab-O-Sil™, colloidal silica, diatomaceous earth, and the like. In a preferred embodiment, a commercial hydrophilic fumed silica product is used for the methods provided herein. Non-limiting examples of these products include those marketed by Evonik Industries under the trade name Aerosil® (e.g., Aerosil 90, Aerosil 130, Aerosil 150, Aerosil 200, Aerosil 300, Aerosil 380, Aerosil OX 50, Aerosil EG 50, Aerosil TT 600, Aerosil 200 SP, Aerosil 300 SP, and Aerosil 300/30).

As used herein, a "disease or disorder associated with Factor H dysfunction" refers to any disease, disorder, or condition in a subject that is caused by, characterized by, or results in a reduced level of Factor H activity in the subject. For purposes of the present invention, Factor H activity may refer to the ability of Factor H to bind a protein or ligand, for example, C3b, C3bBb, C3b2Bb, csbC3b, complement factor B (CFB), C-reactive protein, endothelial cells, glycosaminoglycans (GAGs), or alternatively, may refer to its Factor I cofactor activity or its ability to accelerate the irreversible dissociation of C3bBb and C3b2Bb. In one embodiment, a disease or disorder associated with Factor H dysfunction results in a C3 deficiency and susceptibility to bacterial infections. In some instances, diseases or disorders associated with Factor H dysfunction include conditions that are caused by or linked to mutations and polymorphism in the CFH gene encoding Factor H (for review, see, Barlow et al., Adv Exp Med Biol. 2008; 632:117-42, the disclosure of which is herein incorporated by reference in its entirety for all purposes). Diseases that have been linked to mutations or polymorphisms in the CFH gene include, without limitation, Factor H deficiency, atypical haemolytic uremic syndrome (aHUS), age-related macular degeneration (AMD), membranoproliferative glomulonephritis type II (MPGNII; de Cordoba and de Jorge, Clinical and Experimental Immunology 151, 1-13 (2008)), myocardial infarction (Kardys et al., Journal of the American College of Cardiology 47, 1568-1575 (2006); Mooijaart et al., Experimental Gerontology 42, 1116-1122 (2007); Nicaud et al., Journal of Molecular Medicine 85, 771-775 (2007); Pai et al., European Heart Journal 28, 1297-1303 (2007); Stark et al., Clinical Science (Lond) 113, 213-218 (2007)), coronary heart disease/coronary artery disease (CADiCHD; (Meng et al., BMC Medical Genetics 8, 62 (2007); Pulido et al., Mayo Clinic Proceedings 82, 301-307 (2007); Topol et al., Human Molecular Genetics 15 Spec No 2, R117-R123 (2006)), and Alzheimer's disease (Hamilton et al., Neuromolecular Medicine 9, 331-334 (2007); Zetterberg et al., American Journal of Ophthalmology 143, 1059-1060 (2007)). The disclosures of the forgoing references describing the associations between mutations and polymorphisms in the CFH gene and diseases associated with Factor H dysfunction are herein incorporated by reference in their entireties for all purposes.

As used herein, a "disease or disorder associated with abnormal alternative pathway complement activity" refers to a disease, disorder, or condition that results from uncontrolled or aberrant activation of the alternative pathway of complement. Generally, uncontrolled or aberrant activation of the alternative pathway of complement can result in bystander damage of host cells and tissues, as well as a depletion of C3 and corresponding susceptibility to pathogenic infections (e.g., fungal, bacterial, viral, and protistal). Examples of diseases and disorders associated with abnormal alternative pathway complement activity include, without limitation, various autoimmune diseases (such as rheumatoid arthritis, IgA nephropathy, asthma, systemic lupus erythematosus, multiple sclerosis, Anti-Phospholipid syndrome, ANCA-associated vasculitis, pemphigus, uveitis, myathemia gravis, Hashimoto's thyroiditis), Renal diseases (such as IgA nephropathy, hemolytic uremic syndrome, membranoproliferative glomerulonephritis) other disease such as asthma, Alzheimer disease, adult macular degeneration, proximal nocturnal hemoglobinuria, abdominal aortic aneurism, ischemia, and sepsis.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar.

As used herein, the term "diafiltration" is performed with the same or a similar membrane as ultrafiltration and is typically performed in a tangential flow filtration mode. During diafiltration, buffer is introduced into the recycle tank while filtrate is removed from the unit operation. In processes where the product is in the retentate (for example, Factor H), diafiltration is particularly useful for separating protein from small molecules like sugars and salts. In certain cases, diafiltration can be used to exchange the solution, buffer, or individual components of a buffering system.

As used herein, the term "mixing" describes an act of causing equal distribution of two or more distinct compounds or substances in a solution or suspension by any form of agitation. Complete equal distribution of all ingredients in a solution or suspension is not required as a result of "mixing" as the term is used in this application.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used herein, the term "therapeutically effective amount or dose" or "sufficient/effective amount or dose," refers to a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins; the disclosures of which are herein incorporated by reference in their entireties for all purposes).

As used in this application, the term "spraying" refers to a means of delivering a liquid substance into a system, e.g., during an alcohol precipitation step, such as a Cohn fractionation I or II+III precipitation step, in the form of fine droplets or mist of the liquid substance. Spraying may be achieved by any pressurized device, such as a container (e.g., a spray bottle), that has a spray head or a nozzle and is operated manually or automatically to generate a fine mist from a liquid. Typically, spraying is performed while the system receiving the liquid substance is continuously stirred or otherwise mixed to ensure rapid and equal distribution of the liquid within the system.

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%." As used herein, "about" refers to a range of at or about the specified value.

The terms "dose" and "dosage" are used interchangeably herein. A dose refers to the amount of active ingredient given to an individual at each administration. The dose will vary depending on a number of factors, including frequency of administration; size and tolerance of the individual; severity of the condition; risk of side effects; and the route of administration. One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

As used herein, the term "prevent" refers to a decreased likelihood or reduced frequency of symptoms arising from a condition associated with the lack of function or disfunction of a blood protein.

As used herein, the term "therapy," "treatment," and "amelioration" refer to any reduction in the severity of symptoms arising from a condition associated with the lack of function or disfunction of a blood protein. As used herein, the terms "treat" and "prevent" are not intended to be absolute terms. Treatment can refer to any delay in onset, amelioration of symptoms, improvement in patient survival, increase in survival time or rate, etc. The effect of treatment can be compared to an individual or pool of individuals not receiving the treatment.

As used herein, the term "substantial fraction" refers to at least 10% of the population of a particular protein in a composition. For example, when referring to a substantial fraction of a serine protease in a composition, a substantial fraction of the serine protease corresponds to at least 10% of the serine protease present in the composition. In one embodiment, a substantial fraction refers to at least 25% of the population of a particular protein in a composition. In another embodiment, a substantial fraction refers to at least 50% of the population of a particular protein in a composition. In another embodiment, a substantial fraction refers to at least 75% of the population of a particular protein in a composition. In yet other embodiments, a substantial fraction refers to at least 10% of the population of a particular protein in a composition, or at least 15, 20, 25, 30, 35, 40, 45, 50, 55, 60, 65, 70, 75, 80, 85, 90, 95, 96, 97, 98, 99, or more of the population of a particular protein in a composition.

III. Reduction of Serine Protease and Serine Protease Zymogen Content

In a first aspect, the present invention provides a method for reducing the amount of a serine protease or a serine protease zymogen in a plasma-derived target protein composition by binding the serine protease and/or serine protease zymogen to finely divided silicon dioxide ($SiO_2$) and separating the $SiO_2$ from the composition.

In one embodiment, the method comprises the steps of: (a) contacting the composition with finely divided silicon dioxide ($SiO_2$) under conditions suitable to bind at least one serine protease or serine protease zymogen; and (b) separating the $SiO_2$ from the composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII).

Accordingly, in one embodiment, the invention provides a method for reducing the amount of Factor XI in a plasma-derived protein composition, the method comprising the steps of: (a) contacting the composition with finely divided silicon dioxide ($SiO_2$) under conditions suitable to bind Factor XI; and (b) separating the $SiO_2$ from the composition to remove the bound Factor XI.

In another embodiment, the invention provides a method for reducing the amount of Factor XIa in a plasma-derived protein composition, the method comprising the steps of: (a) contacting the composition with finely divided silicon dioxide ($SiO_2$) under conditions suitable to bind Factor XIa; and (b) separating the $SiO_2$ from the composition to remove the bound Factor XIa.

In another embodiment, the invention provides a method for reducing the amount of Factor XII in a plasma-derived protein composition, the method comprising the steps of: (a) contacting the composition with finely divided silicon dioxide ($SiO_2$) under conditions suitable to bind Factor XII; and (b) separating the $SiO_2$ from the composition to remove the bound Factor XII.

In yet another embodiment, the invention provides a method for reducing the amount of Factor XIIa in a plasma-derived protein composition, the method comprising the steps of: (a) contacting the composition with finely divided silicon dioxide ($SiO_2$) under conditions suitable to bind Factor XIIa; and (b) separating the $SiO_2$ from the composition to remove the bound Factor XIIa.

In certain embodiments, the method described above further comprises the step of performing a first target protein enrichment step to form a first enriched composition, prior to contacting the composition with finely divided silicon dioxide ($SiO_2$). In certain embodiments, the first target protein enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived target protein the method comprises the steps of: (a) forming a first enriched plasma-derived target protein composition by partially precipitating protein in a starting material derived from pooled plasma; (b) contacting the first enriched composition with finely divided silicon dioxide ($SiO_2$) under conditions suitable to bind at least one serine protease or serine protease zymogen; and (c) separating the $SiO_2$ from the composition to remove the bound serine protease or serine protease zymogen. In one embodiment, the partial precipitation is achieved using alcohol. In a preferred embodiment, the alcohol is ethanol. In another preferred embodiment, the serine protease or serine protease zymogen is Factor XIa (FXIa), Factor XIIa (FXIIa), Factor XI (FXI), and/or Factor XII (FXII).

In another embodiment, the invention provides a method for reducing the amount of a serine protease or a serine protease zymogen in a plasma-derived target protein the method comprises the steps of: (a) forming a first enriched plasma-derived target protein composition by ultrafiltering and/or diafiltering a starting material derived from pooled plasma; (b) contacting the first enriched composition with finely divided silicon dioxide ($SiO_2$) under conditions suitable to bind at least one serine protease or serine protease zymogen; and (c) separating the $SiO_2$ from the composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII).

In yet another embodiment, the invention provides a method for reducing the amount of a serine protease or a serine protease zymogen in a plasma-derived target protein the method comprises the steps of: (a) forming a first enriched plasma-derived target protein composition by contacting a starting material derived from pooled plasma with a chromatographic resin; (b) contacting the first enriched composition with finely divided silicon dioxide ($SiO_2$) under conditions suitable to bind at least one serine protease or serine protease zymogen; and (c) separating the $SiO_2$ from the composition to remove the bound serine protease or serine protease zymogen. In certain embodiments, the chromatographic resin is selected from an anion exchange resin, a cation exchange resin, a hydrophobic interaction resin, a mixed mode resin, a hydroxyapatite resin, a ligand affinity resin, an immunoaffinity resin, and a size exclusion resin. In a preferred embodiment, the serine protease or serine protease zymogen is Factor XIa (FXIa), Factor XIIa (FXIIa), Factor XI (FXI), and/or Factor XII (FXII).

In certain embodiments, the methods described above further comprises the step of performing a second target protein enrichment step to form a second enriched composition, prior to contacting the composition with finely divided silicon dioxide ($SiO_2$). In certain embodiments, the first target protein enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived target protein the method comprises the steps of: (a) performing a first target protein enrichment step to form a first enriched plasma-derived target protein composition; (b) performing a second target protein enrichment step to form a second enriched plasma-derived target protein composition; (c) contacting the second enriched composition with finely divided silicon dioxide ($SiO_2$) under conditions suitable to bind at least one serine protease or serine protease zymogen; and (d) separating the $SiO_2$ from the composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

Accordingly, in one embodiment, the invention provides a method for reducing the amount of a serine protease or a serine protease zymogen in a plasma-derived target protein the method comprises the steps of: (a) performing a first target protein enrichment step to form a first enriched plasma-derived target protein composition; (b) contacting the first enriched composition with finely divided silicon dioxide ($SiO_2$) under conditions suitable to bind at least one serine protease or serine protease zymogen; (c) separating the $SiO_2$ from the composition to remove the bound serine protease or serine protease zymogen; and (d) performing a second target protein enrichment step to form a second enriched plasma-derived target protein composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

Likewise, in one embodiment, the invention provides a method for reducing the amount of a serine protease or a serine protease zymogen in a plasma-derived target protein the method comprises the steps of: (a) performing a first target protein enrichment step to form a first enriched plasma-derived target protein composition; (b) performing a second target protein enrichment step to form a second enriched plasma-derived target protein composition; (c) contacting the second enriched composition with finely divided silicon dioxide ($SiO_2$) under conditions suitable to bind at least one serine protease or serine protease zymogen; (d) separating the $SiO_2$ from the composition to remove the bound serine protease or serine protease zymogen; and (e) performing a third target protein enrichment step to form a third enriched plasma-derived target protein composition. In

TABLE 1

Exemplary embodiments for the combination of first and second enrichment steps.

| | | First Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| Second Enrichment Step | Ppt | Var. 1 | Var. 11 | Var. 21 | Var. 31 | Var. 41 | Var. 51 | Var. 61 | Var. 71 | Var. 81 | Var. 91 |
| | UF/DF | Var. 2 | Var. 12 | Var. 22 | Var. 32 | Var. 42 | Var. 52 | Var. 62 | Var. 72 | Var. 82 | Var. 92 |
| | AEC | Var. 3 | Var. 13 | Var. 23 | Var. 33 | Var. 43 | Var. 53 | Var. 63 | Var. 73 | Var. 83 | Var. 93 |
| | CEC | Var. 4 | Var. 14 | Var. 24 | Var. 34 | Var. 44 | Var. 54 | Var. 64 | Var. 74 | Var. 84 | Var. 94 |
| | HIC | Var. 5 | Var. 15 | Var. 25 | Var. 35 | Var. 45 | Var. 55 | Var. 65 | Var. 75 | Var. 85 | Var. 95 |
| | HAC | Var. 6 | Var. 16 | Var. 26 | Var. 36 | Var. 46 | Var. 56 | Var. 66 | Var. 76 | Var. 86 | Var. 96 |
| | MMC | Var. 7 | Var. 17 | Var. 27 | Var. 37 | Var. 47 | Var. 57 | Var. 67 | Var. 77 | Var. 87 | Var. 97 |
| | LAC | Var. 8 | Var. 18 | Var. 28 | Var. 38 | Var. 48 | Var. 58 | Var. 68 | Var. 78 | Var. 88 | Var. 98 |
| | IAC | Var. 9 | Var. 19 | Var. 29 | Var. 39 | Var. 49 | Var. 59 | Var. 69 | Var. 79 | Var. 89 | Var. 99 |
| | SEC | Var. 10 | Var. 20 | Var. 30 | Var. 40 | Var. 50 | Var. 60 | Var. 70 | Var. 80 | Var. 90 | Var. 100 |

*Ppt: Precipitation UF/DF: Ultrafiltration/Diafiltration AEC: Anion Exchange Chromatography CEC: Cation Exchange Chromatography HIC: Hydrophobic Interaction Chromatography HAC: Hydroxyapatite Chromatography MMC: Mixed Mode Chromatography LAC: Ligand Affinity Chromatography LAC: Immuno-Affinity Chromatography SEC: Size Exclusion Chromatography In certain embodiments, the methods described above further comprises the step of performing a target protein enrichment step after contacting the composition with finely divided silicon dioxide ($SiO_2$). In certain embodiments, the target protein enrichment step is selected from a protein precipitation step (e.g., an alcohol fractionation step), an ultrafiltration/diafiltration step, and a chromatographic step.

a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 101 to Var. 1100, found in Table 2, Table 3, Table 4, Table 5, Table 6, Table 7, Table 8, Table 9, Table 10, or Table 11.

TABLE 2

Exemplary embodiments for the combination of a first precipitation enrichment step, a second, and a third enrichment step.

|  |  | Second Enrichment Step* | | | | | | | | | |
|---|---|---|---|---|---|---|---|---|---|---|---|
|  |  | Ppt | UF/DF | AEC | CEC | HIC | HAC | MMC | LAC | IAC | SEC |
| Third Enrichment Step | Ppt | Var. 101 | Var. 111 | Var. 121 | Var. 131 | Var. 141 | Var. 151 | Var. 161 | Var. 171 | Var. 181 | Var. 191 |
|  | UF/DF | Var. 102 | Var. 112 | Var. 122 | Var. 132 | Var. 142 | Var. 152 | Var. 162 | Var. 172 | Var. 182 | Var. 192 |
|  | AEC | Var. 103 | Var. 113 | Var. 123 | Var. 133 | Var. 143 | Var. 153 | Var. 163 | Var. 173 | Var. 183 | Var. 193 |
|  | CEC | Var. 104 | Var. 114 | Var. 124 | Var. 134 | Var. 144 | Var. 154 | Var. 164 | Var. 174 | Var. 184 | Var. 194 |
|  | HIC | Var. 105 | Var. 115 | Var. 125 | Var. 135 | Var. 145 | Var. 155 | Var. 165 | Var. 175 | Var. 185 | Var. 195 |
|  | HAC | Var. 106 | Var. 116 | Var. 126 | Var. 136 | Var. 146 | Var. 156 | Var. 166 | Var. 176 | Var. 186 | Var. 196 |
|  | MMC | Var. 107 | Var. 117 | Var. 127 | Var. 137 | Var. 147 | Var. 157 | Var. 167 | Var. 177 | Var. 187 | Var. 197 |
|  | LAC | Var. 108 | Var. 118 | Var. 128 | Var. 138 | Var. 148 | Var. 158 | Var. 168 | Var. 178 | Var. 188 | Var. 198 |
|  | IAC | Var. 109 | Var. 119 | Var. 129 | Var. 139 | Var. 149 | Var. 159 | Var. 169 | Var. 179 | Var. 189 | Var. 199 |
|  | SEC | Var. 110 | Var. 120 | Var. 130 | Var. 140 | Var. 150 | Var. 160 | Var. 170 | Var. 180 | Var. 190 | Var. 200 |

*As per Table 1.

TABLE 3

Exemplary embodiments for the combination of a first Ultrafiltration/Diafiltration step, a second, and a third enrichment step.

|  |  | Second Enrichment Step* | | | | | | | | | |
|---|---|---|---|---|---|---|---|---|---|---|---|
|  |  | Ppt | UF/DF | AEC | CEC | HIC | HAC | MMC | LAC | IAC | SEC |
| Third Enrichment Step | Ppt | Var. 201 | Var. 211 | Var. 221 | Var. 231 | Var. 241 | Var. 251 | Var. 261 | Var. 271 | Var. 281 | Var. 291 |
|  | UF/DF | Var. 202 | Var. 212 | Var. 222 | Var. 232 | Var. 242 | Var. 252 | Var. 262 | Var. 272 | Var. 282 | Var. 292 |
|  | AEC | Var. 203 | Var. 213 | Var. 223 | Var. 233 | Var. 243 | Var. 253 | Var. 263 | Var. 273 | Var. 283 | Var. 293 |
|  | CEC | Var. 204 | Var. 214 | Var. 224 | Var. 234 | Var. 244 | Var. 254 | Var. 264 | Var. 274 | Var. 284 | Var. 294 |
|  | HIC | Var. 205 | Var. 215 | Var. 225 | Var. 235 | Var. 245 | Var. 255 | Var. 265 | Var. 275 | Var. 285 | Var. 295 |
|  | HAC | Var. 206 | Var. 216 | Var. 226 | Var. 236 | Var. 246 | Var. 256 | Var. 266 | Var. 276 | Var. 286 | Var. 296 |
|  | MMC | Var. 207 | Var. 217 | Var. 227 | Var. 237 | Var. 247 | Var. 257 | Var. 267 | Var. 277 | Var. 287 | Var. 297 |
|  | LAC | Var. 208 | Var. 218 | Var. 228 | Var. 238 | Var. 248 | Var. 258 | Var. 268 | Var. 278 | Var. 288 | Var. 298 |
|  | IAC | Var. 209 | Var. 219 | Var. 229 | Var. 239 | Var. 249 | Var. 259 | Var. 269 | Var. 279 | Var. 289 | Var. 299 |
|  | SEC | Var. 210 | Var. 220 | Var. 230 | Var. 240 | Var. 250 | Var. 260 | Var. 270 | Var. 280 | Var. 290 | Var. 300 |

*As per Table 1.

TABLE 4

Exemplary embodiments for the combination of a first Anion Exchange Chromatography step, a second, and a third enrichment step.

|  |  | Second Enrichment Step* | | | | | | | | | |
|---|---|---|---|---|---|---|---|---|---|---|---|
|  |  | Ppt | UF/DF | AEC | CEC | HIC | HAC | MMC | LAC | IAC | SEC |
| Third Enrichment Step | Ppt | Var. 301 | Var. 311 | Var. 321 | Var. 331 | Var. 341 | Var. 351 | Var. 361 | Var. 371 | Var. 381 | Var. 391 |
|  | UF/DF | Var. 302 | Var. 312 | Var. 322 | Var. 332 | Var. 342 | Var. 352 | Var. 362 | Var. 372 | Var. 382 | Var. 392 |
|  | AEC | Var. 303 | Var. 313 | Var. 323 | Var. 333 | Var. 343 | Var. 353 | Var. 363 | Var. 373 | Var. 383 | Var. 393 |

TABLE 4-continued

Exemplary embodiments for the combination of a first Anion Exchange
Chromatography step, a second, and a third enrichment step.

| | | Second Enrichment Step* | | | | | | | | |
|---|---|---|---|---|---|---|---|---|---|---|
| | | Ppt | UF/DF | AEC | CEC | HIC | HAC | MMC | LAC | IAC | SEC |
| | CEC | Var. 304 | Var. 314 | Var. 324 | Var. 334 | Var. 344 | Var. 354 | Var. 364 | Var. 374 | Var. 384 | Var. 394 |
| | HIC | Var. 305 | Var. 315 | Var. 325 | Var. 335 | Var. 345 | Var. 355 | Var. 365 | Var. 375 | Var. 385 | Var. 395 |
| | HAC | Var. 306 | Var. 316 | Var. 326 | Var. 336 | Var. 346 | Var. 356 | Var. 366 | Var. 376 | Var. 386 | Var. 396 |
| | MMC | Var. 307 | Var. 317 | Var. 327 | Var. 337 | Var. 347 | Var. 357 | Var. 367 | Var. 377 | Var. 387 | Var. 397 |
| | LAC | Var. 308 | Var. 318 | Var. 328 | Var. 338 | Var. 348 | Var. 358 | Var. 368 | Var. 378 | Var. 388 | Var. 398 |
| | IAC | Var. 309 | Var. 319 | Var. 329 | Var. 339 | Var. 349 | Var. 359 | Var. 369 | Var. 379 | Var. 389 | Var. 399 |
| | SEC | Var. 310 | Var. 320 | Var. 330 | Var. 340 | Var. 350 | Var. 360 | Var. 370 | Var. 380 | Var. 390 | Var. 400 |

*As per Table 1.

TABLE 5

Exemplary embodiments for the combination of a first Cation Exchange
Chromatography step, a second, and a third enrichment step.

| | | Second Enrichment Step* | | | | | | | | |
|---|---|---|---|---|---|---|---|---|---|---|
| | | Ppt | UF/DF | AEC | CEC | HIC | HAC | MMC | LAC | IAC | SEC |
| Third Enrichment Step | Ppt | Var. 401 | Var. 411 | Var. 421 | Var. 431 | Var. 441 | Var. 451 | Var. 461 | Var. 471 | Var. 481 | Var. 491 |
| | UF/DF | Var. 402 | Var. 412 | Var. 422 | Var. 432 | Var. 442 | Var. 452 | Var. 462 | Var. 472 | Var. 482 | Var. 492 |
| | AEC | Var. 403 | Var. 413 | Var. 423 | Var. 433 | Var. 443 | Var. 453 | Var. 463 | Var. 473 | Var. 483 | Var. 493 |
| | CEC | Var. 404 | Var. 414 | Var. 424 | Var. 434 | Var. 444 | Var. 454 | Var. 464 | Var. 474 | Var. 484 | Var. 494 |
| | HIC | Var. 405 | Var. 415 | Var. 425 | Var. 435 | Var. 445 | Var. 455 | Var. 465 | Var. 475 | Var. 485 | Var. 495 |
| | HAC | Var. 406 | Var. 416 | Var. 426 | Var. 436 | Var. 446 | Var. 456 | Var. 466 | Var. 476 | Var. 486 | Var. 496 |
| | MMC | Var. 407 | Var. 417 | Var. 427 | Var. 437 | Var. 447 | Var. 457 | Var. 467 | Var. 477 | Var. 487 | Var. 497 |
| | LAC | Var. 408 | Var. 418 | Var. 428 | Var. 438 | Var. 448 | Var. 458 | Var. 468 | Var. 478 | Var. 488 | Var. 498 |
| | IAC | Var. 409 | Var. 419 | Var. 429 | Var. 439 | Var. 449 | Var. 459 | Var. 469 | Var. 479 | Var. 489 | Var. 499 |
| | SEC | Var. 410 | Var. 420 | Var. 430 | Var. 440 | Var. 450 | Var. 460 | Var. 470 | Var. 480 | Var. 490 | Var. 500 |

*As per Table 1.

TABLE 6

Exemplary embodiments for the combination of a first Hydrophobic Interaction
Chromatography step, a second, and a third enrichment step.

| | | Second Enrichment Step* | | | | | | | | |
|---|---|---|---|---|---|---|---|---|---|---|
| | | Ppt | UF/DF | AEC | CEC | HIC | HAC | MMC | LAC | IAC | SEC |
| Third Enrichment Step | Ppt | Var. 501 | Var. 511 | Var. 521 | Var. 531 | Var. 541 | Var. 551 | Var. 561 | Var. 571 | Var. 581 | Var. 591 |
| | UF/DF | Var. 502 | Var. 512 | Var. 522 | Var. 532 | Var. 542 | Var. 552 | Var. 562 | Var. 572 | Var. 582 | Var. 592 |
| | AEC | Var. 503 | Var. 513 | Var. 523 | Var. 533 | Var. 543 | Var. 553 | Var. 563 | Var. 573 | Var. 583 | Var. 593 |
| | CEC | Var. 504 | Var. 514 | Var. 524 | Var. 534 | Var. 544 | Var. 554 | Var. 564 | Var. 574 | Var. 584 | Var. 594 |
| | HIC | Var. 505 | Var. 515 | Var. 525 | Var. 535 | Var. 545 | Var. 555 | Var. 565 | Var. 575 | Var. 585 | Var. 595 |
| | HAC | Var. 506 | Var. 516 | Var. 526 | Var. 536 | Var. 546 | Var. 556 | Var. 566 | Var. 576 | Var. 586 | Var. 596 |

TABLE 6-continued

Exemplary embodiments for the combination of a first Hydrophobic Interaction Chromatography step, a second, and a third enrichment step.

| | | Second Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| | MMC | Var. 507 | Var. 517 | Var. 527 | Var. 537 | Var. 547 | Var. 557 | Var. 567 | Var. 577 | Var. 587 | Var. 597 |
| | LAC | Var. 508 | Var. 518 | Var. 528 | Var. 538 | Var. 548 | Var. 558 | Var. 568 | Var. 578 | Var. 588 | Var. 598 |
| | IAC | Var. 509 | Var. 519 | Var. 529 | Var. 539 | Var. 549 | Var. 559 | Var. 569 | Var. 579 | Var. 589 | Var. 599 |
| | SEC | Var. 510 | Var. 520 | Var. 530 | Var. 540 | Var. 550 | Var. 560 | Var. 570 | Var. 580 | Var. 590 | Var. 600 |

*As per Table 1.

TABLE 7

Exemplary embodiments for the combination of a first Hydroxyapatite Chromatography step, a second, and a third enrichment step.

| | | Second Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| Third Enrichment Step | Ppt | Var. 601 | Var. 611 | Var. 621 | Var. 631 | Var. 641 | Var. 651 | Var. 661 | Var. 671 | Var. 681 | Var. 691 |
| | UF/DF | Var. 602 | Var. 612 | Var. 622 | Var. 632 | Var. 642 | Var. 652 | Var. 662 | Var. 672 | Var. 682 | Var. 692 |
| | AEC | Var. 603 | Var. 613 | Var. 623 | Var. 633 | Var. 643 | Var. 653 | Var. 663 | Var. 673 | Var. 683 | Var. 693 |
| | CEC | Var. 604 | Var. 614 | Var. 624 | Var. 634 | Var. 644 | Var. 654 | Var. 664 | Var. 674 | Var. 684 | Var. 694 |
| | HIC | Var. 605 | Var. 615 | Var. 625 | Var. 635 | Var. 645 | Var. 655 | Var. 665 | Var. 675 | Var. 685 | Var. 695 |
| | HAC | Var. 606 | Var. 616 | Var. 626 | Var. 636 | Var. 646 | Var. 656 | Var. 666 | Var. 676 | Var. 686 | Var. 696 |
| | MMC | Var. 607 | Var. 617 | Var. 627 | Var. 637 | Var. 647 | Var. 657 | Var. 667 | Var. 677 | Var. 687 | Var. 697 |
| | LAC | Var. 608 | Var. 618 | Var. 628 | Var. 638 | Var. 648 | Var. 658 | Var. 668 | Var. 678 | Var. 688 | Var. 698 |
| | IAC | Var. 609 | Var. 619 | Var. 629 | Var. 639 | Var. 649 | Var. 659 | Var. 669 | Var. 679 | Var. 689 | Var. 699 |
| | SEC | Var. 610 | Var. 620 | Var. 630 | Var. 640 | Var. 650 | Var. 660 | Var. 670 | Var. 680 | Var. 690 | Var. 700 |

*As per Table 1.

TABLE 8

Exemplary embodiments for the combination of a first Mixed Mode Chromatography step, a second, and a third enrichment step.

| | | Second Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| Third Enrichment Step | Ppt | Var. 701 | Var. 711 | Var. 721 | Var. 731 | Var. 741 | Var. 751 | Var. 761 | Var. 771 | Var. 781 | Var. 791 |
| | UF/DF | Var. 702 | Var. 712 | Var. 722 | Var. 732 | Var. 742 | Var. 752 | Var. 762 | Var. 772 | Var. 782 | Var. 792 |
| | AEC | Var. 703 | Var. 713 | Var. 723 | Var. 733 | Var. 743 | Var. 753 | Var. 763 | Var. 773 | Var. 783 | Var. 793 |
| | CEC | Var. 704 | Var. 714 | Var. 724 | Var. 734 | Var. 744 | Var. 754 | Var. 764 | Var. 774 | Var. 784 | Var. 794 |
| | HIC | Var. 705 | Var. 715 | Var. 725 | Var. 735 | Var. 745 | Var. 755 | Var. 765 | Var. 775 | Var. 785 | Var. 795 |
| | HAC | Var. 706 | Var. 716 | Var. 726 | Var. 736 | Var. 746 | Var. 756 | Var. 766 | Var. 776 | Var. 786 | Var. 796 |
| | MMC | Var. 707 | Var. 717 | Var. 727 | Var. 737 | Var. 747 | Var. 757 | Var. 767 | Var. 777 | Var. 787 | Var. 797 |
| | LAC | Var. 708 | Var. 718 | Var. 728 | Var. 738 | Var. 748 | Var. 758 | Var. 768 | Var. 778 | Var. 788 | Var. 798 |
| | IAC | Var. 709 | Var. 719 | Var. 729 | Var. 739 | Var. 749 | Var. 759 | Var. 769 | Var. 779 | Var. 789 | Var. 799 |

TABLE 8-continued

Exemplary embodiments for the combination of a first Mixed Mode Chromatography step, a second, and a third enrichment step.

| | | Second Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| | SEC | Var. 710 | Var. 720 | Var. 730 | Var. 740 | Var. 750 | Var. 760 | Var. 770 | Var. 780 | Var. 790 | Var. 800 |

*As per Table 1.

TABLE 9

Exemplary embodiments for the combination of a first Ligand Affinity Chromatography step, a second, and a third enrichment step.

| | | Second Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| Third Enrichment Step | Ppt | Var. 801 | Var. 811 | Var. 821 | Var. 831 | Var. 841 | Var. 851 | Var. 861 | Var. 871 | Var. 881 | Var. 891 |
| | UF/DF | Var. 802 | Var. 812 | Var. 822 | Var. 832 | Var. 842 | Var. 852 | Var. 862 | Var. 872 | Var. 882 | Var. 892 |
| | AEC | Var. 803 | Var. 813 | Var. 823 | Var. 833 | Var. 843 | Var. 853 | Var. 863 | Var. 873 | Var. 883 | Var. 893 |
| | CEC | Var. 804 | Var. 814 | Var. 824 | Var. 834 | Var. 844 | Var. 854 | Var. 864 | Var. 874 | Var. 884 | Var. 894 |
| | HIC | Var. 805 | Var. 815 | Var. 825 | Var. 835 | Var. 845 | Var. 855 | Var. 865 | Var. 875 | Var. 885 | Var. 895 |
| | HAC | Var. 806 | Var. 816 | Var. 826 | Var. 836 | Var. 846 | Var. 856 | Var. 866 | Var. 876 | Var. 886 | Var. 896 |
| | MMC | Var. 807 | Var. 817 | Var. 827 | Var. 837 | Var. 847 | Var. 857 | Var. 867 | Var. 877 | Var. 887 | Var. 897 |
| | LAC | Var. 808 | Var. 818 | Var. 828 | Var. 838 | Var. 848 | Var. 858 | Var. 868 | Var. 878 | Var. 888 | Var. 898 |
| | IAC | Var. 809 | Var. 819 | Var. 829 | Var. 839 | Var. 849 | Var. 859 | Var. 869 | Var. 879 | Var. 889 | Var. 899 |
| | SEC | Var. 810 | Var. 820 | Var. 830 | Var. 840 | Var. 850 | Var. 860 | Var. 870 | Var. 880 | Var. 890 | Var. 900 |

*As per Table 1.

TABLE 10

Exemplary embodiments for the combination of a first Immuno-Affinity Chromatography step, a second, and a third enrichment step.

| | | Second Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| Third Enrichment Step | Ppt | Var. 901 | Var. 911 | Var. 921 | Var. 931 | Var. 941 | Var. 951 | Var. 961 | Var. 971 | Var. 981 | Var. 991 |
| | UF/DF | Var. 902 | Var. 912 | Var. 922 | Var. 932 | Var. 942 | Var. 952 | Var. 962 | Var. 972 | Var. 982 | Var. 992 |
| | AEC | Var. 903 | Var. 913 | Var. 923 | Var. 933 | Var. 943 | Var. 953 | Var. 963 | Var. 973 | Var. 983 | Var. 993 |
| | CEC | Var. 904 | Var. 914 | Var. 924 | Var. 934 | Var. 944 | Var. 954 | Var. 964 | Var. 974 | Var. 984 | Var. 994 |
| | HIC | Var. 905 | Var. 915 | Var. 925 | Var. 935 | Var. 945 | Var. 955 | Var. 965 | Var. 975 | Var. 985 | Var. 995 |
| | HAC | Var. 906 | Var. 916 | Var. 926 | Var. 936 | Var. 946 | Var. 956 | Var. 966 | Var. 976 | Var. 986 | Var. 996 |
| | MMC | Var. 907 | Var. 917 | Var. 927 | Var. 937 | Var. 947 | Var. 957 | Var. 967 | Var. 977 | Var. 987 | Var. 997 |
| | LAC | Var. 908 | Var. 918 | Var. 928 | Var. 938 | Var. 948 | Var. 958 | Var. 968 | Var. 978 | Var. 988 | Var. 998 |
| | IAC | Var. 909 | Var. 919 | Var. 929 | Var. 939 | Var. 949 | Var. 959 | Var. 969 | Var. 979 | Var. 989 | Var. 999 |
| | SEC | Var. 910 | Var. 920 | Var. 930 | Var. 940 | Var. 950 | Var. 960 | Var. 970 | Var. 980 | Var. 990 | Var. 1000 |

*As per Table 1.

TABLE 11

Exemplary embodiments for the combination of a first Size Exclusion Chromatography step, a second, and a third enrichment step.

| | | Second Enrichment Step* | | | | | | | | | |
|---|---|---|---|---|---|---|---|---|---|---|---|
| | | Ppt | UF/DF | AEC | CEC | HIC | HAC | MMC | LAC | IAC | SEC |
| Third Enrichment Step | Ppt | Var. 1001 | Var. 1011 | Var. 1021 | Var. 1031 | Var. 1041 | Var. 1051 | Var. 1061 | Var. 1071 | Var. 1081 | Var. 1091 |
| | UF/DF | Var. 1002 | Var. 1012 | Var. 1022 | Var. 1032 | Var. 1042 | Var. 1052 | Var. 1062 | Var. 1072 | Var. 1082 | Var. 1092 |
| | AEC | Var. 1003 | Var. 1013 | Var. 1023 | Var. 1033 | Var. 1043 | Var. 1053 | Var. 1063 | Var. 1073 | Var. 1083 | Var. 1093 |
| | CEC | Var. 1004 | Var. 1014 | Var. 1024 | Var. 1034 | Var. 1044 | Var. 1054 | Var. 1064 | Var. 1074 | Var. 1084 | Var. 1094 |
| | HIC | Var. 1005 | Var. 1015 | Var. 1025 | Var. 1035 | Var. 1045 | Var. 1055 | Var. 1065 | Var. 1075 | Var. 1085 | Var. 1095 |
| | HAC | Var. 1006 | Var. 1016 | Var. 1026 | Var. 1036 | Var. 1046 | Var. 1056 | Var. 1066 | Var. 1076 | Var. 1086 | Var. 1096 |
| | MMC | Var. 1007 | Var. 1017 | Var. 1027 | Var. 1037 | Var. 1047 | Var. 1057 | Var. 1067 | Var. 1077 | Var. 1087 | Var. 1097 |
| | LAC | Var. 1008 | Var. 1018 | Var. 1028 | Var. 1038 | Var. 1048 | Var. 1058 | Var. 1068 | Var. 1078 | Var. 1088 | Var. 1098 |
| | IAC | Var. 1009 | Var. 1019 | Var. 1029 | Var. 1039 | Var. 1049 | Var. 1059 | Var. 1069 | Var. 1079 | Var. 1089 | Var. 1099 |
| | SEC | Var. 1010 | Var. 1020 | Var. 1030 | Var. 1040 | Var. 1050 | Var. 1060 | Var. 1070 | Var. 1080 | Var. 1090 | Var. 1100 |

*As per Table 1.

In certain embodiments of the methods described above, a chromatographic enrichment step comprises the sub-steps of: (i) contacting the plasma-derived target protein composition with a chromatographic resin under conditions suitable to bind the plasma-derived target protein; and (ii) eluting the plasma-derived target protein from the chromatographic resin. In one specific embodiment, the impurity does not bind to the chromatographic resin in sub-step (i). In another specific embodiment, the impurity binds to the chromatographic resin in sub-step (i), but is not eluted from the chromatographic resin in sub-step (ii).

In other certain embodiments of the methods described above, a chromatographic enrichment step comprises the sub-steps of: (i) contacting the first enriched plasma-derived target protein composition with a chromatographic resin under conditions suitable to bind at least one impurity; and (ii) separating the resin from the plasma-derived protein composition, wherein the plasma-derived target protein does not bind to the chromatographic resin in sub-step (i).

In certain embodiments of the methods described above, the plasma-derived target protein is selected from an immunoglobulin (Ig), albumin, alpha-1-antitrypsin (A1PI), butyrylcholinesterase, a protein of the complement system (e.g., Factor H), and an inter-alpha-trypsin inhibitor (IαI). In a specific embodiment, the protein of the complement system is selected from the group consisting of Factor H (FH), Factor D, complement protein C3, and C4 binding protein. In a preferred embodiment, the protein composition is a manufacturing intermediate.

In certain embodiments of the methods provided herein, the amount of a particular serine protease or serine protease zymogen is reduced by at least 10%. In another embodiment, the amount of a particular serine protease or serine protease zymogen is reduced by at least 25%. In another embodiment, the amount of a particular serine protease or serine protease zymogen is reduced by at least 50%. In another embodiment, the amount of a particular serine protease or serine protease zymogen is reduced by at least 75%. In another embodiment, the amount of a particular serine protease or serine protease zymogen is reduced by at least 90%. In yet other embodiments, the amount of a particular serine protease or serine protease zymogen is reduced by at least 5%, or by at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or to levels below the detection limit of the test system.

Generally, the amount of finely divided silicon dioxide ($SiO_2$) required for the methods described herein will vary dependent on several factors, including without limitation, the total amount of protein present in the composition, the concentration of serine protease and serine protease zymogen (e.g., FXI, FXIa, FXII, and FXIIa) in the composition, the target protein, and the solution conditions (e.g., pH, conductivity, etc.). For example, $SiO_2$ may be added to a target composition at a concentration between about 0.01 g/g protein and about 10 g/g protein. In another embodiment, $SiO_2$ may be added to a target composition at a concentration between about 1 g/g protein and about 5 g/g protein. In another embodiment, $SiO_2$ may be added to a target composition at a concentration between about 2 g/g protein and about 4 g/g protein. In one embodiment, $SiO_2$ is added at a final concentration of at least 1 g per gram total protein. In another specific embodiment, fumed silica is added at a concentration of at least 2 g per gram total protein. In another specific embodiment, fumed silica is added at a concentration of at least 2.5 g per gram total protein. In another embodiment, $SiO_2$ may be added to a target composition at a concentration between about 0.01 g/g protein and about 5 g/g protein. In another embodiment, $SiO_2$ may be added to a target composition at a concentration between about 0.02 g/g protein and about 4 g/g protein. In one embodiment, $SiO_2$ is added at a final concentration of at least 0.1 g per gram total protein. In another specific embodiment, fumed silica is added at a concentration of at least 0.2 g per gram total protein. In another specific embodiment, fumed silica is added at a concentration of at least 0.25 g per gram total protein. In yet other specific embodiments, finely divided silicon dioxide is added at a concentration of at least 0.01 g/g total protein or at least 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g. 0.6 g, 0.7 g, 0.8 g, 0.9 g, 1.0 g, 1.5 g, 2.0 g, 2.5 g. 3.0 g, 3.5 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, or more g/g total protein.

In certain embodiments in which a target protein is extracted from a suspended plasma precipitate fraction, filter aid, for example Celpure C300 (Celpure) or Hyflo-Supper-Cel (World Minerals), will be added after the silica dioxide treatment, to facilitate depth filtration. Filter aid can be added at a final concentration of from about 0.01 kg/kg precipitate to about 1.0 kg/kg precipitate, or from about 0.02 kg/kg precipitate to about 0.8 kg/kg precipitate, or from about 0.03 kg/kg precipitate to about 0.7 kg/kg precipitate. In other embodiments, filter aid can be added at a final concentration of from about 0.01 kg/kg precipitate to about 0.07 kg/kg precipitate, or from about 0.02 kg/kg precipitate to about 0.06 kg/kg precipitate, or from about 0.03 kg/kg precipitate to about 0.05 kg/kg precipitate. In certain embodiments, the filter aid will be added at a final concentration of about 0.01 kg/kg precipitate, or about 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 kg/kg precipitate.

A. Immunoglobulins

In one embodiment, the present invention provides a method for reducing the amount of a serine protease or a serine protease zymogen in a plasma-derived immunoglobulin (Ig) composition. In one specific embodiment, the method comprises the steps of: (a) contacting the Ig composition with finely divided silicon dioxide ($SiO_2$) under conditions suitable to bind at least one serine protease or serine protease zymogen; and (b) separating the $SiO_2$ from the Ig composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII). In one embodiment, the Ig composition is an IgG composition. In other embodiments, the Ig composition is an IgA, IgM, IgG, or mixed composition thereof.

In one embodiment, the method further comprises the step of performing a first Ig protein enrichment step to form a first enriched Ig composition, prior to contacting the composition with finely divided silicon dioxide ($SiO_2$). In certain embodiments, the first Ig protein enrichment step is selected from a protein precipitation step (e.g., an alcohol fractionation step), an ultrafiltration/diafiltration step, and a chromatographic step. In one embodiment, the Ig composition is an IgG composition. In other embodiments, the Ig composition is an IgA, IgM, IgG, or mixed composition thereof.

In certain embodiments, the methods described above further comprises the step of performing a second Ig protein enrichment step to form a second enriched Ig composition, prior to contacting the composition with finely divided silicon dioxide ($SiO_2$). In certain embodiments, the first Ig protein enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived Ig composition, the method comprises the steps of: (a) performing a first Ig enrichment step to form a first enriched plasma-derived Ig composition; (b) performing a second Ig enrichment step to form a second enriched plasma-derived Ig composition; (c) contacting the second enriched composition with finely divided silicon dioxide ($SiO_2$) under conditions suitable to bind at least one serine protease or serine protease zymogen; and (d) separating the $SiO_2$ from the composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

In certain embodiments, the methods described above further comprises the step of performing an Ig enrichment step after contacting the composition with finely divided silicon dioxide ($SiO_2$). In certain embodiments, the Ig enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived Ig composition the method comprises the steps of: (a) performing a first Ig enrichment step to form a first enriched plasma-derived Ig composition; (b) contacting the first enriched composition with finely divided silicon dioxide ($SiO_2$) under conditions suitable to bind at least one serine protease or serine protease zymogen; (c) separating the $SiO_2$ from the composition to remove the bound serine protease or serine protease zymogen; and (d) performing a second Ig enrichment step to form a second enriched plasma-derived Ig composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

Likewise, in one embodiment, the invention provides a method for reducing the amount of a serine protease or a serine protease zymogen in a plasma-derived Ig composition, the method comprising the steps of: (a) performing a first Ig enrichment step to form a first enriched plasma-derived Ig composition; (b) performing a second Ig enrichment step to form a second enriched plasma-derived Ig composition; (c) contacting the second enriched composition with finely divided silicon dioxide ($SiO_2$) under conditions suitable to bind at least one serine protease or serine protease zymogen; (d) separating the $SiO_2$ from the composition to remove the bound serine protease or serine protease zymogen; and (e) performing a third Ig enrichment step to form a third enriched plasma-derived Ig composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 101 to Var. 1100, found in Table 2, Table 3, Table 4, Table 5, Table 6, Table 7, Table 8. Table 9. Table 10, or Table 11.

In a particular embodiment, the Ig composition is a manufacturing intermediate. For example, in certain embodiments, the Ig composition is an IgG manufacturing intermediate from a Cohn fractionation procedure (J. Am. Chem. Soc., 1946, 68(3): 459-475; J. Am. Chem. Soc. 72:465-474 (1950)), an Oncley fractionation procedure (J. Am. Chem. Soc., 1949, 71(2): 541-550), a Deutsch purification procedure (J. Biol. Chem. 164:109-118), a Hoppe purification procedure (Munch Med Wochenschr 1967 (34): 1749-1752), a Falksveden purification procedure (Swedish Patent No. 348942), a Falksveden and Lundblad purification procedure (Methods of Plasma Protein Fractionation 1980), a Lebing purification procedure (Vox Sang 2003 (84): 193-201), a Tanaka purification procedure (Braz J Med Biol Res 2000 (33)37-30)), a Teschner purification procedure (Vox Sang, 2007 (92):42-55), a Nitschmann fractionation procedure (Helv. Chim. Acta 37:866-873), a Kistler/Nitschmann fractionation procedure (Vox Sang. 7:414-424 (1962)), a Barundern purification procedure (Vox Sang. 7:157-74 (1962)), a Koblet purification procedure (Vox Sang. 13:93-102 (1967)) a purification procedure disclosed in U.S. Pat. No. 5,122,373 or 5,177,194, modified procedures thereof, and similar or equivalent purification procedures known in the art.

In one particular embodiment, the IgG composition is a cryo-poor Cohn pool. In another particular embodiment, the IgG composition is a Cohn Fraction I supernatant or equivalent fraction thereof. In another particular embodiment, the IgG composition is a re-suspended Cohn Fraction III precipitate, or equivalent fraction thereof. In another particular embodiment, the IgG composition is a re-suspended Cohn Fraction II+III precipitate, or equivalent fraction thereof. In another particular embodiment, the IgG composition is a re-suspended Cohn Fraction I+II+III precipitate, or equivalent fraction thereof. In another particular embodiment, the IgG composition is a re-suspended Precipitate G precipitate, or equivalent fraction thereof. In another particular embodiment, the IgG composition is a re-suspended Kistler/Nitschmann Precipitate B precipitate, or equivalent fraction thereof.

In a specific embodiment, the present invention provides a method for reducing the amount of serine protease and/or serine protease zymogen in a re-suspended IgG Fraction II+III precipitate. Advantageously, it has been found that the levels of Factor XI, Factor XII, Factor XIa, and/or Factor XIIa in a re-suspended IgG Fraction II+III precipitate can be greatly reduced by the addition of a pretreatment step prior to filtration/centrifugation. In one embodiment, this pretreatment step comprises addition of finely divided silica dioxide particles (e.g., fumed silica, Aerosil)) followed by a 40 to 80 minute incubation period during which the suspension is constantly mixed. In certain embodiments, the incubation period will be between about 50 minutes and about 70 minutes, or about 20, 25, 30, 35, 40, 45, 50, 55, 60, 65, 70, 75, 80, or more minutes. Generally, the treatment will be performed at between about 0° C. and about 10° C., or between about 2° C. and about 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between about 2° C. and about 10° C.

The effect of the fumed silica treatment is exemplified by the results found in Examples 3, 6, and 7. In these examples, Fraction II+III precipitates are re-suspended and treated with varying amounts of finely divided silicon dioxide. As can be seen in Table 22, Table 27, Table 28, and Table 29, Factor XI and XII serine protease activity and zymogen content can be reduced at least 90% by treating the suspension with $SiO_2$.

In certain embodiments, fumed silica is added at a concentration of between about 20 g/kg II+III paste and about 100 g/kg II+III paste (i.e., for a Modified Fraction II+III precipitate that is extracted at a ratio of 1:15, fumed silica should be added at a concentration from about 20 g/16 kg II+III suspension to about 100 g/16 kg II+III suspension, or at a final concentration of about 0.125% (w/w) to about 0.625% (w/w)). In certain embodiments, the fumed silica may be added at a concentration of about 20 g/kg II+III paste, or about 25, 30, 35, 40, 45, 50, 55, 60, 65, 70, 75, 80, 85, 90, 95, or 100 g/kg II+III paste. In one specific embodiment, fumed silica (e.g., Aerosil 380 or equivalent) is added to the Modified Fraction II+III suspension to a final concentration of about 40 g/16 kg II+III. Mixing takes place at about 2 to 8° C. for at least 50 to 70 minutes.

In certain embodiments, $SiO_2$ is added to a an IgG composition at a concentration between about 0.01 g/g protein and about 10 g/g protein. In another embodiment, $SiO_2$ is added to a an IgG composition at a concentration between about 0.01 g/g protein and about 5 g/g protein. In another embodiment, $SiO_2$ is added to an IgG composition at a concentration between about 0.02 g/g protein and about 4 g/g protein. In one embodiment, $SiO_2$ is added at a final concentration of at least 0.1 g per gram total protein. In another specific embodiment, fumed silica is added at a concentration of at least 0.2 g per gram total protein. In another specific embodiment, fumed silica is added at a concentration of at least 0.25 g per gram total protein. In other specific embodiments, fumed silica is added at a concentration of at least 1 g per gram total protein. In another specific embodiment, fumed silica is added at a concentration of at least 2 g per gram total protein. In another specific embodiment, fumed silica is added at a concentration of at least 2.5 g per gram total protein. In yet other specific embodiments, finely divided silicon dioxide is added at a concentration of at least 0.01 g/g total protein or at least 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.5 g, 2.0 g, 2.5 g, 3.0 g, 3.5 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, or more per gram total protein.

In certain embodiments, filter aid, for example Celpure C300 (Celpure) or Hyflo-Supper-Cel (World Minerals), will be added after the silica dioxide treatment, to facilitate depth filtration. Filter aid can be added at a final concentration of from about 0.01 kg/kg II+III paste to about 1.0 kg/kg II+III paste, or from about 0.02 kg/kg II+III paste to about 0.8 kg/kg II+III paste, or from about 0.03 kg/kg II+III paste to about 0.7 kg/kg II+III paste. In other embodiments, filter aid can be added at a final concentration of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste. In certain embodiments, the filter aid will be added at a final concentration of about 0.01 kg/kg II+III paste, or about 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 kg/kg II+III paste.

In one embodiment, the process improvements are realized by inclusion of a fumed silica treatment prior to filtration or centrifugal clarification of a Fraction II+III suspension. In certain embodiments, the fumed silica treatment will include addition of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste, or about 0.02 kg/kg II+III paste, 0.03 kg/kg II+III paste, 0.04 kg/kg II+III paste, 0.05 kg/kg II+III paste, 0.06 kg/kg II+III paste, 0.07 kg/kg II+III paste, 0.08 kg/kg II+III paste, 0.09 kg/kg II+III paste, or 0.1 kg/kg II+III paste, and the mixture will be incubated for between about 50 minutes and about 70 minutes, or about 30, 35, 40, 45, 50, 55, 60, 65, 70, 75, 80, or more minutes at a temperature between about 2° C. and about 8° C. In another embodiment, the process improvements are realized by inclusion of a fumed silica treatment which reduced the levels of residual fibrinogen, amidolytic activity, and/or prekallikrein activator activity. In a specific embodiment, the process improvements are realized by inclusion of a fumed silica treatment, which reduces the levels of FXI, FXIa, FXII, and FXIIa in the immunoglobulin preparation.

Generally, serine protease and/or serine protease zymogen removal from immunoglobulin compositions can be achieved by treating the immunoglobulin-containing solution with finely divided silicon dioxide ($SiO_2$) under pH and conductivity solution conditions in which the serine protease and/or serine protease zymogen binds to the $SiO_2$. As shown in the examples, suitable conditions include low pH and low conductivity.

Accordingly, in one embodiment, the present invention provides a method for reducing the amount of a serine protease or a serine protease zymogen in a plasma-derived immunoglobulin composition, the method comprising contacting the composition with $SiO_2$ at a pH between about 4.0 and about 7.0 to bind a serine protease or a serine protease zymogen and removing the $SiO_2$ from the composition. In another embodiment, the method comprises contacting the composition with $SiO_2$ at a pH between about 4.0 and about 6.5. In another embodiment, the method comprises contacting the composition with $SiO_2$ at a pH between about 4.0 and about 6.0. In another embodiment, the method comprises contacting the composition with $SiO_2$ at a pH between about 4.0 and about 5.5. In another embodiment, the method comprises contacting the composition with $SiO_2$ at a pH between about 4.0 and about 5.0. In another embodiment, the method comprises contacting the composition with $SiO_2$ at a pH between about 4.5 and about 7.0. In another embodiment, the method comprises contacting the composition with $SiO_2$ at a pH between about 4.5 and about 6.5. In another embodiment, the method comprises contacting the composition with $SiO_2$ at a pH between about 4.5 and about 6.0. In another embodiment, the method comprises contacting the composition with $SiO_2$ at a pH between about 4.5 and about 5.5. In another embodiment, the method comprises contacting the composition with $SiO_2$ at a pH between about 4.5 and about 5.0. In another embodiment, the method comprises contacting the composition with $SiO_2$ at a pH between about 5.0 and about 7.0. In another embodiment, the method comprises contacting the composition with $SiO_2$ at a pH between about 5.0 and about 6.5. In another embodiment, the method comprises contacting the composition with $SiO_2$ at a pH between about 5.0 and about 6.0. In another embodiment, the method comprises contacting the composition with $SiO_2$ at a pH between about 5.0 and about 5.5. In yet another embodiment, the method comprises contacting the composition with $SiO_2$ at a pH between about 4.6 and about 5.6. In another embodiment, the method comprises contacting the composition with $SiO_2$ at a pH between about 4.7 and about 5.5. In another embodiment, the method comprises contacting the composition with $SiO_2$ at a pH between about 4.8 and about 5.4. In another embodiment, the method comprises contacting the composition with $SiO_2$ at a pH between about 4.9 and about 5.3. In another embodiment, the method comprises contacting the composition with $SiO_2$ at a pH between about 5.0 and about 5.2. In another embodiment, the method comprises contacting the composition with $SiO_2$ at a pH of about 5.1. In other embodiments, the method comprises contacting the composition with $SiO_2$ at a pH of about 4.0 or about 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or no more than 7.0. In yet other embodiments, the method comprises contacting the composition with $SiO_2$ at a pH of no more than 4.0 or no more than 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or no more than 7.0.

In one embodiment, the present invention provides a method for reducing the amount of a serine protease or a serine protease zymogen in a plasma-derived immunoglobulin composition, the method comprising contacting the composition with $SiO_2$ at an ionic strength between about 0.1 mS/cm and about 3.0 mS/cm to bind a serine protease or a serine protease zymogen and removing the $SiO_2$ from the composition. In another embodiment, the method comprises contacting the composition with $SiO_2$ at an ionic strength between about 0.5 mS/cm and about 2.0 mS/cm. In another embodiment, the method comprises contacting the composition with $SiO_2$ at an ionic strength between about 1.3 mS/cm and about 1.7 mS/cm. In another embodiment, the method comprises contacting the composition with $SiO_2$ at an ionic strength between about 0.1 mS/cm and about 1.9 mS/cm. In another embodiment, the method comprises contacting the composition with $SiO_2$ at an ionic strength between about 0.1 mS/cm and about 1.8 mS/cm. In another embodiment, the method comprises contacting the composition with $SiO_2$ at an ionic strength between about 0.1 mS/cm and about 1.7 mS/cm. In another embodiment, the method comprises contacting the composition with $SiO_2$ at an ionic strength between about 0.1 mS/cm and about 1.6 mS/cm. In another embodiment, the method comprises contacting the composition with $SiO_2$ at an ionic strength between about 0.1 mS/cm and about 1.5 mS/cm. In another embodiment, the method comprises contacting the composition with $SiO_2$ at an ionic strength between about 0.1 mS/cm and about 1.4 mS/cm. In another embodiment, the method comprises contacting the composition with $SiO_2$ at an ionic strength between about 0.1 mS/cm and about 1.3 mS/cm. In another embodiment, the method comprises contacting the composition with $SiO_2$ at an ionic strength between about 0.1 mS/cm and about 1.2 mS/cm. In another embodiment, the method comprises contacting the composition with $SiO_2$ at an ionic strength between about 0.1 mS/cm and about 1.1 mS/cm. In another embodiment, the method comprises contacting the composition with $SiO_2$ at an ionic strength between about 0.1 mS/cm and about 1.0 mS/cm. In another embodiment, the method comprises contacting the composition with $SiO_2$ at an ionic strength between about 0.1 mS/cm and about 0.9 mS/cm. In another embodiment, the method comprises contacting the composition with $SiO_2$ at an ionic strength between about 0.1 mS/cm and about 0.8 mS/cm. In another embodiment, the method comprises contacting the composition with $SiO_2$ at an ionic strength between about 0.2 mS/cm and about 1.0 mS/cm. In another embodiment, the method comprises contacting the composition with $SiO_2$ at an ionic strength between about 0.3 mS/cm and about 1.0 mS/cm. In another embodiment, the method comprises contacting the composition with $SiO_2$ at an ionic strength between about 0.1 mS/cm and about 0.4 mS/cm. In another embodiment, the method comprises contacting the composition with $SiO_2$ at an ionic strength between about 0.5 mS/cm and about 1.0 mS/cm. In another embodiment, the method comprises contacting the composition with $SiO_2$ at an ionic strength between about 0.6 mS/cm and about 1.0 mS/cm. In another embodiment, the method comprises contacting the composition with $SiO_2$ at an ionic strength between about 0.7 mS/cm and about 0.9 mS/cm. In another embodiment, the method comprises contacting the composition with $SiO_2$ at an ionic strength of about 0.8 mS/cm. In other embodiments, the method comprises contacting the composition with $SiO_2$ at an ionic strength of about 0.1 mS/cm or no more than 0.2 mS/cm, 0.3 mS/cm, 0.4 mS/cm, 0.5 mS/cm, 0.6 mS/cm, 0.7 mS/cm, 0.8 mS/cm, 0.9 mS/cm, 1.0 mS/cm, 1.1 mS/cm, 1.2 mS/cm, 1.3 mS/cm, 1.4 mS/cm, 1.5 mS/cm, 1.6 mS/cm, 1.7 mS/cm, 1.8 mS/cm, 1.9 mS/cm, 2.0 mS/cm, 2.1 mS/cm, 2.2 mS/cm, 2.3 mS/cm, 2.4 mS/cm, 2.5 mS/cm, 2.6 mS/cm, 2.7 mS/cm, 2.8 mS/cm, 2.9 mS/cm, or 3.0 mS/cm. In yet other embodiments, the method comprises contacting the composition with $SiO_2$ at an ionic strength of no more than 0.1 mS/cm or no more than 0.2 mS/cm, 0.3 mS/cm, 0.4 mS/cm, 0.5 mS/cm, 0.6 mS/cm, 0.7 mS/cm, 0.8 mS/cm, 0.9 mS/cm, 1.0 mS/cm, 1.1 mS/cm, 1.2 mS/cm, 1.3 mS/cm, 1.4 mS/cm, 1.5 mS/cm, 1.6 mS/cm, 1.7 mS/cm, 1.8 mS/cm, 1.9 mS/cm, 2.0 mS/cm, 2.1 mS/cm, 2.2 mS/cm, 2.3 mS/cm, 2.4 mS/cm, 2.5 mS/cm, 2.6 mS/cm, 2.7 mS/cm, 2.8 mS/cm, 2.9 mS/cm, or 3.0 mS/cm.

In certain embodiments, the present invention provides a method for reducing the amount of a serine protease or a serine protease zymogen in a plasma-derived immunoglobulin composition, the method comprising contacting the composition with $SiO_2$ at a low pH and low ionic strength to bind a serine protease or a serine protease zymogen and removing the $SiO_2$ from the composition. In a particular embodiment, the method comprises contacting the composition with $SiO_2$ at a pH between about 4.8 and about 5.4 at an ionic strength between about 0.6 mS/cm and about 1.0 mS/cm. In a more particular embodiment, the method comprises contacting the composition with $SiO_2$ at a pH between about 4.9 and about 5.3 at an ionic strength between about 0.7 mS/cm and about 0.9 mS/cm. In a yet more particular embodiment, the method comprises contacting the composition with $SiO_2$ at a pH between about 5.0 and about 5.2 at an ionic strength of about 0.8 mS/cm. In yet other embodiments, the method comprises contacting the composition with $SiO_2$ at a pH and ionic strength according to any one of variations Var. 1222 to 3041, as presented in Table 12, Table 13, Table 14, and Table 15.

TABLE 12

Exemplary embodiments of solution conditions useful for binding serine proteases and/or serine protease zymogens to $SiO_2$.

| | | pH | | | | | | | | |
|---|---|---|---|---|---|---|---|---|---|---|
| | | 4.0-7.0 | 4.5-5.0 | 4.5-5.0 | 4.5-5.0 | 4.5-5.0 | 4.5-5.0 | 4.5-5.0 | 4.5-5.0 | 4.5-5.0 |
| Ionic Strength (mS/cm) | 0.1-2.0 | Var. 1222 | Var. 1638 | Var. 1638 | Var. 1638 | Var. 1638 | Var. 1638 | Var. 1638 | Var. 1638 | Var. 1638 |
| | 0.1-1.9 | Var. 1223 | Var. 1639 | Var. 1639 | Var. 1639 | Var. 1639 | Var. 1639 | Var. 1639 | Var. 1639 | Var. 1639 |
| | 0.1-1.8 | Var. 1224 | Var. 1640 | Var. 1640 | Var. 1640 | Var. 1640 | Var. 1640 | Var. 1640 | Var. 1640 | Var. 1640 |
| | 0.1-1.7 | Var. 1225 | Var. 1641 | Var. 1641 | Var. 1641 | Var. 1641 | Var. 1641 | Var. 1641 | Var. 1641 | Var. 1641 |
| | 0.1-1.6 | Var. 1226 | Var. 1642 | Var. 1642 | Var. 1642 | Var. 1642 | Var. 1642 | Var. 1642 | Var. 1642 | Var. 1642 |
| | 0.1-1.5 | Var. 1227 | Var. 1643 | Var. 1643 | Var. 1643 | Var. 1643 | Var. 1643 | Var. 1643 | Var. 1643 | Var. 1643 |
| | 0.1-1.4 | Var. 1228 | Var. 1644 | Var. 1644 | Var. 1644 | Var. 1644 | Var. 1644 | Var. 1644 | Var. 1644 | Var. 1644 |
| | 0.1-1.3 | Var. 1229 | Var. 1645 | Var. 1645 | Var. 1645 | Var. 1645 | Var. 1645 | Var. 1645 | Var. 1645 | Var. 1645 |
| | 0.1-1.2 | Var. 1230 | Var. 1646 | Var. 1646 | Var. 1646 | Var. 1646 | Var. 1646 | Var. 1646 | Var. 1646 | Var. 1646 |
| | 0.1-1.1 | Var. 1231 | Var. 1647 | Var. 1647 | Var. 1647 | Var. 1647 | Var. 1647 | Var. 1647 | Var. 1647 | Var. 1647 |
| | 0.1-1.0 | Var. 1232 | Var. 1648 | Var. 1648 | Var. 1648 | Var. 1648 | Var. 1648 | Var. 1648 | Var. 1648 | Var. 1648 |
| | 0.1-0.9 | Var. 1233 | Var. 1649 | Var. 1649 | Var. 1649 | Var. 1649 | Var. 1649 | Var. 1649 | Var. 1649 | Var. 1649 |
| | 0.1-0.8 | Var. 1234 | Var. 1650 | Var. 1650 | Var. 1650 | Var. 1650 | Var. 1650 | Var. 1650 | Var. 1650 | Var. 1650 |
| | 0.2-2.0 | Var. 1235 | Var. 1651 | Var. 1651 | Var. 1651 | Var. 1651 | Var. 1651 | Var. 1651 | Var. 1651 | Var. 1651 |
| | 0.2-1.5 | Var. 1236 | Var. 1652 | Var. 1652 | Var. 1652 | Var. 1652 | Var. 1652 | Var. 1652 | Var. 1652 | Var. 1652 |
| | 0.2-1.0 | Var. 1237 | Var. 1653 | Var. 1653 | Var. 1653 | Var. 1653 | Var. 1653 | Var. 1653 | Var. 1653 | Var. 1653 |
| | 0.2-0.9 | Var. 1238 | Var. 1654 | Var. 1654 | Var. 1654 | Var. 1654 | Var. 1654 | Var. 1654 | Var. 1654 | Var. 1654 |
| | 0.2-0.8 | Var. 1239 | Var. 1655 | Var. 1655 | Var. 1655 | Var. 1655 | Var. 1655 | Var. 1655 | Var. 1655 | Var. 1655 |
| | 0.3-1.0 | Var. 1240 | Var. 1656 | Var. 1656 | Var. 1656 | Var. 1656 | Var. 1656 | Var. 1656 | Var. 1656 | Var. 1656 |
| | 0.3-0.9 | Var. 1241 | Var. 1657 | Var. 1657 | Var. 1657 | Var. 1657 | Var. 1657 | Var. 1657 | Var. 1657 | Var. 1657 |
| | 0.3-0.8 | Var. 1242 | Var. 1658 | Var. 1658 | Var. 1658 | Var. 1658 | Var. 1658 | Var. 1658 | Var. 1658 | Var. 1658 |
| | 0.4-1.0 | Var. 1243 | Var. 1659 | Var. 1659 | Var. 1659 | Var. 1659 | Var. 1659 | Var. 1659 | Var. 1659 | Var. 1659 |
| | 0.4-0.9 | Var. 1244 | Var. 1660 | Var. 1660 | Var. 1660 | Var. 1660 | Var. 1660 | Var. 1660 | Var. 1660 | Var. 1660 |
| | 0.4-0.8 | Var. 1245 | Var. 1661 | Var. 1661 | Var. 1661 | Var. 1661 | Var. 1661 | Var. 1661 | Var. 1661 | Var. 1661 |
| | 0.5-1.0 | Var. 1246 | Var. 1662 | Var. 1662 | Var. 1662 | Var. 1662 | Var. 1662 | Var. 1662 | Var. 1662 | Var. 1662 |
| | 0.5-0.9 | Var. 1247 | Var. 1663 | Var. 1663 | Var. 1663 | Var. 1663 | Var. 1663 | Var. 1663 | Var. 1663 | Var. 1663 |
| | 0.5-0.8 | Var. 1248 | Var. 1664 | Var. 1664 | Var. 1664 | Var. 1664 | Var. 1664 | Var. 1664 | Var. 1664 | Var. 1664 |
| | 0.6-1.0 | Var. 1249 | Var. 1665 | Var. 1665 | Var. 1665 | Var. 1665 | Var. 1665 | Var. 1665 | Var. 1665 | Var. 1665 |
| | 0.6-0.9 | Var. 1250 | Var. 1666 | Var. 1666 | Var. 1666 | Var. 1666 | Var. 1666 | Var. 1666 | Var. 1666 | Var. 1666 |
| | 0.6-0.8 | Var. 1251 | Var. 1667 | Var. 1667 | Var. 1667 | Var. 1667 | Var. 1667 | Var. 1667 | Var. 1667 | Var. 1667 |
| | 0.7-1.0 | Var. 1252 | Var. 1668 | Var. 1668 | Var. 1668 | Var. 1668 | Var. 1668 | Var. 1668 | Var. 1668 | Var. 1668 |
| | 0.7-0.9 | Var. 1253 | Var. 1669 | Var. 1669 | Var. 1669 | Var. 1669 | Var. 1669 | Var. 1669 | Var. 1669 | Var. 1669 |
| | 0.1 | Var. 1254 | Var. 1670 | Var. 1670 | Var. 1670 | Var. 1670 | Var. 1670 | Var. 1670 | Var. 1670 | Var. 1670 |
| | 0.2 | Var. 1255 | Var. 1671 | Var. 1671 | Var. 1671 | Var. 1671 | Var. 1671 | Var. 1671 | Var. 1671 | Var. 1671 |
| | 0.3 | Var. 1256 | Var. 1672 | Var. 1672 | Var. 1672 | Var. 1672 | Var. 1672 | Var. 1672 | Var. 1672 | Var. 1672 |
| | 0.4 | Var. 1257 | Var. 1673 | Var. 1673 | Var. 1673 | Var. 1673 | Var. 1673 | Var. 1673 | Var. 1673 | Var. 1673 |
| | 0.5 | Var. 1258 | Var. 1674 | Var. 1674 | Var. 1674 | Var. 1674 | Var. 1674 | Var. 1674 | Var. 1674 | Var. 1674 |
| | 0.6 | Var. 1259 | Var. 1675 | Var. 1675 | Var. 1675 | Var. 1675 | Var. 1675 | Var. 1675 | Var. 1675 | Var. 1675 |
| | 0.7 | Var. 1260 | Var. 1676 | Var. 1676 | Var. 1676 | Var. 1676 | Var. 1676 | Var. 1676 | Var. 1676 | Var. 1676 |
| | 0.8 | Var. 1261 | Var. 1677 | Var. 1677 | Var. 1677 | Var. 1677 | Var. 1677 | Var. 1677 | Var. 1677 | Var. 1677 |
| | 0.9 | Var. 1262 | Var. 1678 | Var. 1678 | Var. 1678 | Var. 1678 | Var. 1678 | Var. 1678 | Var. 1678 | Var. 1678 |
| | 1 | Var. 1263 | Var. 1679 | Var. 1679 | Var. 1679 | Var. 1679 | Var. 1679 | Var. 1679 | Var. 1679 | Var. 1679 |
| | 1.1 | Var. 1264 | Var. 1680 | Var. 1680 | Var. 1680 | Var. 1680 | Var. 1680 | Var. 1680 | Var. 1680 | Var. 1680 |
| | 1.2 | Var. 1265 | Var. 1681 | Var. 1681 | Var. 1681 | Var. 1681 | Var. 1681 | Var. 1681 | Var. 1681 | Var. 1681 |
| | 1.3 | Var. 1266 | Var. 1682 | Var. 1682 | Var. 1682 | Var. 1682 | Var. 1682 | Var. 1682 | Var. 1682 | Var. 1682 |
| | 1.4 | Var. 1267 | Var. 1683 | Var. 1683 | Var. 1683 | Var. 1683 | Var. 1683 | Var. 1683 | Var. 1683 | Var. 1683 |
| | 1.5 | Var. 1268 | Var. 1684 | Var. 1684 | Var. 1684 | Var. 1684 | Var. 1684 | Var. 1684 | Var. 1684 | Var. 1684 |
| | 1.6 | Var. 1269 | Var. 1685 | Var. 1685 | Var. 1685 | Var. 1685 | Var. 1685 | Var. 1685 | Var. 1685 | Var. 1685 |

TABLE 12-continued

Exemplary embodiments of solution conditions useful for binding serine proteases and/or serine protease zymogens to $SiO_2$.

| | | pH | | | | | | | | |
|---|---|---|---|---|---|---|---|---|---|---|
| | | 4.0-7.0 | 4.5-5.0 | 4.5-5.0 | 4.5-5.0 | 4.5-5.0 | 4.5-5.0 | 4.5-5.0 | 4.5-5.0 | 4.5-5.0 |
| | 1.7 | Var. 1270 | Var. 1686 | Var. 1686 | Var. 1686 | Var. 1686 | Var. 1686 | Var. 1686 | Var. 1686 | Var. 1686 |
| | 1.8 | Var. 1271 | Var. 1687 | Var. 1687 | Var. 1687 | Var. 1687 | Var. 1687 | Var. 1687 | Var. 1687 | Var. 1687 |
| | 1.9 | Var. 1272 | Var. 1688 | Var. 1688 | Var. 1688 | Var. 1688 | Var. 1688 | Var. 1688 | Var. 1688 | Var. 1688 |
| | 2 | Var. 1273 | Var. 1689 | Var. 1689 | Var. 1689 | Var. 1689 | Var. 1689 | Var. 1689 | Var. 1689 | Var. 1689 |

TABLE 13

Exemplary embodiments of solution conditions useful for binding serine proteases and/or serine protease zymogens to $SiO_2$.

| | | pH | | | | | | | |
|---|---|---|---|---|---|---|---|---|---|
| | | 5.0-7.0 | 5.0-6.5 | 5.0-6.0 | 5.0-5.5 | 4.6-5.6 | 4.7-5.5 | 4.8-5.4 | 4.9-5.3 | 5.0-5.2 |
| Ionic | 0.1-2.0 | Var. 1690 | Var. 1742 | Var. 1794 | Var. 1846 | Var. 1898 | Var. 1950 | Var. 2002 | Var. 2054 | Var. 2106 |
| Strength | 0.1-1.9 | Var. 1691 | Var. 1743 | Var. 1795 | Var. 1847 | Var. 1899 | Var. 1951 | Var. 2003 | Var. 2055 | Var. 2107 |
| (mS/cm) | 0.1-1.8 | Var. 1692 | Var. 1744 | Var. 1796 | Var. 1848 | Var. 1900 | Var. 1952 | Var. 2004 | Var. 2056 | Var. 2108 |
| | 0.1-1.7 | Var. 1693 | Var. 1745 | Var. 1797 | Var. 1849 | Var. 1901 | Var. 1953 | Var. 2005 | Var. 2057 | Var. 2109 |
| | 0.1-1.6 | Var. 1694 | Var. 1746 | Var. 1798 | Var. 1850 | Var. 1902 | Var. 1954 | Var. 2006 | Var. 2058 | Var. 2110 |
| | 0.1-1.5 | Var. 1695 | Var. 1747 | Var. 1799 | Var. 1851 | Var. 1903 | Var. 1955 | Var. 2007 | Var. 2059 | Var. 2111 |
| | 0.1-1.4 | Var. 1696 | Var. 1748 | Var. 1800 | Var. 1852 | Var. 1904 | Var. 1956 | Var. 2008 | Var. 2060 | Var. 2112 |
| | 0.1-1.3 | Var. 1697 | Var. 1749 | Var. 1801 | Var. 1853 | Var. 1905 | Var. 1957 | Var. 2009 | Var. 2061 | Var. 2113 |
| | 0.1-1.2 | Var. 1698 | Var. 1750 | Var. 1802 | Var. 1854 | Var. 1906 | Var. 1958 | Var. 2010 | Var. 2062 | Var. 2114 |
| | 0.1-1.1 | Var. 1699 | Var. 1751 | Var. 1803 | Var. 1855 | Var. 1907 | Var. 1959 | Var. 2011 | Var. 2063 | Var. 2115 |
| | 0.1-1.0 | Var. 1700 | Var. 1752 | Var. 1804 | Var. 1856 | Var. 1908 | Var. 1960 | Var. 2012 | Var. 2064 | Var. 2116 |
| | 0.1-0.9 | Var. 1701 | Var. 1753 | Var. 1805 | Var. 1857 | Var. 1909 | Var. 1961 | Var. 2013 | Var. 2065 | Var. 2117 |
| | 0.1-0.8 | Var. 1702 | Var. 1754 | Var. 1806 | Var. 1858 | Var. 1910 | Var. 1962 | Var. 2014 | Var. 2066 | Var. 2118 |
| | 0.2-2.0 | Var. 1703 | Var. 1755 | Var. 1807 | Var. 1859 | Var. 1911 | Var. 1963 | Var. 2015 | Var. 2067 | Var. 2119 |
| | 0.2-1.5 | Var. 1704 | Var. 1756 | Var. 1808 | Var. 1860 | Var. 1912 | Var. 1964 | Var. 2016 | Var. 2068 | Var. 2120 |
| | 0.2-1.0 | Var. 1705 | Var. 1757 | Var. 1809 | Var. 1861 | Var. 1913 | Var. 1965 | Var. 2017 | Var. 2069 | Var. 2121 |
| | 0.2-0.9 | Var. 1706 | Var. 1758 | Var. 1810 | Var. 1862 | Var. 1914 | Var. 1966 | Var. 2018 | Var. 2070 | Var. 2122 |
| | 0.2-0.8 | Var. 1707 | Var. 1759 | Var. 1811 | Var. 1863 | Var. 1915 | Var. 1967 | Var. 2019 | Var. 2071 | Var. 2123 |
| | 0.3-1.0 | Var. 1708 | Var. 1760 | Var. 1812 | Var. 1864 | Var. 1916 | Var. 1968 | Var. 2020 | Var. 2072 | Var. 2124 |
| | 0.3-0.9 | Var. 1709 | Var. 1761 | Var. 1813 | Var. 1865 | Var. 1917 | Var. 1969 | Var. 2021 | Var. 2073 | Var. 2125 |
| | 0.3-0.8 | Var. 1710 | Var. 1762 | Var. 1814 | Var. 1866 | Var. 1918 | Var. 1970 | Var. 2022 | Var. 2074 | Var. 2126 |
| | 0.4-1.0 | Var. 1711 | Var. 1763 | Var. 1815 | Var. 1867 | Var. 1919 | Var. 1971 | Var. 2023 | Var. 2075 | Var. 2127 |
| | 0.4-0.9 | Var. 1712 | Var. 1764 | Var. 1816 | Var. 1868 | Var. 1920 | Var. 1972 | Var. 2024 | Var. 2076 | Var. 2128 |
| | 0.4-0.8 | Var. 1713 | Var. 1765 | Var. 1817 | Var. 1869 | Var. 1921 | Var. 1973 | Var. 2025 | Var. 2077 | Var. 2129 |
| | 0.5-1.0 | Var. 1714 | Var. 1766 | Var. 1818 | Var. 1870 | Var. 1922 | Var. 1974 | Var. 2026 | Var. 2078 | Var. 2130 |
| | 0.5-0.9 | Var. 1715 | Var. 1767 | Var. 1819 | Var. 1871 | Var. 1923 | Var. 1975 | Var. 2027 | Var. 2079 | Var. 2131 |
| | 0.5-0.8 | Var. 1716 | Var. 1768 | Var. 1820 | Var. 1872 | Var. 1924 | Var. 1976 | Var. 2028 | Var. 2080 | Var. 2132 |
| | 0.6-1.0 | Var. 1717 | Var. 1769 | Var. 1821 | Var. 1873 | Var. 1925 | Var. 1977 | Var. 2029 | Var. 2081 | Var. 2133 |
| | 0.6-0.9 | Var. 1718 | Var. 1770 | Var. 1822 | Var. 1874 | Var. 1926 | Var. 1978 | Var. 2030 | Var. 2082 | Var. 2134 |
| | 0.6-0.8 | Var. 1719 | Var. 1771 | Var. 1823 | Var. 1875 | Var. 1927 | Var. 1979 | Var. 2031 | Var. 2083 | Var. 2135 |
| | 0.7-1.0 | Var. 1720 | Var. 1772 | Var. 1824 | Var. 1876 | Var. 1928 | Var. 1980 | Var. 2032 | Var. 2084 | Var. 2136 |
| | 0.7-0.9 | Var. 1721 | Var. 1773 | Var. 1825 | Var. 1877 | Var. 1929 | Var. 1981 | Var. 2033 | Var. 2085 | Var. 2137 |
| | 0.1 | Var. 1722 | Var. 1774 | Var. 1826 | Var. 1878 | Var. 1930 | Var. 1982 | Var. 2034 | Var. 2086 | Var. 2138 |
| | 0.2 | Var. 1723 | Var. 1775 | Var. 1827 | Var. 1879 | Var. 1931 | Var. 1983 | Var. 2035 | Var. 2087 | Var. 2139 |
| | 0.3 | Var. 1724 | Var. 1776 | Var. 1828 | Var. 1880 | Var. 1932 | Var. 1984 | Var. 2036 | Var. 2088 | Var. 2140 |
| | 0.4 | Var. 1725 | Var. 1777 | Var. 1829 | Var. 1881 | Var. 1933 | Var. 1985 | Var. 2037 | Var. 2089 | Var. 2141 |
| | 0.5 | Var. 1726 | Var. 1778 | Var. 1830 | Var. 1882 | Var. 1934 | Var. 1986 | Var. 2038 | Var. 2090 | Var. 2142 |
| | 0.6 | Var. 1727 | Var. 1779 | Var. 1831 | Var. 1883 | Var. 1935 | Var. 1987 | Var. 2039 | Var. 2091 | Var. 2143 |
| | 0.7 | Var. 1728 | Var. 1780 | Var. 1832 | Var. 1884 | Var. 1936 | Var. 1988 | Var. 2040 | Var. 2092 | Var. 2144 |
| | 0.8 | Var. 1729 | Var. 1781 | Var. 1833 | Var. 1885 | Var. 1937 | Var. 1989 | Var. 2041 | Var. 2093 | Var. 2145 |
| | 0.9 | Var. 1730 | Var. 1782 | Var. 1834 | Var. 1886 | Var. 1938 | Var. 1990 | Var. 2042 | Var. 2094 | Var. 2146 |
| | 1 | Var. 1731 | Var. 1783 | Var. 1835 | Var. 1887 | Var. 1939 | Var. 1991 | Var. 2043 | Var. 2095 | Var. 2147 |
| | 1.1 | Var. 1732 | Var. 1784 | Var. 1836 | Var. 1888 | Var. 1940 | Var. 1992 | Var. 2044 | Var. 2096 | Var. 2148 |
| | 1.2 | Var. 1733 | Var. 1785 | Var. 1837 | Var. 1889 | Var. 1941 | Var. 1993 | Var. 2045 | Var. 2097 | Var. 2149 |
| | 1.3 | Var. 1734 | Var. 1786 | Var. 1838 | Var. 1890 | Var. 1942 | Var. 1994 | Var. 2046 | Var. 2098 | Var. 2150 |
| | 1.4 | Var. 1735 | Var. 1787 | Var. 1839 | Var. 1891 | Var. 1943 | Var. 1995 | Var. 2047 | Var. 2099 | Var. 2151 |
| | 1.5 | Var. 1736 | Var. 1788 | Var. 1840 | Var. 1892 | Var. 1944 | Var. 1996 | Var. 2048 | Var. 2100 | Var. 2152 |
| | 1.6 | Var. 1737 | Var. 1789 | Var. 1841 | Var. 1893 | Var. 1945 | Var. 1997 | Var. 2049 | Var. 2101 | Var. 2153 |
| | 1.7 | Var. 1738 | Var. 1790 | Var. 1842 | Var. 1894 | Var. 1946 | Var. 1998 | Var. 2050 | Var. 2102 | Var. 2154 |
| | 1.8 | Var. 1739 | Var. 1791 | Var. 1843 | Var. 1895 | Var. 1947 | Var. 1999 | Var. 2051 | Var. 2103 | Var. 2155 |
| | 1.9 | Var. 1740 | Var. 1792 | Var. 1844 | Var. 1896 | Var. 1948 | Var. 2000 | Var. 2052 | Var. 2104 | Var. 2156 |
| | 2 | Var. 1741 | Var. 1793 | Var. 1845 | Var. 1897 | Var. 1949 | Var. 2001 | Var. 2053 | Var. 2105 | Var. 2157 |

TABLE 14

Exemplary embodiments of solution conditions useful for binding serine proteases and/or serine protease zymogens to SiO$_2$.

| | | pH | | | | | | | | |
|---|---|---|---|---|---|---|---|---|---|---|
| | | 5.1 | NMT 4.0 | NMT 4.2 | NMT 4.4 | NMT 4.6 | NMT 4.8 | NMT 5.0 | NMT 5.2 | NMT 5.4 |
| Ionic Strength (mS/cm) | 0.1-2.0 | Var. 2158 | Var. 2210 | Var. 2262 | Var. 2314 | Var. 2366 | Var. 2418 | Var. 2470 | Var. 2522 | Var. 2574 |
| | 0.1-1.9 | Var. 2159 | Var. 2211 | Var. 2263 | Var. 2315 | Var. 2367 | Var. 2419 | Var. 2471 | Var. 2523 | Var. 2575 |
| | 0.1-1.8 | Var. 2160 | Var. 2212 | Var. 2264 | Var. 2316 | Var. 2368 | Var. 2420 | Var. 2472 | Var. 2524 | Var. 2576 |
| | 0.1-1.7 | Var. 2161 | Var. 2213 | Var. 2265 | Var. 2317 | Var. 2369 | Var. 2421 | Var. 2473 | Var. 2525 | Var. 2577 |
| | 0.1-1.6 | Var. 2162 | Var. 2214 | Var. 2266 | Var. 2318 | Var. 2370 | Var. 2422 | Var. 2474 | Var. 2526 | Var. 2578 |
| | 0.1-1.5 | Var. 2163 | Var. 2215 | Var. 2267 | Var. 2319 | Var. 2371 | Var. 2423 | Var. 2475 | Var. 2527 | Var. 2579 |
| | 0.1-1.4 | Var. 2164 | Var. 2216 | Var. 2268 | Var. 2320 | Var. 2372 | Var. 2424 | Var. 2476 | Var. 2528 | Var. 2580 |
| | 0.1-1.3 | Var. 2165 | Var. 2217 | Var. 2269 | Var. 2321 | Var. 2373 | Var. 2425 | Var. 2477 | Var. 2529 | Var. 2581 |
| | 0.1-1.2 | Var. 2166 | Var. 2218 | Var. 2270 | Var. 2322 | Var. 2374 | Var. 2426 | Var. 2478 | Var. 2530 | Var. 2582 |
| | 0.1-1.1 | Var. 2167 | Var. 2219 | Var. 2271 | Var. 2323 | Var. 2375 | Var. 2427 | Var. 2479 | Var. 2531 | Var. 2583 |
| | 0.1-1.0 | Var. 2168 | Var. 2220 | Var. 2272 | Var. 2324 | Var. 2376 | Var. 2428 | Var. 2480 | Var. 2532 | Var. 2584 |
| | 0.1-0.9 | Var. 2169 | Var. 2221 | Var. 2273 | Var. 2325 | Var. 2377 | Var. 2429 | Var. 2481 | Var. 2533 | Var. 2585 |
| | 0.1-0.8 | Var. 2170 | Var. 2222 | Var. 2274 | Var. 2326 | Var. 2378 | Var. 2430 | Var. 2482 | Var. 2534 | Var. 2586 |
| | 0.2-2.0 | Var. 2171 | Var. 2223 | Var. 2275 | Var. 2327 | Var. 2379 | Var. 2431 | Var. 2483 | Var. 2535 | Var. 2587 |
| | 0.2-1.5 | Var. 2172 | Var. 2224 | Var. 2276 | Var. 2328 | Var. 2380 | Var. 2432 | Var. 2484 | Var. 2536 | Var. 2588 |
| | 0.2-1.0 | Var. 2173 | Var. 2225 | Var. 2277 | Var. 2329 | Var. 2381 | Var. 2433 | Var. 2485 | Var. 2537 | Var. 2589 |
| | 0.2-0.9 | Var. 2174 | Var. 2226 | Var. 2278 | Var. 2330 | Var. 2382 | Var. 2434 | Var. 2486 | Var. 2538 | Var. 2590 |
| | 0.2-0.8 | Var. 2175 | Var. 2227 | Var. 2279 | Var. 2331 | Var. 2383 | Var. 2435 | Var. 2487 | Var. 2539 | Var. 2591 |
| | 0.3-1.0 | Var. 2176 | Var. 2228 | Var. 2280 | Var. 2332 | Var. 2384 | Var. 2436 | Var. 2488 | Var. 2540 | Var. 2592 |
| | 0.3-0.9 | Var. 2177 | Var. 2229 | Var. 2281 | Var. 2333 | Var. 2385 | Var. 2437 | Var. 2489 | Var. 2541 | Var. 2593 |
| | 0.3-0.8 | Var. 2178 | Var. 2230 | Var. 2282 | Var. 2334 | Var. 2386 | Var. 2438 | Var. 2490 | Var. 2542 | Var. 2594 |
| | 0.4-1.0 | Var. 2179 | Var. 2231 | Var. 2283 | Var. 2335 | Var. 2387 | Var. 2439 | Var. 2491 | Var. 2543 | Var. 2595 |
| | 0.4-0.9 | Var. 2180 | Var. 2232 | Var. 2284 | Var. 2336 | Var. 2388 | Var. 2440 | Var. 2492 | Var. 2544 | Var. 2596 |
| | 0.4-0.8 | Var. 2181 | Var. 2233 | Var. 2285 | Var. 2337 | Var. 2389 | Var. 2441 | Var. 2493 | Var. 2545 | Var. 2597 |
| | 0.5-1.0 | Var. 2182 | Var. 2234 | Var. 2286 | Var. 2338 | Var. 2390 | Var. 2442 | Var. 2494 | Var. 2546 | Var. 2598 |
| | 0.5-0.9 | Var. 2183 | Var. 2235 | Var. 2287 | Var. 2339 | Var. 2391 | Var. 2443 | Var. 2495 | Var. 2547 | Var. 2599 |
| | 0.5-0.8 | Var. 2184 | Var. 2236 | Var. 2288 | Var. 2340 | Var. 2392 | Var. 2444 | Var. 2496 | Var. 2548 | Var. 2600 |
| | 0.6-1.0 | Var. 2185 | Var. 2237 | Var. 2289 | Var. 2341 | Var. 2393 | Var. 2445 | Var. 2497 | Var. 2549 | Var. 2601 |
| | 0.6-0.9 | Var. 2186 | Var. 2238 | Var. 2290 | Var. 2342 | Var. 2394 | Var. 2446 | Var. 2498 | Var. 2550 | Var. 2602 |
| | 0.6-0.8 | Var. 2187 | Var. 2239 | Var. 2291 | Var. 2343 | Var. 2395 | Var. 2447 | Var. 2499 | Var. 2551 | Var. 2603 |
| | 0.7-1.0 | Var. 2188 | Var. 2240 | Var. 2292 | Var. 2344 | Var. 2396 | Var. 2448 | Var. 2500 | Var. 2552 | Var. 2604 |
| | 0.7-0.9 | Var. 2189 | Var. 2241 | Var. 2293 | Var. 2345 | Var. 2397 | Var. 2449 | Var. 2501 | Var. 2553 | Var. 2605 |
| | 0.1 | Var. 2190 | Var. 2242 | Var. 2294 | Var. 2346 | Var. 2398 | Var. 2450 | Var. 2502 | Var. 2554 | Var. 2606 |
| | 0.2 | Var. 2191 | Var. 2243 | Var. 2295 | Var. 2347 | Var. 2399 | Var. 2451 | Var. 2503 | Var. 2555 | Var. 2607 |
| | 0.3 | Var. 2192 | Var. 2244 | Var. 2296 | Var. 2348 | Var. 2400 | Var. 2452 | Var. 2504 | Var. 2556 | Var. 2608 |
| | 0.4 | Var. 2193 | Var. 2245 | Var. 2297 | Var. 2349 | Var. 2401 | Var. 2453 | Var. 2505 | Var. 2557 | Var. 2609 |
| | 0.5 | Var. 2194 | Var. 2246 | Var. 2298 | Var. 2350 | Var. 2402 | Var. 2454 | Var. 2506 | Var. 2558 | Var. 2610 |
| | 0.6 | Var. 2195 | Var. 2247 | Var. 2299 | Var. 2351 | Var. 2403 | Var. 2455 | Var. 2507 | Var. 2559 | Var. 2611 |
| | 0.7 | Var. 2196 | Var. 2248 | Var. 2300 | Var. 2352 | Var. 2404 | Var. 2456 | Var. 2508 | Var. 2560 | Var. 2612 |
| | 0.8 | Var. 2197 | Var. 2249 | Var. 2301 | Var. 2353 | Var. 2405 | Var. 2457 | Var. 2509 | Var. 2561 | Var. 2613 |
| | 0.9 | Var. 2198 | Var. 2250 | Var. 2302 | Var. 2354 | Var. 2406 | Var. 2458 | Var. 2510 | Var. 2562 | Var. 2614 |
| | 1 | Var. 2199 | Var. 2251 | Var. 2303 | Var. 2355 | Var. 2407 | Var. 2459 | Var. 2511 | Var. 2563 | Var. 2615 |
| | 1.1 | Var. 2200 | Var. 2252 | Var. 2304 | Var. 2356 | Var. 2408 | Var. 2460 | Var. 2512 | Var. 2564 | Var. 2616 |
| | 1.2 | Var. 2201 | Var. 2253 | Var. 2305 | Var. 2357 | Var. 2409 | Var. 2461 | Var. 2513 | Var. 2565 | Var. 2617 |
| | 1.3 | Var. 2202 | Var. 2254 | Var. 2306 | Var. 2358 | Var. 2410 | Var. 2462 | Var. 2514 | Var. 2566 | Var. 2618 |
| | 1.4 | Var. 2203 | Var. 2255 | Var. 2307 | Var. 2359 | Var. 2411 | Var. 2463 | Var. 2515 | Var. 2567 | Var. 2619 |
| | 1.5 | Var. 2204 | Var. 2256 | Var. 2308 | Var. 2360 | Var. 2412 | Var. 2464 | Var. 2516 | Var. 2568 | Var. 2620 |
| | 1.6 | Var. 2205 | Var. 2257 | Var. 2309 | Var. 2361 | Var. 2413 | Var. 2465 | Var. 2517 | Var. 2569 | Var. 2621 |
| | 1.7 | Var. 2206 | Var. 2258 | Var. 2310 | Var. 2362 | Var. 2414 | Var. 2466 | Var. 2518 | Var. 2570 | Var. 2622 |
| | 1.8 | Var. 2207 | Var. 2259 | Var. 2311 | Var. 2363 | Var. 2415 | Var. 2467 | Var. 2519 | Var. 2571 | Var. 2623 |
| | 1.9 | Var. 2208 | Var. 2260 | Var. 2312 | Var. 2364 | Var. 2416 | Var. 2468 | Var. 2520 | Var. 2572 | Var. 2624 |
| | 2 | Var. 2209 | Var. 2261 | Var. 2313 | Var. 2365 | Var. 2417 | Var. 2469 | Var. 2521 | Var. 2573 | Var. 2625 |

NMT = No More Than

TABLE 15

Exemplary embodiments of solution conditions useful for binding serine proteases and/or serine protease zymogens to SiO$_2$.

| | | pH | | | | | | |
|---|---|---|---|---|---|---|---|---|
| | | NMT 5.6 | NMT 5.8 | NMT 6.0 | NMT 6.2 | NMT 6.4 | NMT 6.6 | NMT 6.8 | NMT 7.0 |
| Ionic Strength (mS/cm) | 0.1-2.0 | Var. 2626 | Var. 2678 | Var. 2730 | Var. 2782 | Var. 2834 | Var. 2886 | Var. 2938 | Var. 2990 |
| | 0.1-1.9 | Var. 2627 | Var. 2679 | Var. 2731 | Var. 2783 | Var. 2835 | Var. 2887 | Var. 2939 | Var. 2991 |
| | 0.1-1.8 | Var. 2628 | Var. 2680 | Var. 2732 | Var. 2784 | Var. 2836 | Var. 2888 | Var. 2940 | Var. 2992 |
| | 0.1-1.7 | Var. 2629 | Var. 2681 | Var. 2733 | Var. 2785 | Var. 2837 | Var. 2889 | Var. 2941 | Var. 2993 |
| | 0.1-1.6 | Var. 2630 | Var. 2682 | Var. 2734 | Var. 2786 | Var. 2838 | Var. 2890 | Var. 2942 | Var. 2994 |
| | 0.1-1.5 | Var. 2631 | Var. 2683 | Var. 2735 | Var. 2787 | Var. 2839 | Var. 2891 | Var. 2943 | Var. 2995 |
| | 0.1-1.4 | Var. 2632 | Var. 2684 | Var. 2736 | Var. 2788 | Var. 2840 | Var. 2892 | Var. 2944 | Var. 2996 |

TABLE 15-continued

Exemplary embodiments of solution conditions useful for binding
serine proteases and/or serine protease zymogens to SiO$_2$.

| | pH | | | | | | | |
|---|---|---|---|---|---|---|---|---|
| | NMT 5.6 | NMT 5.8 | NMT 6.0 | NMT 6.2 | NMT 6.4 | NMT 6.6 | NMT 6.8 | NMT 7.0 |
| 0.1-1.3 | Var. 2633 | Var. 2685 | Var. 2737 | Var. 2789 | Var. 2841 | Var. 2893 | Var. 2945 | Var. 2997 |
| 0.1-1.2 | Var. 2634 | Var. 2686 | Var. 2738 | Var. 2790 | Var. 2842 | Var. 2894 | Var. 2946 | Var. 2998 |
| 0.1-1.1 | Var. 2635 | Var. 2687 | Var. 2739 | Var. 2791 | Var. 2843 | Var. 2895 | Var. 2947 | Var. 2999 |
| 0.1-1.0 | Var. 2636 | Var. 2688 | Var. 2740 | Var. 2792 | Var. 2844 | Var. 2896 | Var. 2948 | Var. 3000 |
| 0.1-0.9 | Var. 2637 | Var. 2689 | Var. 2741 | Var. 2793 | Var. 2845 | Var. 2897 | Var. 2949 | Var. 3001 |
| 0.1-0.8 | Var. 2638 | Var. 2690 | Var. 2742 | Var. 2794 | Var. 2846 | Var. 2898 | Var. 2950 | Var. 3002 |
| 0.2-2.0 | Var. 2639 | Var. 2691 | Var. 2743 | Var. 2795 | Var. 2847 | Var. 2899 | Var. 2951 | Var. 3003 |
| 0.2-1.5 | Var. 2640 | Var. 2692 | Var. 2744 | Var. 2796 | Var. 2848 | Var. 2900 | Var. 2952 | Var. 3004 |
| 0.2-1.0 | Var. 2641 | Var. 2693 | Var. 2745 | Var. 2797 | Var. 2849 | Var. 2901 | Var. 2953 | Var. 3005 |
| 0.2-0.9 | Var. 2642 | Var. 2694 | Var. 2746 | Var. 2798 | Var. 2850 | Var. 2902 | Var. 2954 | Var. 3006 |
| 0.2-0.8 | Var. 2643 | Var. 2695 | Var. 2747 | Var. 2799 | Var. 2851 | Var. 2903 | Var. 2955 | Var. 3007 |
| 0.3-1.0 | Var. 2644 | Var. 2696 | Var. 2748 | Var. 2800 | Var. 2852 | Var. 2904 | Var. 2956 | Var. 3008 |
| 0.3-0.9 | Var. 2645 | Var. 2697 | Var. 2749 | Var. 2801 | Var. 2853 | Var. 2905 | Var. 2957 | Var. 3009 |
| 0.3-0.8 | Var. 2646 | Var. 2698 | Var. 2750 | Var. 2802 | Var. 2854 | Var. 2906 | Var. 2958 | Var. 3010 |
| 0.4-1.0 | Var. 2647 | Var. 2699 | Var. 2751 | Var. 2803 | Var. 2855 | Var. 2907 | Var. 2959 | Var. 3011 |
| 0.4-0.9 | Var. 2648 | Var. 2700 | Var. 2752 | Var. 2804 | Var. 2856 | Var. 2908 | Var. 2960 | Var. 3012 |
| 0.4-0.8 | Var. 2649 | Var. 2701 | Var. 2753 | Var. 2805 | Var. 2857 | Var. 2909 | Var. 2961 | Var. 3013 |
| 0.5-1.0 | Var. 2650 | Var. 2702 | Var. 2754 | Var. 2806 | Var. 2858 | Var. 2910 | Var. 2962 | Var. 3014 |
| 0.5-0.9 | Var. 2651 | Var. 2703 | Var. 2755 | Var. 2807 | Var. 2859 | Var. 2911 | Var. 2963 | Var. 3015 |
| 0.5-0.8 | Var. 2652 | Var. 2704 | Var. 2756 | Var. 2808 | Var. 2860 | Var. 2912 | Var. 2964 | Var. 3016 |
| 0.6-1.0 | Var. 2653 | Var. 2705 | Var. 2757 | Var. 2809 | Var. 2861 | Var. 2913 | Var. 2965 | Var. 3017 |
| 0.6-0.9 | Var. 2654 | Var. 2706 | Var. 2758 | Var. 2810 | Var. 2862 | Var. 2914 | Var. 2966 | Var. 3018 |
| 0.6-0.8 | Var. 2655 | Var. 2707 | Var. 2759 | Var. 2811 | Var. 2863 | Var. 2915 | Var. 2967 | Var. 3019 |
| 0.7-1.0 | Var. 2656 | Var. 2708 | Var. 2760 | Var. 2812 | Var. 2864 | Var. 2916 | Var. 2968 | Var. 3020 |
| 0.7-0.9 | Var. 2657 | Var. 2709 | Var. 2761 | Var. 2813 | Var. 2865 | Var. 2917 | Var. 2969 | Var. 3021 |
| 0.1 | Var. 2658 | Var. 2710 | Var. 2762 | Var. 2814 | Var. 2866 | Var. 2918 | Var. 2970 | Var. 3022 |
| 0.2 | Var. 2659 | Var. 2711 | Var. 2763 | Var. 2815 | Var. 2867 | Var. 2919 | Var. 2971 | Var. 3023 |
| 0.3 | Var. 2660 | Var. 2712 | Var. 2764 | Var. 2816 | Var. 2868 | Var. 2920 | Var. 2972 | Var. 3024 |
| 0.4 | Var. 2661 | Var. 2713 | Var. 2765 | Var. 2817 | Var. 2869 | Var. 2921 | Var. 2973 | Var. 3025 |
| 0.5 | Var. 2662 | Var. 2714 | Var. 2766 | Var. 2818 | Var. 2870 | Var. 2922 | Var. 2974 | Var. 3026 |
| 0.6 | Var. 2663 | Var. 2715 | Var. 2767 | Var. 2819 | Var. 2871 | Var. 2923 | Var. 2975 | Var. 3027 |
| 0.7 | Var. 2664 | Var. 2716 | Var. 2768 | Var. 2820 | Var. 2872 | Var. 2924 | Var. 2976 | Var. 3028 |
| 0.8 | Var. 2665 | Var. 2717 | Var. 2769 | Var. 2821 | Var. 2873 | Var. 2925 | Var. 2977 | Var. 3029 |
| 0.9 | Var. 2666 | Var. 2718 | Var. 2770 | Var. 2822 | Var. 2874 | Var. 2926 | Var. 2978 | Var. 3030 |
| 1 | Var. 2667 | Var. 2719 | Var. 2771 | Var. 2823 | Var. 2875 | Var. 2927 | Var. 2979 | Var. 3031 |
| 1.1 | Var. 2668 | Var. 2720 | Var. 2772 | Var. 2824 | Var. 2876 | Var. 2928 | Var. 2980 | Var. 3032 |
| 1.2 | Var. 2669 | Var. 2721 | Var. 2773 | Var. 2825 | Var. 2877 | Var. 2929 | Var. 2981 | Var. 3033 |
| 1.3 | Var. 2670 | Var. 2722 | Var. 2774 | Var. 2826 | Var. 2878 | Var. 2930 | Var. 2982 | Var. 3034 |
| 1.4 | Var. 2671 | Var. 2723 | Var. 2775 | Var. 2827 | Var. 2879 | Var. 2931 | Var. 2983 | Var. 3035 |
| 1.5 | Var. 2672 | Var. 2724 | Var. 2776 | Var. 2828 | Var. 2880 | Var. 2932 | Var. 2984 | Var. 3036 |
| 1.6 | Var. 2673 | Var. 2725 | Var. 2777 | Var. 2829 | Var. 2881 | Var. 2933 | Var. 2985 | Var. 3037 |
| 1.7 | Var. 2674 | Var. 2726 | Var. 2778 | Var. 2830 | Var. 2882 | Var. 2934 | Var. 2986 | Var. 3038 |
| 1.8 | Var. 2675 | Var. 2727 | Var. 2779 | Var. 2831 | Var. 2883 | Var. 2935 | Var. 2987 | Var. 3039 |
| 1.9 | Var. 2676 | Var. 2728 | Var. 2780 | Var. 2832 | Var. 2884 | Var. 2936 | Var. 2988 | Var. 3040 |
| 2 | Var. 2677 | Var. 2729 | Var. 2781 | Var. 2833 | Var. 2885 | Var. 2937 | Var. 2989 | Var. 3041 |

NMT = No More Than

A. Modified Alcohol Precipitation/Ion Exchange Chromatography Fractionation Methods In one aspect, the present invention provides improved methods for the manufacture of IgG compositions suitable for use in IVIG therapy. Generally, these methods provide IgG preparations having higher yields and comparable if not higher purity than current methods employed for the production of commercial IVIG products.

In one specific aspect, the present invention provides a method for preparing a composition of concentrated IgG from plasma, e.g., 10% IVIG, the method comprising performing at least one alcohol precipitation step and at least one ion exchange chromatography step. In particular, several steps in the improved upstream process are different from prior processes, e.g., the use of 25% ethanol at lower temperatures, ethanol addition by spraying, pH adjustment by spraying, and the use of finely divided silica particles.

In a certain embodiment, the method comprises the steps of (a) precipitating a cryo-poor plasmid fraction, in a first precipitation step, with between about 6% and about 10% alcohol at a pH of between about 6.7 and about 7.3 to obtain a supernatant enriched in IgG, (b) precipitating IgG from the supernatant with between about 20% and about 30% alcohol at a lower temperature and at a pH of between about 6.7 and about 7.3 to form a first precipitate, (c) re-suspending the first precipitate formed in step (b) to form a suspension, (d) treating the suspension formed in step (c) with a detergent, (e) precipitating IgG from the suspension with between about 20% and about 30% alcohol at a pH of between about 6.7 and about 7.3 to form a second precipitate, (f) re-suspending the second precipitate formed in step (e) to form a suspension, (g) treating the suspension formed in step (f) with a solvent and/or detergent, and (h) performing at least one ion exchange chromatography fractionation thereby preparing a composition of concentrated IgG. In one embodiment, the method further comprises treating the suspension formed in step (c) with finely divided silica dioxide ($SiO_2$) and filtering the solution prior to step (d).

In one embodiment, a method for preparing a concentrated IgG composition from plasma is provided, the method comprising the steps of (a) adjusting the pH of a cryo-poor plasma fraction to about 7.0, (b) adjusting the ethanol concentration of the cryo-poor plasma fraction of step (a) to at or about 25% (v/v) at a temperature between about −5° C. and about −9° C., thereby forming a mixture, wherein the ethanol concentration may be adjusted by spraying, (c) separating liquid and precipitate from the mixture of step (b), (d) re-suspending the precipitate of step (c) with a buffer containing phosphate and acetate, wherein the pH of the buffer is adjusted with between about 400 and about 700 ml of glacial acetic acid per 1000 L of buffer, thereby forming a suspension, (e) mixing finely divided silicon dioxide (SiO2) with the suspension from step (d) for at least about 30 minutes, (f) filtering the suspension with a filter press, thereby forming a filtrate, (g) washing the filter press with at least 3 filter press dead volumes of a buffer containing phosphate and acetate, wherein the pH of the buffer is adjusted with about 150 ml of glacial acetic acid per 1000 L of buffer, thereby forming a wash solution, (h) combining the filtrate of step (f) with the wash solution of step (g), thereby forming a solution, and treating the solution with a detergent, (i) adjusting the pH of the solution of step (h) to about 7.0 and adding ethanol to a final concentration of at or about 25%, thereby forming a precipitate, wherein the ethanol concentration and/or pH may be adjusted by spraying (j) separating liquid and precipitate from the mixture of step (i), (k) dissolving the precipitate in an aqueous solution comprising a solvent or detergent and maintaining the solution for at least 60 minutes, (l) passing the solution after step (k) through a cation exchange chromatography column and eluting proteins absorbed on the column in an eluate, (m) passing the eluate from step (l) through an anion exchange chromatography column to generate an effluent (i.e., flow-through), (n) passing the effluent from step (m) through a nanofilter to generate a nanofiltrate, (o) passing the nanofiltrate from step (n) through an ultrafiltration membrane to generate an ultrafiltrate, and (p) diafiltrating the ultrafiltrate from step (o) against a diafiltration buffer to generate a diafiltrate having a protein concentration between about 8% (w/v) and about 22% (w/v), thereby obtaining a composition of concentrated IgG. In one embodiment, the temperature of step (b) is at or about −7° C. In one specific embodiment, the suspension buffer in step (d) is adjusted with about 600 mL glacial acetic acid.

In certain embodiments, the diafiltrate will have a protein concentration between about 8% and about 12%, for example, about 8%, or about 9%, 10%, 11%, or 12%. In a preferred embodiment, the diafiltrate will have a protein concentration of at or about 10%. In another preferred embodiment, the diafiltrate will have a protein concentration of at or about 1%. In yet another preferred embodiment, the diafiltrate will have a protein concentration of at or about 12%. In other embodiments, the diafiltrate will have a protein concentration between about 13% and about 17%, for example, about 13%, or about 14%, 15%, 16%, or 17%. In yet other embodiments, the diafiltrate will have a protein concentration between about 18% and about 22%, for example, about 18%, or about 19%, 20%, 21%, or 22%. In a preferred embodiment, the diafiltrate will have a protein concentration of at or about 20%. In another preferred embodiment, the diafiltrate will have a protein concentration of at or about 21%. In yet another preferred embodiment, the diafiltrate will have a protein concentration of at or about 22%.

In certain embodiments of the present invention, the methods provided herein may comprise improvements in two or more of the fractionation process steps described above. For example, embodiments may include improvements in the first precipitation step, the Modified Fraction II+III precipitation step, the Modified Fraction II+III dissolution step, and/or the Modified Fraction II+III suspension filtration step.

In one embodiment, the improvement made in the first precipitation step is the addition of alcohol by spraying. In another embodiment, the improvement made in the first precipitation step is the addition of a pH modifying agent by spraying. In yet embodiment, the improvement made in the first precipitation step is the adjustment of the pH of the solution after addition of the alcohol. In a related embodiment, the improvement made in the first precipitation step is the maintenance of the pH during the addition of the alcohol. In another related embodiment, the improvement made in the first precipitation step is the maintenance of the pH during the precipitation incubation time by continuously adjusting the pH of the solution. In certain embodiments, the first precipitation step may be improved by implementing more than one of these improvements. Further improvements that may be realized in this step will be evident from the section provided below discussing the first precipitation step—Modified Fractionation I. By implementing one or more of the improvements described above, a reduced amount of IgG is lost in the precipitate fraction of the first precipitation step and/or a reduced fraction of IgG is irreversibly denatured during the precipitation step.

In one embodiment, the improvement made in the Modified Fraction II+III precipitation step is the addition of alcohol by spraying. In another embodiment, the improvement made in the Modified Fraction II+III precipitation step is the addition of a pH modifying agent by spraying. In yet embodiment, the improvement made in the Modified Fraction II+III precipitation step is the adjustment of the pH of the solution after addition of the alcohol. In a related embodiment, the improvement made in the Modified Fraction II+III precipitation step is the maintenance of the pH during the addition of the alcohol. In another related embodiment, the improvement made in the Modified Fraction II+III precipitation step is the maintenance of the pH during the precipitation incubation time by continuously adjusting the pH of the solution. In another aspect, the Modified Fraction II+III precipitation step is improved by increasing the concentration of alcohol to at or about 25%. In yet another embodiment, the Modified Fraction II+III precipitation step is improved by lowering the incubation temperature to between about −7° C. and −9° C. In certain embodiments, the Modified Fraction II+III precipitation step may be improved by implementing more than one of these improvements. Further improvements that may be realized in this step will be evident from the section provided below discussing the second precipitation step—Modified Fractionation II+III. By implementing one or more of the improvements described above, a reduced amount of IgG is lost in the supernatant fraction of the Modified Fraction II+III precipitation step and/or a reduced fraction of IgG is irreversibly denatured during the precipitation step.

In one embodiment, the improvement made in the Modified Fraction II+III dissolution step is achieved by increasing the glacial acetic acid content of the dissolution buffer to about 0.06%. In another embodiment, the improvement made in the Modified Fraction II+III dissolution step is achieved by maintaining the pH of the solution during the dissolution incubation time by continuously adjusting the pH of the solution. In another embodiment, the improvement made in the Modified Fraction II+III dissolution step is achieved by mixing finely divided silicon dioxide ($SiO_2$)

with the Fraction II+III suspension prior to filtration. In certain embodiments, the Modified Fraction II+III dissolution step may be improved by implementing more than one of these improvements. Further improvements that may be realized in this step will be evident from the section provided below discussing the Modified Fraction II+III dissolution step—Extraction of the Modified Fraction II+III Precipitate. By implementing one or more of the improvements described above, an increased amount of IgG is recovered in the Fraction II+III suspension and/or the amount of impurities is reduced in the Fraction II+III suspension.

An exemplary improvement made in the Modified Fraction II+III suspension filtration step is realized by post-washing the filter with at least about 3.6 dead volumes of dissolution buffer containing at or about 150 mL glacial acetic acid per 1000 L. Further improvements that may be realized in this step will be evident from the section provided below discussing the Modified Fraction II+III suspension filtration step—Pretreatment and Filtration of the Modified Fraction II+III Suspension. By implementing one or more of the improvements described above, a reduced amount of IgG is lost during the Modified Fraction II+III suspension filtration step.

In one embodiment, the method may comprise an improvement in the first precipitation step and the Modified Fraction II+III precipitation step.

In another embodiment, the method may comprise an improvement in the first precipitation step and the Modified Fraction II+III dissolution step.

In another embodiment, the method may comprise an improvement in the first precipitation step and the Modified Fraction II+III suspension filtration step.

In another embodiment, the method may comprise an improvement in the Modified Fraction II+III precipitation step and the Modified Fraction II+III dissolution step.

In another embodiment, the method may comprise an improvement in the Modified Fraction II+III precipitation step and the Modified Fraction II+III suspension filtration step.

In another embodiment, the method may comprise an improvement in the Modified Fraction II+III dissolution step and the Modified Fraction II+III suspension filtration step.

In another embodiment, the method may comprise an improvement in the first precipitation step, the Modified Fraction II+III precipitation step, and the Modified Fraction II+III dissolution step.

In another embodiment, the method may comprise an improvement in the first precipitation step, the Modified Fraction II+III precipitation step, and the Modified Fraction II+III suspension filtration step.

In another embodiment, the method may comprise an improvement in the first precipitation step, the Modified Fraction II+III dissolution step, and the Modified Fraction 1+III suspension filtration step.

In another embodiment, the method may comprise an improvement in the Modified Fraction II+III precipitation step, the Modified Fraction II+III dissolution step, and the Modified Fraction II+III suspension filtration step.

In another embodiment, the method may comprise an improvement in all of the first precipitation step, the Modified Fraction II+III precipitation step, the Modified Fraction II+III dissolution step, and the Modified Fraction II+III suspension filtration step.

In certain embodiments, one process improvement in the IgG purification methods provided herein comprises the spray addition of one or more solutions that would otherwise be introduced into a plasma fraction by fluent addition. For example, in certain embodiments the process improvement comprises the addition of alcohol (e.g., ethanol) into a plasma fraction for the purposes of precipitation of one or more protein species by spraying. In other embodiments, solutions that may be added to a plasma fraction by spraying include, without limitation, a pH modifying solution, a solvent solution, a detergent solution, a dilution buffer, a conductivity modifying solution, and the like. In a preferred embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, another process improvement, which may be combined with any other process improvement, comprises the adjustment of the pH of a plasma fraction being precipitated after and/or concomitant with the addition of the precipitating agent (e.g., alcohol or polyethylene glycol). In some embodiments, a process improvement is provided in which the pH of a plasma fraction being actively precipitated is maintained throughout the entire precipitation incubation or hold step by continuous monitoring and adjustment of the pH. In preferred embodiments the adjustment of the pH is performed by the spray addition of a pH modifying solution.

In other embodiments, another process improvement, which may be combined with any other process improvement, comprises the use of a finely divided silica treatment step to remove impurities.

1. Preparation of Cryo-Poor Plasma

The starting material used for the preparation of concentrated IgG compositions generally consists of either recovered plasma (i.e., plasma that has been separated from whole blood ex vivo) or source plasma (i.e., plasma collected via plasmapheresis). The purification process typically starts with thawing previously frozen pooled plasma, which has already been assayed for safety and quality considerations. Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step can be performed by filtration rather than centrifugation. The liquid supernatant (also referred to as "cryo-poor plasma," after cold-insoluble proteins removed by centrifugation from fresh thawed plasma) is then processed in the next step. Various additional steps can be taken at this juncture for the isolation of factor eight inhibitor bypass activity (FEIBA), Factor IX-complex, Factor VII-concentrate, or Antithrombin III-complex.

2. First Precipitation Event—Modified Fractionation I

In this step, cryo-poor plasma is typically cooled to about 0+° C. and the pH is adjusted to between about 7.0 and about 7.5, preferably between about 7.1 and about 7.3, most preferably about 7.2. In one embodiment, the pH of the cryo-poor plasma is adjusted to a pH of at or about 7.2. Pre-cooled ethanol is then added while the plasma is stirred to a target concentration of ethanol at or about 8% v/v. At the same time the temperature is further lowered to between about −4 and about 0° C. In a preferred embodiment, the temperature is lowered to at or about −2° C., to precipitate contaminants such as $\alpha_2$-macroglobulin, $\beta_{1A}$- and $\beta_{1C}$- globulin, fibrinogen, and Factor VIII. Typically, the precipitation event will include a hold time of at least about 1 hour, although shorter or longer hold times may also be employed. Subsequently, the supernatant (Supernatant I), ideally containing the entirety of the IgG content present in the cryo-poor plasma, is then collected by centrifugation, filtration, or another suitable method.

As compared to conventional methods employed as a first fractionation step for cryo-poor plasma (Cohn et al., supra; Oncley et al., supra), the present invention provides, in several embodiments, methods that result in improved IgG yields in the Supernatant I fraction. In one embodiment, the improved IgG yield is achieved by adding the alcohol by spraying. In another embodiment, the improved IgG yield is achieved by adding a pH modifying agent by spraying. In yet another embodiment, the improved IgG yield is achieved by adjusting the pH of the solution after addition of the alcohol. In a related embodiment, the improved IgG yield is achieved by adjusting the pH of the solution during the addition of the alcohol.

In one specific aspect, the improvement relates to a method in which a reduced amount of IgG is lost in the precipitate fraction of the first precipitation step. For example, in certain embodiments, a reduced amount of IgG is lost in the precipitate fraction of the first precipitation step as compared to the amount of IgG lost in the first precipitation step of the Cohn method 6 protocol.

In certain embodiments, the process improvement is realized by adjusting the pH of the solution to between about 7.0 and about 7.5 after the addition of the precipitating alcohol. In other embodiments, the pH of the solution is adjusted to between about 7.1 and about 7.3 after addition of the precipitating alcohol. In yet other embodiments, the pH of the solution is adjusted to about 7.0 or about 7.1, 7.2, 7.3, 7.4, or 7.5 after addition of the precipitating alcohol. In a particular embodiment, the pH of the solution is adjusted to about 7.2 after addition of the precipitating alcohol. As such, in certain embodiments, a reduced amount of IgG is lost in the precipitate fraction of the first precipitation step as compared to an analogous precipitation step in which the pH of the solution is adjusted prior to but not after addition of the precipitating alcohol. In one embodiment, the pH is maintained at the desired pH during the precipitation hold or incubation time by continuously adjusting the pH of the solution. In one embodiment, the alcohol is ethanol.

In other certain embodiments, the process improvement is realized by adding the precipitating alcohol and/or the solution used to adjust the pH by spraying, rather than by fluent addition. As such, in certain embodiments, a reduced amount of IgG is lost in the precipitate fraction of the first precipitation step as compared to an analogous precipitation step in which the alcohol and/or solution used to adjust the pH is introduced by fluent addition. In one embodiment, the alcohol is ethanol.

In yet other certain embodiments, the improvement is realized by adjusting the pH of the solution to between about 7.0 and about 7.5. In a preferred embodiment, the pH of the solution is adjusted to between about 7.1 and about 7.3. In other embodiments, the pH of the solution is adjusted to at or about 7.0, 7.1, 7.2, 7.3, 7.4, or 7.5 after the addition of the precipitating alcohol and by adding the precipitating alcohol and/or the solution used to adjust the pH by spraying, rather than by fluent addition. In a particular embodiment, the pH of the solution is adjusted to at or about 7.2 after addition of the precipitating alcohol and by adding the precipitating alcohol and/or the solution used to adjust the pH by spraying, rather than by fluent addition. In one embodiment, the alcohol is ethanol.

3. Second Precipitation Event—Modified Fractionation II+III

To further enrich the IgG content and purity of the fractionation, Supernatant I is subjected to a second precipitation step, which is a modified Cohn-Oncley Fraction II+III fractionation. Generally, the pH of the solution is adjusted to a pH of between about 6.6 and about 6.8. In a preferred embodiment, the pH of the solution is adjusted to at or about 6.7. Alcohol, preferably ethanol, is then added to the solution while being stirred to a final concentration of between about 20% and about 25% (v/v) to precipitate the IgG in the fraction. In a preferred embodiment, alcohol is added to a final concentration of at or about 25% (v/v) to precipitate the IgG in the fraction. Generally, contaminants such as $\alpha_1$-lipoprotein, $\alpha_1$-antitrypsin, Gc-globulins, $\alpha_{1x}$-glycoprotin, haptoglobulin, ceruloplasmin, transferrin, hemopexin, a fraction of the Christmas factor, thyroxin binding globulin, cholinesterase, hypertensinogen, and albumin will not be precipitated by these conditions.

Prior to or concomitant with alcohol addition, the solution is further cooled to between about −7° C. and about −9° C. In a preferred embodiment, the solution is cooled to a temperature at or about −7° C. After completion of the alcohol addition, the pH of the solution is immediately adjusted to between about 6.8 and about 7.0. In a preferred embodiment, the pH of the solution is adjusted to at or about 6.9. Typically, the precipitation event will include a hold time of at least about 10 hours, although shorter or longer hold times may also be employed. Subsequently, the precipitate (Modified Fraction II+III), which ideally contains at least about 85%, preferably at least about 90%, more preferably at least about 95%, of the IgG content present in the cryo-poor plasma, is separated from the supernatant by centrifugation, filtration, or another suitable method and collected. As compared to conventional methods employed as a second fractionation step for cryo-poor plasma (Cohn et al., supra; Oncley et al., supra), the present invention provides, in several embodiments, methods that result in improved IgG yields in the Modified Fraction II+III precipitate. In a related embodiment, the present invention provides methods that result in a reduced loss of IgG in the Modified II+III supernatant.

As compared to conventional methods employed as a second fractionation step for cryo-poor plasma (Cohn et al., supra; Oncley et al., supra), the present invention provides, in several embodiments, methods that result in improved IgG yields in the Modified Fraction II+III precipitate. In one embodiment, the improvement is realized by the addition of alcohol by spraying. In another embodiment, the improvement is realized by the addition of a pH modifying agent by spraying. In another embodiment, the improvement is realized by adjusting the pH of the solution after addition of the alcohol. In a related embodiment, the improvement is realized by adjusting the pH of the solution during addition of the alcohol. In another embodiment, the improvement is realized by increasing the concentration of alcohol (e.g., ethanol) to about 25% (v/v). In another embodiment, the improvement is realized by lowering the temperature of the precipitation step to between about −7° C. and −9° C. In a preferred embodiment, the improvement is realized by increasing the concentration of alcohol (e.g., ethanol) to about 25% (v/v) and lowering the temperature to between about −7° C. and −9° C. In comparison, both Cohn et al. and Oncley et al. perform precipitation at −5° C. and Oncley et al. use 20% alcohol, in order to reduce the level of contaminants in the precipitate. Advantageously, the methods provided herein allow for maximal IgG yield without high levels of contamination in the final product.

It has been discovered that when the pH of the solution is adjusted to a pH of about 6.9 prior to addition of the precipitating alcohol, the pH of the solution shift from 6.9 to between about 7.4 and about 7.7, due in part to protein precipitation. As the pH of the solution shifts away from 6.9, precipitation of IgG becomes less favorable and the precipitation of certain contaminants becomes more favorable. Advantageously, the inventors have found that by adjusting the pH of the solution after addition of the precipitating alcohol, that a higher percentage of IgG is recovered in the Fraction II+III precipitate.

Accordingly, in one aspect, the improvement relates to a method in which a reduced amount of IgG is lost in the supernatant fraction of the modified Fraction II+III precipitation step. In other words, an increased percentage of the starting IgG is present in the Fraction II+III precipitate. In certain embodiments, the process improvement is realized by adjusting the pH of the solution to between about 6.7 and about 7.1 immediately after or during the addition of the precipitating alcohol. In another embodiment, the process improvement is realized by maintaining the pH of the solution to between about 6.7 and about 7.1 continuously during the precipitation incubation period. In other embodiments, the pH of the solution is adjusted to between about 6.8 and about 7.0 immediately after or during the addition of the precipitating alcohol, or to a pH of about 6.7, 6.8, 6.9, 7.0, or 7.1 immediately after or during the addition of the precipitating alcohol. In a particular embodiment, the pH of the solution is adjusted to about 6.9 immediately after or during the addition of the precipitating alcohol. In certain embodiments, the pH of the solution is maintained at between about 6.8 to about 7.0 continuously during the precipitation incubation period, or at a pH of about 6.9 continuously during the precipitation incubation period. As such, in certain embodiments, a reduced amount of IgG is lost in the supernatant fraction of the second precipitation step as compared to an analogous precipitation step in which the pH of the solution is adjusted prior to but not after addition of the precipitating alcohol or to an analogous precipitation step in which the pH of the solution is not maintained during the entirety of the precipitation incubation period. In one embodiment, the pH is maintained at the desired pH during the precipitation hold or incubation time by continuously adjusting the pH of the solution. In one embodiment, the alcohol is ethanol.

In another embodiment, the process improvement is realized by adding the precipitating alcohol and/or the solution used to adjust the pH by spraying, rather than by fluent addition. As such, in certain embodiments, a reduced amount of IgG is lost in the supernatant fraction of the second precipitation step as compared to an analogous precipitation step in which the alcohol and/or solution used to adjust the pH is introduced by fluent addition. In one embodiment, the alcohol is ethanol.

In another embodiment, the process improvement is realized by performing the precipitation step at a temperature between about −7° C. and about −9° C. In one embodiment, the precipitation step is performed at a temperature of at or about −7° C. In another embodiment, the precipitation step is performed at a temperature of at or about −8° C. In another embodiment, the precipitation step is performed at a temperature of at or about −9° C. In certain embodiments, the alcohol concentration of the precipitation step is between about 23% and about 27%. In a preferred embodiment, the alcohol concentration is between about 24% and about 26%. In another preferred embodiment, the alcohol concentration is at or about 25%. In other embodiments, the alcohol concentration may be at or about 23%, 24%, 25%, 26%, or 27%. In a particular embodiment, the second precipitation step is performed at a temperature of at or about −7° C. with an alcohol concentration of at or about 25%. In one embodiment, the alcohol is ethanol.

The effect of increasing the alcohol concentration of the second precipitation from 20%, as used in Oncley et al., supra, to 25% and lowering the temperature of the incubation from −5° C., as used in the Cohn and Oncley methods, to at or about −7° C. is a 5% to 6% increase in the IgG content of the modified Fraction II+III precipitate.

In another embodiment, the process improvement is realized by adjusting the pH of the solution to between about 6.7 and about 7.1, preferably at or about 6.9, immediately after or during the addition of the precipitating alcohol, maintaining the pH of the solution at a pH of between about 6.7 and about 7.1, preferably at or about 6.9, by continuously adjusting the pH during the precipitation incubation period, and by adding the precipitating alcohol and/or the solution used to adjust the pH by spraying, rather than by fluent addition. In another particular embodiment, the process improvement is realized by performing the precipitation step at a temperature between about −7° C. and about −9° C., preferably at or about −7° C. and by precipitating the IgG with an alcohol concentration of between about 23% and about 27%, preferably at or about 25%. In yet another particular embodiment, the process improvement is realized by incorporating all of the Modified Fraction II+III improvements provided above. In a preferred embodiment, the process improvement is realized by precipitating IgG at a temperature of at or about −7° C. with at or about 25% ethanol added by spraying and then adjusting the pH of the solution to at or about 6.9 after addition of the precipitating alcohol. In yet another preferred embodiment, the pH of the solution is maintained at or about 6.9 for the entirety of the precipitation incubation or hold time.

4. Extraction of the Modified Fraction II+III Precipitate

In order to solubilize the IgG content of the modified Fraction II+III precipitate, a cold extraction buffer is used to re-suspend the Fractionation II+III precipitate at a typical ratio of 1 part precipitate to 15 parts of extraction buffer. Other suitable re-suspension ratios may be used, for example from about 1:8 to about 1:30, or from about 1:10 to about 1:20, or from about 1:12 to about 1:18, or from about 1:13 to about 1:17, or from about 1:14 to about 1:16. In certain embodiments, the re-suspension ratio may be about 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or higher.

Suitable solutions for the extraction of the modified II+III precipitate will generally have a pH between about 4.0 and about 5.5. In certain embodiments, the solution will have a pH between about 4.5 and about 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer will be at or about 4.5. In another preferred embodiment, the pH of the extraction buffer will be at or about 4.7. In another preferred embodiment, the pH of the extraction buffer will be at or about 4.9. Generally, these pH requirements can be met using a buffering agent selected from, for example, acetate, citrate, monobasic phosphate, dibasic phosphate, mixtures thereof, and the like. Suitable buffer concentrations typically range from about 5 to about 100 mM, or from about 10 to about 50 mM, or about 5, 10, 15, 20, 25, 30, 35, 40, 45, 50, 55, 60, 65, 70, 75, 80, 85, 90, 95, or 100 mM buffering agent.

The extraction buffer will preferably have a conductivity of from about 0.5 mS·cm$^{-1}$ to about 2.0 mS·cm$^{-1}$. For example, in certain embodiments, the conductivity of the extraction buffer will be about 0.5 mS·cm$^{-1}$, or about 0.6, 0.7, 0.8, 0.9, 1.0, 1.1, 1.2, 1.3, 1.4, 1.5, 1.6, 1.7, 1.8, 1.9, or about 2.0 mS·cm$^{-1}$. One of ordinary skill in the art will know how to generate extraction buffers having an appropriate conductivity.

In one particular embodiment, an exemplary extraction buffer may contain at or about 5 mM monobasic sodium phosphate and at or about 5 mM acetate at a pH of at or about 4.5±0.2 and conductivity of at or about 0.7 to 0.9 mS/cm.

Generally, the extraction is performed at between about 0° C. and about 10° C., or between about 2° C. and about 8° C. In certain embodiments, the extraction may be performed at about 0° C., 1° C., 2° C., 3° C., 4° C., 5° C., 6° C., 7° C., 8° C., 9° C., or 10° C. In a particular embodiment, the extraction is performed at between about 2° C. and about 10° C. Typically, the extraction process will proceed for between about 60 and about 300 minutes, or for between about 120 and 240 min, or for between about 150 and 210 minutes, while the suspension is continuously stirred. In certain embodiments, the extraction process will proceed for about 60, 70, 80, 90, 100, 110, 120, 130, 140, 150, 160, 170, 180, 190, 200, 210, 220, 230, 240, 250, 260, 270, 280, 290, or about 300 minutes. In a preferred embodiment, the extraction process will proceed for at least 160 minutes with continuous stirring.

It has been found that employing an extraction buffer containing 5 mM monobasic sodium phosphate, 5 mM acetate, and 0.051% to 0.06% glacial acetic acid (v/v), a substantial increase in the yield increase in the final IgG composition can be obtained without jeopardizing the purity of the final product. In a preferred embodiment, the Fraction II+III precipitate is extracted with a paste to buffer ration of at or about 1:15 at a pH of at or about 4.5±0.2.

Advantageously, it has been found that compared to the current manufacturing process for GAMMAGARD® LIQUID (Baxter Healthcare), which employs an extraction buffer containing 5 mM monobasic sodium phosphate, 5 mM acetate, and 0.051% glacial acetic acid (v/v), that by increasing the glacial acetic acid content to at or about 0.06% (v/v), a substantial increase in the yield increase in the final IgG composition can be obtained. As compared to methods previously employed for the extraction of the precipitate formed by the second precipitation step (GAMMAGARD® LIQUID), the present invention provides, in several embodiments, methods that result in improved IgG yields in the Modified Fraction II+III suspension.

In one aspect, the improvement relates to a method in which a reduced amount of IgG is lost in the non-solubilized fraction of the Modified Fraction II+III precipitate. In one embodiment, the process improvement is realized by extracting the Modified Fraction II+III precipitate at a ratio of 1:15 (precipitate to buffer) with a solution containing 5 mM monobasic sodium phosphate, 5 mM acetate, and 0.06% glacial acetic acid (v/v). In another embodiment, the improvement is realized by maintaining the pH of the solution during the duration of the extraction process. In one embodiment, the pH of the solution is maintained at between about 4.1 and about 4.9 for the duration of the extraction process. In a preferred embodiment, the pH of the solution is maintained at between about 4.2 and about 4.8 for the duration of the extraction process. In a more preferred embodiment, the pH of the solution is maintained at between about 4.3 and about 4.7 for the duration of the extraction process. In another preferred embodiment, the pH of the solution is maintained at between about 4.4 and about 4.6 for the duration of the extraction process. In yet another preferred embodiment, the pH of the solution is maintained at or at about 4.5 for the duration of the extraction process.

In another aspect, the improvement relates to a method in which an increased amount of IgG is solubilized from the Fraction II+III precipitate in the Fraction II+III dissolution step. In one embodiment, the process improvement is realized by solubilizing the Fraction II+III precipitate in a dissolution buffer containing 600 mL glacial acetic acid per 1000 L. In another embodiment, the improvement relates to a method in which impurities are reduced after the IgG in the Fraction II+III precipitate is solubilized. In one embodiment, the process improvement is realized by mixing finely divided silicon dioxide ($SiO_2$) with the Fraction II+III suspension for at least about 30 minutes.

5. Pretreatment and Filtration of the Modified Fraction II+III Suspension

In order to remove the non-solubilized fraction of the Modified Fraction II+III precipitate (i.e., the Modified Fraction II+III filter cake), the suspension is filtered, typically using depth filtration. Depth filters that may be employed in the methods provided herein include, metallic, glass, ceramic, organic (such as diatomaceous earth) depth filters, and the like. Example of suitable filters include, without limitation, Cuno 50SA, Cuno 90SA, and Cuno VR06 filters (Cuno). Alternatively, the separation step can be performed by centrifugation rather than filtration.

Although the manufacturing process improvements described above minimize IgG losses in the initial steps of the purification process, critical impurities, including PKA activity, amidolytic activity, and fibrinogen content, are much higher when, for example, the II+III paste is extracted at pH 4.5 or 4.6, as compared to when the extraction occurs at a pH around 4.9 to 5.0 (see, Examples 2 to 5).

In order to counter act the impurities extracted in the methods provided herein, it has now been found that the purity of the IgG composition can be greatly enhanced by the addition of a pretreatment step prior to filtration/centrifugation. In one embodiment, this pretreatment step comprises addition of finely divided silica dioxide particles (e.g., fumed silica, Aerosil®) followed by a 40 to 80 minute incubation period during which the suspension is constantly mixed. In certain embodiments, the incubation period will be between about 50 minutes and about 70 minutes, or about 30, 35, 40, 45, 50, 55, 60, 65, 70, 75, 80, or more minutes. Generally, the treatment will be performed at between about 0° C. and about 10° C., or between about 2° C. and about 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between about 2° C. and about 10° C.

The effect of the fumed silica treatment is exemplified by the results of an experiment where a Fraction II+III precipitate is suspended and split into two samples, one of which is clarified with filter aid only prior to filtration and one of which is treated with fumed silica prior to addition of the filter aid and filtration. The chromatographs and quantitated data show the filtrate sample pretreated with fumed silica had a much higher IgG purity than the sample only treated with filter aid (68.8% vs. 55.7%).

In certain embodiments, fumed silica is added at a concentration of between about 20 g/kg II+III paste and about 100 g/kg II+III paste (i.e., for a Modified Fraction II+III precipitate that is extracted at a ratio of 1:15, fumed silica should be added at a concentration from about 20 g/16 kg II+III suspension to about 100 g/16 kg II+III suspension, or at a final concentration of about 0.125% (w/w) to about 0.625% (w/w)). In certain embodiments, the fumed silica may be added at a concentration of about 20 g/kg II+III paste, or about 25, 30, 35, 40, 45, 50, 55, 60, 65, 70, 75, 80, 85, 90, 95, or 100 g/kg II+III paste. In one specific embodiment, fumed silica (e.g., Aerosil 380 or equivalent) is added to the Modified Fraction II+III suspension to a final concentration of about 40 g/16 kg II+III. Mixing takes place at about 2 to 8° C. for at least 50 to 70 minutes.

In certain embodiments, $SiO_2$ is added to a an IgG composition at a concentration between about 0.01 g/g protein and about 10 g/g protein. In another embodiment, $SiO_2$ is added to a an IgG composition at a concentration between about 0.01 g/g protein and about 5 g/g protein. In another embodiment, $SiO_2$ is added to an IgG composition at a concentration between about 0.02 g/g protein and about 4 g/g protein. In one embodiment, $SiO_2$ is added at a final concentration of at least 0.1 g per gram total protein. In another specific embodiment, fumed silica is added at a concentration of at least 0.2 g per gram total protein. In another specific embodiment, fumed silica is added at a concentration of at least 0.25 g per gram total protein. In other specific embodiments, fumed silica is added at a concentration of at least 1 g per gram total protein. In another specific embodiment, fumed silica is added at a concentration of at least 2 g per gram total protein. In another specific embodiment, fumed silica is added at a concentration of at least 2.5 g per gram total protein. In yet other specific embodiments, finely divided silicon dioxide is added at a concentration of at least 0.01 g/g total protein or at least 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.5 g, 2.0 g, 2.5 g, 3.0 g, 3.5 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, or more per gram total protein.

In certain embodiments, filter aid, for example Celpure C300 (Celpure) or Hyflo-Supper-Cel (World Minerals), will be added after the silica dioxide treatment, to facilitate depth filtration. Filter aid can be added at a final concentration of from about 0.01 kg/kg II+III paste to about 1.0 kg/kg II+III paste, or from about 0.02 kg/kg II+III paste to about 0.8 kg/kg II+III paste, or from about 0.03 kg/kg II+III paste to about 0.7 kg/kg II+III paste. In other embodiments, filter aid can be added at a final concentration of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste. In certain embodiments, the filter aid will be added at a final concentration of about 0.01 kg/kg II+III paste, or about 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 kg/kg II+III paste.

A significant fraction of IgG was being lost during the filtration step of the GAMMAGARD® LIQUID manufacturing process. It was found that the current methods of post-filtration wash, using 1.8 dead volumes of suspension buffer to purge the filter press frames and lines, were insufficient for maximal recovery of IgG at this step. Surprisingly, it was found that at least 3.0 dead volumes, preferably 3.6 dead volumes, of suspension buffer were required in order for efficient recovery of total IgG in the Modified Fraction II+III clarified suspension. In certain embodiments, the filter press may be washed with any suitable suspension buffer. In a particular embodiment, the wash buffer will comprise, for example, 5 mM monobasic sodium phosphate, 5 mM acetate, and 0.015% glacial acetic acid (v/v).

In one aspect, the improvement relates to a method in which a reduced amount of IgG is lost during the Fraction II+III suspension filtration step. In one embodiment, the process improvement is realized by post-washing the filter with at least about 3.6 dead volumes of dissolution buffer containing 150 mL glacial acetic acid per 1000 L. In one embodiment, the pH of the post-wash extraction buffer is between about 4.6 and about 5.3. In a preferred embodiment, the pH of the post-wash buffer is between about 4.7 and about 5.2. In another preferred embodiment, the pH of the post-wash buffer is between about 4.8 and about 5.1. In yet another preferred embodiment, the pH of the post-wash buffer is between about 4.9 and about 5.0.

As compared to methods previously employed for the clarification of the suspension formed from the second precipitation step (GAMMAGARD® LIQUID), the present invention provides, in several embodiments, methods that result in improved IgG yields and purity in the clarified Fraction II+III suspension. In one aspect, the improvement relates to a method in which a reduced amount of IgG is lost in the Modified Fraction II+III filter cake. In other aspect, the improvement relates to a method in which a reduced amount of an impurity is found in the clarified Fraction I+III suspension.

In one embodiment, the process improvements are realized by inclusion of a fumed silica treatment prior to filtration or centrifugal clarification of a Fraction II+III suspension. In certain embodiments, the fumed silica treatment will include addition of from about 0.01 kg/kg II+III paste to about 0.07 kg/kg II+III paste, or from about 0.02 kg/kg II+III paste to about 0.06 kg/kg I+III paste, or from about 0.03 kg/kg II+III paste to about 0.05 kg/kg II+III paste, or about 0.02 kg/kg II+III paste, 0.03 kg/kg II+III paste, 0.04 kg/kg II+III paste, 0.05 kg/kg II+III paste, 0.06 kg/kg II+III paste, 0.07 kg/kg II+III paste, 0.08 kg/kg II+III paste, 0.09 kg/kg II+III paste, or 0.1 kg/kg II+III paste, and the mixture will be incubated for between about 50 minutes and about 70 minutes, or about 30, 35, 40, 45, 50, 55, 60, 65, 70, 75, 80, or more minutes at a temperature between about 2° C. and about 8° C. In another embodiment, the process improvements are realized by inclusion of a fumed silica treatment which reduced the levels of residual fibrinogen, amidolytic activity, and/or prekallikrein activator activity. In a specific embodiment, the process improvements are realized by inclusion of a fumed silica treatment, which reduces the levels of FXI, FXIa, FXII, and FXIIa in the immunoglobulin preparation.

In another embodiment, the process improvements are realized by washing the depth filter with between about 3 and about 5 volumes of the filter dead volume after completing the Modified Fraction II+III suspension filtration step. In certain embodiments, the filter will be washed with between about 3.5 volumes and about 4.5 volumes, or at least about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 volumes of the filter dead volume. In a particular embodiment, the filter press will be washed with at least about 3.6 dead volumes of suspension buffer.

6. Detergent Treatment

In order to remove additional contaminants from the Modified Fraction II+III filtrate, the sample is next subjected to a detergent treatment. Methods for the detergent treatment of plasma derived fractions are well known in the art. Generally, any standard non-ionic detergent treatment may be used in conjunction with the methods provided herein. For example, an exemplary protocol for a detergent treatment is provided below.

Briefly, polysorbate-80 is added to the Modified Fraction II+III filtrate at a final concentration of about 0.2% (w/v) with stirring and the sample is incubated for at least 30 minutes at a temperature between about 2 to 8° C. Sodium citrate dehydrate is then mixed into the solution at a final concentration of about 8 g/L and the sample is incubated for an additional 30 minutes, with continuous of stirring at a temperature between about 2 to 8° C.

In certain embodiments, any suitable non-ionic detergent can be used. Examples of suitable non-ionic detergents include, without limitation, Octylglucoside, Digitonin, C12E8, Lubrol, Triton X-100, Nonidet P-40, Tween-20 (i.e., polysorbate-20), Tween-80 (i.e., polysorbate-80), an alkyl poly(ethylene oxide), a Brij detergent, an alkylphenol poly(ethylene oxide), a poloxamer, octyl glucoside, decyl maltoside, and the like.

In one embodiment, a process improvement is realized by adding the detergent reagents (e.g., polysorbate-80 and sodium citrate dehydrate) by spraying rather than by fluent addition. In other embodiments, the detergent reagents may be added as solids to the Modified Fraction II+III filtrate while the sample is being mixed to ensure rapid distribution of the additives. In certain embodiments, it is preferable to add solid reagents by sprinkling the solids over a delocalized surface area of the filtrate such that local overconcentration does not occur, such as in fluent addition.

7. Third Precipitation Event—Precipitation G

In order to remove several residual small proteins, such as albumin and transferrin, a third precipitation is performed at a concentration of 25% alcohol. Briefly, the pH of the detergent treated II+III filtrate is adjusted to between about 6.8 and 7.2, preferably between about 6.9 and about 7.1, most preferably about 7.0 with a suitable pH modifying solution (e.g., 1M sodium hydroxide or 1M acetic acid). Cold alcohol is then added to the solution to a final concentration of about 25% (v/v) and the mixture is incubated while stirring at between about −6° C. to about −10° C. for at least 1 hour to form a third precipitate (i.e., precipitate G). In one embodiment, the mixture is incubated for at lease 2 hours, or at least 3, 4, 5, 6, 7, 8, 9, 10, 11, 12, 13, 14, 15, 16, 17, 18, 19, 20, 21, 22, 23, 24, or more hours. In a preferred embodiment, the mixture is incubated for at least 2 hours. In a more preferred embodiment, the mixture is incubated for at least 4 hours. In an even more preferred embodiment, the mixture is incubated for at least 8 hours.

In one aspect, a process improvement relates to a method in which a reduced amount of IgG is lost in the supernatant fraction of the third precipitation step. In certain embodiments, the process improvement is realized by adjusting the pH of the solution to between about 6.8 and about 7.2 immediately after or during the addition of the precipitating alcohol. In another embodiment, the process improvement is realized by maintaining the pH of the solution to between about 6.8 and about 7.2 continuously during the precipitation incubation period. In other embodiments, the pH of the solution is adjusted to between about 6.9 and about 7.1 immediately after or during the addition of the precipitating alcohol, or to a pH of about 6.8, 6.9, 7.0, 7.1, or 7.2 immediately after or during the addition of the precipitating alcohol. In a particular embodiment, the pH of the solution is adjusted to about 7.0 immediately after or during the addition of the precipitating alcohol. In certain embodiments, the pH of the solution is maintained at between about 6.9 to about 7.1 continuously during the precipitation incubation period, or at a pH of about 7.0 continuously during the precipitation incubation period. As such, in certain embodiments, a reduced amount of IgG is lost in the supernatant fraction of the third precipitation step as compared to an analogous precipitation step in which the pH of the solution is adjusted prior to but not after addition of the precipitating alcohol or to an analogous precipitation step in which the pH of the solution is not maintained during the entirety of the precipitation incubation period. In one embodiment, the pH is maintained at the desired pH during the precipitation hold or incubation time by continuously adjusting the pH of the solution. In one embodiment, the alcohol is ethanol.

In another embodiment, the process improvement is realized by adding the precipitating alcohol and/or the solution used to adjust the pH by spraying, rather than by fluent addition. As such, in certain embodiments, a reduced amount of IgG is lost in the supernatant fraction of the third precipitation step as compared to an analogous precipitation step in which the alcohol and/or solution used to adjust the pH is introduced by fluent addition. In one embodiment, the alcohol is ethanol.

8. Suspension and Filtration of Precipitate G (PptG)

In order to solubilize the IgG content of the precipitate G, a cold extraction buffer is used to re-suspend the PptG. Briefly, the precipitate G is dissolved 1 to 3.5 in Water for Injection (WFI) at between about 0° C. and about 8° C. to achieve an $AU_{280-320}$ value of between about 40 to 95. The final pH of the solution, which is stirred for at least 2 hours, is then adjusted to at or about 5.2±0.2. In one embodiment, this pH adjustment is performed with 1M acetic acid. To increase the solubility of IgG, the conductivity of the suspension is increased to between about 2.5 and about 6.0 mS/cm. In one embodiment, the conductivity is increased by the addition of sodium chloride. The suspended PptG solution is then filtered with a suitable depth filter having a nominal pore size of between about 0.1 μm and about 0.4 μm in order to remove any undissolved particles. In one embodiment, the nominal pore size of the depth filter is about 0.2 μm (e.g., Cuno VR06 filter or equivalent) to obtain a clarified filtrate. In another embodiment, the suspended PptG solution is centrifuged to recover a clarified supernatant. Post-wash of the filter is performed using a sodium chloride solution with a conductivity of between about 2.5 and about 6.0 mS/cm. Typically, suitable solutions for the extraction of precipitate G include, WFI and low conductivity buffers. In one embodiment, a low conductivity buffer has a conductivity of less than about 10 mS/cm. In a preferred embodiment, the low conductivity buffer has a conductivity of less than about 9, 8, 7, 6, 5, 4, 3, 2, or 1 mS/cm. In a preferred embodiment, the low conductivity buffer has a conductivity of less than about 6 mS/cm. In another preferred embodiment, the low conductivity buffer has a conductivity of less than about 4 mS/cm. In another preferred embodiment, the low conductivity buffer has a conductivity of less than about 2 mS/cm.

9. Solvent Detergent Treatment

In order to inactivate various viral contaminants which may be present in plasma-derived products, the clarified PptG filtrate is next subjected to a solvent detergent (S/D) treatment. Methods for the detergent treatment of plasma derived fractions are well known in the art (for review see, Pelletier J P el al., *Best Pract Res Clin Haematol.* 2006; 19(1):205-42). Generally, any standard S/D treatment may be used in conjunction with the methods provided herein. For example, an exemplary protocol for an S/D treatment is provided below.

Briefly, Triton X-100, Tween-20, and tri(n-butyl)phosphate (TNBP) are added to the clarified PptG filtrate at final concentrations of about 1.0%, 0.3%, and 0.3%, respectively. The mixture is then stirred at a temperature between about 18° C. and about 25° C. for at least about an hour.

In one embodiment, a process improvement is realized by adding the S/D reagents (e.g., Triton X-100, Tween-20, and TNBP) by spraying rather than by fluent addition. In other embodiments, the detergent reagents may be added as solids to the clarified PptG filtrate, which is being mixed to ensure rapid distribution of the S/D components. In certain embodiments, it is preferable to add solid reagents by sprinkling the solids over a delocalized surface area of the filtrate such that local overconcentration does not occur, such as in fluent addition.

10. Ion Exchange Chromatography

In order to further purify and concentrate IgG from the S/D treated PptG filtrate, cation exchange and/or anion exchange chromatography can be employed. Methods for purifying and concentrating IgG using ion exchange chromatography are well known in the art. For example, U.S. Pat. No. 5,886,154 describes a method in which a Fraction II+III precipitate is extracted at low pH (between about 3.8 and 4.5), followed by precipitation of IgG using caprylic acid, and finally implementation of two anion exchange chromatography steps. U.S. Pat. No. 6,069,236 describes a chromatographic IgG purification scheme that does not rely on alcohol precipitation at all. PCT Publication No. WO 2005/073252 describes an IgG purification method involving the extraction of a Fraction II+III precipitate, caprylic acid treatment, PEG treatment, and a single anion exchange chromatography step. U.S. Pat. No. 7,186,410 describes an IgG purification method involving the extraction of either a Fraction I+II+III or a Fraction II precipitate followed by a single anion exchange step performed at an alkaline pH. U.S. Pat. No. 7,553,938 describes a method involving the extraction of either a Fraction 1+II+III or a Fraction II+III precipitate, caprylate treatment, and either one or two anion exchange chromatography steps. U.S. Pat. No. 6,093,324 describes a purification method comprising the use of a macroporous anion exchange resin operated at a pH between about 6.0 and about 6.6. U.S. Pat. No. 6,835,379 describes a purification method that relies on cation exchange chromatography in the absence of alcohol fractionation. The disclosures of the above publications are hereby incorporated by reference in their entireties for all purposes In one embodiment of the methods of the present invention, the S/D treated PptG filtrate may be subjected to both cation exchange chromatography and anion exchange chromatography. For example, in one embodiment, the S/D treated PptG filtrate is passed through a cation exchange column, which binds the IgG in the solution. The S/D reagents can then be washed away from the absorbed IgG, which is subsequently eluted off of the column with a high pH elution buffer having a pH between about 8.0 and 9.0. In this fashion, the cation exchange chromatography step can be used to remove the S/D reagents from the preparation, concentrate the IgG containing solution, or both. In certain embodiments, the pH elution buffer may have a pH between about 8.2 and about 8.8, or between about 8.4 and about 8.6, or a pH of about 8.0, 8.1, 8.2, 8.3, 8.4, 8.5, 8.6, 8.7, 8.8, 8.9, or 9.0. In a preferred embodiment, the pH of the elution buffer is about 8.5±0.1.

In certain embodiments, the eluate from the cation exchange column may be adjusted to a lower pH, for example between about 5.5 and about 6.5, and diluted with an appropriate buffer such that the conductivity of the solution is reduced. In certain embodiments, the pH of the cation exchange eluate may be adjusted to a pH between about 5.7 and about 6.3, or between about 5.9 and about 6.1, or a pH of about 5.5, 5.6, 5.7, 5.8, 5.9, 6.0, 6.1, 6.2, 6.3, 6.4, or 6.5. In a preferred embodiment, the pH of the eluate is adjusted to a pH of about 6.0±0.1. The eluate is then loaded onto an anion exchange column, which binds several contaminants found in the preparation. The column flow through, containing the IgG fraction, is collected during column loading and washing. In certain embodiments, the ion exchange chromatographic steps of the present invention can be performed in column mode, batch mode, or in a combination of the two.

In certain embodiments, a process improvement is realized by adding the solution used to adjust the pH by spraying, rather than by fluent addition.

11. Nanofiltration and Ultra/Diafiltration

In order to further reduce the viral load of the IgG composition provided herein, the anion exchange column effluent may be nanofiltered using a suitable nanofiltration device. In certain embodiments, the nanofiltration device will have a mean pore size of between about 15 nm and about 200 nm. Examples of nanofilters suitable for this use include, without limitation, DVD, DV 50, DV 20 (PaII), Viresolve NFP, Viresolve NFR (Millipore), Planova 15N, 20N, 35N, and 75N (Planova). In a specific embodiment, the nanofilter may have a mean pore size of between about 15 nm and about 72 nm, or between about 19 nm and about 35 nm, or of about 15 nm, 19 nm, 35 nm, or 72 nm. In a preferred embodiment, the nanofilter will have a mean pore size of about 35 nm, such as an Asahi PLANOVA 35N filter or equivalent thereof.

Optionally, ultrafiltration/diafiltration may performed to further concentrate the nanofiltrate. In one embodiment, an open channel membrane is used with a specifically designed post-wash and formulation near the end the production process render the resulting IgG compositions about twice as high in protein concentration (200 mg/mL) compared to state of the art IVIGs (e.g., GAMMAGARD® LIQUID) without affecting yield and storage stability. With most of the commercial available ultrafiltration membranes a concentration of 200 mg/mL IgG cannot be reached without major protein losses. These membranes will be blocked early and therefore adequate post-wash is difficult to achieve. Therefore open channel membrane configurations have to be used. Even with open channel membranes, a specifically designed post-wash procedure has to be used to obtain the required concentration without significant protein loss (less than 2% loss). Even more surprising is the fact that the higher protein concentration of 200 mg/mL does not effect the virus inactivation capacity of the low pH storage step.

Subsequent to nanofiltration, the filtrate may be further concentrated by ultrafiltration/diafiltration. In one embodiment, the nanofiltrate may be concentrated by ultrafiltration to a protein concentration of between about 2% and about 10% (w/v). In certain embodiments, the ultrafiltration is carried out in a cassette with an open channel screen and the ultrafiltration membrane has a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa.

Upon completion of the ultrafiltration step, the concentrate may further be concentrated via diafiltration against a solution suitable for intravenous or intramuscular administration. In certain embodiments, the diafiltration solution may comprise a stabilizing and/or buffering agent. In a preferred embodiment, the stabilizing and buffering agent is glycine at an appropriate concentration, for example between about 0.20 M and about 0.30M, or between about 0.22M and about 0.28M, or between about 0.24M and about 0.26 mM, or at a concentration of about 2.0, 2.1, 2.2, 2.3, 2.4, 2.5, 2.6, 2.7, 2.8, 2.9, or 3.0. In a preferred embodiment, the diafiltration buffer contains at or about 0.25 M glycine.

Typically, the minimum exchange volume is at least about 3 times the original concentrate volume or at least about 4, 5, 6, 7, 8, 9, or more times the original concentrate volume. The IgG solution may be concentrated to a final protein concentration of between about 5% and about 25% (w/v), or between about 6% and about 18% (w/v), or between about 7% and about 16% (w/v), or between about 8% and about 14% (w/v), or between about 9% and about 12%, or to a final concentration of about 5%, or 6%, 7%, 8%, 9%, 10%, 11%, 12%, 13%, 14%, 15%, 16%, 17%, 18%, 19%, 20%, 21%, 22%, 23%, 24%, 25% or higher. In one embodiment, a final protein concentration of at least about 23% is achieved without adding the post-wash fraction to the concentrated solution. In another embodiment, a final protein concentration of at least about 24% is achieved without adding the post-wash fraction to the concentrated solution, a final protein concentration of at least about 25% is achieved without adding the post-wash fraction to the concentrated solution. Typically, at the end of the concentration process, the pH of the solution will be between about 4.6 to 5.1.

In an exemplary embodiment, the pH of the IgG composition is adjusted to about 4.5 prior to ultrafiltration. The solution is concentrated to a protein concentration of 5±2% w/v through ultrafiltration. The UF membrane has a nominal molecular weight cut off (NMWCO) of 50,000 Daltons or less (Millipore Pellicon Polyether sulfon membrane). The concentrate is diafiltered against ten volumes of 0.25 M glycine solution, pH 4.5±0.2. Throughout the ultra-diafiltration operation the solution is maintained at a temperature of between about 2° C. to about 8° C. After diafiltration, the solution is concentrated to a protein concentration of at least 11% (w/v).

12. Formulation

Upon completion of the diafiltration step, the protein concentration of the solution is adjusted to with the diafiltration buffer to a final concentration of between about 5% and about 20% (w/v), or between about 6% and about 18% (w/v), or between about 7% and about 16% (w/v), or between about 8% and about 14% (w/v), or between about 9% and about 12%, or to a final concentration of about 5%, or 6%, 7%, 8%, 9%, 10%, 11%, 12%, 13%, 14%, 15%, 16%, 17%, 18%, 19%, or 20%. In a preferred embodiment, the final protein concentration of the solution is between about 9% and about 11%, more preferably about 10%.

The formulated bulk solution is further sterilized by filtering through a membrane filter with an absolute pore size of no more than about 0.22 micron, for example about 0.2 micron. Then the solution is aseptically dispensed into final containers for proper sealing, with samples taken for testing.

In one embodiment, the IgG composition is further adjusted to a concentration of about 10.2±0.2% (w/v) with diafiltration buffer. The pH is adjusted to about 4.4 to about 4.9 if necessary. Finally, the solution is sterile filtered and incubated for three weeks at or about 30° C.

B. Factor H

In one embodiment, the present invention provides a method for reducing the amount of a serine protease or a serine protease zymogen in a plasma-derived Factor H composition. In one specific embodiment, the method comprises the steps of: (a) contacting the Factor H composition with finely divided silicon dioxide ($SiO_2$) under conditions suitable to bind at least one serine protease or serine protease zymogen; and (b) separating the $SiO_2$ from the Factor H composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII).

In one embodiment, the method further comprises the step of performing a first Factor H protein enrichment step to form a first enriched Factor H composition, prior to contacting the composition with finely divided silicon dioxide ($SiO_2$). In certain embodiments, the first Factor H protein enrichment step is selected from a protein precipitation step (e.g., an alcohol fractionation step), an ultrafiltration/diafiltration step, and a chromatographic step.

In certain embodiments, the methods described above further comprises the step of performing a second Factor H protein enrichment step to form a second enriched Factor H composition, prior to contacting the composition with finely divided silicon dioxide ($SiO_2$). In certain embodiments, the first Factor H protein enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived Factor H composition, the method comprises the steps of: (a) performing a first Factor H enrichment step to form a first enriched plasma-derived Factor H composition; (b) performing a second Factor H enrichment step to form a second enriched plasma-derived Factor H composition; (c) contacting the second enriched composition with finely divided silicon dioxide ($SiO_2$) under conditions suitable to bind at least one serine protease or serine protease zymogen; and (d) separating the $SiO_2$ from the composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

In certain embodiments, the methods described above further comprises the step of performing an Factor H enrichment step after contacting the composition with finely divided silicon dioxide ($SiO_2$). In certain embodiments, the Factor H enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived Factor H composition the method comprises the steps of: (a) performing a first Factor H enrichment step to form a first enriched plasma-derived Factor H composition; (b) contacting the first enriched composition with finely divided silicon dioxide ($SiO_2$) under conditions suitable to bind at least one serine protease or serine protease zymogen; (c) separating the $SiO_2$ from the composition to remove the bound serine protease or serine protease zymogen; and (d) performing a second Factor H enrichment step to form a second enriched plasma-derived Factor H composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

Likewise, in one embodiment, the invention provides a method for reducing the amount of a serine protease or a serine protease zymogen in a plasma-derived Factor H composition, the method comprising the steps of: (a) performing a first Factor H enrichment step to form a first enriched plasma-derived Factor H composition; (b) performing a second Factor H enrichment step to form a second enriched plasma-derived Factor H composition; (c) contacting the second enriched composition with finely divided silicon dioxide ($SiO_2$) under conditions suitable to bind at least one serine protease or serine protease zymogen; (d) separating the $SiO_2$ from the composition to remove the bound serine protease or serine protease zymogen; and (e) performing a third Factor H enrichment step to form a third enriched plasma-derived Factor H composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 101 to Var. 1100, found in Table 2, Table 3, Table 4, Table 5, Table 6, Table 7, Table 8, Table 9, Table 10, or Table 11.

1. Methods for the Manufacture of Plasma-Derived Factor H

Regarding production, the claimed processes starting from human plasma shall be based on the sub-fractionation of typical industrial intermediates obtained by, e.g., the fractional precipitation by ethanol in the cold (reviewed in Schultze H E, Heremans J F; Molecular Biology of Human Proteins. Volume I: Nature and Metabolism of Extracellular Proteins 1966, Elsevier Publishing Company; p. 236-317). A preferred embodiment of such purification is the purification of functional Factor H from side fractions of industrial scale plasma fractionation in such a way that established and licensed manufacturing processes of plasma products, which are under control of pharmaceutical regulatory authorities, like immunoglobulins, are not affected. For example, the filter cake obtained after filtration of a Fraction II+III paste suspension (Teschner W et al., Vox Sang. 2007 January; 92(1):42-55). Fraction I precipitate (Cohn et al., (1946) supra), Precipitate III (Schultze H E, Heremans J F; Molecular Biology of Human Proteins. Volume I: Nature and Metabolism of Extracellular Proteins 1966, Elsevier Publishing Company; p. 236-317 at p. 253) and precipitate B (method of Kistler and Nitschmann; supra at p. 253) are examples of such industrial sources for Factor H. Starting from those side fractions, purification procedures known in the art can be used to purify Factor H. They may be based on precipitation with polyethylene glycol (Nagasawa S, Stroud R M; Mol Immunol 1980; 17:1365-72), affinity chromatography via immobilized heparin (citation as before), ion exchange chromatography (Crossley L G, Porter R R; Biochem J 1980; 191:173-82) and hydrophobic interaction chromatography (Ripoche J, Al Salihi A, Rousseaux J, Fontaine B; Biochem J 1984; 221, 89-96).

In one embodiment, the starting material for the invention is prepared using Cohn fractions. This fractionation is a well known fractionation used for the preparation of immunoglobulin preparations can be prepared from donor serum or monoclonal or recombinant immunoglobulins. In a typical example, blood is collected from healthy donors. Usually, the blood is collected from the same species of animal as the subject to which the immunoglobulin preparation will be administered (typically referred to as "homologous" immunoglobulins). The immunoglobulins are isolated from the blood by suitable procedures, such as, for example, Cohn fractionation, ultracentrifugation, electrophoretic preparation, ion exchange chromatography, affinity chromatography, immunoaffinity chromatography, polyethylene glycol fractionation, or the like. (See, e.g., Cohn et al., J. Am. Chem. Soc. 68:459-75 (1946); Oncley et al., J. Am. Chem. Soc. 71:541-50 (1949); Barundern et al., Vox Sang. 7:157-74 (1962); Koblet et al., Vox Sang. 13:93-102 (1967); U.S. Pat. Nos. 5,122,373 and 5,177,194; the disclosures of which are incorporated herein by reference in their entireties for all purposes.) In one embodiment, the present invention uses the discarded fractions from the preparation of immunoglobulins. In a particular embodiment, the present invention uses the fraction that is found in a $SiO_2$ filtration cake once the Fraction II+III extract is filtered.

Generally, Factor H preparations according to the present invention can be prepared from any suitable starting materials, for example, recovered plasma or source plasma. In a typical example, blood or plasma is collected from healthy donors. Usually, the blood is collected from the same species of animal as the subject to which the Factor H preparation will be administered (typically referred to as "homologous" Factor H). The Factor H is isolated from the blood or plasma by suitable procedures, such as, for example, precipitation (alcohol fractionation or polyethylene glycol fractionation), chromatographic methods (ion exchange chromatography, affinity chromatography, immunoaffinity chromatography, etc.) ultracentrifugation, and electrophoretic preparation, and the like. (See, e.g., Cohn et al., J. Am. Chem. Soc. 68:459-75 (1946); Deutsch et al., J. Biol. Chem. 164:109-118; Oncley et al., J. Am. Chem. Soc. 71:541-50 (1949); Cohn et al., J. Am. Chem. Soc. 72:465-474 (1950); Cohn et al., Blood Cells and Plasma Proteins: Their State in Nature (J. L. Tullis, ed), pp. 1-58, Academic Press, New York and London (1953); Nitschmann et al., Helv. Chim. Acta 37:866-873; Kistler and Nitschmann, Vox Sang. 7:414-424 (1962); Barundern et al., Vox Sang. 7:157-74 (1962); Koblet et al., Vox Sang. 13:93-102 (1967); U.S. Pat. Nos. 5,122,373 and 5,177,194; the disclosures of which are hereby incorporated by reference in their entireties for all purposes).

In certain embodiments, Factor H is recovered from material otherwise discarded during the manufacture of other commercially important blood products by plasma fractionation. For example, in an exemplary embodiment, Factor H is extracted from a Fraction I precipitate and/or extracted from a filter cake formed after centrifugation or filtration of a re-suspended Fraction II+III paste. Advantageously, according to the methods provided herein, industrial-scale preparation of Factor H can be achieved without the need for additional input plasma or the redesign and regulatory re-approval of existing manufacturing processes for other commercially important plasma-derived blood products, such as IgG gamma globulins for intravenous (IVIG) or subcutaneous administration.

In one aspect, the present invention provides a method for preparing an enriched Factor H composition having reduced serine protease and/or serine protease zymogen content from plasma by extracting Factor H from a plasma fraction and reducing the FXI, FXIa, FXII, and/or FXIIa content with a $SiO_2$ treatment method provided herein.

In one embodiment, a method is provided for preparing an enriched Factor H composition from plasma, the method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating Factor H from the first supernatant, in a second precipitation step, with between about 20% and about 30% alcohol at a pH of between about 6.7 and about 7.3 to form a second precipitate; (c) re-suspending the second precipitate to form a suspension; (d) mixing finely divided silicon dioxide ($SiO_2$) with the suspension from step (c); (e) separating the suspension to form a filter cake and a supernatant; and (f) extracting Factor H from the $SiO_2$ filter cake under solution conditions that reduce the level of a serine protease or serine protease zymogen in the final composition. In a preferred embodiment, the filter cake is separated from the supernatant by filtering the suspension through a filter press containing a suitable filter. In one embodiment, Factor H can be extracted by re-circulating an extraction buffer through a filter press containing a filter cake.

In a second aspect, the present invention provides a method for preparing an enriched Factor H composition with reduced serine protease and/or serine protease zymogen content from plasma by extracting Factor H from a Fraction I precipitate.

In a preferred embodiment, a method is provided for preparing an enriched Factor H composition from plasma, the method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) extracting Factor H from the precipitate with a Factor H extraction buffer, and (c) reducing the level of a serine protease or serine protease zymogen by treating the composition with $SiO_2$, using a suitable method provided herein.

In one aspect, a method is provided for preparing an enriched Factor H composition from plasma, by extracting Factor H from a pool of two or more manufacturing byproduct fractions created by a process designed to provide a second blood protein, for example, IgG gamma globulins. In one embodiment, the method comprises pooling a Fraction I precipitate and a Fraction II+III filter cake formed during the manufacture of IgG gamma globulins (e.g., IVIG) and extracting Factor H from the pooled fractions.

In certain embodiments, an enriched Factor H composition having reduced serine protease and/or serine protease zymogen content may be further purified subsequent to extraction from a Fraction I precipitate and/or Fraction II+III filter cake. Various methods are available for further purifying Factor H, including without limitation, additional precipitation steps or fractionations, affinity chromatography, ion exchange chromatography, hydrophobic interaction chromatography, size exclusion chromatography, solvent/detergent (S/D) treatment, nanofiltration, ultrafiltration, diafiltration, and the like.

In one embodiment, the method further comprises precipitating impurities from an enriched Factor H composition. In certain embodiments, this step comprises precipitating at least one impurity, for example a lipid or protein, from the composition and then separating the precipitate from the supernatant containing Factor H. Optionally, Factor H can then be precipitated from the supernatant in a separate precipitation.

In a specific embodiment, a Factor H composition extracted from a plasma fraction (e.g., fraction I precipitate, fraction II+III precipitate, Precipitate B precipitate, etc.) is further enriched by precipitating at least one impurity out of the solution using PEG at a final concentration of between about 2.5% and about 7.5%. In another embodiment, PEG is used at a final concentration of between about 3% and about 7%. In another embodiment, PEG is used at a final concentration of between about 4% and about 6%. In yet another embodiment, PEG is used at a final concentration of about 5%.

In another specific embodiment, a Factor H composition extracted from a plasma fraction (e.g., fraction I precipitate, fraction II+III precipitate, Precipitate B precipitate, etc.) is further enriched by precipitating Factor H out of the solution using PEG at a final concentration of between about 9% and about 15%. In another embodiment, PEG is used at a final concentration of between about 10% and about 14%. In another embodiment, PEG is used at a final concentration of between about 11% and about 13%. In yet another embodiment, PEG is used at a final concentration of about 12%.

In another specific embodiment, a Factor H composition extracted from a plasma fraction (e.g., fraction I precipitate, fraction II+III precipitate, Precipitate B precipitate, etc.) is further enriched by (a) precipitating at least one impurity out of the solution; (b) precipitating Factor H out of the solution; and (c) recovering the precipitate containing Factor H. In certain embodiments, the precipitation steps are performed with alcohol (e.g., methanol or ethanol), PEG, or a combination thereof. In a particular embodiment, the precipitation steps are performed with PEG. In certain embodiments, the PEG concentration of the first precipitation step is between about 2.5% and about 7.5% and the PEG concentration of the second precipitation step is between about 9% and about 15%. In a specific embodiment, the PEG concentration of the first step is between about 4% and about 6% and the PEG concentration of the second step is between about 11% and about 13%. In a more specific embodiment, the PEG concentration of the first precipitation step is about 5% and the PEG concentration of the second precipitation step is about 12%. In yet other embodiments, the PEG concentration of the first and second precipitation steps is selected from variations Var. 1101 and Var. 1221 listed in Table 16.

TABLE 16

PEG concentrations for enrichment of Factor H compositions.

| | | PEG Concentration - First Precipitation | | | | | | | | | | |
|---|---|---|---|---|---|---|---|---|---|---|---|---|
| | | 2.5% | 3.0% | 3.5% | 4.0% | 4.5% | 5.0% | 5.5% | 6.0% | 6.5% | 7.0% | 7.5% |
| PEG Concentration - Second Precipitation | 2.5% | Var. 1101 | Var. 1112 | Var. 1123 | Var. 1134 | Var. 1145 | Var. 1156 | Var. 1167 | Var. 1178 | Var. 1189 | Var. 1200 | Var. 1211 |
| | 3.0% | Var. 1102 | Var. 1113 | Var. 1124 | Var. 1135 | Var. 1146 | Var. 1157 | Var. 1168 | Var. 1179 | Var. 1190 | Var. 1201 | Var. 1212 |

TABLE 16-continued

PEG concentrations for enrichment of Factor H compositions.

| | PEG Concentration - First Precipitation | | | | | | | | | | |
|---|---|---|---|---|---|---|---|---|---|---|---|
| | 2.5% | 3.0% | 3.5% | 4.0% | 4.5% | 5.0% | 5.5% | 6.0% | 6.5% | 7.0% | 7.5% |
| 3.5% | Var. 1103 | Var. 1114 | Var. 1125 | Var. 1136 | Var. 1147 | Var. 1158 | Var. 1169 | Var. 1180 | Var. 1191 | Var. 1202 | Var. 1213 |
| 4.0% | Var. 1104 | Var. 1115 | Var. 1126 | Var. 1137 | Var. 1148 | Var. 1159 | Var. 1170 | Var. 1181 | Var. 1192 | Var. 1203 | Var. 1214 |
| 4.5% | Var. 1105 | Var. 1116 | Var. 1127 | Var. 1138 | Var. 1149 | Var. 1160 | Var. 1171 | Var. 1182 | Var. 1193 | Var. 1204 | Var. 1215 |
| 5.0% | Var. 1106 | Var. 1117 | Var. 1128 | Var. 1139 | Var. 1150 | Var. 1161 | Var. 1172 | Var. 1183 | Var. 1194 | Var. 1205 | Var. 1216 |
| 5.5% | Var. 1107 | Var. 1118 | Var. 1129 | Var. 1140 | Var. 1151 | Var. 1162 | Var. 1173 | Var. 1184 | Var. 1195 | Var. 1206 | Var. 1217 |
| 6.0% | Var. 1108 | Var. 1119 | Var. 1130 | Var. 1141 | Var. 1152 | Var. 1163 | Var. 1174 | Var. 1185 | Var. 1196 | Var. 1207 | Var. 1218 |
| 6.5% | Var. 1109 | Var. 1120 | Var. 1131 | Var. 1142 | Var. 1153 | Var. 1164 | Var. 1175 | Var. 1186 | Var. 1197 | Var. 1208 | Var. 1219 |
| 7.0% | Var. 1110 | Var. 1121 | Var. 1132 | Var. 1143 | Var. 1154 | Var. 1165 | Var. 1176 | Var. 1187 | Var. 1198 | Var. 1209 | Var. 1220 |
| 7.5% | Var. 1111 | Var. 1122 | Var. 1133 | Var. 1144 | Var. 1155 | Var. 1166 | Var. 1177 | Var. 1188 | Var. 1199 | Var. 1210 | Var. 1221 |

In certain embodiments, the method for preparing an enriched Factor H composition further comprises at least one, preferably two, chromatographic steps to further enrich the purity of the composition. Generally, any suitable chromatographic method may be employed to further enrich the Factor H composition, for example, extracted from a Fraction I precipitate or Fraction I+III filter cake. In certain embodiments, prior to chromatographic enrichment, the extracted Factor H composition will be subjected one or more additional precipitation steps, as described above, to reduce the impurities present in the composition, reduce the load volume for the chromatographic step, and/or exchange the buffer of the composition.

In certain embodiments, a Factor H composition may be further enriched by a chromatographic step comprising anion exchange chromatography (AEC), cation exchange chromatography (CEC), heparin affinity chromatography, hydrophobic exchange chromatography (HIC), hydroxyapatite chromatography (HAP), immunoaffinity chromatography, size exclusion chromatography (i.e., gel filtration), or other suitable chromatographic step. Chromatographic steps may be performed in either batch or column mode.

In a preferred embodiment, the method comprises the use of anion exchange chromatography and heparin affinity chromatography.

In certain embodiments, the methods provided herein for the preparation of an enriched Factor H composition will further include at least one, preferably at least two, most preferably at least three, viral inactivation or removal steps. Non-limiting examples of viral inactivation or removal steps that may be employed with the methods provided herein include, solvent detergent treatment (Horowitz et al., Blood Coagul Fibrinolysis 1994 (5 Suppl 3):S21-S28 and Kreil et al., Transfusion 2003 (43): 1023-1028, both of which are herein expressly incorporated by reference in their entirety for all purposes), nanofiltration (Hamamoto et al., Vox Sang 1989 (56)230-236 and Yuasa et al., J Gen Virol. 1991 (72 (pt 8)):2021-2024, both of which are herein expressly incorporated by reference in their entirety for all purposes), low pH incubation at high temperatures (Kempf et al., Transfusion 1991 (31)423-427 and Louie et al., Biologicals 1994 (22): 13-19), and heat treatment of lyophilized Factor H compositions (Piszkiewicz et al., Thromb Res. 1987 Jul. 15; 47(2):235-41; Piszkiewicz et al., Curr Stud Hematol Blood Transfus. 1989; (56):44-54; Epstein and Fricke, Arch Pathol Lab Med. 1990 March 114(3):335-40).

In a preferred embodiment, the present invention provides a method of preparing a virally safe enriched Factor H composition having reduced serine protease and/or serine protease zymogen content comprising (i) extracting Factor H from a Fraction II+III filter cake using $SiO_2$, (ii) performing a first precipitation step to precipitate at least one impurity from the Factor H composition, (iii) performing a second precipitation step to precipitate Factor H from the composition, and (iv) performing at least one viral inactivation or removal step, thereby preparing a virally safe enriched Factor H composition. In one embodiment, the precipitation steps comprise PEG precipitation. In a specific embodiment, the PEG concentration of the first and second precipitation steps is selected from variations Var. 1101 and Var. 1221 listed in Table 16.

2. Co-Binding and Differential Elution

In one aspect, the present invention provides a method for preparing a plasma-derived Factor H composition having a reduced amount of a serine protease or a serine protease zymogen, the method comprising co-extracting Factor H and a serine protease and/or serine protease zymogen from a composition derived from pooled plasma by binding the proteins to finely divided silicon dioxide ($SiO_2$), eluting the serine protease and/or serine protease zymogen from the $SiO_2$ under a first solution condition, and subsequently eluting Factor H from the $SiO_2$ under a second solution condition. In a preferred embodiment, the starting composition is a re-suspended Fraction II+III precipitate or equivalent precipitate thereof.

In a specific embodiment, the method comprises the steps of: (a) contacting a composition containing Factor H and at least one serine protease or serine protease zymogen with finely divided silicon dioxide ($SiO_2$) under conditions suitable to bind the Factor H and at least one serine protease or serine protease zymogen; (b) separating the $SiO_2$ from the composition; (c) eluting the serine protease or serine protease zymogen from the $SiO_2$ under a solution condition in which the Factor H remains bound; and (d) eluting the Factor H from the $SiO_2$.

In certain embodiments, a solution condition in which the Factor H remains bound refers to a condition that preferentially elutes the serine protease or serine protease zymogen, while a substantial fraction of Factor H remains bound to the $SiO_2$. In one embodiment, a substantial fraction refers to at least 10% of the Factor H bound to the $SiO_2$. In another embodiment, a substantial fraction refers to at least 25% of the Factor H bound to the $SiO_2$. In another embodiment, a substantial fraction refers to at least 50% of the Factor H bound to the $SiO_2$. In another embodiment, a substantial fraction refers to at least 75% of the Factor H bound to the $SiO_2$. In yet other embodiments, a substantial fraction refers to at least 10% of the Factor H bound to the $SiO_2$, or at least 15, 20, 25, 30, 35, 40, 45, 50, 55, 60, 65, 70, 75, 80, 85, 90, 95, 96, 97, 98, 99, or more of the Factor H bound to the $SiO_2$.

In certain embodiments, differential elution of the serine protease or serine protease zymogen and Factor H is achieved by sequentially contacting (i.e., step-wise elution) the $SiO_2$ with a first solution condition (e.g., a first elution buffer) suitable to elute the majority of the serine protease or serine protease zymogen but not a substantial fraction of the bound Factor H, and a second solution condition (e.g., a second elution buffer) suitable to elute the substantial fraction of bound Factor H from the $SiO_2$.

In other embodiments, differential elution of the serine protease or serine protease zymogen and Factor H is achieved by gradually changing the solution conditions (i.e., with an elution gradient) from a first solution condition suitable to elute the majority of the serine protease or serine protease zymogen but not a substantial fraction of the bound Factor H to a second solution condition suitable to elute the substantial fraction of bound Factor H from the $SiO_2$. In this fashion, the serine protease or serine protease zymogen and Factor H content eluted off of the $SiO_2$ may be partially overlapping. By fractionating the elution and characterizing the individual fractions, a Factor H pool may be created from fractions having high Factor H content and low serine protease or serine protease zymogen content.

Solution conditions that may be varied to achieve a desired result from a method described above include, without limitation, the pH of the solution, the conductivity of the solution, the temperature of the solution, the concentration of Factor H in the composition, and the concentration of $SiO_2$ used in the method. Generally, suitable pH ranges for methods of reducing serine protease and/or serine protease zymogen content in a Factor H enriched composition range from about 3 to about 11. Suitable conductivities for the methods described above range from about 0.1 mS/cm to about 100 mS/cm. Suitable temperatures for performing the methods described above range from about −10° C. to about 90° C. Finely divided silicon dioxide may be used at a final concentration ranging from about 0.01 g/g protein to about 10 g/g protein. Finally, Factor H compositions may vary in concentration from about 0.001 mg/mL to about 100 mg/mL.

In one embodiment, the solution condition under which the serine protease or serine protease zymogen is eluted from the $SiO_2$ and a significant fraction of the Factor H remains bound comprises a pH between about 5.0 and about 11.0. In another embodiment, the pH is between about 6.0 and about 1.0. In another embodiment, the pH is between about 7.0 and about 9.0. In another embodiment, the pH is between about 7.5 and about 8.5. In yet another embodiment, the pH is between about 7.0 and about 8.0.

In a particular embodiment, the solution condition under which the serine protease or serine protease zymogen is eluted from the $SiO_2$ and a significant fraction of the Factor H remains bound comprises a pH of about 7.0. In another specific embodiment, the pH is about 7.5. In another embodiment, the pH is about 8.0. In yet other embodiments, the pH is about 3.0 or about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, or 11.0.

In one embodiment, the solution condition under which the serine protease or serine protease zymogen is eluted from the $SiO_2$ and a significant fraction of the Factor H remains bound comprises a pH of at least 6.0. In another embodiment, the pH is at least 6.5. In another embodiment, the pH is at least 7.0. In yet another embodiment, the pH is at least 7.5. In yet other embodiments, the pH of the solution is at least 3.0 or at least 3.5, 4.0, 4.5, 5.0, 5.5, 6.0, 6.5, 7.0, 7.5, 8.0, 8.5, 9.0, 9.5, 10.0, 10.5, or higher.

In another embodiment, of any of the methods described above, the solution condition under which the serine protease or serine protease zymogen is eluted from the $SiO_2$ and a significant fraction of the Factor H remains bound comprises a pH of no greater than about 11.0. In another embodiment, the pH is no greater about 10.0. In another embodiment, the pH is no greater about 9.0. In another embodiment, the pH is no greater about 8.0. In yet other embodiments, the pH is no greater than about 11.0, or 10.5, 10.0, 9.5, 9.0, 8.5, 8.0, 7.5, 7.0, 6.5, 6.0, 5.5, 5.0, 4.5, 4.0, 3.5, or lower.

In one embodiment, the solution condition under which the serine protease or serine protease zymogen is eluted from the $SiO_2$ and a significant fraction of the Factor H remains bound comprises a conductivity of at least 10 mS/cm. In another embodiment, the conductivity is at least 20 mS/cm. In yet other embodiments, the conductivity of the solution is at least 2 mS/cm, or at least 3 mS/cm, 4 mS/cm, 5 mS/cm, 6 mS/cm, 7 mS/cm, 8 mS/cm, 9 mS/cm, 10 mS/cm, 11 mS/cm, 12 mS/cm, 13 mS/cm, 14 mS/cm, 15 mS/cm, 16 mS/cm, 17 mS/cm, 18 mS/cm, 19 mS/cm, 20 mS/cm, 21 mS/cm, 22 mS/cm, 23 mS/cm, 24 mS/cm, 25 mS/cm, 26 mS/cm, 27 mS/cm, 28 mS/cm, 29 mS/cm, 30 mS/cm, 31 mS/cm, 32 mS/cm, 33 mS/cm, 34 mS/cm, 35 mS/cm, 36 mS/cm, 37 mS/cm, 38 mS/cm, 39 mS/cm, 40 mS/cm, 41 mS/cm, 42 mS/cm, 43 mS/cm, 44 mS/cm, 45 mS/cm, 46 mS/cm, 47 mS/cm, 48 mS/cm, 49 mS/cm, 50 mS/cm, 55 mS/cm, 60 mS/cm, 65 mS/cm, 70 mS/cm, 75 mS/cm, 80 mS/cm, 85 mS/cm, 90 mS/cm, 95 mS/cm, 100 mS/cm, or greater.

In one embodiment, the solution condition under which the serine protease or serine protease zymogen is eluted from the $SiO_2$ and a significant fraction of the Factor H remains bound comprises a conductivity between about 10 mS/cm and about 100 mS/cm. In another embodiment, the conductivity is between about 10 mS/cm and about 50 mS/cm. In another embodiment, the conductivity is between about 20 mS/cm and about 100 mS/cm. In yet another embodiment, the conductivity is between about 20 mS/cm and about 50 mS/cm.

Figure 3:
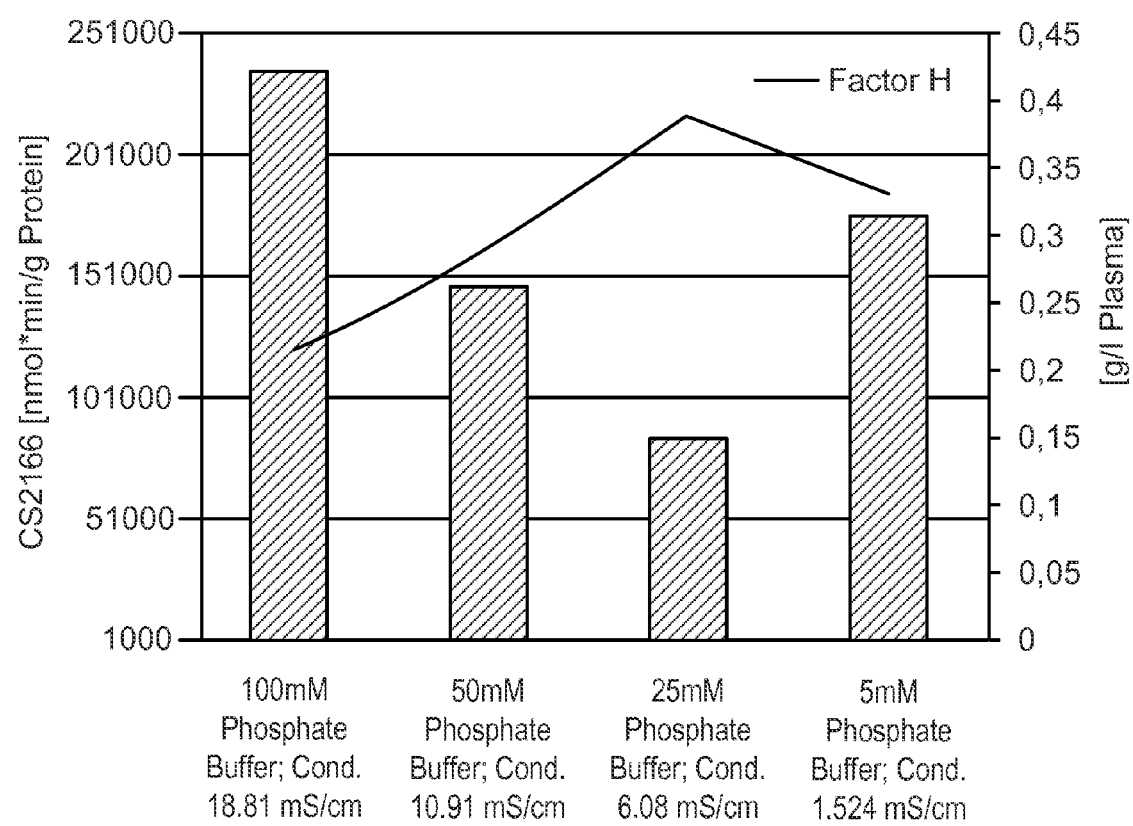

As shown in Example 5 and illustrated in FIG. 3, it was found that the use of solution conditions having a pH greater than 6.0 (e.g., 7.5) and increasing conductivity (e.g., greater than 6.0 mS/cm), results in increased elution of serine proteases and/or serine protease zymogens from $SiO_2$, and decreased elution of Factor H from $SiO_2$. Advantageously, these findings can be used to provide methods for reducing the levels of serine protease and serine protease zymogen present in Factor H compositions. In a particular embodiment of the methods described above, the solution condition under which the serine protease or serine protease zymogen is eluted from the SiO$_2$ and a significant fraction of the Factor H remains bound comprises a conductivity of at least about 10 mS/cm and a pH of at least 7.0. In another particular embodiment, the solution condition comprises a conductivity of at least 10 mS/cm and a pH of at least 7.5. In another embodiment, the solution condition comprises a conductivity of at least 20 mS/cm and a pH of at least 7.0. In yet another embodiment, the solution condition comprises a conductivity of at least 20 mS/cm and a pH of at least 7.5.

3. Co-Binding and Preferential Factor H Elution

In one aspect, the present invention provides a method for preparing a plasma-derived Factor H composition having a reduced amount of a serine protease or a serine protease zymogen, the method comprising co-extracting Factor H and a serine protease and/or serine protease zymogen from a composition derived from pooled plasma by binding the proteins to finely divided silicon dioxide (SiO$_2$), and eluting the Factor H from the SiO$_2$ under conditions in which a substantial fraction of the bound serine protease and/or serine protease zymogen remains bound to the SiO$_2$. In a preferred embodiment, the starting composition is a re-suspended Fraction II+III precipitate or equivalent precipitate thereof.

In a specific embodiment, the method comprises the steps of: (a) contacting a composition containing Factor H and at least one serine protease or serine protease zymogen with finely divided silicon dioxide (SiO$_2$) under conditions suitable to bind the Factor H and at least one serine protease or serine protease zymogen; (b) separating the SiO$_2$ from the composition; and (c) eluting the Factor H from the SiO$_2$ under a solution condition in which the serine protease or serine protease zymogen remains bound.

In certain embodiments, a solution condition in which the serine protease or serine protease zymogen remains bound refers to a condition that preferentially elutes the Factor H, while a substantial fraction of the serine protease or serine protease zymogen remains bound to the SiO$_2$. In one embodiment, a substantial fraction refers to at least 10% of the serine protease or serine protease zymogen bound to the SiO$_2$. In another embodiment, a substantial fraction refers to at least 25% of the serine protease or serine protease zymogen bound to the SiO$_2$. In another embodiment, a substantial fraction refers to at least 50% of the serine protease or serine protease zymogen bound to the SiO$_2$. In another embodiment, a substantial fraction refers to at least 75% of the serine protease or serine protease zymogen bound to the SiO$_2$. In yet other embodiments, a substantial fraction refers to at least 10% of the serine protease or serine protease zymogen bound to the SiO$_2$, or at least 15, 20, 25, 30, 35, 40, 45, 50, 55, 60, 65, 70, 75, 80, 85, 90, 95, 96, 97, 98, 99, or more of the serine protease or serine protease zymogen bound to the SiO$_2$.

Solution conditions that may be varied to achieve a desired result from a method described above include, without limitation, the pH of the solution, the conductivity of the solution, the temperature of the solution, the concentration of Factor H in the composition, and the concentration of SiO$_2$ used in the method. Generally, suitable pH ranges for methods of reducing serine protease and/or serine protease zymogen content in a Factor H enriched composition range from about 3 to about 11. Suitable conductivities for the methods described above range from about 0.1 mS/cm to about 100 mS/cm. Suitable temperatures for performing the methods described above range from about −10° C. to about 90° C. Finely divided silicon dioxide may be used at a final concentration ranging from about 0.01 g/g protein to about 10 g/g protein. Finally, Factor H compositions may vary in concentration from about 0.001 mg/mL to about 100 mg/mL.

In one embodiment, the solution condition under which the Factor H is eluted from the SiO$_2$ and a significant fraction of the serine protease or serine protease zymogen remains bound comprises a pH between about 5.0 and about 11.0. In another embodiment, the pH is between about 6.0 and about 1.0. In another embodiment, the pH is between about 7.0 and about 9.0. In another embodiment, the pH is between about 7.5 and about 8.5. In yet another embodiment, the pH is between about 7.0 and about 8.0.

In a particular embodiment, the solution condition under which the Factor H is eluted from the SiO$_2$ and a significant fraction of the serine protease or serine protease zymogen remains bound comprises a pH of about 7.0. In another specific embodiment, the pH is about 7.5. In another embodiment, the pH is about 8.0. In yet other embodiments, the pH is about 3.0 or about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, or 11.0.

In one embodiment, the solution condition under which the Factor H is eluted from the SiO$_2$ and a significant fraction of the serine protease or serine protease zymogen remains bound comprises a pH of at least 6.0. In another embodiment, the pH is at least 6.5. In another embodiment, the pH is at least 7.0. In yet another embodiment, the pH is at least 7.5. In yet other embodiments, the pH of the solution is at least 3.0 or at least 3.5, 4.0, 4.5, 5.0, 5.5, 6.0, 6.5, 7.0, 7.5, 8.0, 8.5, 9.0, 9.5, 10.0, 10.5, or higher.

In another embodiment, of any of the methods described above, the solution condition under which the Factor H is eluted from the SiO$_2$ and a significant fraction of the serine protease or serine protease zymogen remains bound comprises a pH of no greater than about 11.0. In another embodiment, the pH is no greater about 10.0. In another embodiment, the pH is no greater about 9.0. In another embodiment, the pH is no greater about 8.0. In yet other embodiments, the pH is no greater than about 11.0, or 10.5, 10.0, 9.5, 9.0, 8.5, 8.0, 7.5, 7.0, 6.5, 6.0, 5.5, 5.0, 4.5, 4.0, 3.5, or lower.

In one embodiment, the solution condition under which the Factor H is eluted from the SiO$_2$ and a significant fraction of the serine protease or serine protease zymogen remains bound comprises a conductivity of no more than about 20 mS/cm. In another embodiment, the conductivity is no more than about 10 mS/cm. In yet other embodiments, the conductivity of the solution condition is no more than about 20 mS/cm, or no more than about 19 mS/cm, 18 mS/cm, 17 mS/cm, 16 mS/cm, 15 mS/cm, 14 mS/cm, 13 mS/cm, 12 mS/cm, 11 mS/cm, 10 mS/cm, 9 mS/cm, 8 mS/cm, 7 mS/cm, 6 mS/cm, 5 mS/cm, 4 mS/cm, 3 mS/cm, 2 mS/cm, or less.

In one embodiment, the solution condition under which the serine protease or serine protease zymogen is eluted from the SiO$_2$ and a significant fraction of the Factor H remains bound comprises a conductivity between about 2 mS/cm and about 20 mS/cm. In another embodiment, the conductivity is between about 2 mS/cm and about 10 mS/cm. In another embodiment, the conductivity is between about 20 mS/cm and about 6 mS/cm. In yet another embodiment, the conductivity is between about 10 mS/cm and about 6 mS/cm.

As shown in Example 5 and illustrated in FIG. 3, it was found that the use of solution conditions having a pH greater than 6.0 (e.g., 7.5) and decreasing conductivity (e.g., less than 20 mS/cm), results in increased elution of Factor H from $SiO_2$, and decreased elution of serine proteases and/or serine protease zymogens from $SiO_2$. Advantageously, these findings can be used to provide methods for reducing the levels of serine protease and serine protease zymogen present in Factor H compositions. In a particular embodiment of the methods described above, the solution condition under which the Factor H is eluted from the $SiO_2$ and a significant fraction of the serine protease or serine protease zymogen remains bound comprises a conductivity of at no more than about 20 mS/cm and a pH of at least 7.0. In another particular embodiment, the solution condition comprises a conductivity of no more than about 10 mS/cm and a pH of at least 7.5. In another embodiment, the solution condition comprises a conductivity between about 10 mS/cm and about 2 mS/cm and a pH of at least 7.0. In yet another embodiment, the solution condition comprises a conductivity between about 10 mS/cm and about 2 mS/cm and a pH of at least 7.5.

4. Preferential Binding of Factor H

In one aspect, the present invention provides a method for preparing a plasma-derived Factor H composition having a reduced amount of a serine protease or a serine protease zymogen, the method comprising (a) contacting a composition containing Factor H and at least one serine protease or serine protease zymogen with finely divided silicon dioxide ($SiO_2$) under conditions suitable to bind the Factor H but not the at least one serine protease or serine protease zymogen; (b) separating the $SiO_2$ from the composition; and (c) eluting the Factor H from the $SiO_2$.

In certain embodiments, a solution condition in which the serine protease or serine protease zymogen does not bind to the $SiO_2$ refers to a condition that preferentially allows Factor H binding to the $SiO_2$, while a substantial fraction of the serine protease or serine protease zymogen remains unbound in the solution. In one embodiment, a substantial fraction refers to at least 10% of the serine protease or serine protease zymogen in the starting composition. In another embodiment, a substantial fraction refers to at least 25% of the serine protease or serine protease zymogen in the starting composition. In another embodiment, a substantial fraction refers to at least 50% of the serine protease or serine protease zymogen in the starting composition. In another embodiment, a substantial fraction refers to at least 75% of the serine protease or serine protease zymogen in the starting composition. In yet other embodiments, a substantial fraction refers to at least 10% of the serine protease or serine protease zymogen in the starting composition, or at least 15, 20, 25, 30, 35, 40, 45, 50, 55, 60, 65, 70, 75, 80, 85, 90, 95, 96, 97, 98, 99, or more of the serine protease or serine protease zymogen in the starting composition.

Solution conditions that may be varied to achieve a desired result from a method described above include, without limitation, the pH of the solution, the conductivity of the solution, the temperature of the solution, the concentration of Factor H in the composition, and the concentration of $SiO_2$ used in the method. Generally, suitable pH ranges for methods of reducing serine protease and/or serine protease zymogen content in a Factor H enriched composition range from about 3 to about 11. Suitable conductivities for the methods described above range from about 0.1 mS/cm to about 100 mS/cm. Suitable temperatures for performing the methods described above range from about –10° C. to about 90° C. Finely divided silicon dioxide may be used at a final concentration ranging from about 0.01 g/g protein to about 10 g/g protein. Finally, Factor H compositions may vary in concentration from about 0.001 mg/mL to about 100 mg/mL.

In one embodiment, the solution condition under which Factor H binds to $SiO_2$ and a significant fraction of the serine protease or serine protease zymogen does not bind comprises a pH between about 5.0 and about 11.0. In another embodiment, the pH is between about 6.0 and about 1.0. In another embodiment, the pH is between about 7.0 and about 9.0. In another embodiment, the pH is between about 7.5 and about 8.5. In yet another embodiment, the pH is between about 7.0 and about 8.0.

In a particular embodiment, the solution condition under which Factor H binds to $SiO_2$ and a significant fraction of the serine protease or serine protease zymogen does not bind comprises a pH of about 7.0. In another specific embodiment, the pH is about 7.5. In another embodiment, the pH is about 8.0. In yet other embodiments, the pH is about 3.0 or about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, or 11.0.

In one embodiment, the solution condition under which Factor H binds to $SiO_2$ and a significant fraction of the serine protease or serine protease zymogen does not bind comprises a pH of at least 6.0. In another embodiment, the pH is at least 6.5. In another embodiment, the pH is at least 7.0. In yet another embodiment, the pH is at least 7.5. In yet other embodiments, the pH of the solution is at least 3.0 or at least 3.5, 4.0, 4.5, 5.0, 5.5, 6.0, 6.5, 7.0, 7.5, 8.0, 8.5, 9.0, 9.5, 10.0, 10.5, or higher.

In another embodiment, of any of the methods described above, the solution condition under which Factor H binds to $SiO_2$ and a significant fraction of the serine protease or serine protease zymogen does not bind comprises a pH of no greater than about 11.0. In another embodiment, the pH is no greater about 10.0. In another embodiment, the pH is no greater about 9.0. In another embodiment, the pH is no greater about 8.0. In yet other embodiments, the pH is no greater than about 11.0, or 10.5, 10.0, 9.5, 9.0, 8.5, 8.0, 7.5, 7.0, 6.5, 6.0, 5.5, 5.0, 4.5, 4.0, 3.5, or lower.

In one embodiment, the solution condition under which Factor H binds to $SiO_2$ and a significant fraction of the serine protease or serine protease zymogen does not bind comprises a conductivity of at least 10 mS/cm. In another embodiment, the conductivity is at least 20 mS/cm. In yet other embodiments, the conductivity of the solution condition is at least 2 mS/cm, or at least 3 mS/cm, 4 mS/cm, 5 mS/cm, 6 mS/cm, 7 mS/cm, 8 mS/cm, 9 mS/cm, 10 mS/cm, 11 mS/cm, 12 mS/cm, 13 mS/cm, 14 mS/cm, 15 mS/cm, 16 mS/cm, 17 mS/cm, 18 mS/cm, 19 mS/cm, 20 mS/cm, 21 mS/cm, 22 mS/cm, 23 mS/cm, 24 mS/cm, 25 mS/cm, 26 mS/cm, 27 mS/cm, 28 mS/cm, 29 mS/cm, 30 mS/cm, 31 mS/cm, 32 mS/cm, 33 mS/cm, 34 mS/cm, 35 mS/cm, 36 mS/cm, 37 mS/cm, 38 mS/cm, 39 mS/cm, 40 mS/cm, 41 mS/cm, 42 mS/cm, 43 mS/cm, 44 mS/cm, 45 mS/cm, 46 mS/cm, 47 mS/cm, 48 mS/cm, 49 mS/cm, 50 mS/cm, 55 mS/cm, 60 mS/cm, 65 mS/cm, 70 mS/cm, 75 mS/cm, 80 mS/cm, 85 mS/cm, 90 mS/cm, 95 mS/cm, 100 mS/cm, or greater.

In one embodiment, the solution condition under which Factor H binds to $SiO_2$ and a significant fraction of the serine protease or serine protease zymogen does not bind comprises a conductivity between about 10 mS/cm and about 100 mS/cm. In another embodiment, the conductivity is between about 10 mS/cm and about 50 mS/cm. In another embodiment, the conductivity is between about 20 mS/cm and about 100 mS/cm. In yet another embodiment, the conductivity is between about 20 mS/cm and about 50 mS/cm.

As shown in Example 5 and illustrated in FIG. 3, it was found that the use of solution conditions having a pH greater than 6.0 (e.g., 7.5) and increasing conductivity (e.g., greater than 6.0 mS/cm), results in a decreased affinity of serine proteases and/or serine protease zymogens for $SiO_2$, and increased affinity of Factor H for $SiO_2$. Advantageously, these findings can be used to provide methods for reducing the levels of serine protease and serine protease zymogen present in Factor H compositions. In a particular embodiment of the methods described above, the solution condition under which Factor H binds to $SiO_2$ and a significant fraction of the serine protease or serine protease zymogen does not bind comprises a conductivity of at least about 10 mS/cm and a pH of at least 7.0. In another particular embodiment, the solution condition comprises a conductivity of at least 10 mS/cm and a pH of at least 7.5. In another embodiment, the solution condition comprises a conductivity of at least 20 mS/cm and a pH of at least 7.0. In yet another embodiment, the solution condition comprises a conductivity of at least 20 mS/cm and a pH of at least 7.5.

5. Preferential Binding of Serine Protease or Serine Protease Zymogen

In one aspect, the present invention provides a method for preparing a plasma-derived Factor H composition having a reduced amount of a serine protease or a serine protease zymogen, the method comprising (a) contacting a composition containing Factor H and at least one serine protease or serine protease zymogen with finely divided silicon dioxide ($SiO_2$) under conditions suitable to bind the serine protease and/or serine protease zymogen but not the Factor H; and (b) separating the $SiO_2$ from the composition.

In certain embodiments, a solution condition in which the Factor H does not bind to the $SiO_2$ refers to a condition that preferentially allows serine protease or serine protease zymogen binding to the $SiO_2$, while a substantial fraction of the Factor H remains unbound in the solution. In one embodiment, a substantial fraction refers to at least 10% of the Factor H in the starting composition. In another embodiment, a substantial fraction refers to at least 25% of the Factor H in the starting composition. In another embodiment, a substantial fraction refers to at least 50% of the Factor H in the starting composition. In another embodiment, a substantial fraction refers to at least 75% of the Factor H in the starting composition. In yet other embodiments, a substantial fraction refers to at least 10% of the Factor H in the starting composition, or at least 15, 20, 25, 30, 35, 40, 45, 50, 55, 60, 65, 70, 75, 80, 85, 90, 95, 96, 97, 98, 99, or more of the Factor H in the starting composition.

Solution conditions that may be varied to achieve a desired result from a method described above include, without limitation, the pH of the solution, the conductivity of the solution, the temperature of the solution, the concentration of Factor H in the composition, and the concentration of $SiO_2$ used in the method. Generally, suitable pH ranges for methods of reducing serine protease and/or serine protease zymogen content in a Factor H enriched composition range from about 3 to about 11. Suitable conductivities for the methods described above range from about 0.1 mS/cm to about 100 mS/cm. Suitable temperatures for performing the methods described above range from about −10° C. to about 90° C. Finely divided silicon dioxide may be used at a final concentration ranging from about 0.01 g/g protein to about 10 g/g protein. Finally, Factor H compositions may vary in concentration from about 0.001 mg/mL to about 100 mg/mL.

In one embodiment, the solution condition under which the serine protease or serine protease zymogen binds to $SiO_2$ and a significant fraction of the Factor H does not bind comprises a pH between about 5.0 and about 11.0. In another embodiment, the pH is between about 6.0 and about 1.0. In another embodiment, the pH is between about 7.0 and about 9.0. In another embodiment, the pH is between about 7.5 and about 8.5. In yet another embodiment, the pH is between about 7.0 and about 8.0.

In a particular embodiment, the solution condition under which the serine protease or serine protease zymogen binds to $SiO_2$ and a significant fraction of the Factor H does not bind comprises a pH of about 7.0. In another specific embodiment, the pH is about 7.5. In another embodiment, the pH is about 8.0. In yet other embodiments, the pH is about 3.0 or about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, or 11.0.

In one embodiment, the solution condition under which the serine protease or serine protease zymogen binds to $SiO_2$ and a significant fraction of the Factor H does not bind comprises a pH of at least 6.0. In another embodiment, the pH is at least 6.5. In another embodiment, the pH is at least 7.0. In yet another embodiment, the pH is at least 7.5. In yet other embodiments, the pH of the solution is at least 3.0 or at least 3.5, 4.0, 4.5, 5.0, 5.5, 6.0, 6.5, 7.0, 7.5, 8.0, 8.5, 9.0, 9.5, 10.0, 10.5, or higher.

In another embodiment, of any of the methods described above, the solution condition under which the serine protease or serine protease zymogen binds to $SiO_2$ and a significant fraction of the Factor H does not bind comprises a pH of no greater than about 11.0. In another embodiment, the pH is no greater about 10.0. In another embodiment, the pH is no greater about 9.0. In another embodiment, the pH is no greater about 8.0. In yet other embodiments, the pH is no greater than about 11.0, or 10.5, 10.0, 9.5, 9.0, 8.5, 8.0, 7.5, 7.0, 6.5, 6.0, 5.5, 5.0, 4.5, 4.0, 3.5, or lower.

In one embodiment, the solution condition under which the serine protease or serine protease zymogen binds to $SiO_2$ and a significant fraction of the Factor H does not bind comprises a conductivity of no more than about 20 mS/cm. In another embodiment, the conductivity is no more than about 10 mS/cm. In yet other embodiments, the conductivity of the solution condition is no more than about 20 mS/cm, or no more than about 19 mS/cm, 18 mS/cm, 17 mS/cm, 16 mS/cm, 15 mS/cm, 14 mS/cm, 13 mS/cm, 12 mS/cm, 11 mS/cm, 10 mS/cm, 9 mS/cm, 8 mS/cm, 7 mS/cm, 6 mS/cm, 5 mS/cm, 4 mS/cm, 3 mS/cm, 2 mS/cm, or less.

In one embodiment, the solution condition under which the serine protease or serine protease zymogen binds to $SiO_2$ and a significant fraction of the Factor H does not bind comprises a conductivity between about 2 mS/cm and about 20 mS/cm. In another embodiment, the conductivity is between about 2 mS/cm and about 10 mS/cm. In another embodiment, the conductivity is between about 20 mS/cm and about 6 mS/cm. In yet another embodiment, the conductivity is between about 10 mS/cm and about 6 mS/cm.

As shown in Example 5 and illustrated in FIG. 3, it was found that the use of solution conditions having a pH greater than 6.0 (e.g., 7.5) and decreasing conductivity (e.g., less than 20 mS/cm), results in increased affinity of Factor H for $SiO_2$, and decreased affinity of serine proteases and/or serine protease zymogens from $SiO_2$. Advantageously, these findings can be used to provide methods for reducing the levels of serine protease and serine protease zymogen present in Factor H compositions. In a particular embodiment of the methods described above, the solution condition under which the serine protease or serine protease zymogen binds to $SiO_2$ and a significant fraction of the Factor H does not bind comprises a conductivity of at no more than about 20 mS/cm and a pH of at least 7.0. In another particular embodiment, the solution condition comprises a conductivity of no more than about 10 mS/cm and a pH of at least 7.5. In another embodiment, the solution condition comprises a conductivity between about 10 mS/cm and about 2 mS/cm and a pH of at least 7.0. In yet another embodiment, the solution condition comprises a conductivity between about 10 mS/cm and about 2 mS/cm and a pH of at least 7.5.

6. Method for Factor H Extraction from a Plasma Precipitate

In one aspect, the present invention provides a method for preparing a Factor H composition, the method comprising the steps of: (a) contacting a suspended plasma precipitate composition containing Factor H and at least one serine protease or serine protease zymogen with finely divided silicon dioxide ($SiO_2$) under conditions suitable to bind the Factor H, (b) washing the $SiO_2$ with a solution comprising a pH between 5.0 and 7.0 and a conductivity of less than 4 mS/cm, and (c) eluting the Factor H from the $SiO_2$ with a solution comprising a pH between 7.0 and 8.0 and a conductivity greater than 10 mS/cm, thereby providing an enriched Factor H composition. In a preferred embodiment, the serine protease or serine protease zymogen is one or more of FXI, FXIa, FXII, and FXIIa. In certain embodiments, the plasma precipitate is a Cohn fraction I precipitate, a Cohn fraction II+III precipitate, a Cohn fraction I+II+III precipitate, a Kistler/Nitschmann Precipitate A, a Kistler/Nitschmann Precipitate B, or an equivalent fraction thereof. In one embodiment, the solution used to wash the $SiO_2$ comprises a pH between 5.5 and 6.5. In a specific embodiment, the solution used to wash the $SiO_2$ comprises a pH of 6.0±0.2. In one embodiment, the solution used to elute Factor H comprises a conductivity of at least 20 mS/cm. In a specific embodiment, the solution used to elute Factor H comprises a conductivity of between 25 mS/cm and 40 mS/cm.

In certain embodiments, the method described above further comprises an enrichment step comprising precipitating at least one impurity from the enriched Factor H composition, wherein Factor H is not co-precipitated. In a specific embodiment, the method comprises the steps of (a) contacting a suspended plasma precipitate composition containing Factor H and at least one serine protease or serine protease zymogen with finely divided silicon dioxide ($SiO_2$) under conditions suitable to bind the Factor H, (b) washing the $SiO_2$ with a solution comprising a pH between 5.0 and 7.0 and a conductivity of less than 4 mS/cm, (c) eluting the Factor H from the $SiO_2$ with a solution comprising a pH between 7.0 and 8.0 and a conductivity greater than 10 mS/cm, and (d) precipitating at least one impurity from the Factor H elution, wherein Factor H is not precipitated, thereby providing an enriched Factor H composition. In a preferred embodiment, the serine protease or serine protease zymogen is one or more of FXI, FXIa, FXII, and FXIIa. In certain embodiments, the plasma precipitate is a Cohn fraction I precipitate, a Cohn fraction II+III precipitate, a Cohn fraction I+II+III precipitate, a Kistler/Nitschmann Precipitate A, a Kistler/Nitschmann Precipitate B, or an equivalent fraction thereof. In one embodiment, the solution used to wash the $SiO_2$ comprises a pH between 5.5 and 6.5. In a specific embodiment, the solution used to wash the $SiO_2$ comprises a pH of 6.0±0.2. In one embodiment, the solution used to elute Factor H comprises a conductivity of at least 20 mS/cm. In a specific embodiment, the solution used to elute Factor H comprises a conductivity of between 25 mS/cm and 40 mS/cm. In one embodiment, the impurity precipitation step is PEG precipitation. In a specific embodiment, the impurity PEG precipitation comprises precipitation with PEG 4000 at a final concentration between 3% and 7%. In a more specific embodiment, the final concentration of PEG 4000 in the impurity precipitation step is 5±0.5%.

In certain embodiments, the methods described above further comprises an enrichment step comprising precipitating Factor H from an enriched Factor H composition. In a specific embodiment, the method comprises the steps of (a) contacting a suspended plasma precipitate composition containing Factor H and at least one serine protease or serine protease zymogen with finely divided silicon dioxide ($SiO_2$) under conditions suitable to bind the Factor H, (b) washing the $SiO_2$ with a solution comprising a pH between 5.0 and 7.0 and a conductivity of less than 4 mS/cm, (c) eluting the Factor H from the $SiO_2$ with a solution comprising a pH between 7.0 and 8.0 and a conductivity greater than 10 mS/cm, (d) precipitating at least one impurity from the Factor H elution, to form a supernatant comprising Factor H, and (e) precipitating Factor H from the supernatant, thereby providing an enriched Factor H composition. In a preferred embodiment, the serine protease or serine protease zymogen is one or more of FXI, FXIa, FXII, and FXIIa. In certain embodiments, the plasma precipitate is a Cohn fraction I precipitate, a Cohn fraction II+III precipitate, a Cohn fraction 1+II+III precipitate, a Kistler/Nitschmann Precipitate A, a Kistler/Nitschmann Precipitate B, or an equivalent fraction thereof. In one embodiment, the solution used to wash the $SiO_2$ comprises a pH between 5.5 and 6.5. In a specific embodiment, the solution used to wash the $SiO_2$ comprises a pH of 6.0±0.2. In one embodiment, the solution used to elute Factor H comprises a conductivity of at least 20 mS/cm. In a specific embodiment, the solution used to elute Factor H comprises a conductivity of between 25 mS/cm and 40 mS/cm. In one embodiment, the impurity precipitation step is PEG precipitation. In a specific embodiment, the impurity PEG precipitation comprises precipitation with PEG 4000 at a final concentration between 3% and 7%. In a more specific embodiment, the final concentration of PEG 4000 in the impurity precipitation step is 5±0.5%. In one embodiment, the Factor H precipitation step is PEG precipitation. In a specific embodiment, the Factor H PEG precipitation comprises precipitation with PEG 4000 at a final concentration between 10% and 15%. In a more specific embodiment, the final concentration of PEG 4000 is 12±0.5% in the Factor H precipitation step.

In certain embodiments, the methods described above further comprises an enrichment step comprising performing anion exchange chromatography with an enriched Factor H composition. In a specific embodiment, the method comprises the steps of (a) contacting a suspended plasma precipitate composition containing Factor H and at least one serine protease or serine protease zymogen with finely divided silicon dioxide (SiO$_2$) under conditions suitable to bind the Factor H, (b) washing the SiO$_2$ with a solution comprising a pH between 5.0 and 7.0 and a conductivity of less than 4 mS/cm, (c) eluting the Factor H from the SiO$_2$ with a solution comprising a pH between 7.0 and 8.0 and a conductivity greater than 10 mS/cm, (d) precipitating at least one impurity from the Factor H elution, to form a supernatant comprising Factor H, (e) precipitating Factor H from the supernatant, (f) re-suspending the precipitate comprising Factor H, (g) binding Factor H present in the re-suspended precipitate to an anion exchange resin, and (h) eluting Factor H from the anion exchange resin, thereby providing an enriched Factor H composition. In a preferred embodiment, the serine protease or serine protease zymogen is one or more of FXI, FXIa, FXII, and FXIIa. In certain embodiments, the plasma precipitate is a Cohn fraction I precipitate, a Cohn fraction II+III precipitate, a Cohn fraction I+II+III precipitate, a Kistler/Nitschmann Precipitate A, a Kistler/Nitschmann Precipitate B, or an equivalent fraction thereof. In one embodiment, the solution used to wash the SiO$_2$ comprises a pH between 5.5 and 6.5. In a specific embodiment, the solution used to wash the SiO$_2$ comprises a pH of 6.0±0.2. In one embodiment, the solution used to elute Factor H comprises a conductivity of at least 20 mS/cm. In a specific embodiment, the solution used to elute Factor H comprises a conductivity of between 25 mS/cm and 40 mS/cm. In one embodiment, the impurity precipitation step is PEG precipitation. In a specific embodiment, the impurity PEG precipitation comprises precipitation with PEG 4000 at a final concentration between 3% and 7%. In a more specific embodiment, the final concentration of PEG 4000 in the impurity precipitation step is 5±0.5%. In one embodiment, the Factor H precipitation step is PEG precipitation. In a specific embodiment, the Factor H PEG precipitation comprises precipitation with PEG 4000 at a final concentration between 10% and 15%. In a more specific embodiment, the final concentration of PEG 4000 is 12±0.5% in the Factor H precipitation step.

In certain embodiments, the methods described above further comprises an enrichment step comprising performing heparin affinity chromatography with an enriched Factor H composition. In a specific embodiment, the method comprises the steps of (a) contacting a suspended plasma precipitate composition containing Factor H and at least one serine protease or serine protease zymogen with finely divided silicon dioxide (SiO$_2$) under conditions suitable to bind the Factor H, (b) washing the SiO$_2$ with a solution comprising a pH between 5.0 and 7.0 and a conductivity of less than 4 mS/cm, (c) eluting the Factor H from the SiO$_2$ with a solution comprising a pH between 7.0 and 8.0 and a conductivity greater than 10 mS/cm, (d) precipitating at least one impurity from the Factor H elution, to form a supernatant comprising Factor H, (e) precipitating Factor H from the supernatant, (f) re-suspending the precipitate comprising Factor H, (g) binding Factor H present in the re-suspended precipitate to an anion exchange resin, (h) eluting Factor H from the anion exchange resin, (i) binding Factor H present in the anion exchange eluate to a heparin affinity resin, and (j) eluting Factor H from the heparin affinity resin, thereby providing an enriched Factor H composition. In a preferred embodiment, the serine protease or serine protease zymogen is one or more of FXI, FXIa, FXII, and FXIIa. In certain embodiments, the plasma precipitate is a Cohn fraction I precipitate, a Cohn fraction II+III precipitate, a Cohn fraction I+II+III precipitate, a Kistler/Nitschmann Precipitate A, a Kistler/Nitschmann Precipitate B, or an equivalent fraction thereof. In one embodiment, the solution used to wash the SiO$_2$ comprises a pH between 5.5 and 6.5. In a specific embodiment, the solution used to wash the SiO$_2$ comprises a pH of 6.0±0.2. In one embodiment, the solution used to elute Factor H comprises a conductivity of at least 20 mS/cm. In a specific embodiment, the solution used to elute Factor H comprises a conductivity of between 25 mS/cm and 40 mS/cm. In one embodiment, the impurity precipitation step is PEG precipitation. In a specific embodiment, the impurity PEG precipitation comprises precipitation with PEG 4000 at a final concentration between 3% and 7%. In a more specific embodiment, the final concentration of PEG 4000 in the impurity precipitation step is 5±0.5%. In one embodiment, the Factor H precipitation step is PEG precipitation. In a specific embodiment, the Factor H PEG precipitation comprises precipitation with PEG 4000 at a final concentration between 10% and 15%. In a more specific embodiment, the final concentration of PEG 4000 is 12±0.5% in the Factor H precipitation step.

In certain embodiments, the methods described above further comprises subjecting a Factor H composition to a dedicated viral removal and/or inactivation step. In a specific embodiment, the method comprises the steps of (a) contacting a suspended plasma precipitate composition containing Factor H and at least one serine protease or serine protease zymogen with finely divided silicon dioxide (SiO$_2$) under conditions suitable to bind the Factor H, (b) washing the SiO$_2$ with a solution comprising a pH between 5.0 and 7.0 and a conductivity of less than 4 mS/cm, (c) eluting the Factor H from the SiO$_2$ with a solution comprising a pH between 7.0 and 8.0 and a conductivity greater than 10 mS/cm, (d) precipitating at least one impurity from the Factor H elution, to form a supernatant comprising Factor H, (e) precipitating Factor H from the supernatant, (f) re-suspending the precipitate comprising Factor H, (g) binding Factor H present in the re-suspended precipitate to an anion exchange resin, (h) eluting Factor H from the anion exchange resin, (i) binding Factor H present in the anion exchange eluate to a heparin affinity resin, (j) eluting Factor H from the heparin affinity resin, and (k) performing a dedicated viral removal and/or inactivation step selected from nanofiltration, solvent/detergent (S/D) treatment, heat treatment, and incubation at low pH, thereby providing an enriched Factor H composition. In a preferred embodiment, the serine protease or serine protease zymogen is one or more of FXI, FXIa, FXII, and FXIIa. In certain embodiments, the plasma precipitate is a Cohn fraction I precipitate, a Cohn fraction II+III precipitate, a Cohn fraction I+II+III precipitate, a Kistler/Nitschmann Precipitate A, a Kistler/Nitschmann Precipitate B, or an equivalent fraction thereof. In one embodiment, the solution used to wash the SiO$_2$ comprises a pH between 5.5 and 6.5. In a specific embodiment, the solution used to wash the SiO$_2$ comprises a pH of 6.0±0.2. In one embodiment, the solution used to elute Factor H comprises a conductivity of at least 20 mS/cm. In a specific embodiment, the solution used to elute Factor H comprises a conductivity of between 25 mS/cm and 40 mS/cm. In one embodiment, the impurity precipitation step is PEG precipitation. In a specific embodiment, the impurity PEG precipitation comprises precipitation with PEG 4000 at a final concentration between 3% and 7%. In a more specific embodiment, the final concentration of PEG 4000 in the impurity precipitation step is 5±0.5%. In one embodiment, the Factor H precipitation step is PEG precipitation. In a specific embodiment, the Factor H PEG precipitation comprises precipitation with PEG 4000 at a final concentration between 10% and 15%. In a more specific embodiment, the final concentration of PEG 4000 is 12±0.5% in the Factor H precipitation step.

In certain embodiments, the methods described above further comprises a step of concentrating an enriched Factor H composition by ultrafiltration/diafiltration. In a specific embodiment, the method comprises the steps of (a) contacting a suspended plasma precipitate composition containing Factor H and at least one serine protease or serine protease zymogen with finely divided silicon dioxide ($SiO_2$) under conditions suitable to bind the Factor H, (b) washing the $SiO_2$ with a solution comprising a pH between 5.0 and 7.0 and a conductivity of less than 4 mS/cm, (c) eluting the Factor H from the $SiO_2$ with a solution comprising a pH between 7.0 and 8.0 and a conductivity greater than 10 mS/cm, (d) precipitating at least one impurity from the Factor H elution, to form a supernatant comprising Factor H, (e) precipitating Factor H from the supernatant, (f) re-suspending the precipitate comprising Factor H, (g) binding Factor H present in the re-suspended precipitate to an anion exchange resin, (h) eluting Factor H from the anion exchange resin, (i) binding Factor H present in the anion exchange eluate to a heparin affinity resin, (j) eluting Factor H from the heparin affinity resin, (k) performing a dedicated viral removal and/or inactivation step selected from nano-filtration, solvent/detergent (S/D) treatment, heat treatment, and incubation at low pH, and (l) concentrating Factor H by ultrafiltration/diafiltration, thereby providing an enriched Factor H composition. In a preferred embodiment, the serine protease or serine protease zymogen is one or more of FXI, FXIa, FXII, and FXIIa. In certain embodiments, the plasma precipitate is a Cohn fraction I precipitate, a Cohn fraction II+III precipitate, a Cohn fraction I+II+III precipitate, a Kistler/Nitschmann Precipitate A, a Kistler/Nitschmann Precipitate B, or an equivalent fraction thereof. In one embodiment, the solution used to wash the $SiO_2$ comprises a pH between 5.5 and 6.5. In a specific embodiment, the solution used to wash the $SiO_2$ comprises a pH of 6.0±0.2. In one embodiment, the solution used to elute Factor H comprises a conductivity of at least 20 mS/cm. In a specific embodiment, the solution used to elute Factor H comprises a conductivity of between 25 mS/cm and 40 mS/cm. In one embodiment, the impurity precipitation step is PEG precipitation. In a specific embodiment, the impurity PEG precipitation comprises precipitation with PEG 4000 at a final concentration between 3% and 7%. In a more specific embodiment, the final concentration of PEG 4000 in the impurity precipitation step is 5±0.5%. In one embodiment, the Factor H precipitation step is PEG precipitation. In a specific embodiment, the Factor H PEG precipitation comprises precipitation with PEG 4000 at a final concentration between 10% and 15%. In a more specific embodiment, the final concentration of PEG 4000 is 12±0.5% in the Factor H precipitation step.

C. Inter-alpha-Trypsin Inhibitor (IαI)

In one embodiment, the present invention provides a method for reducing the amount of a serine protease or a serine protease zymogen in a plasma-derived IαI composition. In one specific embodiment, the method comprises the steps of: (a) contacting the IαI composition with finely divided silicon dioxide ($SiO_2$) under conditions suitable to bind at least one serine protease or serine protease zymogen; and (b) separating the $SiO_2$ from the IαI composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII).

In one embodiment, the method further comprises the step of performing a first IαI protein enrichment step to form a first enriched IαI composition, prior to contacting the composition with finely divided silicon dioxide ($SiO_2$). In certain embodiments, the first IαI protein enrichment step is selected from a protein precipitation step (e.g., an alcohol fractionation step), an ultrafiltration/diafiltration step, and a chromatographic step.

In certain embodiments, the methods described above further comprises the step of performing a second IαI protein enrichment step to form a second enriched IαI composition, prior to contacting the composition with finely divided silicon dioxide ($SiO_2$). In certain embodiments, the first IαI protein enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived IαI composition, the method comprises the steps of: (a) performing a first IαI enrichment step to form a first enriched plasma-derived IαI composition; (b) performing a second IαI enrichment step to form a second enriched plasma-derived IαI composition; (c) contacting the second enriched composition with finely divided silicon dioxide ($SiO_2$) under conditions suitable to bind at least one serine protease or serine protease zymogen; and (d) separating the $SiO_2$ from the composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

In certain embodiments, the methods described above further comprises the step of performing an IαI enrichment step after contacting the composition with finely divided silicon dioxide ($SiO_2$). In certain embodiments, the IαI enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived IαI composition the method comprises the steps of: (a) performing a first IαI enrichment step to form a first enriched plasma-derived IαI composition; (b) contacting the first enriched composition with finely divided silicon dioxide ($SiO_2$) under conditions suitable to bind at least one serine protease or serine protease zymogen; (c) separating the $SiO_2$ from the composition to remove the bound serine protease or serine protease zymogen; and (d) performing a second IαI enrichment step to form a second enriched plasma-derived IαI composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

Likewise, in one embodiment, the invention provides a method for reducing the amount of a serine protease or a serine protease zymogen in a plasma-derived IαI composition, the method comprising the steps of: (a) performing a first IαI enrichment step to form a first enriched plasma-derived IαI composition; (b) performing a second IαI enrichment step to form a second enriched plasma-derived IαI composition; (c) contacting the second enriched composition with finely divided silicon dioxide (SiO$_2$) under conditions suitable to bind at least one serine protease or serine protease zymogen; (d) separating the SiO$_2$ from the composition to remove the bound serine protease or serine protease zymogen; and (e) performing a third IαI enrichment step to form a third enriched plasma-derived IαI composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 101 to Var. 1100, found in Table 2, Table 3, Table 4, Table 5, Table 6, Table 7, Table 8, Table 9, Table 10, or Table 11.

1. Co-Binding and Differential Elution

In one aspect, the present invention provides a method for preparing a plasma-derived IαI composition having a reduced amount of a serine protease or a serine protease zymogen, the method comprising co-extracting IαI and a serine protease and/or serine protease zymogen from a composition derived from pooled plasma by binding the proteins to finely divided silicon dioxide (SiO$_2$), eluting the serine protease and/or serine protease zymogen from the SiO$_2$ under a first solution condition, and subsequently eluting IαI from the SiO$_2$ under a second solution condition. In a preferred embodiment, the starting composition is a re-suspended Fraction II+III precipitate or equivalent precipitate thereof.

In a specific embodiment, the method comprises the steps of: (a) contacting a composition containing IαI and at least one serine protease or serine protease zymogen with finely divided silicon dioxide (SiO$_2$) under conditions suitable to bind the IαI and at least one serine protease or serine protease zymogen; (b) separating the SiO$_2$ from the composition; (c) eluting the serine protease or serine protease zymogen from the SiO$_2$ under a solution condition in which the IαI remains bound; and (d) eluting the IαI from the SiO$_2$.

In certain embodiments, a solution condition in which the IαI remains bound refers to a condition that preferentially elutes the serine protease or serine protease zymogen, while a substantial fraction of IαI remains bound to the SiO$_2$. In one embodiment, a substantial fraction refers to at least 10% of the IαI bound to the SiO$_2$. In another embodiment, a substantial fraction refers to at least 25% of the IαI bound to the SiO$_2$. In another embodiment, a substantial fraction refers to at least 50% of the IαI bound to the SiO$_2$. In another embodiment, a substantial fraction refers to at least 75% of the IαI bound to the SiO$_2$. In yet other embodiments, a substantial fraction refers to at least 10% of the IαI bound to the SiO$_2$, or at least 15, 20, 25, 30, 35, 40, 45, 50, 55, 60, 65, 70, 75, 80, 85, 90, 95, 96, 97, 98, 99, or more of the IαI bound to the SiO$_2$.

In certain embodiments, differential elution of the serine protease or serine protease zymogen and IαI is achieved by sequentially contacting (i.e., step-wise elution) the SiO$_2$ with a first solution condition (e.g., a first elution buffer) suitable to elute the majority of the serine protease or serine protease zymogen but not a substantial fraction of the bound IαI, and a second solution condition (e.g., a second elution buffer) suitable to elute the substantial fraction of bound IαI from the SiO$_2$.

In other embodiments, differential elution of the serine protease or serine protease zymogen and IαI is achieved by gradually changing the solution conditions (i.e., with an elution gradient) from a first solution condition suitable to elute the majority of the serine protease or serine protease zymogen but not a substantial fraction of the bound IαI to a second solution condition suitable to elute the substantial fraction of bound IαI from the SiO$_2$. In this fashion, the serine protease or serine protease zymogen and IαI content eluted off of the SiO$_2$ may be partially overlapping. By fractionating the elution and characterizing the individual fractions, a IαI pool may be created from fractions having high IαI content and low serine protease or serine protease zymogen content.

2. Co-Binding and Preferential IαI Elution

In one aspect, the present invention provides a method for preparing a plasma-derived IαI composition having a reduced amount of a serine protease or a serine protease zymogen, the method comprising co-extracting IαI and a serine protease and/or serine protease zymogen from a composition derived from pooled plasma by binding the proteins to finely divided silicon dioxide (SiO$_2$), and eluting the IαI from the SiO$_2$ under conditions in which a substantial fraction of the bound serine protease and/or serine protease zymogen remains bound to the SiO$_2$. In a preferred embodiment, the starting composition is a re-suspended Fraction II+III precipitate or equivalent precipitate thereof.

In a specific embodiment, the method comprises the steps of: (a) contacting a composition containing IαI and at least one serine protease or serine protease zymogen with finely divided silicon dioxide (SiO$_2$) under conditions suitable to bind the IαI and at least one serine protease or serine protease zymogen; (b) separating the SiO$_2$ from the composition; and (c) eluting the IαI from the SiO$_2$ under a solution condition in which the serine protease or serine protease zymogen remains bound.

In certain embodiments, a solution condition in which the serine protease or serine protease zymogen remains bound refers to a condition that preferentially elutes the IαI, while a substantial fraction of the serine protease or serine protease zymogen remains bound to the SiO$_2$. In one embodiment, a substantial fraction refers to at least 10% of the serine protease or serine protease zymogen bound to the SiO$_2$. In another embodiment, a substantial fraction refers to at least 25% of the serine protease or serine protease zymogen bound to the SiO$_2$. In another embodiment, a substantial fraction refers to at least 50% of the serine protease or serine protease zymogen bound to the SiO$_2$. In another embodiment, a substantial fraction refers to at least 75% of the serine protease or serine protease zymogen bound to the SiO$_2$. In yet other embodiments, a substantial fraction refers to at least 10% of the serine protease or serine protease zymogen bound to the SiO$_2$, or at least 15, 20, 25, 30, 35, 40, 45, 50, 55, 60, 65, 70, 75, 80, 85, 90, 95, 96, 97, 98, 99, or more of the serine protease or serine protease zymogen bound to the SiO$_2$.

3. Preferential Binding of IαI

In one aspect, the present invention provides a method for preparing a plasma-derived IαI composition having a reduced amount of a serine protease or a serine protease zymogen, the method comprising (a) contacting a composition containing IαI and at least one serine protease or serine protease zymogen with finely divided silicon dioxide (SiO$_2$) under conditions suitable to bind the IαI but not the at least one serine protease or serine protease zymogen; (b) separating the SiO$_2$ from the composition; and (c) eluting the IαI from the SiO$_2$.

In certain embodiments, a solution condition in which the serine protease or serine protease zymogen does not bind to the SiO$_2$ refers to a condition that preferentially allows IαI binding to the SiO$_2$, while a substantial fraction of the serine protease or serine protease zymogen remains unbound in the solution. In one embodiment, a substantial fraction refers to at least 10% of the serine protease or serine protease zymogen in the starting composition. In another embodiment, a substantial fraction refers to at least 25% of the serine protease or serine protease zymogen in the starting composition. In another embodiment, a substantial fraction refers to at least 50% of the serine protease or serine protease zymogen in the starting composition. In another embodiment, a substantial fraction refers to at least 75% of the serine protease or serine protease zymogen in the starting composition. In yet other embodiments, a substantial fraction refers to at least 10% of the serine protease or serine protease zymogen in the starting composition, or at least 15, 20, 25, 30, 35, 40, 45, 50, 55, 60, 65, 70, 75, 80, 85, 90, 95, 96, 97, 98, 99, or more of the serine protease or serine protease zymogen in the starting composition.

4. Preferential Binding of Serine Protease or Serine Protease Zymogen

In one aspect, the present invention provides a method for preparing a plasma-derived IαI composition having a reduced amount of a serine protease or a serine protease zymogen, the method comprising (a) contacting a composition containing IαI and at least one serine protease or serine protease zymogen with finely divided silicon dioxide ($SiO_2$) under conditions suitable to bind the serine protease and/or serine protease zymogen but not the IαI; and (b) separating the $SiO_2$ from the composition.

In certain embodiments, a solution condition in which the IαI does not bind to the $SiO_2$ refers to a condition that preferentially allows serine protease or serine protease zymogen binding to the $SiO_2$, while a substantial fraction of the IαI remains unbound in the solution. In one embodiment, a substantial fraction refers to at least 10% of the IαI in the starting composition. In another embodiment, a substantial fraction refers to at least 25% of the IαI in the starting composition. In another embodiment, a substantial fraction refers to at least 50% of the IαI in the starting composition. In another embodiment, a substantial fraction refers to at least 75% of the IαI in the starting composition. In yet other embodiments, a substantial fraction refers to at least 10% of the IαI in the starting composition, or at least 15, 20, 25, 30, 35, 40, 45, 50, 55, 60, 65, 70, 75, 80, 85, 90, 95, 96, 97, 98, 99, or more of the IαI in the starting composition.

D. Alpha-1-Antitrypsin (A1PI)

In one embodiment, the present invention provides a method for reducing the amount of a serine protease or a serine protease zymogen in a plasma-derived alpha-1-antitrypsin (A1PI) composition. In one specific embodiment, the method comprises the steps of: (a) contacting an A1PI composition with finely divided silicon dioxide ($SiO_2$) under conditions suitable to bind at least one serine protease or serine protease zymogen; and (b) separating the $SiO_2$ from the A1PI composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII).

In one embodiment, the method further comprises the step of performing a first A1PI protein enrichment step to form a first enriched A1PI composition, prior to contacting the composition with finely divided silicon dioxide ($SiO_2$). In certain embodiments, the first A1PI protein enrichment step is selected from a protein precipitation step (e.g., an alcohol fractionation step), an ultrafiltration/diafiltration step, and a chromatographic step. In certain embodiments, the methods described above further comprises the step of performing a second A1PI protein enrichment step to form a second enriched A1PI composition, prior to contacting the composition with finely divided silicon dioxide ($SiO_2$). In certain embodiments, the first A1PI protein enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived A1PI composition, the method comprises the steps of: (a) performing a first A1PI enrichment step to form a first enriched plasma-derived A1PI composition; (b) performing a second A1PI enrichment step to form a second enriched plasma-derived A1PI composition; (c) contacting the second enriched composition with finely divided silicon dioxide ($SiO_2$) under conditions suitable to bind at least one serine protease or serine protease zymogen; and (d) separating the $SiO_2$ from the composition to remove the bound serine protease or serine protease zymogen. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

In certain embodiments, the methods described above further comprises the step of performing an A1PI enrichment step after contacting the composition with finely divided silicon dioxide ($SiO_2$). In certain embodiments, the A1PI enrichment step is selected from a protein precipitation step (e.g., an alcohol fractionation step), an ultrafiltration/diafiltration step, and a chromatographic step.

Accordingly, in one embodiment, the invention provides a method for reducing the amount of a serine protease or a serine protease zymogen in a plasma-derived A1PI composition the method comprises the steps of: (a) performing a first A1PI enrichment step to form a first enriched plasma-derived A1PI composition; (b) contacting the first enriched composition with finely divided silicon dioxide ($SiO_2$) under conditions suitable to bind at least one serine protease or serine protease zymogen; (c) separating the $SiO_2$ from the composition to remove the bound serine protease or serine protease zymogen; and (d) performing a second A1PI enrichment step to form a second enriched plasma-derived A1PI composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var. 1 to Var. 100, found in Table 1.

Likewise, in one embodiment, the invention provides a method for reducing the amount of a serine protease or a serine protease zymogen in a plasma-derived A1PI composition, the method comprising the steps of: (a) performing a first A1PI enrichment step to form a first enriched plasma-derived A1PI composition; (b) performing a second A1PI enrichment step to form a second enriched plasma-derived Ig composition; (c) contacting the second enriched composition with finely divided silicon dioxide ($SiO_2$) under conditions suitable to bind at least one serine protease or serine protease zymogen; (d) separating the $SiO_2$ from the composition to remove the bound serine protease or serine protease zymogen; and (e) performing a third A1PI enrichment step to form a third enriched plasma-derived A1PI composition. In a preferred embodiment, the serine protease or serine protease zymogen is Factor XIa (FXIa), Factor XIIa (FXIIa), Factor XI (FXI), and/or Factor XII (FXII). In certain embodiments, the combination of first and second enrichment steps is selected from any one of variations Var.

101 to Var. 1100, found in Table 2, Table 3, Table 4, Table 5, Table 6, Table 7, Table 8, Table 9, Table 10, or Table 11.

In a particular embodiment, the A1PI composition is a manufacturing intermediate. For example, in certain embodiments, the A1PI composition is a manufacturing intermediate from a Cohn fractionation procedure (J. Am. Chem. Soc., 1946, 68(3): 459-475; J. Am. Chem. Soc. 72:465-474 (1950)), an Oncley fractionation procedure (J. Am. Chem. Soc., 1949, 71(2): 541-550), a Kistler/Nitschmann fractionation procedure (Vox Sang. 7:414-424 (1962)), a purification procedure disclosed in U.S. Pat. No. 6,974,792 or 7,807,435, modified procedures thereof, and similar or equivalent purification procedures known in the art. The aforementioned references are hereby incorporated by reference in their entireties for all purposes.

For example, a number of production methods for A1PI are known which comprise the fractionated precipitation of plasma with polyethylene glycol 4000, but also the processing of various plasma fractions (Cohn fraction IV-1-precipitate or Kistler and Nitschmann Supernatant A or A+1) (Feldman and Winkelman, Blood Separation and Plasma Fractionation (1991), Wiley-Liss, Inc., pp. 341-383). In more elaborate purifications, the respective blood fractions have been purified by means of DEAE cellulose, e.g. (Basis et al. (Vopr. Med. Khim. 33 (1) (1987), 54-59)), treated with affinity chromatographic materials or with cation exchanger chromatographic materials (EP 0 698 615 A1). U.S. Pat. No. 6,974,792 describes a purification process yielding A1PI with high specific activity utilizing a Cohn fraction V precipitate. U.S. Pat. No. 7,807,435 describes a purification process providing higher yields of A1PI, utilizing a Cohn fraction IV-1 and/or fraction IV-4 precipitate.

In one particular embodiment, the A1PI composition is a cryo-poor Cohn pool. In another particular embodiment, the A1PI composition is a re-suspended Cohn Fraction V precipitate or equivalent fraction thereof. In another particular embodiment, the A1PI composition is a re-suspended Cohn Fraction IV-1 precipitate, or equivalent fraction thereof. In another particular embodiment, the A1PI composition is a re-suspended Cohn Fraction IV-4 precipitate, or equivalent fraction thereof. In another particular embodiment, the A1PI composition is a Kistler/Nitschmann Supernatant A, or equivalent fraction thereof.

Generally, serine protease and/or serine protease zymogen removal from A1PI compositions can be achieved by treating the A1PI-containing composition with finely divided silicon dioxide ($SiO_2$) under pH and conductivity solution conditions in which the serine protease and/or serine protease zymogen binds to the $SiO_2$.

In one embodiment, the process improvements are realized by inclusion of a fumed silica treatment prior to filtration or centrifugal clarification of a plasma precipitate comprising A1PI. In one embodiment, the $SiO_2$ treatment step comprises addition of finely divided silica dioxide particles (e.g., fumed silica, Aerosil®) followed by a 40 minute to 16 hour incubation period during which the suspension is constantly mixed. In certain embodiments, the incubation period will be between about 50 minutes and about 70 minutes, or about 20, 25, 30, 35, 40, 45, 50, 55, 60, 65, 70, 75, 80, or more minutes. In other embodiments, the incubation period will be at least 1 hour, or at least 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, or more hours. In a particular embodiment, the incubation period will be at least 15 hours. Generally, the treatment will be performed at between about 0° C. and about 25° C., or between about 2° C. and about 8° C. In certain embodiments, the treatment may be performed at about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., or 25° C. In a particular embodiment, the treatment is performed at between about 2° C. and about 25° C. In a specific embodiment, the process improvements are realized by inclusion of a fumed silica treatment, which reduces the levels of FXI, FXIa, FXII, and FXIIa in the immunoglobulin preparation.

In certain embodiments, fumed silica is added at a concentration of between about 20 g/kg precipitate and about 100 g/kg precipitate. In certain embodiments, the fumed silica may be added at a concentration of about 20 g/kg precipitate, or about 25, 30, 35, 40, 45, 50, 55, 60, 65, 70, 75, 80, 85, 90, 95, or 100 g/kg precipitate. In one specific embodiment, fumed silica (e.g., Aerosil 380 or equivalent) is added to the precipitate re-suspension to a final concentration of about 40 g/kg precipitate.

In certain embodiments, $SiO_2$ is added to an A1PI composition at a concentration between about 0.01 g/g protein and about 10 g/g protein. In another embodiment, $SiO_2$ is added to an A1PI composition at a concentration between about 0.01 g/g protein and about 5 g/g protein. In another embodiment, $SiO_2$ is added to an A1PI composition at a concentration between about 0.02 g/g protein and about 4 g/g protein. In one embodiment, $SiO_2$ is added to an A1PI composition at a final concentration of at least 0.1 g per gram total protein. In another specific embodiment, fumed silica is added at a concentration of at least 0.2 g per gram total protein. In another specific embodiment, fumed silica is added at a concentration of at least 0.25 g per gram total protein. In other specific embodiments, fumed silica is added at a concentration of at least 1 g per gram total protein. In another specific embodiment, fumed silica is added at a concentration of at least 2 g per gram total protein. In another specific embodiment, fumed silica is added at a concentration of at least 2.5 g per gram total protein. In yet other specific embodiments, finely divided silicon dioxide is added at a concentration of at least 0.01 g/g total protein or at least 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, or more g/g total protein.

In certain embodiments, filter aid, for example Celpure C300 (Celpure) or Hyflo-Supper-Cel (World Minerals), will be added after the silica dioxide treatment, to facilitate depth filtration. Filter aid can be added at a final concentration of from about 0.01 kg/kg precipitate to about 1.0 kg/kg precipitate, or from about 0.02 kg/kg precipitate to about 0.8 kg/kg precipitate, or from about 0.03 kg/kg precipitate to about 0.7 kg/kg precipitate. In certain embodiments, the filter aid will be added at a final concentration of at least 0.01 kg/kg precipitate, or at least 0.02 kg/kg, 0.03 kg/kg, 0.04 kg/kg, 0.05 kg/kg, 0.06 kg/kg, 0.07 kg/kg, 0.08 kg/kg, 0.09 kg/kg, 0.1 kg/kg, 0.2 kg/kg, 0.3 kg/kg, 0.4 kg/kg, 0.5 kg/kg, 0.6 kg/kg, 0.7 kg/kg, 0.8 kg/kg, 0.9 kg/kg, or 1.0 kg/kg precipitate. In certain embodiments, the filter aid will be added at a final concentration of about 0.01 kg/kg precipitate, or about 0.02 kg/kg, 0.03 kg/kg, 0.04 kg/kg, 0.05 kg/kg, 0.06 kg/kg, 0.07 kg/kg, 0.08 kg/kg, 0.09 kg/kg, 0.1 kg/kg, 0.2 kg/kg, 0.3 kg/kg, 0.4 kg/kg, 0.5 kg/kg, 0.6 kg/kg, 0.7 kg/kg, 0.8 kg/kg, 0.9 kg/kg, or 1.0 kg/kg precipitate.

Accordingly, in one embodiment, the present invention provides a method for reducing the amount of a serine protease or a serine protease zymogen in a plasma-derived A1PI composition, the method comprising contacting the composition with SiO$_2$ at a pH between about 4.0 and about 7.0 to bind a serine protease or a serine protease zymogen. In another embodiment, the method comprises contacting the composition with SiO$_2$ at a pH between about 4.0 and about 6.5. In another embodiment, the method comprises contacting the composition with SiO$_2$ at a pH between about 4.0 and about 6.0. In another embodiment, the method comprises contacting the composition with SiO$_2$ at a pH between about 4.0 and about 5.5. In another embodiment, the method comprises contacting the composition with SiO$_2$ at a pH between about 4.0 and about 5.0. In another embodiment, the method comprises contacting the composition with SiO$_2$ at a pH between about 4.5 and about 7.0. In another embodiment, the method comprises contacting the composition with SiO$_2$ at a pH between about 4.5 and about 6.5. In another embodiment, the method comprises contacting the composition with SiO$_2$ at a pH between about 4.5 and about 6.0. In another embodiment, the method comprises contacting the composition with SiO$_2$ at a pH between about 4.5 and about 5.5. In another embodiment, the method comprises contacting the composition with SiO$_2$ at a pH between about 4.5 and about 5.0. In another embodiment, the method comprises contacting the composition with SiO$_2$ at a pH between about 5.0 and about 7.0. In another embodiment, the method comprises contacting the composition with SiO$_2$ at a pH between about 5.0 and about 6.5. In another embodiment, the method comprises contacting the composition with SiO$_2$ at a pH between about 5.0 and about 6.0. In another embodiment, the method comprises contacting the composition with SiO$_2$ at a pH between about 5.0 and about 5.5. In yet another embodiment, the method comprises contacting the composition with SiO$_2$ at a pH between about 4.6 and about 5.6. In another embodiment, the method comprises contacting the composition with SiO$_2$ at a pH between about 4.7 and about 5.5. In another embodiment, the method comprises contacting the composition with SiO$_2$ at a pH between about 4.8 and about 5.4. In another embodiment, the method comprises contacting the composition with SiO$_2$ at a pH between about 4.9 and about 5.3. In another embodiment, the method comprises contacting the composition with SiO$_2$ at a pH between about 5.0 and about 5.2. In another embodiment, the method comprises contacting the composition with SiO$_2$ at a pH of about 5.1. In other embodiments, the method comprises contacting the composition with SiO$_2$ at a pH of about 4.0 or about 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or no more than 7.0. In yet other embodiments, the method comprises contacting the composition with SiO$_2$ at a pH of no more than 4.0 or no more than 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or no more than 7.0.

In one embodiment, the present invention provides a method for reducing the amount of a serine protease or a serine protease zymogen in a plasma-derived A1PI composition, the method comprising contacting the composition with SiO$_2$ at an ionic strength between about 0.1 mS/cm and about 2.0 mS/cm to bind a serine protease or a serine protease zymogen. In another embodiment, the method comprises contacting the composition with SiO$_2$ at an ionic strength between about 0.1 mS/cm and about 1.9 mS/cm. In another embodiment, the method comprises contacting the composition with SiO$_2$ at an ionic strength between about 0.1 mS/cm and about 1.8 mS/cm. In another embodiment, the method comprises contacting the composition with SiO$_2$ at an ionic strength between about 0.1 mS/cm and about 1.7 mS/cm. In another embodiment, the method comprises contacting the composition with SiO$_2$ at an ionic strength between about 0.1 mS/cm and about 1.6 mS/cm. In another embodiment, the method comprises contacting the composition with SiO$_2$ at an ionic strength between about 0.1 mS/cm and about 1.5 mS/cm. In another embodiment, the method comprises contacting the composition with SiO$_2$ at an ionic strength between about 0.1 mS/cm and about 1.4 mS/cm. In another embodiment, the method comprises contacting the composition with SiO$_2$ at an ionic strength between about 0.1 mS/cm and about 1.3 mS/cm. In another embodiment, the method comprises contacting the composition with SiO$_2$ at an ionic strength between about 0.1 mS/cm and about 1.2 mS/cm. In another embodiment, the method comprises contacting the composition with SiO$_2$ at an ionic strength between about 0.1 mS/cm and about 1.1 mS/cm. In another embodiment, the method comprises contacting the composition with SiO$_2$ at an ionic strength between about 0.1 mS/cm and about 1.0 mS/cm. In another embodiment, the method comprises contacting the composition with SiO$_2$ at an ionic strength between about 0.1 mS/cm and about 0.9 mS/cm. In another embodiment, the method comprises contacting the composition with SiO$_2$ at an ionic strength between about 0.1 mS/cm and about 0.8 mS/cm. In another embodiment, the method comprises contacting the composition with SiO$_2$ at an ionic strength between about 0.2 mS/cm and about 1.0 mS/cm. In another embodiment, the method comprises contacting the composition with SiO$_2$ at an ionic strength between about 0.3 mS/cm and about 1.0 mS/cm. In another embodiment, the method comprises contacting the composition with SiO$_2$ at an ionic strength between about 0.1 mS/cm and about 0.4 mS/cm. In another embodiment, the method comprises contacting the composition with SiO$_2$ at an ionic strength between about 0.5 mS/cm and about 1.0 mS/cm. In another embodiment, the method comprises contacting the composition with SiO$_2$ at an ionic strength between about 0.6 mS/cm and about 1.0 mS/cm. In another embodiment, the method comprises contacting the composition with SiO$_2$ at an ionic strength between about 0.7 mS/cm and about 0.9 mS/cm. In another embodiment, the method comprises contacting the composition with SiO$_2$ at an ionic strength of about 0.8 mS/cm. In other embodiments, the method comprises contacting the composition with SiO$_2$ at an ionic strength of about 0.1 mS/cm or no more than 0.2 mS/cm, 0.3 mS/cm, 0.4 mS/cm, 0.5 mS/cm, 0.6 mS/cm, 0.7 mS/cm, 0.8 mS/cm, 0.9 mS/cm, 1.0 mS/cm, 1.1 mS/cm, 1.2 mS/cm, 1.3 mS/cm, 1.4 mS/cm, 1.5 mS/cm, 1.6 mS/cm, 1.7 mS/cm, 1.8 mS/cm, 1.9 mS/cm, 2.0 mS/cm, 2.1 mS/cm, 2.2 mS/cm, 2.3 mS/cm, 2.4 mS/cm, 2.5 mS/cm, 2.6 mS/cm, 2.7 mS/cm, 2.8 mS/cm, 2.9 mS/cm, or 3.0 mS/cm. In yet other embodiments, the method comprises contacting the composition with SiO$_2$ at an ionic strength of no more than 0.1 mS/cm or no more than 0.2 mS/cm, 0.3 mS/cm, 0.4 mS/cm, 0.5 mS/cm, 0.6 mS/cm, 0.7 mS/cm, 0.8 mS/cm, 0.9 mS/cm, 1.0 mS/cm, 1.1 mS/cm, 1.2 mS/cm, 1.3 mS/cm, 1.4 mS/cm, 1.5 mS/cm, 1.6 mS/cm, 1.7 mS/cm, 1.8 mS/cm, 1.9 mS/cm, 2.0 mS/cm, 2.1 mS/cm, 2.2 mS/cm, 2.3 mS/cm, 2.4 mS/cm, 2.5 mS/cm, 2.6 mS/cm, 2.7 mS/cm, 2.8 mS/cm, 2.9 mS/cm, or 3.0 mS/cm.

In certain embodiments, the present invention provides a method for reducing the amount of a serine protease or a serine protease zymogen in a plasma-derived A1PI composition, the method comprising contacting the composition with SiO$_2$ at a low pH and low ionic strength to bind a serine protease or a serine protease zymogen. In a particular embodiment, the method comprises contacting the composition with SiO$_2$ at a pH between about 4.8 and about 5.4 at an ionic strength between about 0.6 mS/cm and about 1.0 mS/cm. In a more particular embodiment, the method comprises contacting the composition with $SiO_2$ at a pH between about 4.9 and about 5.3 at an ionic strength between about 0.7 mS/cm and about 0.9 mS/cm. In a yet more particular embodiment, the method comprises contacting the composition with $SiO_2$ at a pH between about 5.0 and about 5.2 at an ionic strength of about 0.8 mS/cm. In yet other embodiments, the method comprises contacting the composition with $SiO_2$ at a pH and ionic strength according to any one of variations Var. 1222 to 3041, as presented in Table 12, Table 13, Table 14, and Table 15.

1. Binding and Elution of Serine Proteases or Serine Protease Zymogens

In one aspect, the present invention provides a method for reducing the amount of serine protease and/or serine protease zymogen in a re-suspended plasma precipitate comprising A1PI. Generally, the precipitate may be any precipitated during the fractionation of pooled plasma, preferably human plasma In one embodiment, the method comprises contacting a re-suspended plasma precipitate comprising A1PI in an insoluble state with finely divided silicon dioxide ($SiO_2$) under a first low pH solution condition to bind the serine protease and/or serine protease zymogen and to maintain the A1PI in an insoluble state, separating the soluble and insoluble portions of the suspension, eluting the serine and/or serine protease zymogen from $SiO_2$ under a second low pH solution condition suitable to maintain a substantial fraction of the A1PI in an insoluble state, separating the soluble and insoluble portions of the suspension, and extracting the A1PI from the insoluble portion. In one embodiment, the $SiO_2$ is admixed prior to or during the precipitation reaction and recovered along with the precipitate. In a specific embodiment, the precipitate is a Cohn fraction IV-1 precipitate. In another embodiment, the precipitate is a Cohn fraction IV-4 precipitate. In another embodiment, the precipitate is a Cohn fraction V precipitate. In another embodiment, the precipitate is a Kistler/Nitschmann precipitate IV. In yet another embodiment, the precipitate is a Kistler/Nitschmann precipitate C.

In one embodiment of the methods provided above, the first low pH solution condition comprises a pH of between 4.0 and 7.0 and an ionic strength of less than about 5.0 mS/cm. In another embodiment, the solution condition comprises a pH of between 5.0 and 7.0 and an ionic strength of less than about 5.0 mS/cm. In another embodiment, the solution condition comprises a pH of between 5.0 and 6.5 and an ionic strength of less than about 5.0 mS/cm. In another embodiment, the solution condition comprises a pH of between 5.0 and 6.0 and an ionic strength of less than about 5.0 mS/cm. In another embodiment, the solution condition comprises a pH of between 5.5 and 6.0 and an ionic strength of less than about 5.0 mS/cm. In a specific embodiment, the solution condition comprises a pH of 5.5±0.2 and an ionic strength of less than about 5.0 mS/cm. In another specific embodiment, the solution condition comprises a pH of 6.0±0.2 and an ionic strength of less than about 5.0 mS/cm.

In another embodiment of the methods provided above, the first low pH solution condition comprises a pH of between 5.0 and 6.5 and an ionic strength of less than about 4.0 mS/cm. In another embodiment, the solution condition comprises a pH of between 5.0 and 6.5 and an ionic strength of less than about 3.0 mS/cm. In another embodiment, the solution condition comprises a pH of between 5.0 and 6.5 and an ionic strength of less than about 2.0 mS/cm. In another embodiment, the solution condition comprises a pH of between 5.0 and 6.5 and an ionic strength of less than about 1.0 mS/cm. In another embodiment, the solution condition comprises a pH of between 5.0 and 6.5 and an ionic strength of less than about 0.5 mS/cm. In another embodiment, the solution condition comprises a pH of between 5.5 and 6.0 and an ionic strength of less than about 4.0 mS/cm. In another embodiment, the solution condition comprises a pH of between 5.5 and 6.0 and an ionic strength of less than about 3.0 mS/cm. In another embodiment, the solution condition comprises a pH of between 5.5 and 6.0 and an ionic strength of less than about 2.0 mS/cm. In another embodiment, the solution condition comprises a pH of between 5.5 and 6.0 and an ionic strength of less than about 1.0 mS/cm. In another embodiment, the solution condition comprises a pH of between 5.5 and 6.0 and an ionic strength of less than about 0.5 mS/cm. In a specific embodiment, the solution conditions comprises a pH of 5.5±0.2 and an ionic strength of less than about 3.0 mS/cm. In another specific embodiment, the solution condition comprises a pH of 6.0±0.2 and an ionic strength of less than about 3.0 mS/cm. In yet other embodiments, the first low pH solution condition comprises a pH and ionic strength according to any one of variations Var. 1222 to 3041, as presented in Table 12, Table 13, Table 14, and Table 15.

In one embodiment of the methods provided above, the second low pH solution condition comprises a pH of between 4.0 and 7.0 and an ionic strength of greater than about 5.0 mS/cm. In another embodiment, the solution condition comprises a pH of between 5.0 and 7.0 and an ionic strength of greater than about 5.0 mS/cm. In another embodiment, the solution condition comprises a pH of between 5.0 and 6.5 and an ionic strength of greater than about 5.0 mS/cm. In another embodiment, the solution condition comprises a pH of between 5.0 and 6.0 and an ionic strength of greater than about 5.0 mS/cm. In another embodiment, the solution condition comprises a pH of between 5.5 and 6.0 and an ionic strength of greater than about 5.0 mS/cm. In a specific embodiment, the solution condition comprises a pH of 5.5±0.2 and an ionic strength of greater than about 5.0 mS/cm. In another specific embodiment, the solution conditions comprises a pH of 6.0±0.2 and an ionic strength of greater than about 5.0 mS/cm.

In another embodiment of the methods provided above, the second low pH solution condition comprises a pH of between 5.0 and 6.5 and an ionic strength of greater than about 3.0 mS/cm. In another embodiment, the solution condition comprises a pH of between 5.0 and 6.5 and an ionic strength of greater than about 4.0 mS/cm. In another embodiment, the solution condition comprises a pH of between 5.0 and 6.5 and an ionic strength of greater than about 6.0 mS/cm. In another embodiment, the solution condition comprises a pH of between 5.0 and 6.5 and an ionic strength of greater than about 7.0 mS/cm. In another embodiment, the solution condition comprises a pH of between 5.0 and 6.5 and an ionic strength of greater than about 10 mS/cm. In another embodiment, the solution condition comprises a pH of between 5.5 and 6.0 and an ionic strength of greater than about 3.0 mS/cm. In another embodiment, the solution condition comprises a pH of between 5.5 and 6.0 and an ionic strength of greater than about 4.0 mS/cm. In another embodiment, the solution condition comprises a pH of between 5.5 and 6.0 and an ionic strength of greater than about 6.0 mS/cm. In another embodiment, the solution condition comprises a pH of between 5.5 and 6.0 and an ionic strength of greater than about 7.0 mS/cm. In another embodiment, the solution condition comprises a pH of between 5.5 and 6.0 and an ionic strength of greater than about 10 mS/cm. In a specific embodiment, the solution conditions comprises a pH of 5.5±0.2 and an ionic strength of greater than about 10 mS/cm. In another specific embodiment, the solution condition comprises a pH of 6.0±0.2 and an ionic strength of greater than about 10 mS/cm.

In one specific embodiment, the present invention provides a method for reducing the amount of serine protease and/or serine protease zymogen in a re-suspended plasma precipitate comprising A1PI, comprising the steps of contacting a re-suspended plasma precipitate comprising A1PI in an insoluble state with finely divided silicon dioxide ($SiO_2$) under a first low pH solution condition comprising a pH between about 5.0 and about 6.5 and an ionic strength of less than 5.0 mS to bind the serine protease and/or serine protease zymogen and to maintain the A1PI in an insoluble state, separating the soluble and insoluble portions of the suspension, eluting the serine and/or serine protease zymogen from $SiO_2$ under a second low pH solution condition comprising a pH between about 5.0 and about 6.5 and an ionic strength of greater than 5.0 mS to maintain a substantial fraction of the A1PI in an insoluble state, separating the soluble and insoluble portions of the suspension, and extracting the A1PI from the insoluble portion. In one embodiment, the $SiO_2$ is admixed prior to or during the precipitation reaction and recovered along with the precipitate. In a specific embodiment, the precipitate is a Cohn fraction IV-1 precipitate. In another embodiment, the precipitate is a Cohn fraction IV-4 precipitate. In another embodiment, the precipitate is a Cohn fraction V precipitate. In another embodiment, the precipitate is a Kistler/Nitschmann precipitate IV. In yet another embodiment, the precipitate is a Kistler/Nitschmann precipitate C.

2. Binding of Serine Proteases or Serine Protease Zymogens and Extraction of A1PI In another aspect, the present invention provides a method for reducing the amount of serine protease and/or serine protease zymogen in a re-suspended plasma precipitate comprising A1PI. Generally, the precipitate may be any precipitated during the fractionation of pooled plasma, preferably human plasma In one embodiment, the method comprises contacting a re-suspended plasma precipitate comprising A1PI in an insoluble state with finely divided silicon dioxide ($SiO_2$) under a first solution condition comprising low pH to bind the serine protease and/or serine protease zymogen and to maintain the A1PI in an insoluble state, separating the soluble and insoluble portions of the suspension, extracting the A1PI from the insoluble portion under a second solution condition comprising high pH, and separating the soluble portion from the insoluble portion, wherein a substantial fraction of the serine protease and/or serine protease zymogen remains bound to the $SiO_2$ during the extraction of A1PI from the insoluble portion. In one embodiment, the $SiO_2$ is admixed prior to or during the precipitation reaction and recovered along with the precipitate. In a specific embodiment, the precipitate is a Cohn fraction IV-I precipitate. In another embodiment, the precipitate is a Cohn fraction IV-4 precipitate. In another embodiment, the precipitate is a Cohn fraction V precipitate. In another embodiment, the precipitate is a Kistler/Nitschmann precipitate IV. In yet another embodiment, the precipitate is a Kistler/Nitschmann precipitate C.

In one embodiment of the methods provided above, the first solution condition comprises a pH of between 4.0 and 7.0 and an ionic strength of less than about 5.0 mS/cm. In another embodiment, the solution condition comprises a pH of between 5.0 and 7.0 and an ionic strength of less than about 5.0 mS/cm. In another embodiment, the solution condition comprises a pH of between 5.0 and 6.5 and an ionic strength of less than about 5.0 mS/cm. In another embodiment, the solution condition comprises a pH of between 5.0 and 6.0 and an ionic strength of less than about 5.0 mS/cm. In another embodiment, the solution condition comprises a pH of between 5.5 and 6.0 and an ionic strength of less than about 5.0 mS/cm. In a specific embodiment, the solution condition comprises a pH of 5.5±0.2 and an ionic strength of less than about 5.0 mS/cm. In another specific embodiment, the solution condition comprises a pH of 6.0±0.2 and an ionic strength of less than about 5.0 mS/cm.

In another embodiment of the methods provided above, the first solution condition comprises a pH of between 5.0 and 6.5 and an ionic strength of less than about 4.0 mS/cm. In another embodiment, the solution condition comprises a pH of between 5.0 and 6.5 and an ionic strength of less than about 3.0 mS/cm. In another embodiment, the solution condition comprises a pH of between 5.0 and 6.5 and an ionic strength of less than about 2.0 mS/cm. In another embodiment, the solution condition comprises a pH of between 5.0 and 6.5 and an ionic strength of less than about 1.0 mS/cm. In another embodiment, the solution condition comprises a pH of between 5.0 and 6.5 and an ionic strength of less than about 0.5 mS/cm. In another embodiment, the solution condition comprises a pH of between 5.5 and 6.0 and an ionic strength of less than about 4.0 mS/cm. In another embodiment, the solution condition comprises a pH of between 5.5 and 6.0 and an ionic strength of less than about 3.0 mS/cm. In another embodiment, the solution condition comprises a pH of between 5.5 and 6.0 and an ionic strength of less than about 2.0 mS/cm. In another embodiment, the solution condition comprises a pH of between 5.5 and 6.0 and an ionic strength of less than about 1.0 mS/cm. In another embodiment, the solution condition comprises a pH of between 5.5 and 6.0 and an ionic strength of less than about 0.5 mS/cm. In a specific embodiment, the solution conditions comprises a pH of 5.5±0.2 and an ionic strength of less than about 3.0 mS/cm. In another specific embodiment, the solution condition comprises a pH of 6.0±0.2 and an ionic strength of less than about 3.0 mS/cm. In yet other embodiments, the first low pH solution condition comprises a pH and ionic strength according to any one of variations Var. 1222 to 3041, as presented in Table 12, Table 13, Table 14, and Table 15.

In one embodiment of the methods provided above, the second solution condition comprises a pH of between 7.0 and 10.0 and an ionic strength of less than about 10.0 mS/cm. In another embodiment, the solution condition comprises a pH of between 7.0 and 9.0 and an ionic strength of less than about 10.0 mS/cm. In another embodiment, the solution condition comprises a pH of between 7.0 and 8.5 and an ionic strength of less than about 10.0 mS/cm. In another embodiment, the solution condition comprises a pH of between 7.5 and 8.5 and an ionic strength of less than about 10.0 mS/cm. In another embodiment, the solution condition comprises a pH of between 7.5 and 8.0 and an ionic strength of less than about 10.0 mS/cm. In a specific embodiment, the solution condition comprises a pH of 7.5±0.2 and an ionic strength of less than about 10.0 mS/cm. In another specific embodiment, the solution condition comprises a pH of 8.0±0.2 and an ionic strength of less than about 10.0 mS/cm.

In another embodiment of the methods provided above, the second solution condition comprises a pH of between 7.0 and 8.5 and an ionic strength of less than about 9.0 mS/cm. In another embodiment, the solution condition comprises a pH of between 7.0 and 8.5 and an ionic strength of less than about 8.0 mS/cm. In another embodiment, the solution condition comprises a pH of between 7.0 and 8.5 and an ionic strength of less than about 7.0 mS/cm. In another embodiment, the solution condition comprises a pH of between 7.0 and 8.5 and an ionic strength of less than about 6.0 mS/cm. In another embodiment, the solution condition comprises a pH of between 7.0 and 8.5 and an ionic strength of less than about 5 mS/cm. In another embodiment, the solution condition comprises a pH of between 7.0 and 8.5 and an ionic strength of less than about 4.0 mS/cm. In another embodiment, the solution condition comprises a pH of between 7.0 and 8.5 and an ionic strength of less than about 3.0 mS/cm. In another embodiment, the solution condition comprises a pH of between 7.0 and 8.5 and an ionic strength of less than about 2 mS/cm. In another embodiment, the solution condition comprises a pH of between 7.0 and 8.5 and an ionic strength of between 2 mS/cm and 10 mS/cm.

In another embodiment of the methods provided above, the second solution condition comprises a pH of between 7.5 and 8.0 and an ionic strength of less than about 9.0 mS/cm. In another embodiment, the solution condition comprises a pH of between 7.5 and 8.0 and an ionic strength of less than about 8.0 mS/cm. In another embodiment, the solution condition comprises a pH of between 7.5 and 8.0 and an ionic strength of less than about 7.0 mS/cm. In another embodiment, the solution condition comprises a pH of between 7.5 and 8.0 and an ionic strength of less than about 6.0 mS/cm. In another embodiment, the solution condition comprises a pH of between 7.5 and 8.0 and an ionic strength of less than about 5 mS/cm. In another embodiment, the solution condition comprises a pH of between 7.5 and 8.0 and an ionic strength of less than about 4.0 mS/cm. In another embodiment, the solution condition comprises a pH of between 7.5 and 8.0 and an ionic strength of less than about 3.0 mS/cm. In another embodiment, the solution condition comprises a pH of between 7.5 and 8.0 and an ionic strength of less than about 2 mS/cm. In another embodiment, the solution condition comprises a pH of between 7.5 and 8.5 and an ionic strength of between 2 mS/cm and 10 mS/cm. In a specific embodiment, the solution condition comprises a pH of 7.5±0.2 and an ionic strength of between 2 mS/cm and 10 mS/cm. In another specific embodiment, the solution condition comprises a pH of 8.0±0.2 and an ionic strength of between 2 mS/cm and 10 mS/cm.

IV. Pharmaceutical Compositions

In one aspect, the present invention provides compositions of plasma-derived proteins having reduced levels of serine protease and/or serine protease zymogen, which are prepared according to any of the methods described herein. In certain embodiments, these compositions will be formulated for pharmaceutical administration (i.e., pharmaceutical compositions). Generally, the plasma-derived blood protein compositions prepared according to the methods provided herein will have reduced amidolytic activity and will provide better safety profiles than existing plasma-derived biologics currently available. In a preferred embodiment, the compositions provided herein will have reduced Factor XI, Factor XIa, Factor XII, and/or Factor XIIa content.

In one embodiment, the present invention provides a plasma-derived protein composition prepared by a method comprising the steps of: (a) contacting the composition with finely divided silicon dioxide ($SiO_2$) under conditions suitable to bind at least one serine protease or serine protease zymogen; and (b) separating the $SiO_2$ from the composition to remove the bound serine protease or serine protease zymogen. In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In certain embodiments, the compositions described above are prepared by a method further comprising the step of performing a first target protein enrichment step to form a first enriched composition, prior to contacting the composition with finely divided silicon dioxide ($SiO_2$). In certain embodiments, the first target protein enrichment step is selected from a protein precipitation step (e.g., an alcohol fractionation step), an ultrafiltration/diafiltration step, and a chromatographic step.

In one embodiment, the present invention provides a plasma-derived protein composition prepared by a method comprising the steps of: (a) forming a first enriched plasma-derived target protein composition by partially precipitating protein in a starting material derived from pooled plasma; (b) contacting the first enriched composition with finely divided silicon dioxide ($SiO_2$) under conditions suitable to bind at least one serine protease or serine protease zymogen; and (c) separating the $SiO_2$ from the composition to remove the bound serine protease or serine protease zymogen. In one embodiment, the partial precipitation is achieved using alcohol. In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one embodiment, the present invention provides a plasma-derived protein composition prepared by a method comprising the steps of: (a) forming a first enriched plasma-derived target protein composition by ultrafiltering and/or diafiltering a starting material derived from pooled plasma; (b) contacting the first enriched composition with finely divided silicon dioxide ($SiO_2$) under conditions suitable to bind at least one serine protease or serine protease zymogen; and (c) separating the $SiO_2$ from the composition to remove the bound serine protease or serine protease zymogen. In one embodiment, the partial precipitation is achieved using alcohol. In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one embodiment, the present invention provides a plasma-derived protein composition prepared by a method comprising the steps of: (a) forming a first enriched plasma-derived target protein composition by contacting a starting material derived from pooled plasma with a chromatographic resin; (b) contacting the first enriched composition with finely divided silicon dioxide ($SiO_2$) under conditions suitable to bind at least one serine protease or serine protease zymogen; and (c) separating the $SiO_2$ from the composition to remove the bound serine protease or serine protease zymogen. In one embodiment, the partial precipitation is achieved using alcohol. In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In certain embodiments, the compositions described above are prepared by a method further comprising the step of performing a second target protein enrichment step to form a second enriched composition, prior to contacting the composition with finely divided silicon dioxide ($SiO_2$). In certain embodiments, the first target protein enrichment step is selected from a protein precipitation step (e.g., an alcohol fractionation step), an ultrafiltration/diafiltration step, and a chromatographic step.

In one embodiment, the present invention provides a plasma-derived protein composition prepared by a method comprising the steps of: (a) performing a first target protein enrichment step to form a first enriched plasma-derived target protein composition; (b) performing a second target protein enrichment step to form a second enriched plasma-derived target protein composition; (c) contacting the second enriched composition with finely divided silicon dioxide ($SiO_2$) under conditions suitable to bind at least one serine protease or serine protease zymogen; and (d) separating the $SiO_2$ from the composition to remove the bound serine protease or serine protease zymogen. In certain embodiments, the combination of first and second enrichment steps is selected from any one of variations Var. 1 to Var. 100, found in Table 1. In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In certain embodiments, the compositions described above are prepared by a method further comprising the step of performing a target protein enrichment step after contacting the composition with finely divided silicon dioxide ($SiO_2$). In certain embodiments, the target protein enrichment step is selected from a protein precipitation step (e.g., an alcohol fractionation step), an ultrafiltration/diafiltration step, and a chromatographic step.

In one embodiment, the present invention provides a plasma-derived protein composition prepared by a method comprising the steps of: (a) performing a first target protein enrichment step to form a first enriched plasma-derived target protein composition; (b) contacting the first enriched composition with finely divided silicon dioxide ($SiO_2$) under conditions suitable to bind at least one serine protease or serine protease zymogen; (c) separating the $SiO_2$ from the composition to remove the bound serine protease or serine protease zymogen; and (d) performing a second target protein enrichment step to form a second enriched plasma-derived target protein composition. In certain embodiments, the combination of first and second enrichment steps is selected from any one of variations Var. 1 to Var. 100, found in Table 1. In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one aspect, the present invention provides a plasma-derived protein composition having reduced levels of serine protease and/or serine protease zymogen for use in the treatment of a condition associated with a blood protein deficiency or dysfunction. In certain embodiments, the plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one embodiment, the present invention provides a plasma-derived protein composition prepared by a method comprising the steps of: (a) performing a first target protein enrichment step to form a first enriched plasma-derived target protein composition; (b) performing a second target protein enrichment step to form a second enriched plasma-derived target protein composition; (c) contacting the second enriched composition with finely divided silicon dioxide ($SiO_2$) under conditions suitable to bind at least one serine protease or serine protease zymogen; (d) separating the $SiO_2$ from the composition to remove the bound serine protease or serine protease zymogen; and (e) performing a third target protein enrichment step to form a third enriched plasma-derived target protein composition. In certain embodiments, the combination of first and second enrichment steps is selected from any one of variations Var. 101 to Var. 1100, found in Table 2, Table 3, Table 4, Table 5, Table 6, Table 7, Table 8, Table 9, Table 10, or Table 11. In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In certain embodiments of the compositions described above, a chromatographic enrichment step comprises the sub-steps of: (i) contacting the plasma-derived target protein composition with a chromatographic resin under conditions suitable to bind the plasma-derived target protein; and (ii) eluting the plasma-derived target protein from the chromatographic resin. In one specific embodiment, the impurity does not bind to the chromatographic resin in sub-step (i). In another specific embodiment, the impurity binds to the chromatographic resin in sub-step (i), but is not eluted from the chromatographic resin in sub-step (ii).

In other certain embodiments of the compositions described above, a chromatographic enrichment step comprises the sub-steps of: (i) contacting the first enriched plasma-derived target protein composition with a chromatographic resin under conditions suitable to bind at least one impurity; and (ii) separating the resin from the plasma-derived protein composition, wherein the plasma-derived target protein does not bind to the chromatographic resin in sub-step (i).

In certain embodiments of the compositions provided herein, the amount of a particular serine protease or serine protease zymogen is reduced by at least 10%. In another embodiment, the amount of a particular serine protease or serine protease zymogen is reduced by at least 25%. In another embodiment, the amount of a particular serine protease or serine protease zymogen is reduced by at least 50%. In another embodiment, the amount of a particular serine protease or serine protease zymogen is reduced by at least 75%. In another embodiment, the amount of a particular serine protease or serine protease zymogen is reduced by at least 90%. In yet other embodiments, the amount of a particular serine protease or serine protease zymogen is reduced by at least 5%, or by at least 10%, 15%, 20%, 25%, 30%, 35%, 40%, 45%, 50%, 55%, 60%, 65%, 70%, 75%. 80%, 85%, 90%, 91%, 92%, 93%, 94%. 95%, 96%, 97%, 98%, or 99%. In one embodiment, the reduction of serine protease or serine protease zymogen refers to the reduction achieved within the individual $SiO_2$ treatment step. In another embodiment, the reduction of serine protease or serine protease zymogen refers to the level of the contaminant in the final composition, as compared to a composition prepared in a similar fashion excluding a $SiO_2$ treatment step.

In one embodiment, the pharmaceutical compositions provided herein are prepared by formulating a plasma-derived protein composition isolated using a method provided herein. Generally, the formulated composition will have been subjected to at least one, preferably at least two, most preferably at least three, viral inactivation or removal steps. Non-limiting examples of viral inactivation or removal steps that may be employed with the methods provided herein include, solvent detergent treatment (Horowitz et al., Blood Coagul Fibrinolysis 1994 (5 Suppl 3):S21-S28 and Kreil et al., Transfusion 2003 (43):1023-1028, both of which are herein expressly incorporated by reference in their entirety for all purposes), nanofiltration (Hamamoto et al., Vox Sang 1989 (56)230-236 and Yuasa et al., J Gen Virol. 1991 (72 (pt 8)):2021-2024, both of which are herein expressly incorporated by reference in their entirety for all purposes), and low pH incubation at high temperatures (Kempf et al., Transfusion 1991 (31)423-427 and Louie et al., Biologicals 1994 (22): 13-19). In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one embodiment, the pharmaceutical compositions provided herein will comprise one or more buffering agents or pH stabilizing agents suitable for intravenous, subcutaneous, intramuscular, and/or intraocular administration. Non-limiting examples of buffering agents suitable for formulating a plasma-derived protein composition provided herein include glycine, citrate, phosphate, acetate, glutamate, tartrate, benzoate, lactate, histidine or other amino acids, gluconate, malate, succinate, formate, propionate, carbonate, or any combination thereof adjusted to an appropriate pH. Generally, the buffering agent will be sufficient to maintain a suitable pH in the formulation for an extended period of time. In a preferred embodiment, the buffering agent is glycine. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In some embodiments, the pharmaceutical compositions provided herein may optionally further comprise an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, sodium chloride, potassium chloride, calcium chloride, calcium gluconoglucoheptonate, dimethyl sulfone, and the like.

Typically, the formulations provided herein will have osmolarities that are comparable to physiologic osmolarity, about 285 to 295 mOsmol/kg (Lacy et al., Drug Information Handbook—Lexi-Comp 1999:1254. In certain embodiments, the osmolarity of the formulation will be between about 200 mOsmol/kg and about 350 mOsmol/kg, preferably between about 240 and about 300 mOsmol/kg. In particular embodiments, the osmolarity of the formulation will be about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg.

The plasma-derived formulations provided herein are generally stable in liquid form for an extended period of time. In certain embodiments, the formulations are stable for at least about 3 months at room temperature, or at least about 4, 5, 6, 7, 8, 9, 10, 11, 12, 13, 14, 15, 16, 17, 18, 19, 20, 21, 22, 23, or 24 months at room temperature. The formulation will also generally be stable 6 or at least about 18 months under refrigerated conditions (typically between about 2° C. and about 8° C.), or for at least about 21, 24, 27, 30, 33, 36, 39, 42, or 45 months under refrigerated conditions.

V. Methods of Treatment

In one aspect, the present invention provides methods for treating a disease or disorder associated with a blood protein deficiency or dysfunction in a subject in need thereof by administering a therapeutically effective dose of a plasma-derived protein composition having reduced levels of serine protease and/or serine protease zymogen prepared according to a method provided herein. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one aspect, the present invention provides the use of a plasma-derived protein composition having reduced levels of serine protease and/or serine protease zymogen for the manufacture of a medicament for use in the treatment of a condition associated with a blood protein deficiency or dysfunction. In certain embodiments, the plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

A. Immunoglobulins

As routinely practiced in the modern medicine, sterilized preparations of concentrated immunoglobulins (especially IgGs) are used for treating medical conditions that fall into these three main classes: immune deficiencies, inflammatory and autoimmune diseases, and acute infections. These IgG preparations may also be useful for treating multiple sclerosis (especially relapsing-remitting multiple sclerosis or RRMS), Alzheimer's disease, and Parkinson's disease. The purified IgG preparation of this invention is suitable for these purposes, as well as other clinically accepted uses of IgG preparations.

The FDA has approved the use of IVIG to treat various indications, including allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), and kidney transplant with a high antibody recipient or with an ABO incompatible donor. In certain embodiments, the IVIG compositions provided herein are useful for the treatment or management of these diseases and conditions.

Furthermore, off-label uses for IVIG are commonly provided to patients for the treatment or management of various indications, for example, chronic fatigue syndrome, clostridium difficile colitis, dermatomyositis and polymyositis, Graves' ophthalmopathy, Guillain-Barré syndrome, muscular dystrophy, inclusion body myositis, Lambert-Eaton syndrome, Lupus crythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, and hypogammaglobulinemia. In certain embodiments, the IVIG compositions provided herein are useful for the treatment or management of these diseases and conditions.

Finally, experimental use of IVIG for the treatment or management of diseases including primary immune deficiency, RRMS, Alzheimer's disease, and Parkinson's disease has been proposed (U.S. Patent Application Publication No. U.S. 2009/0148463, which is herein incorporated by reference in its entirety for all purposes). In certain embodiments, the IVIG compositions provided herein are useful for the treatment or management of primary immune deficiency, RRMS, Alzheimer's disease, or Parkinson's disease. In certain embodiments comprising daily administration, an effective amount to be administered to the subject can be determined by a physician with consideration of individual differences in age, weight, disease severity, route of administration (e.g., intravenous v, subcutaneous) and response to the therapy. In certain embodiments, an immunoglobulin preparation of this invention can be administered to a subject at about 5 mg/kilogram to about 2000 mg/kilogram each day. In additional embodiments, the immunoglobulin preparation can be administered in amounts of at least about 10 mg/kilogram, at last 15 mg/kilogram, at least 20 mg/kilogram, at least 25 mg/kilogram, at least 30 mg/kilogram, or at least 50 mg/kilogram. In additional embodiments, the immunoglobulin preparation can be administered to a subject at doses up to about 100 mg/kilogram, to about 150 mg/kilogram, to about 200 mg/kilogram, to about 250 mg/kilogram, to about 300 mg/kilogram, to about 400 mg/kilogram each day. In other embodiments, the doses of the immunoglobulin preparation can be greater or less. Further, the immunoglobulin preparations can be administered in one or more doses per day. Clinicians familiar with the diseases treated by IgG preparations can determine the appropriate dose for a patient according to criteria known in the art.

In accordance with the present invention, the time needed to complete a course of the treatment can be determined by a physician and may range from as short as one day to more than a month. In certain embodiments, a course of treatment can be from 1 to 6 months.

An effective amount of an IVIG preparation is administered to the subject by intravenous means. The term "effective amount" refers to an amount of an IVIG preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, an IVIG preparation can be administered to a subject at dose of about 5 mg/kilogram to about 2000 mg/kilogram per administration. In certain embodiments, the dose may be at least about 5 mg/kg, or at least about 10 mg/kg, or at least about 20 mg/kg, 30 mg/kg, 40 mg/kg, 50 mg/kg, 60 mg/kg, 70 mg/kg, 80 mg/kg. 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg. 600 mg/kg. 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or at least about 2000 mg/kg.

The dosage and frequency of IVIG treatment will depend upon, among other factors, the disease or condition being treated and the severity of the disease or condition in the patient. Generally, for primary immune dysfunction a dose of between about 100 mg/kg and about 400 mg/kg body weight will be administered about every 3 to 4 weeks. For neurological and autoimmune diseases, up to 2 g/kg body weight is implemented for three to six months over a five day course once a month. This is generally supplemented with maintenance therapy comprising the administration of between about 100 mg/kg and about 400 mg/kg body weight about once every 3 to 4 weeks. Generally, a patient will receive a dose or treatment about once every 14 to 35 days, or about every 21 to 28 days. The frequency of treatment will depend upon, among other factors, the disease or condition being treated and the severity of the disease or condition in the patient.

In a preferred embodiment, a method of treating an immunodeficiency, autoimmune disease, or acute infection in a human in need thereof is provided, the method comprising administering a pharmaceutical IVIG composition of the present invention. In a related embodiment, the present invention provides IVIG compositions manufactured according to a method provided herein for the treatment of an immunodeficiency, autoimmune disease, or acute infection in a human in need thereof.

In certain embodiments, the immunodeficiency, autoimmune disease, or acute infection is selected from allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), kidney transplant with a high antibody recipient or with an ABO incompatible donor, chronic fatigue syndrome, clostridium difficile colitis, dermatomyositis and polymyositis, Graves' ophthalmopathy, Guillain-Barré syndrome, muscular dystrophy, inclusion body myositis, Lambert-Eaton syndrome, Lupus erythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, hypogammaglobulinemia, primary immune deficiency, RRMS, Alzheimer's disease, and Parkinson's disease.

B. Factor H

In one aspect, the present invention provides methods for treating a disease or disorder associated with a Factor H dysfunction or abnormal alternative pathway complement activity in a subject in need thereof by administering a therapeutically effective dose of a Factor H composition prepared according to a method provided herein. In one embodiment, the Factor H composition is prepared by extracting Factor H from a Fraction I precipitate. In another embodiment, the Factor H composition is prepared by extracting Factor H from a Fraction II+III filter cake.

In certain embodiments, the disease or disorder associated with a Factor H dysfunction is selected from atypical haemolytic uremic syndrome (aHUS), age-related macular degeneration (AMD), membranoproliferative glomulonephritis type II (MPGNII), myocardial infarction, coronary heart disease/coronary artery disease (CADiCHD), and Alzheimer's disease. In one particular embodiment, the disease is atypical haemolytic uremic syndrome (aHUS). In another particular embodiment, the disease is age-related macular degeneration (AMD). In yet another particular embodiment, the disease is membranoproliferative glomulonephritis type II (MPGNII).

In certain embodiments, a method is provided for treating a disease or disorder associated with a abnormal alternative pathway complement activity in a subject in need thereof by administering to the subject a therapeutically effective dose of a Factor H composition provided herein. In one embodiment, the Factor H composition is prepared by extracting Factor H from a Fraction I precipitate. In another embodiment, the Factor H composition is prepared by extracting Factor H from a Fraction II+III filter cake.

In certain embodiments, the disease or disorder associated with abnormal alternative pathway complement activity is selected from an autoimmune disease (such as rheumatoid arthritis, IgA nephropathy, asthma, systemic lupus erythematosus, multiple sclerosis, Anti-Phospholipid syndrome, ANCA-associated vasculitis, pemphigus, uveitis, myathemia gravis, Hashimoto's thyroiditis), a renal disease (such as IgA nephropathy, hemolytic uremic syndrome, membranoproliferative glomerulonephritis) asthma, Alzheimer disease, adult macular degeneration, proximal nocturnal hemoglobinuria, abdominal aortic aneurism, ischemia reperfusion injury, and sepsis.

The pharmaceutical compositions provided by the invention may be administered alone or in conjunction with other therapeutic agents. These agents may be incorporated as part of the same pharmaceutical.

1. Administration

In accordance with the present invention, the time needed to complete a course of the treatment can be determined by a physician and may range from as short as one day to more than a month. In certain embodiments, a course of treatment can be from 1 to 6 months.

An effective amount of a Factor H preparation is administered to the subject by any suitable means to treat the disease or disorder. For example, in certain embodiments, Factor H may be administered by intravenous, intraocular, subcutaneous, and/or intramuscular means. In a preferred embodiment, a method for treating age-related macular degeneration in a subject in need thereof is provided comprising the intraocular administration of a Factor H composition to the patient.

In certain embodiments, the Factor H compositions provided herein can be administered either systemically or locally. Systemic administration includes: oral, transdermal, subdermal, intraperitioneal, subcutaneous, transnasal, sublingual, or rectal. The most preferred systemic route of administration is oral. Local administration for ocular administration includes: topical, intravitreal, periocular, transcleral, retrobulbar, juxtascleral, sub-tenon, or via an intraocular device. Preferred methods for local delivery include transsscleral delivery to the macula by posterior juxtascleral administration; via intravitreal injection; or via cannula, such as that described in U.S. Pat. No. 6,413,245, the disclosure of which is incorporated by reference herein in its entirety for all purposes. Alternatively, the inhibitors may be delivered via a sustained delivery device implanted intravitreally or transsclerally, or by other known means of local ocular delivery.

In certain embodiments, the term "effective amount" refers to an amount of a Factor H preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, an Factor H preparation can be administered to a subject at dose of at or about between 5 mg/kilogram and 2000 mg/kilogram per administration. In certain embodiments, the dose may be at least at or about 5 mg/kg, or at least at or about 10 mg/kg, or at least at or about 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg. 350 mg/kg. 400 mg/kg. 450 mg/kg. 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg. 1400 mg/kg, 1500 mg/kg, 1600 mg/kg, 1700 mg/kg, 1800 mg/kg, 1900 mg/kg, or 2000 mg/kg. The dosage and frequency of Factor H treatment will depend upon, among other factors, the disease or condition being treated and the severity of the disease or condition in the patient.

2. Age-Related Macular Degeneration (AMD)

In a preferred embodiment, the present invention provides a method of treating age-related macular degeneration in a subject in need thereof by administering to the subject a therapeutically effective dose of a Factor H composition provided herein.

Age-related macular degeneration (AMD) is the number one cause of blindness for the elderly population over 60 years of age. Today, it is estimated that 35-40% of those over 75 years of age have some degree of AMD. It has been estimated that approximately 50 million people are affected world-wide, with 10 million in the US alone. Currently, about 155,000 new diagnoses of AMD are made every year. As the worldwide population continues to age, the number of annual diagnoses are expected to triple by the year 2020. It is a devastating disease that destroys central vision in the affected individuals, robbing them of their ability to perform activities necessary for everyday life such as reading and driving.

AMD is a slow, progressive disease that involves cells of the outer retinal layers (including photoreceptors and the retinal pigment epithelial (RPE) cells that support the photoreceptors), as well as cells in the adjacent vascular layer of the eye known as the choroid. Macular degeneration is characterized by the breakdown of the macula, a small portion of the central retina (about 2 mm in diameter) responsible for high-acuity vision. Late-onset macular degeneration (i.e., AMD) is generally defined as either "dry" or "wet." The wet ("exudative") neovascular form of AMD affects approximately 10% of those with the disease, and is characterized by abnormal blood vessels growing from the choriocapillaris through the RPE, typically resulting in hemorrhage, exudation, scarring, and/or serous retinal detachment. Approximately 90% of patients with AMD have the non-neovascular, or dry form of the disease, which is characterized by atrophy of the RPE and loss of macular photoreceptors.

AMD is characterized by the presence of deposits of debris-like material, termed "drusen," that accumulate on Bruch's membrane, a multilayered composite of extracellular matrix components separating the RPE (the outermost layer of the retina) from the underlying choroid. Drusen can be observed by funduscopic eye examination. These deposits have been extensively characterized in microscopic studies of donor eyes from patients with AMD. The deposits observed in the living eye upon clinical examination are classified as either soft drusen or hard drusen, according to several criteria including relative size, abundance, and shape of the deposits. Histochemical and immunocytochemical studies have shown that drusen contain a variety of lipids, polysaccharides, glycosaminoglycans and proteins.

Presently, there no known cure for AMD, although several types of treatments has been shown to be effective at managing the disease. Laser photocoagulation of abnormal vessels in the wet form of the disease is the standard treatment. This treatment is limited by the fact that only well-delineated neovascular lesions can be treated in this way and that 50% of patients will suffer recurrence of the leakage from the vessels (Fine et al., 2000). Because of the energy of the laser required for this treatment, the photoreceptors in the treated area will also die, and the patient will also often suffer central blindness immediately after the treatment. New neovascular lesions will eventually develop, requiring repeated treatments. Other interventions include changing lifestyles by cessation of smoking and beginning therapy with antioxidants. Antiangiogenic treatments using VEGF inhibitors e.g., intravitrial injection of ranibizumab or bevacizumab also have been suggested.

Recently it was discovered that about 35% of individuals carry at an at-risk single nucleotide polymorphism (SNP) in one or both copies of their Factor H gene. Homozygous individuals have an approximately sevenfold increased chance of developing age-related macular degeneration, while heterozygotes have a two-to-threefold increased likelihood of developing the disease. This SNP, located in CCP module 7 of Factor H, has been shown to affect the interactions between Factor H and both C-reactive protein and heparin indicating a causal relationship between the SNP and disease. The polymorphism is a Y420H polymorphism.

In one embodiment of a method for limiting complement activation resulting in delayed progression or onset of the development of age related macular degeneration (AMD) in a subject, the subject does not have any symptoms of AMD.

In another embodiment of a method for limiting complement activation resulting in delayed progression or onset of the development of age related macular degeneration (AMD) in a subject, the subject has drusen.

In another embodiment of a method for limiting complement activation resulting in delayed progression or onset of the development of age related macular degeneration (AMD) in a subject, the subject is at increased risk of developing AMD.

In another embodiment of a method for limiting complement activation resulting in delayed progression or onset of the development of age related macular degeneration (AMD) in a subject, the administration is intravenous.

In another embodiment of a method for limiting complement activation resulting in delayed progression or onset of the development of age related macular degeneration (AMD) in a subject, the method further comprises treating a subject having signs and/or symptoms of AMD.

In another embodiment of a method for limiting complement activation resulting in delayed progression or onset of the development of age related macular degeneration (AMD) in a subject, the subject has been diagnosed with AMD.

In another aspect, the present invention provides a method of treating a human subject judged to be at risk for the development of age related macular degeneration, comprising the step of administering to the subject a prophylactically or therapeutically effective amount of a Factor H preparation provided herein, and periodically repeating said administration.

In one embodiment of a method of treating a human subject judged to be at risk for the development of age related macular degeneration, the administration is repeated for a time effective to delay the progression or onset of the development of macular degeneration in said subject.

In another embodiment of a method of treating a human subject judged to be at risk for the development of age related macular degeneration, the human subject is judged to be at risk for the development of age-related macular degeneration as identified based on the presence of one or more genetic markers associated with development of age-related macular degeneration.

In another embodiment of a method of treating a human subject judged to be at risk for the development of age related macular degeneration, the genetic marker is a polymorphism.

In another embodiment of a method for limiting complement activation resulting in delayed progression or onset of the development of age related macular degeneration (AMD) in a subject, the subject is not diagnosed with AMD.

C. Inter-alpha-Trypsin Inhibitor (IαI)

In yet other aspects, it is an object of the invention to provide methods for treating disorders and diseases associated with reduced IαIp function or IαI p dysfunction by administering a therapeutically effective amount of an IαIp composition provided herein. In one embodiment, the disease or disorder associated with reduced IαIp function or IαIp dysfunction is sepsis.

In one embodiment, the present invention provides a therapeutically effective dose of an IαIp composition prepared by a method disclosed herein for use in a method for treating a disease or disorder associated with reduced IαIp function or IαIp dysfunction in a subject in need thereof. In one embodiment, the disease or disorder associated with reduced IαIp function or IαIp dysfunction is sepsis.

In another aspect, it is an object of the invention to provide methods for treating diseases and disorders associated with increased plasma serine protease activity by administering a therapeutically effective amount of an IαIp composition provided herein. In one embodiment, the disease or disorder associated increased plasma serine protease activity is selected from sepsis, septic shock, endotoxic shock, disseminated intravascular coagulation, fibroproliferation, anthrax intoxication, cancer metastasis, tissue injury during surgery, kidney disease, vascular disease, coagulation, diabetes, and systemic inflammation.

In one embodiment, the present invention provides a therapeutically effective dose of an IαIp composition prepared by a method disclosed herein for use in a method for treating a disease or disorder associated with increased plasma serine protease activity in a subject in need thereof. In one embodiment, the disease or disorder associated increased plasma serine protease activity is selected from sepsis, septic shock, endotoxic shock, disseminated intravascular coagulation, fibroproliferation, anthrax intoxication, cancer metastasis, tissue injury during surgery, kidney disease, vascular disease, coagulation, diabetes, and systemic inflammation.

A. Administration

In accordance with the present invention, the time needed to complete a course of the treatment can be determined by a physician and may range from as short as one day to more than a month. In certain embodiments, a course of treatment can be from 1 to 6 months.

An effective amount of an IαIp preparation is administered to the subject by any suitable means to treat the disease or disorder. For example, in certain embodiments, IαIp may be administered by intravenous, subcutaneous, and/or intramuscular means. In a preferred embodiment, a method for treating sepsis in a subject in need thereof is provided comprising the intravenous (IV) administration of an IαIp composition to the patient.

In certain embodiments, the IαIp compositions provided herein can be administered either systemically or locally. Systemic administration includes: oral, subdermal, intraperitoneal, subcutaneous, transnasal, sublingual, or rectal routes of administration. Local administration includes: topical, subcutaneous, intramuscular, and intraperitoneal routes of administration.

In certain embodiments, the term "effective amount" refers to an amount of a IαI p preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, an IαIp preparation can be administered to a subject at dose of about 5 mg/kilogram to about 2000 mg/kilogram per administration. In certain embodiments, the dose may be at least about 5 mg/kg, or at least about 10 mg/kg, or at least about 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or at least about 2000 mg/kg. The dosage and frequency of IαIp treatment will depend upon, among other factors, the disease or condition being treated and the severity of the disease or condition in the patient.

VI. Examples

Example 1

In order to determine the residual serine protease content and activity present in plasma-derived protein compositions, the amidolytic activity profile was determined for two commercially available IgG preparations that were manufactured without the use of $SiO_2$ treatment: OCTAGAM® (5% Intravenous Immune Globulin; Octapharma) and Subcuvia (16% Subcutaneous Immune Globulin; Baxter); two lots of a commercially available IgG preparation manufactured using $SiO_2$ treatment: Gammagard Liquid (10% Intravenous Immune Globulin; Baxter), and a Factor H purification method currently in development. Notably, the Factor H composition was purified as described above, by binding and subsequently eluting Factor H from finely divided $SiO_2$.

Briefly, the amidolytic activity profile for each of the plasma-derived protein compositions was determined by assaying with the following chromogenic substrates with different enzyme specificities: PL-1 (broad spectrum), S-2288 (broad spectrum), S-2266 (FXIa, glandular kallikreins), S-2222 (FXa, trypsin), S-2251 (Plasmin), and S-2302 (Kallikrein, FXIa, and FXIIa). Pre-kallikrein activator activity (PKKA) and amount of Factor XIa Units was also determined. As shown in Table 17, the plasma-derived IgG compositions manufactured without the use of an $SiO_2$ adsorption step contained significant levels of amidolytic activity and FXIa content. In contrast, both tested lots of the Gammagard Liquid contained minimal amidolytic activity and FXIa content. Consistent with these results, the Factor H composition prepared by binding and eluting from finely divided $SiO_2$, contains extremely high levels of amidolytic activity and FXIa content.

TABLE 17

Amidolytic activity of various plasma-derived protein compositions.

| | | | Commercially available IGIV preparations | | |
| | | Factor H Sample FH012 FC steril | Octagam 5% (Octapharma) #B82A8432 | Gammagard Liquid 10% lot 1 (Baxter) #LE12G142AD | Gammagard Liquid 10% lot 2 (Baxter) #LE12HE76 | IGSC Subcuvia 16% (Baxter) #VNG1H020 |
| Specificity | Chromogenic substrate | | | Hydrolysis rate [nmol/ml × min] | | |
| --- | --- | --- | --- | --- | --- | --- |
| Broad spectrum | PL-1 | 73.7 | 18.3 | <10 | <10 | 22.1 |
| Broad spectrum | S-2288 | 241 | 29 | <5 | <5 | 46 |

TABLE 17-continued

Amidolytic activity of various plasma-derived protein compositions.

| | | | Commercially available IGIV preparations | | | |
|---|---|---|---|---|---|---|
| Specificity | Chromogenic substrate | Factor H Sample FH012 FC steril | Octagam 5% (Octapharma) #B82A8432 | Gammagard Liquid 10% lot 1 (Baxter) #LE12G142AD | Gammagard Liquid 10% lot 2 (Baxter) #LE12HE76 | IGSC Subcuvia 16% (Baxter) #VNG1H020 |
| | | | Hydrolysis rate [nmol/ml × min] | | | |
| FXIa, glandular kallikreins | S-2266 | 171 | 27.1 | <5 | <5 | 34.2 |
| FXa, Trypsin | S-2222 | 8.3 | <5 | <5 | <5 | <5 |
| Plasmin | S-2251 | 7.3 | <5 | <5 | <5 | <5 |
| Kallikrein, FXIa, FXIIa | S-2302 | 563 | 70.1 | <5 | 7.6 | 99.6 |
| PKKA | IE/mL | 9.5 | <4 | <4 | <4 | <4 |
| F-XIa | mU/mL | 510.8 | 1.37 | <0.04 | <0.04 | 0.79 |

Example 2

Figure 2:
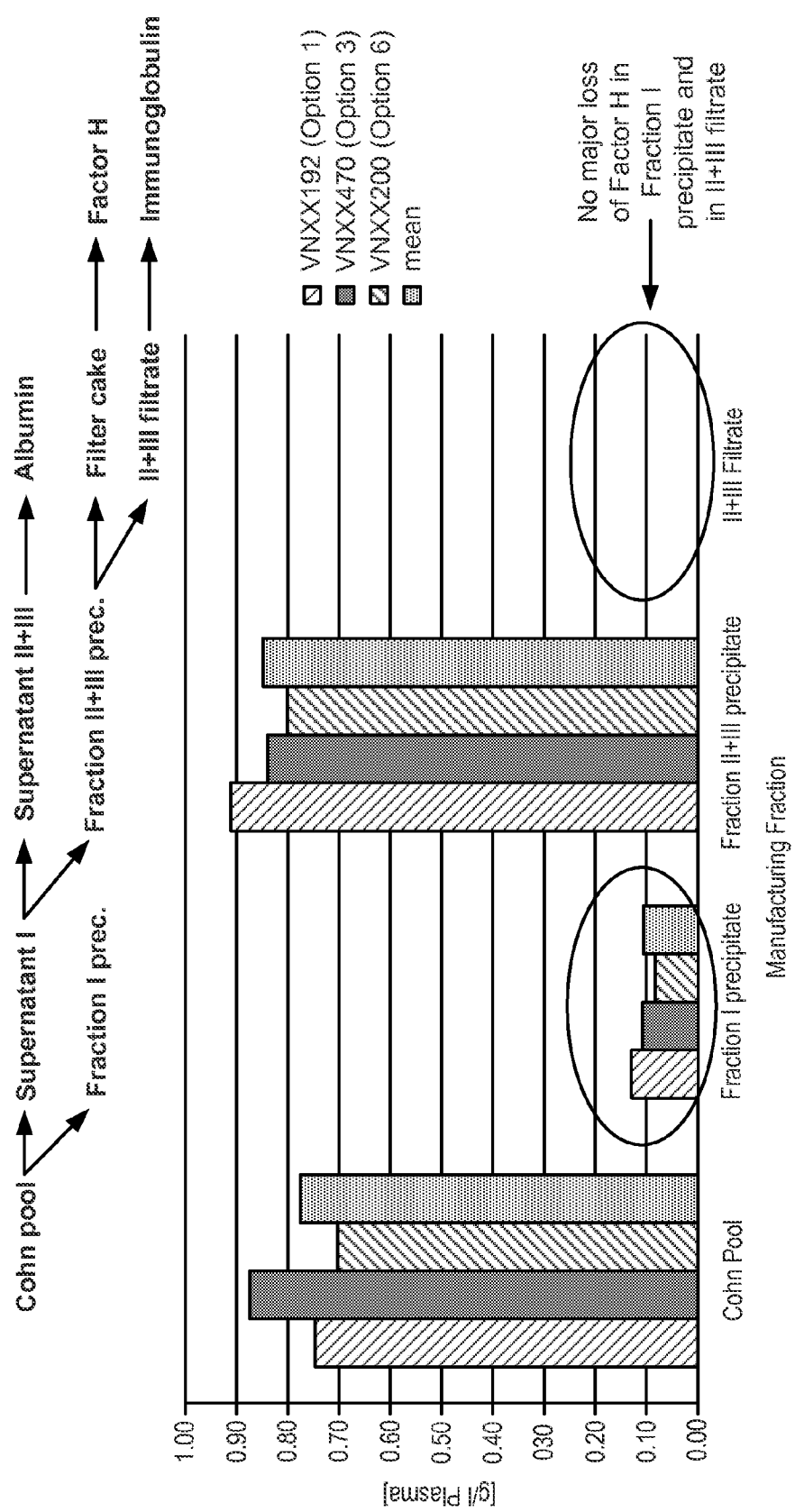
FIG. 2. Factor H content in select fractions of an industrial-scale plasma protein fractionation, as measured by ELISA FIG. 3. Illustration of Factor H and amidolytic activity (as measured using substrate CS2166) eluted from $SiO_2$ under solution conditions with varying conductivities at pH 7.5.

To determine an economically beneficial scheme for the manufacture of Factor H from a plasma sample, which allows for the recovery of additional blood factors from the same plasma sample, a lot of pooled human plasma was subjected to fractionation according to the scheme outlined in the flow-diagram shown in FIG. 1. As shown in FIG. 2, the majority of Factor H (about 90%) present in a human plasma cryo-poor Cohn pool can be found in the fraction II+III precipitate. A smaller, yet significant, amount of Factor H (about 10%) can also be found in the fraction I precipitate. This is consistent with the results shown in PCT Publication No. WO 2011/011753, the contents of which are hereby incorporated by reference in their entirety for all purposes.

Factor H was extracted from the finely divided $SiO_2$ filter cake byproduct formed as a result of filtering the "Aerosil Treatment" composition directly upstream of composition 6, the "Fraction II+III Filtrate," by re-circulating a Factor H extraction buffer through the filter press. Salts and various impurities were then removed from the filter cake extract by a first precipitation step performed at pH 8.0 via addition of ethanol to a final concentration of 15% and incubation at −6° C. for a minimum of four hours. The pH of the precipitation reaction was readjusted to 8.0 after 1 hour of incubation time. The precipitate was then removed from the supernatant by centrifugation. Factor H was further enriched by a second precipitation step performed at pH 6.0 via addition of ethanol to a final concentration of 25% and incubation at −10° C. for a minimum of 8 hours. The precipitate containing Factor H was then recovered by centrifugation.

The precipitate formed by the second precipitation step was dissolved at a ratio of 1:9 in a low ionic strength dissolution buffer and S/D treated to inactivate lipid enveloped viruses. Factor H was subsequently enriched by anion exchange chromatography using a DEAE-Sepharose FF resin. Briefly, Factor H was bound to DEAE-Sepharose resin under low ionic strength conditions and eluted by increasing the ionic strength of the solution. The conductivity of the DEAE-Sepharose eluate was then reduced and Factor H was further enriched by Heparin-affinity chromatography. Briefly, Factor H was bound to Heparin-Sepharose FF resin under low ionic strength conditions and eluted by increasing the ionic strength of the solution. As shown in Table 18, the majority of Factor H bound to the DEAE and Heparin resins.

TABLE 18

Binding of Factor H to chromatographic resins.

| | 1. DEAE-Sepharose FF | | 2. Heparin-Sepharose FF | |
|---|---|---|---|---|
| LOT | FH006 | FH012 | FH006 | FH012 |
| Loading (Protein) | 30.6 mg/ml | 28.0 mg/ml | 3.3 mg/ml | 2.1 mg/ml |
| FH binding to resine | 87.4% | 96.3% | 100% | 99.4% |

Factor H eluted from the Heparin resin was then subjected to ultrafiltration/diafiltration according to standard procedures, followed by size exclusion chromatography on a Superdex 200 column. Factor H recovered from the size exclusion chromatography was then concentrated by ultrafiltration, sterile filtered, and formulated at a final protein concentration of 50 mg/mL in PBS-buffer.

The final Factor H composition (FH012) was then characterized for homogeneity, impurities, and amidolytic activity. The monodispersity of the Factor H composition was characterized by size exclusion chromatography. As shown in Table 19, the majority of the protein present in the Factor H final composition migrated with an estimated size of 400 kDa when loaded onto an HP-SEC column.

TABLE 19

Molecular size distribution of final FH012 composition as determined by HP-SEC.

| sample | Peak 1 >450 kDa | Peak 2 400 kDa % area | Peak 3 160 kDa |
|---|---|---|---|
| FC FH012 | 0.3 | 97.6 | 2.1 |

The level of endotoxins, pH, visual appearance, and final protein concentration was then determined for the final Factor H composition. As shown in Table 20, the composition had low endotoxin levels (<0.5 EU/mL) as determined by limulus amebocyte lysate (LAL) assay.

TABLE 20

LAL, pH, visual appearance, and protein content of the final FH012 composition.

| LAL | <0.5 EU/mL (pyrogen free) |
|---|---|
| pH | 7.1 |

TABLE 20-continued

LAL, pH, visual appearance, and protein
content of the final FH012 composition.

| Visual Appearance | Colorless and free of visual particles |
|---|---|
| Protein Concentration | 4.54% |

The level of various protein impurities in the final Factor H composition was then determined. As shown in Table 21, complement proteins and IgG immunoglobulins accounted for less than 1% of the final protein concentration in the Factor H composition.

TABLE 21

Impurities in the final FH012 composition.

| Impurity | Concentration | Percentage of Total Protein |
|---|---|---|
| IgG | 51 µg/mL | 0.11% |
| C3 | 321.5 µg/mL | 0.71% |
| C3a | 17.5 µg/mL | 0.04% |
| C5a | 3.7 ng/mL | <0.01% |
| C4 | 1.94 µg/mL | <0.01% |
| EDTA | 72 µg/mL | |

Finally, the level of amidolytic activity and protease content was determined as reported in Example 1. As shown in Table 17, plasma-derived Factor H purified according to the scheme outlined in this example contained high levels of amidolytic activity and FXIa content.

Example 3

In order to show the capability of removing amidolytic activity from a plasma-derived protein composition, re-suspended Cohn Fraction II+III precipitates were treated with finely divided silicon dioxide ($SiO_2$). Briefly, pooled cryo-poor human plasma was fractionated according to the IgG purification scheme described herein, to provide a Fraction II+III precipitate. The fraction II+III precipitate was re-suspended in low conductivity extraction buffer (pH 5.1±0.2; ~0.8 mS/cm) at a temperature maintained between 0° C. and 8° C. Aerosil®380 (Evonik Industries AG) was added to a final concentration of between 40 and 60 g/kg II+III precipitate. After the additional of CELPURE® C300 filter aid (Advanced Minerals Corporation) to a final concentration of 0.5 kg/kg II+III precipitate, the suspension was filtered using a depth filter. The immunoglobulin composition in the filtrate was then tested for FXI zymogen content. As shown in Table 22, treatment of the fraction II+III suspension with finely divided $SiO_2$ resulted in nearly 90% reduction in the Factor XI zymogen content of the composition.

Example 4

To evaluate the elution of serine proteases from a finely divided $SiO_2$ filter cake, as prepared in Example 3, elution buffers containing varying concentrations of phosphate buffer (100, 50, 25, and 5 mM) were used to elute proteins from the $SiO_2$ at two different pH (6.0, 7.5). Briefly, the filtercake was dissolved at a ratio of 1:5 in the appropriate buffer system and filtrated through depth filters (Cuno 50 SA). The amidolytic activity and Factor H composition of each eluate was then determined (Table 23 and Table 24). As shown in Table 23, at lower conductivity and pH (i.e., 6.0), the elution of amidolytic activity measured with the substrate CS2166 (FXIa, activated Protein C) was reduced.

Under elution conditions at pH 7.5 (Table 24), Factor H elution decreased with increasing conductivity, while serine protease elution increased with increasing conductivity. Surprisingly, at extremely low conductivity (5 mM phosphate; 0.882 mS/cm), serine protease elution increased substantially, while Factor H elution decreased. The data obtained for elution at pH 7.5 is shown graphically in FIG. 3.

TABLE 23

Elution of Factor H and serine protease activity from finely divided $SiO_2$ at pH 6.0.

| Buffer System: pH = 6.0 | Sample | Substrate: CS2166 total nmol * min | Factor H [g/l Plasma] | Protein [nmol/g] |
|---|---|---|---|---|
| 100 mM Phosphate buffer; Cond. 11.88 mS/cm | Filtrate | 72745 | 0.27 | 61944 |
| 50 mM Phosphate buffer; Cond. 6.55 mS/cm | Filtrate | 65055 | 0.19 | 64600 |
| 25 mM Phosphate buffer; Cond. 3.48 mS/cm | Filtrate | 28591 | 0.05 | 63694 |
| 5 mM Phosphate buffer: Cond. 0.882 mS/cm | Filtrate | 4816 | 0.0003 | 57331 |

TABLE 24

Elution of Factor H and serine protease activity from finely divided $SiO_2$ at pH 7.5.

| Buffer System: pH = 7.5 | Sample | Substrate: CS2166 total nmol * min | Factor H [g/l Plasma] | Protein [nmol/g] |
|---|---|---|---|---|
| 100 mM Phosphate buffer; Cond. 18.81 mS/cm | Filtrate | 236456 | 0.21 | 156718 |

TABLE 22

Impurities in the final FH012 composition.

| | Fraction II + III Re-suspension | | | | | Fraction II + III Extract Cuno Filtrate | | | | |
|---|---|---|---|---|---|---|---|---|---|---|
| Lot | Fr. II + III paste, (kg) | Fr. II + III dissolved (L) | F-XI zymogen (U/mL) | F-XI zymogen (1000s of U) | F-XI zymogen (%) | Fr. II + III Filtrate volume, (L) | F-XI zymogen (U/mL) | F-XI zymogen (1000s of U) | F-XI zymogen (% of II + III re-suspension) | % Removal |
| 1 | 117 | 469 | 5.25 | 2460 | 100 | 2250 | 0.11 | 247 | 10.1% | 89.9% |
| 2 | 118 | 475 | 5.13 | 2435 | 100 | 2290 | 0.11 | 251 | 10.3% | 89.7% |
| 3 | 119 | 479 | 4.51 | 2162 | 100 | 2300 | 0.12 | 276 | 12.8% | 87.2% |

TABLE 24-continued

Elution of Factor H and serine protease activity from finely divided SiO$_2$ at pH 7.5.

| Buffer System: pH = 7.5 | Sample | Substrate: CS2166 total nmol * min | Factor H [g/l Plasma] | Protein [nmol/g] |
|---|---|---|---|---|
| 50 mM Phosphate Buffer; Cond. 10.91 mS/cm | Filtrate | 147829 | 0.29 | 109228 |
| 25 mM Phosphate buffer; Cond. 6.08 mS/cm | Filtrate | 84622 | 0.39 | 57892 |
| 5 mM Phosphate buffer: Cond. 1.524 mS/cm | Filtrate | 176685 | 0.33 | 134051 |

Example 5

In order to demonstrate the ability to differentially elute serine proteases and Factor H co-bound to SiO$_2$, a two step elution procedure was developed. Briefly, a fraction II+III filter cake formed after SiO$_2$ treatment was prepared as before. The filter cake was then subjected to a first elution under solution conditions comprising an ionic strength between 0.882 mS/cm and 11.88 mS/cm at pH 6.0. As demonstrated in Example 4, treatment of bound SiO$_2$ at low pH (pH 6.0) and low ionic strength (less than 6.5 mS/cm) results in elution of serine proteases (e.g., FXIa), while a substantial fraction of Factor H remains bound. Subsequent treatment at high pH (pH 7.5) and high ionic strength results in the elution of Factor H from the SiO$_2$ (Table 25). Furthermore, consistent with the results provided in Example 4, initial treatment of SiO$_2$ at high pH (7.5) results in elution of Factor H (Table 26). As shown, an initial elution at lower conductivity and pH 6.0 could be used to partially reduce amidolytic activity from the filter cake and then Factor H can be eluted at 100 mM phosphate concentration, 150 mM NaCl, pH 7.6. This procedure resulted in a filtrate, Factor H yield of 0.31 g/l plasma, with reduced amidolytic activity (CS2166) for further processing.

TABLE 25

Two-step differential elution of serine protease and Factor H from SiO$_2$ at pH 6.0/7.6.

| First Elution buffer System pH 6.0 | Second Elution buffer | Sample | Factor H [g/l Plasma] |
|---|---|---|---|
| 100 mM Phosphate buffer; Cond. 11.88 mS/cm | 100 mM Phosphate buffer + 150 mM NaCl, pH 7.6 | Filtrate second elution | 0.06 |
| 50 mM Phosphate buffer; Cond. 6.55 mS/cm | 100 mM Phosphate buffer + 150 mM NaCl, pH 7.6 | Filtrate second elution | 0.11 |
| 25 mM Phosphate buffer; Cond. 3.48 mS/cm | 100 mM Phosphate buffer + 150 mM NaCl, pH 7.6 | Filtrate second elution | 0.25 |
| 5 mM Phosphate buffer: Cond. 0.882 mS/cm | 100 mM Phosphate buffer + 150 mM NaCl, pH 7.6 | Filtrate second elution | 0.31 |

TABLE 26

Two-step differential elution of serine protease and Factor H from SiO$_2$ at pH 7.5/7.6.

| First Elution buffer System pH 7.5 | Second Elution buffer | Sample | Factor H [g/l Plasma] |
|---|---|---|---|
| 100 mM Phosphate buffer; Cond. 11.88 mS/cm | 100 mM Phosphate buffer + 150 mM NaCl, pH 7.6 | Filtrate second elution | 0.05 |
| 50 mM Phosphate buffer; Cond. 6.55 mS/cm | 100 mM Phosphate buffer + 150 mM NaCl, pH 7.6 | Filtrate second elution | 0.06 |
| 25 mM Phosphate buffer; Cond. 3.48 mS/cm | 100 mM Phosphate buffer + 150 mM NaCl, pH 7.6 | Filtrate second elution | 0.06 |
| 5 mM Phosphate buffer: Cond. 0.882 mS/cm | 100 mM Phosphate buffer + 150 mM NaCl, pH 7.6 | Filtrate second elution | 0.07 |

Example 6

To determine the amount of finely divided SiO$_2$ required for efficient removal of serine proteases and serine protease zymogens from a plasma-derived protein composition, a fraction II+III precipitate (i.e., II+III filtercake) was dissolved, filtered, treated with SiO$_2$, filter aid was admixed, and subjected to a second filtration. Briefly, the fraction II+III filtercake was first dissolved in 0.1 M phosphate buffer containing 150 mM sodium chloride (pH 7.5; 30 mS/cm). This suspension was then filtered through a Cuno 50 SA filter and the filtrate collected. Aerosil 380 was admixed with the filtrate at a final concentration of either 1.0 or 2.5 g/g protein and then incubated for at least 50 minutes. CEL-PURE filter aid was added and filtration was performed using a Cuno 50 SA filter. The resulting filtrate was then characterized for amidolytic activity, as reported in Table 27. Significantly, the results show that addition of Aerosil at a final concentration of 2.5 g/g protein reduced the amidolytic activity of Kallikrein, FXIa, and FXIIa in the composition by greater than 90%, as compared to the sample treated with Aerosil at a final concentration of 1.0 g/g protein.

TABLE 27

Amidolytic activity present in re-suspended Fraction II + III precipitate after treatment with finely divided silicon dioxide.

| Kallikrein, FXIa, FXIIa sample | Substrate: S-2302 total: nmol * min | Reduction by increased Aerosil addition [%] |
|---|---|---|
| FH027 Cuno filtrate, after addition of 1 g Aerosil per g Protein | 83347 | — |
| FH027 Cuno filtrate, after addition of 2.5 g Aerosil per g Protein | 6227 | 92.5 |

Example 7

To evaluate the efficiency of SiO$_2$ treatment for the removal of Factor XI zymogen during the industrial-scale manufacture of plasma-derived protein compositions, the FXI zymogen content of six industrial-scale manufacturing batches was characterized. Table 28 and Table 29 show the average FXI zymogen content of each upstream process step from three purifications performed at the same manufacturing site. The data in Table 28 and Table 29 demonstrate that SiO$_2$ treatment of manufacturing-scale purifications can reduce the FXI zymogen content of the composition by at least 90%. Notably, manufacturing sites 1 admixed Aerosil at a final concentration of 50 g/kg II+III precipitate, while site 2 used Aerosil at a final concentration of 40 g/kg II+III precipitate. Surprisingly, this small difference in the amount of aerosil used resulted in a significant difference in the Factor XI zymogen content of the filtrate after aerosil treatment (8.1% of Cohn starting pool for site 2 vs. 2.8% of Cohn starting pool for site 1).

TABLE 28

Mean value of Factor XI zymogen content in each fraction of three large-scale manufacturing batches processed at site 1.

| | | F-XI zymogen | | |
|---|---|---|---|---|
| Sample | Volume | (U/mL) | (U) | (% of Cohn pool) |
| Cohn pool | 3379 | 1.25 | 4233923 | 100.0 |
| Supernatant I | 3632 | 1.01 | 3669081 | 87.2 |
| Supernatant II + II | 3927 | 0.21 | 812077 | 19.1 |
| II + III paste* | 2302 | 1.31 | 3026261 | 71.6 |
| Filtrate after Aerosil | 2993 | 0.04 | 119107 | 2.8 |
| Ppt G dissolved | 248 | 0.31 | 77300 | 1.8 |

TABLE 29

Mean value of Factor XI zymogen content in each fraction of three large-scale manufacturing batches processed at site 2.

| | | F-XI zymogen | | |
|---|---|---|---|---|
| Sample | Volume | (U/mL) | (U) | (% of Cohn pool) |
| Cohn pool | 2885 | 1.11 | 3193460 | 100.0 |
| Supernatant I | 3076 | 1.04 | 3208517 | 100.5 |
| Supernatant II + II | 3376 | 0.29 | 968120 | 30.2 |
| II + III paste* | 474.3 | 4.96 | 2352714 | 74.0 |
| Filtrate after Aerosil | 2280 | 0.11 | 258466.7 | 8.1 |
| Ppt G dissolved | 238.1 | 1.07 | 253912.33 | 8.0 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing an inter-alpha-trypsin inhibitor (IαI) composition having a reduced amount of a serine protease or a serine protease zymogen, the method comprising the steps of:
   (a) contacting a blood-plasma derived solution containing IαI and at least one serine protease with from 0.01 grams to 10 grams finely divided silicon dioxide (SiO$_2$) per gram protein under conditions suitable to bind the IαI and at least one serine protease, the conditions including a pH of from 4.0 to 7.0 and a conductivity of from 0.1 mS/cm to 2.0 mS/cm;
   (b) separating the SiO$_2$ from the composition;
   (c) eluting the serine protease or serine protease zymogen from the SiO$_2$ under conditions in which at least 50% of the IαI remains bound, the conditions including a pH of from 5.0 to 7.0 and a conductivity of less than 5 mS/cm; and
   (d) eluting the IαI from the SiO$_2$ under conditions including a pH of from 7.0 to 8.0 and a conductivity of at least 2 mS/cm.

2. A method for preparing an inter-alpha-trypsin inhibitor (IαI) composition having a reduced amount of a serine protease or a serine protease zymogen, the method comprising the steps of:
   (a) contacting a blood-plasma derived solution containing IαI and at least one serine protease with from 0.01 grams to 10 grams finely divided silicon dioxide (SiO$_2$) per gram protein under conditions suitable to bind the IαI and at least one serine protease, the conditions including a pH of from 4.0 to 7.0 and a conductivity of from 0.1 mS/cm to 2.0 mS/cm;

(b) separating the SiO$_2$ from the composition; and (c) eluting the IαI from the SiO$_2$ under conditions in which at least 50% of the serine protease or serine protease zymogen remains bound to the SiO$_2$, the conditions including a pH of from 7.0 to 8.0 and a conductivity of no more than 10 mS/cm.

3. A method for preparing an inter-alpha-trypsin inhibitor (IαI) composition having a reduced amount of a serine protease or a serine protease zymogen, the method comprising the steps of:

(a) contacting a blood-plasma derived solution containing IαI and at least one serine protease with from 0.01 grams to 10 grams finely divided silicon dioxide (SiO$_2$) per gram protein under conditions suitable to bind the IαI but not at least 50% of the at least one serine protease or serine protease zymogen, the conditions including a pH of from 7.0 to 9.0 and a conductivity of at least 10 mS/cm;

(b) separating the SiO$_2$ from the composition; and (c) eluting the IαI from the SiO$_2$ under conditions including a pH of from 7.0 to 9.0 and a conductivity of less than 10 mS/cm.

4. A method for preparing an inter-alpha-trypsin inhibitor (IαI) composition having a reduced amount of a serine protease or a serine protease zymogen, the method comprising the steps of:

(a) contacting a blood-plasma derived solution containing inter-alpha-trypsin inhibitor (IαI) and at least one serine protease with from 0.01 grams to 10 grams finely divided silicon dioxide (SiO$_2$) per gram protein under conditions suitable to bind the serine protease or serine protease zymogen but not at least 50% of the inter-alpha-trypsin inhibitor (IαI), the conditions including a pH of from 7.0 to 9.0 and a conductivity of less than 10 mS/cm; and (b) separating the SiO$_2$ from the composition.

5. The method of claim 1, wherein the composition is contacted with SiO$_2$ at a final concentration of at least 1 g SiO$_2$/g protein.

6. The method of claim 5, wherein the composition is contacted with SiO$_2$ at a final concentration of at least 2 g SiO$_2$/g protein.

7. The method of claim 5, wherein the composition is contacted with SiO$_2$ at a final concentration of at least 2.5 g SiO$_2$/g protein.

8. The method of claim 1, wherein the serine protease or serine protease zymogen is Factor XI.

9. The method of claim 1, wherein the serine protease or serine protease zymogen is Factor XII.

10. The method of claim 1, wherein the serine protease or serine protease zymogen is Factor XIa.

11. The method of claim 1, wherein the serine protease or serine protease zymogen is Factor XIIa.

12. The method of claim 1, wherein the finely divided silicon dioxide (SiO$_2$) is fumed silica.

13. The method of claim 1, wherein the conditions in step (c) include a pH of from 6.0±0.5.

14. The method of claim 1, wherein the conditions in step (c) include a pH of rom 6.0±0.2.

15. The method of claim 2, wherein the conditions in step (c) include a conductivity of about 6.0.

16. The method of claim 3, wherein the conditions in step (a) include a conductivity of at least 20 mS/cm.

17. The method of claim 4, wherein the conditions in step (a) include a conductivity of about 6.0.

18. The method of claim 2, wherein the finely divided silicon dioxide (SiO$_2$) is fumed silica.

19. The method of claim 3, wherein the finely divided silicon dioxide (SiO$_2$) is fumed silica.

20. The method of claim 4, wherein the finely divided silicon dioxide (SiO$_2$) is fumed silica.

* * * * *